United States Patent
Mason

(10) Patent No.: US 10,842,765 B2
(45) Date of Patent: *Nov. 24, 2020

(54) METHODS OF REDUCING OR PREVENTING OXIDATION OF SMALL DENSE LDL OR MEMBRANE POLYUNSATURATED FATTY ACIDS

(71) Applicant: Amarin Pharmaceuticals Ireland Limited, Dublin (IE)

(72) Inventor: Richard Preston Mason, Bedminster, NJ (US)

(73) Assignee: Amarin Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,307

(22) Filed: Jun. 28, 2019

(65) Prior Publication Data
US 2019/0358185 A1    Nov. 28, 2019

Related U.S. Application Data

(63) Continuation of application No. 15/415,667, filed on Jan. 25, 2017, now Pat. No. 10,406,130.

(60) Provisional application No. 62/308,525, filed on Mar. 15, 2016.

(51) Int. Cl.
*A61K 31/202* (2006.01)
*A61K 31/40* (2006.01)

(52) U.S. Cl.
CPC ............ *A61K 31/202* (2013.01); *A61K 31/40* (2013.01)

(58) Field of Classification Search
CPC .................................................. A61K 31/202
See application file for complete search history.

(56) References Cited

U.S. PATENT DOCUMENTS

| | | | |
|---|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

Gabir et al., Diabetes Care, 23:1108-1112.2000 (Year: 2000).*

(Continued)

*Primary Examiner* — San Ming R Hui
(74) *Attorney, Agent, or Firm* — Perkins Coie LLP

(57) ABSTRACT

In various embodiments, the present invention provides methods of treating and/or preventing cardiovascular-related disease and, in particular, a method of reducing or preventing sdLDL oxidation in a subject, the method comprising administering to the subject a pharmaceutical composition comprising eicosapentaenoic acid or a derivative thereof.

13 Claims, 48 Drawing Sheets

*$p<0.01$ and **$p<0.001$ versus control; †$p<0.001$ versus glucose treatment (Student-Newman-Keuls multiple comparisons test).

(56) References Cited

U.S. PATENT DOCUMENTS

| | | |
|---|---|---|
| 5,343,389 A | 8/1994 | Otvos |
| 5,385,929 A | 1/1995 | Bjorge et al. |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,618,558 A | 4/1997 | Horrobin et al. |
| 5,656,667 A | 8/1997 | Breivik et al. |
| 5,698,594 A | 12/1997 | Breivik et al. |
| 5,760,081 A | 6/1998 | Leaf et al. |
| 5,763,496 A | 6/1998 | Holland |
| 5,776,978 A | 7/1998 | Bruzzese |
| 5,792,795 A | 8/1998 | Buser et al. |
| 5,837,731 A | 11/1998 | Vaddadi |
| 5,840,944 A | 11/1998 | Furihata et al. |
| 5,886,037 A | 3/1999 | Klor et al. |
| 5,888,541 A | 3/1999 | Horrobin et al. |
| 5,948,818 A | 9/1999 | Buser et al. |
| 6,025,008 A | 2/2000 | Akahoshi |
| 6,069,168 A | 5/2000 | Horrobin et al. |
| 6,193,999 B1 | 2/2001 | Gennadios |
| 6,207,699 B1 | 3/2001 | Rothman |
| 6,284,268 B1 | 9/2001 | Mishra et al. |
| 6,313,330 B1 | 11/2001 | Kiyohara et al. |
| 6,326,031 B1 | 12/2001 | Hsia et al. |
| 6,326,355 B1 | 12/2001 | Abbruzzese et al. |
| 6,331,568 B1 | 12/2001 | Horrobin |
| 6,368,621 B1 | 4/2002 | Engel et al. |
| 6,384,077 B1 | 5/2002 | Peet et al. |
| 6,479,544 B1 | 11/2002 | Horrobin |
| 6,482,421 B2 | 11/2002 | Weidner |
| 6,531,150 B1 | 3/2003 | Sunohara et al. |
| 6,555,700 B1 | 4/2003 | Horrobin et al. |
| 6,596,766 B1 | 7/2003 | Igarashi et al. |
| 6,620,821 B2 | 9/2003 | Robl |
| 6,689,812 B2 | 2/2004 | Peet |
| 6,846,942 B2 | 1/2005 | Rubin |
| 7,022,713 B2 | 4/2006 | Aoki et al. |
| 7,112,609 B2 | 9/2006 | Hermelin et al. |
| 7,119,118 B2 | 10/2006 | Peet |
| 7,179,491 B1 | 2/2007 | Mag |
| 7,205,329 B2 | 4/2007 | Chien et al. |
| 7,405,302 B2 | 7/2008 | Hutchinson et al. |
| 7,498,359 B2 | 3/2009 | Yokoyama et al. |
| 7,511,131 B2 | 3/2009 | Crooke et al. |
| 7,598,227 B2 | 10/2009 | Crooke et al. |
| 7,776,881 B2 | 8/2010 | Aoki et al. |
| 8,188,146 B2 | 5/2012 | Peet et al. |
| 8,293,727 B2 | 10/2012 | Manku et al. |
| 8,293,728 B2 | 10/2012 | Manku et al. |
| 8,298,554 B2 | 10/2012 | Manku |
| 8,314,086 B2 | 11/2012 | Manku et al. |
| 8,318,715 B2 | 11/2012 | Manku et al. |
| 8,324,195 B2 | 12/2012 | Manku et al. |
| 8,357,677 B1 | 1/2013 | Manku et al. |
| 8,367,652 B2 | 2/2013 | Manku et al. |
| 8,377,920 B2 | 2/2013 | Manku et al. |
| 8,410,086 B2 | 4/2013 | Osterloh et al. |
| 8,431,560 B1 | 4/2013 | Manku et al. |
| 8,440,650 B1 | 5/2013 | Manku et al. |
| 8,455,472 B2 | 6/2013 | Osterloh et al. |
| 8,518,929 B2 | 8/2013 | Manku et al. |
| 8,524,698 B2 | 9/2013 | Manku et al. |
| 8,546,372 B2 | 10/2013 | Manku et al. |
| 8,551,521 B2 | 10/2013 | Manku et al. |
| 8,563,608 B2 | 10/2013 | Manku et al. |
| 8,617,593 B2 | 12/2013 | Manku et al. |
| 8,617,594 B2 | 12/2013 | Manku et al. |
| 8,618,168 B2 | 12/2013 | Fujii et al. |
| 8,623,406 B2 | 1/2014 | Manku et al. |
| 8,642,077 B2 | 2/2014 | Manku et al. |
| 8,669,245 B2 | 3/2014 | Osterloh et al. |
| 8,680,144 B2 | 3/2014 | Osterloh et al. |
| 8,691,871 B2 | 4/2014 | Osterloh et al. |
| 8,703,185 B2 | 4/2014 | Manku et al. |
| 8,709,475 B2 | 4/2014 | Manku et al. |
| 8,906,964 B2 | 12/2014 | Bobotas et al. |
| 9,006,285 B2 | 4/2015 | Ohnishi |
| 9,060,981 B2 | 6/2015 | Sato et al. |
| 9,138,415 B2 | 9/2015 | Manku et al. |
| 9,452,121 B2 | 9/2016 | Manku et al. |
| 9,452,150 B2 | 9/2016 | Ueshima et al. |
| 9,603,826 B2 | 3/2017 | Soni |
| 9,610,272 B2 | 4/2017 | Soni |
| 9,623,001 B2 | 4/2017 | Soni |
| 9,693,984 B2 | 7/2017 | Soni |
| 9,693,985 B2 | 7/2017 | Soni |
| 9,693,986 B2 | 7/2017 | Soni |
| 9,855,237 B2 | 1/2018 | Osterloh et al. |
| 9,918,954 B2 | 3/2018 | Soni |
| 10,058,521 B2 | 8/2018 | Bobotas et al. |
| 10,166,209 B2 | 1/2019 | Manku et al. |
| 10,220,013 B2 | 3/2019 | Osterloh et al. |
| 10,265,290 B2 | 4/2019 | Manku et al. |
| 10,278,935 B2 | 5/2019 | Soni |
| 2001/0035125 A1 | 11/2001 | Talieh et al. |
| 2002/0016312 A1 | 2/2002 | Seed et al. |
| 2002/0025983 A1 | 2/2002 | Horrobin |
| 2002/0035125 A1 | 3/2002 | Shear |
| 2002/0055529 A1 | 5/2002 | Bisgaier et al. |
| 2002/0055539 A1 | 5/2002 | Bockow et al. |
| 2002/0077361 A1 | 6/2002 | Peet et al. |
| 2002/0169209 A1 | 11/2002 | Horrobin |
| 2002/0183389 A1 | 12/2002 | Peet |
| 2002/0193439 A1 | 12/2002 | Peet et al. |
| 2002/0198177 A1 | 12/2002 | Horrobin et al. |
| 2003/0100610 A1 | 5/2003 | Shibuya |
| 2003/0104048 A1 | 6/2003 | Patel et al. |
| 2003/0161918 A1 | 8/2003 | Kendrick et al. |
| 2003/0166614 A1 | 9/2003 | Harrison |
| 2003/0232385 A1 | 12/2003 | Breit et al. |
| 2004/0009208 A1 | 1/2004 | Edson |
| 2004/0048919 A1 | 3/2004 | Dreon et al. |
| 2004/0062847 A1 | 4/2004 | Koiki et al. |
| 2004/0077723 A1 | 4/2004 | Granata |
| 2004/0106591 A1 | 6/2004 | Pacioretty et al. |
| 2004/0121000 A1 | 6/2004 | Bowe et al. |
| 2004/0162348 A1 | 8/2004 | Peet et al. |
| 2004/0204356 A1 | 10/2004 | Guenzler-Pukall |
| 2004/0258645 A1 | 12/2004 | Trejo et al. |
| 2005/0042214 A1 | 2/2005 | Gershwin et al. |
| 2005/0137253 A1 | 6/2005 | Phinney et al. |
| 2005/0147665 A1 | 7/2005 | Horrobin et al. |
| 2005/0187292 A1 | 8/2005 | Aoki et al. |
| 2005/0244367 A1 | 11/2005 | Hui et al. |
| 2005/0272095 A1 | 12/2005 | Wang |
| 2006/0034815 A1 | 2/2006 | Guzman et al. |
| 2006/0051418 A1 | 3/2006 | Cowen et al. |
| 2006/0088502 A1 | 4/2006 | Sata et al. |
| 2006/0111437 A1 | 5/2006 | Aoki et al. |
| 2006/0134178 A1 | 6/2006 | Doisaki et al. |
| 2006/0134206 A1 | 6/2006 | Iyer et al. |
| 2006/0135607 A1 | 6/2006 | Kobayashi et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0172012 A1 | 8/2006 | Finley et al. |
| 2006/0189682 A1 | 8/2006 | Payne et al. |
| 2006/0211749 A1 | 9/2006 | Bobotas et al. |
| 2006/0211761 A1 | 9/2006 | Kumar et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0223838 A1 | 10/2006 | Jiang et al. |
| 2006/0252833 A1 | 11/2006 | Peet et al. |
| 2007/0021504 A1 | 1/2007 | Yokoyama et al. |
| 2007/0060532 A1 | 3/2007 | Junien et al. |
| 2007/0098787 A1 | 5/2007 | Kakiuchi |
| 2007/0104779 A1 | 5/2007 | Rongen et al. |
| 2007/0105793 A1 | 5/2007 | Hendrix |
| 2007/0105954 A1 | 5/2007 | Puri |
| 2007/0141138 A1 | 6/2007 | Feuerstein et al. |
| 2007/0167520 A1 | 7/2007 | Bruzzese |

(56) References Cited

U.S. PATENT DOCUMENTS

| | | |
|---|---|---|
| 2007/0185198 A1 | 8/2007 | Yokoyama et al. |
| 2007/0191467 A1 | 8/2007 | Rongen et al. |
| 2007/0202159 A1 | 8/2007 | Mathur et al. |
| 2007/0212411 A1 | 9/2007 | Fawzy et al. |
| 2007/0219271 A1 | 9/2007 | Mittmann et al. |
| 2007/0265340 A1 | 11/2007 | Shalwitz et al. |
| 2007/0269507 A1 | 11/2007 | Sachetto et al. |
| 2008/0020018 A1 | 1/2008 | Moodley et al. |
| 2008/0057115 A1 | 3/2008 | Okamoto |
| 2008/0085911 A1 | 4/2008 | Rongen et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0139604 A1 | 6/2008 | Fitzpatrick et al. |
| 2008/0185198 A1 | 8/2008 | Jones |
| 2008/0200453 A1 | 8/2008 | Cincotta |
| 2008/0200547 A1 | 8/2008 | Peet et al. |
| 2008/0200707 A1 | 8/2008 | Shimano et al. |
| 2008/0214531 A1 | 9/2008 | Saxena et al. |
| 2008/0299187 A1 | 12/2008 | Opheim et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0018125 A1 | 1/2009 | Mittmann et al. |
| 2009/0042979 A1 | 2/2009 | Guzman et al. |
| 2009/0054329 A1 | 2/2009 | Willemsen et al. |
| 2009/0105340 A1 | 4/2009 | Yokoyama |
| 2009/0148543 A1 | 6/2009 | Theoharides |
| 2009/0156675 A1 | 6/2009 | Yokoyama et al. |
| 2009/0182049 A1 | 7/2009 | Opheim |
| 2009/0227602 A1 | 9/2009 | Griffin et al. |
| 2009/0233843 A1 | 9/2009 | Marin |
| 2009/0239927 A1 | 9/2009 | Bobotas et al. |
| 2009/0304784 A1 | 12/2009 | Mane et al. |
| 2009/0311322 A1 | 12/2009 | Dlugatch et al. |
| 2010/0021555 A1 | 1/2010 | Geiringer et al. |
| 2010/0063018 A1 | 3/2010 | Pellicciari et al. |
| 2010/0069492 A1 | 3/2010 | Geiringen et al. |
| 2010/0113506 A1 | 5/2010 | Kawano et al. |
| 2010/0113811 A1 | 5/2010 | Yadav et al. |
| 2010/0119598 A1 | 5/2010 | Yoshinari et al. |
| 2010/0130608 A1 | 5/2010 | Ryan et al. |
| 2010/0160261 A1 | 6/2010 | Fortin |
| 2010/0233280 A1 | 9/2010 | Driscoll |
| 2010/0254951 A1 | 10/2010 | Shido et al. |
| 2010/0278879 A1 | 11/2010 | Manku |
| 2010/0285121 A1 | 11/2010 | Uchiyama et al. |
| 2010/0298379 A1 | 11/2010 | Jacobsen |
| 2010/0305205 A1 | 12/2010 | Yokoyama et al. |
| 2010/0311834 A1 | 12/2010 | Manku et al. |
| 2011/0034555 A1 | 2/2011 | Osterloh et al. |
| 2011/0065793 A1 | 3/2011 | Peet et al. |
| 2011/0071176 A1 | 3/2011 | Rowe |
| 2011/0082119 A1 | 4/2011 | Yano |
| 2011/0092592 A1 | 4/2011 | Yano |
| 2011/0105510 A1 | 5/2011 | Ishikawa |
| 2011/0130458 A1 | 6/2011 | Breivik et al. |
| 2011/0178105 A1 | 7/2011 | Gillies et al. |
| 2011/0195061 A1 | 8/2011 | Minatelli |
| 2011/0218243 A1 | 9/2011 | Rowe |
| 2011/0223158 A1 | 9/2011 | Sacks et al. |
| 2011/0236476 A1 | 9/2011 | Manku |
| 2011/0268811 A1 | 11/2011 | Minatelli et al. |
| 2011/0288171 A1 | 11/2011 | Manku et al. |
| 2012/0035105 A1 | 2/2012 | Geho et al. |
| 2012/0035262 A1 | 2/2012 | Osterloh et al. |
| 2012/0039997 A1 | 2/2012 | Manku et al. |
| 2012/0046251 A1 | 2/2012 | Schaefer et al. |
| 2012/0093922 A1 | 4/2012 | Manku et al. |
| 2012/0093924 A1 | 4/2012 | Manku et al. |
| 2012/0100208 A1 | 4/2012 | Manku |
| 2012/0108659 A1 | 5/2012 | Manku et al. |
| 2012/0108660 A1 | 5/2012 | Manku et al. |
| 2012/0108663 A1 | 5/2012 | Manku et al. |
| 2012/0121698 A1 | 5/2012 | Manku et al. |
| 2012/0156285 A1 | 6/2012 | Manku et al. |
| 2012/0157530 A1 | 6/2012 | Manku et al. |
| 2012/0157531 A1 | 6/2012 | Osterloh et al. |
| 2012/0172432 A1 | 7/2012 | Manku et al. |
| 2012/0184595 A1 | 7/2012 | Macdonald et al. |
| 2012/0195963 A1 | 8/2012 | Peet et al. |
| 2012/0207800 A1 | 8/2012 | Abu-Baker |
| 2012/0214771 A1 | 8/2012 | Sampalis |
| 2012/0225120 A1 | 9/2012 | Manku et al. |
| 2012/0232145 A1 | 9/2012 | Osterloh et al. |
| 2012/0237594 A1 | 9/2012 | Manku et al. |
| 2012/0264824 A1 | 10/2012 | Mizuguchi et al. |
| 2012/0295976 A1 | 11/2012 | Yokoyama |
| 2012/0302589 A1 | 11/2012 | Manku et al. |
| 2012/0329852 A1 | 12/2012 | Yokoyama |
| 2013/0004566 A1 | 1/2013 | Manku et al. |
| 2013/0004567 A1 | 1/2013 | Manku et al. |
| 2013/0004568 A1 | 1/2013 | Manku et al. |
| 2013/0004572 A1 | 1/2013 | Manku et al. |
| 2013/0005757 A1 | 1/2013 | Osterloh et al. |
| 2013/0005809 A1 | 1/2013 | Manku et al. |
| 2013/0011471 A1 | 1/2013 | Manku et al. |
| 2013/0011472 A1 | 1/2013 | Manku et al. |
| 2013/0012580 A1 | 1/2013 | Osterloh et al. |
| 2013/0017256 A1 | 1/2013 | Manku et al. |
| 2013/0065956 A1 | 3/2013 | Yokoyama |
| 2013/0079409 A1 | 3/2013 | Manku et al. |
| 2013/0090383 A1 | 4/2013 | Manku et al. |
| 2013/0095178 A1 | 4/2013 | Manku |
| 2013/0095179 A1 | 4/2013 | Davidson et al. |
| 2013/0096197 A1 | 4/2013 | Manku |
| 2013/0102674 A1 | 4/2013 | Manku |
| 2013/0115284 A1 | 5/2013 | Fujii |
| 2013/0131170 A1 | 5/2013 | Manku |
| 2013/0156852 A1 | 6/2013 | Manku et al. |
| 2013/0158120 A1 | 6/2013 | Manku et al. |
| 2013/0164375 A1 | 6/2013 | Manku et al. |
| 2013/0165513 A1 | 6/2013 | Manku et al. |
| 2013/0171249 A1 | 7/2013 | Manku et al. |
| 2013/0171250 A1 | 7/2013 | Manku et al. |
| 2013/0171251 A1 | 7/2013 | Manku et al. |
| 2013/0172413 A1 | 7/2013 | Manku |
| 2013/0189355 A1 | 7/2013 | Manku et al. |
| 2013/0195972 A1 | 8/2013 | Manku et al. |
| 2013/0252989 A1 | 9/2013 | Manku et al. |
| 2013/0252990 A1 | 9/2013 | Manku et al. |
| 2013/0253030 A1 | 9/2013 | Osterloh et al. |
| 2013/0253031 A1 | 9/2013 | Osterloh et al. |
| 2013/0260403 A1 | 10/2013 | Button et al. |
| 2013/0261180 A1 | 10/2013 | Gillies et al. |
| 2013/0281534 A1 | 10/2013 | Osterloh et al. |
| 2013/0295173 A1 | 11/2013 | Machielse et al. |
| 2013/0303614 A1 | 11/2013 | Kanehiro et al. |
| 2013/0324607 A1 | 12/2013 | Mason |
| 2013/0331447 A1 | 12/2013 | Manku et al. |
| 2014/0004183 A1 | 1/2014 | Soni et al. |
| 2014/0005264 A1 | 1/2014 | Soni et al. |
| 2014/0005265 A1 | 1/2014 | Soni et al. |
| 2014/0017306 A1 | 1/2014 | Manku |
| 2014/0057981 A1 | 2/2014 | Fujii |
| 2014/0073692 A1 | 3/2014 | Peet |
| 2014/0080850 A1 | 3/2014 | Mason |
| 2014/0080909 A1 | 3/2014 | Manku |
| 2014/0088194 A1 | 3/2014 | Manku |
| 2014/0094520 A1 | 4/2014 | Bobotas et al. |
| 2014/0107199 A1 | 4/2014 | Fawzy et al. |
| 2014/0127289 A1 | 5/2014 | Osterloh et al. |
| 2014/0128453 A1 | 5/2014 | Mullick et al. |
| 2014/0128464 A1 | 5/2014 | Rowe |
| 2014/0154310 A1 | 6/2014 | Osterloh et al. |
| 2014/0155455 A1 | 6/2014 | Osterloh et al. |
| 2014/0155481 A1 | 6/2014 | Osterloh et al. |
| 2014/0186438 A1 | 7/2014 | Manku et al. |
| 2014/0187633 A1 | 7/2014 | Manku et al. |
| 2014/0213648 A1 | 7/2014 | Manku et al. |
| 2014/0221358 A1 | 8/2014 | Zakrzewski |
| 2014/0221452 A1 | 8/2014 | Zakrzewski |
| 2014/0221486 A1 | 8/2014 | Manku et al. |
| 2014/0221676 A1 | 8/2014 | Braeckman et al. |

(56) References Cited

U.S. PATENT DOCUMENTS

| | | |
|---|---|---|
| 2014/0234410 A1 | 8/2014 | Moodley et al. |
| 2014/0235716 A1 | 8/2014 | Manku et al. |
| 2014/0243389 A1 | 8/2014 | Zakrzewski |
| 2014/0249200 A1 | 9/2014 | Braeckman et al. |
| 2014/0249214 A1 | 9/2014 | Braeckman et al. |
| 2014/0249220 A1 | 9/2014 | Braeckman et al. |
| 2014/0249225 A1 | 9/2014 | Mason |
| 2014/0256809 A1 | 9/2014 | Zakrzewski |
| 2014/0271841 A1 | 9/2014 | Grandolfi |
| 2014/0271907 A1 | 9/2014 | Zakrzewski |
| 2014/0275252 A1 | 9/2014 | Zakrzewski |
| 2014/0275253 A1 | 9/2014 | Zakrzewski |
| 2014/0322314 A1 | 10/2014 | Fawzy et al. |
| 2014/0357717 A1 | 12/2014 | Braeckman et al. |
| 2014/0364459 A1 | 12/2014 | Zakrzewski |
| 2015/0045431 A1 | 2/2015 | Zakrzewski |
| 2015/0051143 A1 | 2/2015 | Harada et al. |
| 2015/0051282 A1 | 2/2015 | Zakrzewski |
| 2015/0065572 A1 | 3/2015 | Zakrzewski |
| 2015/0073050 A1 | 3/2015 | Zakrzewski |
| 2015/0141510 A1 | 5/2015 | Kiyohara et al. |
| 2015/0157592 A1 | 6/2015 | Soni |
| 2015/0157593 A1 | 6/2015 | Braeckman et al. |
| 2015/0164850 A1 | 6/2015 | Osterloh et al. |
| 2015/0190361 A1 | 7/2015 | Osterloh et al. |
| 2015/0216831 A1 | 8/2015 | Manku et al. |
| 2015/0250754 A1 | 9/2015 | Ohta |
| 2015/0250756 A1 | 9/2015 | Mason |
| 2015/0250757 A1 | 9/2015 | Soni |
| 2015/0258051 A1 | 9/2015 | Manku et al. |
| 2015/0265566 A1 | 9/2015 | Osterloh et al. |
| 2015/0265574 A1 | 9/2015 | Rowe |
| 2015/0272917 A1 | 10/2015 | Manku et al. |
| 2015/0283074 A1 | 10/2015 | Fujii |
| 2015/0290154 A1 | 10/2015 | Roberts et al. |
| 2015/0335607 A1 | 11/2015 | Rowe |
| 2015/0359775 A1 | 12/2015 | Osterloh et al. |
| 2016/0058729 A1 | 3/2016 | Manku et al. |
| 2016/0120837 A1 | 5/2016 | Manku et al. |
| 2016/0143875 A1 | 5/2016 | Zakrzewski |
| 2016/0151319 A1 | 6/2016 | Kimura |
| 2016/0158184 A1 | 6/2016 | Ito |
| 2016/0213636 A1 | 7/2016 | Manku et al. |
| 2016/0213639 A1 | 7/2016 | Suzuki et al. |
| 2016/0220522 A1 | 8/2016 | Osterloh et al. |
| 2016/0287546 A1 | 10/2016 | Osterloh et al. |
| 2017/0014366 A1 | 1/2017 | Osterloh et al. |
| 2017/0035722 A1 | 2/2017 | Soni |
| 2017/0056361 A1 | 3/2017 | Soni |
| 2017/0079946 A1 | 3/2017 | Ohta |
| 2017/0087111 A1 | 3/2017 | Mason |
| 2017/0100363 A9 | 4/2017 | Zakrzewski |
| 2017/0119721 A1 | 5/2017 | Zakrzewski |
| 2017/0119722 A1 | 5/2017 | Manku et al. |
| 2017/0119723 A1 | 5/2017 | Soni |
| 2017/0119724 A1 | 5/2017 | Fujii |
| 2017/0128402 A1 | 5/2017 | Manku et al. |
| 2017/0128405 A1 | 5/2017 | Osterloh et al. |
| 2017/0128406 A1 | 5/2017 | Rowe |
| 2017/0136055 A1 | 5/2017 | Zakrzewski |
| 2017/0143656 A1 | 5/2017 | Soni |
| 2017/0143657 A1 | 5/2017 | Braeckman et al. |
| 2017/0143658 A1 | 5/2017 | Soni |
| 2017/0151202 A1 | 6/2017 | Mason |
| 2017/0151206 A1 | 6/2017 | Yokoyama |
| 2017/0258753 A1 | 9/2017 | Soni |
| 2017/0258754 A1 | 9/2017 | Soni |
| 2017/0258755 A1 | 9/2017 | Soni |
| 2017/0273928 A1 | 9/2017 | Yokoyama |
| 2017/0304249 A1 | 10/2017 | Abu-Baker |
| 2017/0333377 A1 | 11/2017 | Mason |
| 2017/0348268 A1 | 12/2017 | Kimura |
| 2017/0348273 A1 | 12/2017 | Ito |
| 2017/0368184 A1 | 12/2017 | Ito |
| 2018/0015038 A1 | 1/2018 | Ito |
| 2018/0015071 A1 | 1/2018 | Braeckman et al. |
| 2018/0028480 A1 | 2/2018 | Mason |
| 2018/0028505 A1 | 2/2018 | Oshima |
| 2018/0042880 A1 | 2/2018 | Osterloh et al. |
| 2018/0042883 A1 | 2/2018 | Manku et al. |
| 2018/0064676 A1 | 3/2018 | Zakrzewski |
| 2018/0085334 A1 | 3/2018 | Soni |
| 2018/0153846 A1 | 6/2018 | Soni |
| 2018/0185320 A1 | 7/2018 | Manku et al. |

FOREIGN PATENT DOCUMENTS

| | | |
|---|---|---|
| CA | 2675836 | 7/2008 |
| CA | 2724983 | 11/2009 |
| CA | 2772378 | 12/2010 |
| CN | 101252837 | 8/2008 |
| EP | 273708 | 7/1988 |
| EP | 277747 | 8/1988 |
| EP | 0302482 | 2/1989 |
| EP | 347509 | 12/1989 |
| EP | 0460917 | 12/1991 |
| EP | 606012 | 7/1994 |
| EP | 0610506 | 8/1994 |
| EP | 0641562 A1 | 3/1995 |
| EP | 0843972 | 5/1998 |
| EP | 1125914 | 8/2001 |
| EP | 1157692 | 11/2001 |
| EP | 1296670 | 4/2003 |
| EP | 1549299 | 12/2003 |
| EP | 1743644 | 1/2007 |
| EP | 1 790 339 A1 | 5/2007 |
| EP | 1 834 639 A1 | 9/2007 |
| EP | 1 982 710 A1 | 10/2008 |
| EP | 2022495 | 2/2009 |
| EP | 2395991 | 8/2010 |
| EP | 2308493 A1 | 4/2011 |
| EP | 2343066 A1 | 7/2011 |
| EP | 2719382 A1 | 4/2014 |
| EP | 2792746 | 10/2014 |
| FR | 2635263 | 2/1990 |
| GB | 2148713 | 6/1985 |
| GB | 2221843 | 2/1990 |
| GB | 2229363 | 9/1990 |
| GB | 9901809.5 | 1/1999 |
| GB | 2480146 | 11/2011 |
| IL | 55227 | 12/1982 |
| JP | 61035356 | 2/1986 |
| JP | 04182426 | 6/1992 |
| JP | 2003306690 | 10/2003 |
| JP | 07 238598 | 9/2007 |
| JP | 08 050367 | 3/2008 |
| KR | 10-2006-0109988 | 10/2006 |
| KR | 10-2007-0058460 | 6/2007 |
| RU | 2290185 | 12/2006 |
| RU | 2402326 C1 | 10/2010 |
| WO | WO 1990/004391 | 5/1990 |
| WO | WO 1992/021335 | 12/1992 |
| WO | WO 1994/028891 | 12/1994 |
| WO | WO 1995/024459 | 9/1995 |
| WO | WO 1996/036329 | 11/1996 |
| WO | WO 1997/039759 | 10/1997 |
| WO | WO 1998/016216 | 4/1998 |
| WO | WO 1999/26583 | 6/1999 |
| WO | WO 1999/029316 | 6/1999 |
| WO | WO 2000/044361 | 8/2000 |
| WO | WO 2000/051573 | 9/2000 |
| WO | WO 2001/015552 | 3/2001 |
| WO | WO 2002/002105 | 1/2002 |
| WO | WO 2002/058793 | 8/2002 |
| WO | WO 2002/089787 | 11/2002 |
| WO | WO 2002/096408 | 12/2002 |
| WO | WO 2003/068216 | 8/2003 |
| WO | WO 2003/092673 | 11/2003 |
| WO | WO 2004/050913 | 6/2004 |
| WO | WO 2004/064716 | 8/2004 |
| WO | WO 2004/078166 | 9/2004 |
| WO | WO 2004/082402 | 9/2004 |
| WO | WO 2005/060954 | 7/2005 |
| WO | WO 2005/079797 | 9/2005 |

(56) References Cited

FOREIGN PATENT DOCUMENTS

| WO | WO 2005/079853 | 9/2005 |
|---|---|---|
| WO | WO2005/102301 | 11/2005 |
| WO | WO 2005/123060 | 12/2005 |
| WO | WO 2005/123061 | 12/2005 |
| WO | WO 2006/017627 | 2/2006 |
| WO | WO 2006/029577 | 3/2006 |
| WO | WO 2006/062748 | 6/2006 |
| WO | WO 2006/096806 | 9/2006 |
| WO | WO 2007/011886 | 1/2007 |
| WO | WO 2007/016256 | 2/2007 |
| WO | WO 2007/017240 | 2/2007 |
| WO | WO 2007/073176 | 6/2007 |
| WO | WO 2007/075841 | 7/2007 |
| WO | WO 2007/091338 | 8/2007 |
| WO | WO 2007/128801 | 11/2007 |
| WO | WO 2007/142118 | 12/2007 |
| WO | WO 2008/004900 | 1/2008 |
| WO | WO 2008/045465 | 4/2008 |
| WO | WO 2008/088415 | 7/2008 |
| WO | WO 2008/106787 | 9/2008 |
| WO | WO 2008/115529 | 9/2008 |
| WO | WO 2008/145170 | 12/2008 |
| WO | WO 2009/004999 | 1/2009 |
| WO | WO2009/085386 | 7/2009 |
| WO | WO2009/085388 | 7/2009 |
| WO | WO 2010/028067 | 3/2010 |
| WO | WO 2010/093634 | 8/2010 |
| WO | WO 2010/127099 | 11/2010 |
| WO | WO 2010/127103 | 11/2010 |
| WO | WO 2010/147994 | 12/2010 |
| WO | WO2011/028689 | 3/2011 |
| WO | WO 2011/038122 | 3/2011 |
| WO | WO2011/085211 | 7/2011 |
| WO | WO 2011/109724 | 9/2011 |
| WO | WO 2012/074930 | 6/2012 |
| WO | WO2012/128587 | 9/2012 |
| WO | WO 2013/070735 | 5/2013 |
| WO | WO2013/103958 | 7/2013 |
| WO | WO2013/148136 | 10/2013 |
| WO | WO2014/004861 | 1/2014 |
| WO | WO2014/004993 | 1/2014 |
| WO | WO2014/005013 | 1/2014 |
| WO | WO 2014/057522 | 4/2014 |
| WO | WO2014/074552 | 5/2014 |
| WO | WO2014/130200 | 8/2014 |
| WO | WO2014/134466 | 9/2014 |
| WO | WO2014/143469 | 9/2014 |
| WO | WO2014/143523 | 9/2014 |
| WO | WO2015/021141 | 2/2015 |
| WO | WO2015/066512 | 5/2015 |
| WO | WO2015/195662 | 12/2015 |
| WO | WO2016/140949 | 9/2016 |

OTHER PUBLICATIONS

WHO classification of Diabetes Mellitus 2019, p. 1-23 (Year: 2019).*
Standards of Medical care in Diabetes-2019, Diabetes Care, 42, Suppl. 1, S13-S28, 2019 (Year: 2019).*
A study of AMR101 to evaluate its ability to reduce cardiovascular events in high risk patients with hypertriglyceridemia and on statin (REDUCE-IT). Available at: http://clinicaltrials.gov/show/NCT01492361. (3 pages).
Aarsland, et al., "On the Effect of Peroximsomal beta-Oxidation and Carnitine Palmitoyltransferase Activity by Eicosapentaenoic Aid in Live and Heart of Rats." Lipids, 25:546-548, (Sep. 1990).
Aas, V., et al., "Eicosapentaenoic acid (20:5 n-3) increases fatty acid and glucose uptake in cultured human skeletal muscle cells." Journal of Lipid Research, 47:366-374 (Feb. 2006).
Abbey, M., et al., "Effect of fish oil on lipoproteins, lecithin:cholesterol acyltransferase, and lipidtransfer protein activity in humans." Arterioscler. Thromb. Vasc. Biol. 10:85-94 (Jan./Feb. 1990).

Abele GS, Aziz K. "Cholesterol crystals cause mechanical damage to biological membranes: a proposed mechanism of plaque rupture and erosion leading to arterial thrombosis." Clin. Cardiol. (Sep. 2005);28(9):413-420.
Abelo A, Andersson TB, Antonsson M, et al. "Stereoselective metabolism of omeprazole by human cytochrome P450 enzymes." Drug Metab. Dispos. Aug. 28, 2000 (8): 966-72.
Ackman et al., "The 'Basic' Fatty Acid Composition of Atlantic Fish Oils: Potential Similarties Useful for Enrichment of Polyunsaturated Fatty Acids by Urea Complexation," JAOCS, vol. 65, 1:136-138 (Jan. 1988).
Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (Jan. 1999).
Adan, Y., et al., "Concentration of serum lipids and aortic lesion size in female and male apo E-deficient mice fed docosahexaenoic acid." Biosci. Biotechnol. Biochem. 63(2):309-313 (Feb. 1999).
Adorini et al., "Farnesoid X receptor targeting to treat nonalcoholic steatohepatitis," Drug Discover Today, 14(17-18):988-997 (Sep. 2012)(available online May 28, 2012).
Agren JJ, Vaisanen S, Hanninen O, et al. "Hemostatic factors and platelet aggregation after a fish-enriched diet or fish oil or docosahexaenoic acid supplementation." Prostaglandins Leukot Essent Fatty Acids (Oct. 1997) 57 (4-5): 419-21.
Agren, J.J., et al., "Fatty acid composition of erythrocyte, platelet, and serum lipids in strict vegans." Lipids 30:365-369 (Apr. 1995).
Agren, J.J., et al., "Fish diet, fish oil and docosahexaenoic acid rich oil lower fasting and postprandial plasma lipid levels." Eur J Clin Nutr., 50:765-771. (Nov. 1996).
Aguilar-Salinas et al., "High Prevalence of Low HDL Cholesterol Concentrations and Mixed Hyperlipidemia in a Mexican Nationwide Survey," J Lipid Res., (Aug. 2001), 42:1298-1307.
Ai M, Otokozawa S, Asztalos BF, Ito Y, Nakajima K, White CC, Cupples LA, Wilson PW, Schaefer EJ. "Small dense LDL cholesterol and coronary heart disease: results from the Framingham Offspring Study." Clin. Chem. (Jun. 2010);56(6):967-976.
Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (Feb. 2003).
Alderman, J.D., et al., "Effect of a modified, well-tolerated niacin regimen on serum total cholesterol, high density lipoprotein cholesterol and the cholesterol to high density lipoprotein ratio," Am. J. Cardio, 64: 725-729.A (Oct. 1989).
Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (Jan. 2008).
Allard et al. "Nutritional assessment and hepatic fatty acid composition in non-alcoholic fatty liver disease (NAFLD): a cross-sectional study." J Hepatol. Feb. 2008;48(2):300-7.
Allred, C., et al., "PPARγ1 as a molecular target of eicosapentaenoic acid in human colon cancer (HT-29) cells." J. Nutr. 138:250-256 (Feb. 2008).
Almeida et al., "Effect of nebicapone on the pharmacokinetics and pharmacodynamics of warfarin in healthy subjects." Eur J Clin Pharmacol. (Oct. 2008);64(10):961-6.
Amarin Appoints Medpace as CRO for Two Phase 3 Cardiovascular Trials, published Oct. 19, 2009 (2 pages).
Amarin Corporation Announces First Patients Enrolled in Two Phase 3 Clinical Trials Assessing AMR101 for the Treatment of Cardiovascular Disease [online], Amarin Corporation, Jan. 11, 2010 [retrieved Apr. 27, 2011], Retrieved from the Internet: <http://inestor.amarincorp.com/releasedetail.cfm?ReleaseID=504380> (2 pages).
Amarin Corporation, Annual Report, Jun. 24, 2010 (245 pages total)(submitted in three parts; Part I: Cover and pp. 1-39 (81 pages); Part II: pp. 40 through F-10 (81 pages); Part III: pp. F11-F51 (83 pages)).
Amarin Corporation, Executive Informational Overview, "Neurological Disease-Focused Biopharmaceutical Opportunity," SEC filing dated Oct. 11, 2005 (99 pages).

(56) References Cited

OTHER PUBLICATIONS

Amarin Corporation, press release (Jan. 18, 2008)(1 page).
Amarin Presentation "Next Generation Lipid Modification in Cardiovascular Disease," (Aug. 2011)(27 pages).
Amarin Presentation "Next Generation Lipid Modification in Cardiovascular Disease," (Mar. 2010)(25 pages).
Amarin Proceeding to Phase 3 with AMR101 for Hypertriglyceridemia, published Jul. 23, 2008 (1 page).
Amarin's Vascepa® Briefing Document for the Endocrinologic and Metabolic Drugs Advisory Committee Meeting dated Oct. 16, 2013, (117 pages).
Anber V, Griffin BA, McConnell M, Packard CJ, Shepherd J. Influence of plasma lipid and LDL-subfraction profile on the interaction between low density lipoprotein with human arterial wall proteoglycans. *Atherosclerosis.* Aug. 1996;124(2):261-271.
Anderson TJ, Gregoire J, Hegele RA, et al. 2012 update of the Canadian Cardiovascular Society guidelines for the diagnosis and treatment of dyslipidemia for the prevention of cardiovascular disease in the adult. Can. J. Cardiol. Feb. 2013;29:151-167.
Anderson TJ, Meredith IT, Yeung AC, Frei B, Selwyn AP, Ganz P. The effect of cholesterol-lowering and antioxidant therapy on endothelium-dependent coronary vasomotion. N. Engl. J. Med. Feb. 1995;332:488-493.
Anderson, "Lipoprotein-Associated Phospholipase A2: An Independent Predictor of Coronary Artery Disease Events in Primary and Secondary Prevention," 101 Am. J. Cardiology 23F-33F (Jun. 2008).
Ando, M., et al., "Eicosapentanoic acid reduces plasma levels of remnant lipoproteins and prevents in vivo peroxidation of LDL in dialysis patients." J. Am. Soc. Nephrol., 10:2177-2184 (Oct. 1999).
Ando, Y., et al., "Positional distribution of highly unsaturated fatty acids in triacyl-sn-glycerols of Artemia Nauplii enriched with docosahexaenoic acid ethyl ester." Lipids 36:733-740 (Jul. 2001).
Andrade, SE. et al., "Discontinuation of antihyperlipidaemic drugs_ do rates reported in clinical trials reflect rates in primary care settings?" New Eng. J. Med. 332: 1125-1131. (Apr. 1995).
Andrews HE, Bruckdorfer KR, Dunn RC, Jacobs M. Low-density lipoproteins inhibit endotheliumdependent relaxation in rabbit aorta. Nature. May 1987;327:237-239.
Angerer et al., "n-3 Polyunsaturated Fatty Acids and the Cardiovascular System", Current Opinion in Lipidology, 11(1):57-63, (Feb. 2000).
Anil, Eliz, "The Impact of EPA and DHA on Blood Lipids and Lipoprotein Metabolism: Influence of ApoE Genotype", Proceedings of the Nutrition Society, 66:60-68, (Feb. 2007).
Annex to Rule 161 Response dated Apr. 16, 2012 (4 pages).
Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu; 70:625-631. (1993) (with English translation).
Appendix A to Defendants' Invalidity Contentions, 3:14-CV-02550-MLC-DEA (D.N.J.), 478 pages (Dec. 5, 2014).
Appleton, Katherine M., et al., "Effects of n-3 long-chain polyunsaturated fatty acids on depressed mood: systematic review of published trials", Am. J. Clin. Nutr., 84(6):1308-1316, (Dec. 2006).
Arca et al., "Treating statin-intolerant patients," Diabetes, Metabolic Syndrome and Obesity: Targets and Therapy, 4:155-156 (Apr. 28, 2011).
Arrol, S. et al., "The effects of fatty acids on apolipoprotein B secretion by human hepatoma cells (HEP G2)," Atherosclerosis 150:255-264. (Jun. 2000).
Arshad, A., et al., "Sudden cardiac death and the role of medical therapy." Progress in Cardiovascular Diseases, vol. 50, No. 6, 420-438, (May/Jun. 2008).
Arterburn, L., et al., "Distribution, interconversion, and dose response of n-3 fatty acids in humans." Am J Clin Nutr., 83:1467S-76S (Jun. 2006).

Asahara, EPA Products What is the Clinical Significance of Epadel? Obesity and Diabetes 10(6):903-905 (2011) (with English translation).
Asano, M., et al., "Eicosapentaenoic acid inhibits vasopressin-activated Ca2q influx and cell proliferation in rat aortic smooth muscle cell lines." European Journal of Pharmacology 379:199-209 (Aug. 1999).
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (Apr. 1997).
Ascenta Health "Fish Oil as Triglycerides vs. Ethyl Esters: Why this Matters." (2015)(14 pages).
Atorvastatin Package Leaflet, Reg. No. LSR-005205/08, Sep. 30, 2016 [retrieved Sep. 30, 2016] retrieved from the internet: academ-clinic.ru/drugs/atorvastatin (6 pages).
ATP III guidelines, NIH publication No. 01-3305 (2001).(6 pages).
Attie AD, et al., "Relationship between stearoyl-CoA desaturase activity and plasma triglycerides in human and mouse hypertriglyceridemia," J. Lipid Res. 2002;43:1899-907.
Ault, "Prescription omega-3 fatty acid formulation approved," Ob.Gyn.News, (Jan. 15, 2005).
Avandia [package insert]. Research Triangle Park, NC: GlaxoSmithKline; 2011.(45 pages).
Avery et al., "Upper Gastrointestinal System," Integrating Therapeutic and Complementary Nutrition, Edited by Mary Marian, CRC Press (2006)(14 pages).
Aviram M, Rosenblat M, Bisgaier CL, Newton RS. Atorvastatin and gemfibrozil metabolites, but not the parent drugs, are potent anti-oxidants against lipoprotein oxidation. Atherosclerosis. Jun. 1998; 138(2):271-280.
Ayton, et al., "A pilot open case series of Ethyl-EPA supplementation in the treatment of anorexia nervosa," Prostaglandins, Leukotrienes and Essential Fatty Acids 71, pp. 205-209. (Oct. 2004).
Ayton, et al., "Rapid improvement of severe anorexia nervosa during treatment with ethyl-eicosapentaenoate and micronutrients," European Psychiatry 19, pp. 317-319. (Aug. 2004).
Baigent, C., et al., "Efficacy and safety of cholesterol-lowering treatment: prospective meta-analysis of data from 90,056 participants in 14 randomised trials of statins." Lancet; 366:1267-1278. (Oct. 2005).
Baldwin RM, Ohlsson S, Pedersen RS, et al. Increased omeprazole metabolism in carriers of the CYP2C19*17 allele; a pharmacokinetic study in healthy volunteers. *Br. J. Clin. Pharmacol.* May 2008 65 (5): 767-74.
Baldwin SJ, Clarke SE, Chenery RJ. Characterization of the cytochrome P450 enzymes involved in the in vitro metabolism of rosiglitazone. Br. J. Clin. Pharmacol. Sep. 1999;48:424-432.
Balk, E.M., et al., "Effects of omega-3 fatty acids on serum markers of cardiovascular disease risk: a systematic review. Atherosclerosis." 189:19-30. (Nov. 2006).
Ballantyne CM, Bays HE, Kastelein JJ, et al. Efficacy and safety of eicosapentaenoic acid ethyl ester (AMR 101) therapy in statin-treated patients with persistent high triglycerides (from the ANCHOR study). Am J Cardiol Oct. 2012 110 (7): 984-92.
Ballantyne et al., "Abstract 15071: AMR101 Lowers Triglycerides, Atherogenic Lipoprotein, Phospholipase A$_2$, and High-sensitivity C-reactive Protein Levels in Patients with High Triglycerides and on Background Statin Therapy (the ANCHOR Study)," Circulation, Lippincott Williams and Wilkins, vol. 124, No. 21, Suppl., Nov. 22, 2011.
Ballantyne et al., "Effects of icosapent ethyl on lipoprotein particle concentration and the fatty acid desaturation index in statiotreated patients with persistent high triglycerides (the ANCHOR study)." Journ. Clin. Lipidology, 2013, 7(3):270-271.
Ballantyne et al., Influence of low-high density lipoprotein cholesterol and elevated triglyceride on coronary heart disease events and response to simvastatin therapy in 4S, Circulation, 104:3046-3051. (Dec. 2001).
Bang HO, Dyerberg J. "Plasma lipids and Lipoproteins in Greenlandic west coast Eskimos" Acta Med Scand, 192:85-94. (Jul./Aug. 1972).

(56) References Cited

OTHER PUBLICATIONS

Banga, A., et al., "Adiponectin translation is increased by the PPARy agonists pioglitazone and ω-3 fatty acids." Am J Physiol Endocrinol Metab 296:480-489 (Mar. 2009).
Bangham et al., "Diffusion of univalent ions across the lamellae of swolloen phospholipids." J. Mol. Biol. (Aug. 1965) 13(1):238-252.
Bansal S, Buring JE, Rifai N, Mora S, Sacks FM, Ridker PM, "Fasting Compared With Nonfasting Triglycerides and Risk of Cardiovascular Events in Women," JAMA, 298:309-316 (Jul. 2007).
Barter et al., "Effectiveness of Combined Statin Plus Omega-3 Fatty Acid Therapy for Mixed Dyslipidemia." Am. J. Cardiol. 102(8):1040-1045 (Oct. 15, 2008).
Basu, A., et al., "Dietary Factors That Promote or Retard Inflammation." Arterioscler. Thromb. Vasc. Biol. 26:995-1001 (May 2006).
Baynes JW. Role of oxidative stress in development of complications in diabetes. Diabetes. Apr. 1991;40(4):405-412.
Bays HE et al. "Prescription omega 3 fatty acids and their lipid effects: physiologic mechanisms of action and clinical implications," Expert Rev Cardiovasc Ther., 6:391-409. (Mar. 2008).
Bays HE, Ballantyne CM, Braeckman RA, Stirlen WG, Soni PN. Icosapent ethyl, a pure ethyl ester of eicosapentaenoic acid: effects on circulating markers of inflammation from the MARINE and ANCHOR studies. Am. J. Cardiovasc. Drugs. Feb. 2013;13(1):37-46.
Bays HE, Braeckman RA, Ballantyne CM, et al. Icosapent ethyl, a pure EPA omega-3 fatty acid: Effects on lipoprotein particle concentration and size in patients with very high triglyceride levels (the MARINE study). J. Clin. Lipidol. Nov./Dec. 2012;6:565-572.
Bays HE, Safety considerations with omega-3 fatty acid therapy. Am. J. Cardiol. Mar. 2007 99 (6A): 35C-43C.
Bays, H., Clinical Overview of Omacor: A Concentrated Formulation of Omega-3 Polyunsaturated Fatty Acids, Am J Cardiol.; 98[suppl]:71i-76i (Aug. 2006).
Bays, H., "Rationale for Prescription Omega-3-Acid Ethyl Ester Therapy for Hypertriglyceridemia: A Primer for Clinicians," Drugs of Today, 44(3); 205-246. (Mar. 2008).
Bays, H.E., Eicosapentaenoic Acid Ethyl Ester (AMR101) Therapy in Patients With Very High Triglyceride Levels (from the Multicenter, plAcebo-controlled, Randomized, double-bIINd, 12-week study with an open-label Extension [MARINE] Trial) Am J Cardiol;108:682-690. (Sep. 2011).
Bays, H.E., et al., "Long-term up to 24-month efficacy and safety of concomitant prescription omega-3-acid ethyl esters and simvastatin in hypertriglyceridemic patients." Curr Med Res Opin.; 26:907-915. (Apr. 2010).
Beal, M.F., Annals of Neurology, vol. 38, No. 3, "Aging, Energy, and Oxidative Stress in Neurodegenerative Diseases", pp. 357-366, (Sep. 1995).
Beaumont et al., Design of Ester Prodrugs to Enhance Oral Absorption of Poorly Permeable Compounds: Challenges to the Discovery Scientist, Current Drug and Metabolism. (Dec. 2003) 4:461-485.
Belarbi et al., "A process for high yield and scaleable recovery of high purity eicosapentaenoic acid esters from microalgae and fish oil," Enzyme and Microbail Technology 26:516-529 (Apr. 2000).
Belger et al., "Assessment of prefrontal activation by infrequent visual targets and non-target noval stimuli in schisophrenia: a function MRI study, " Presented at the 9th Biennial winter workshop on schizophrenia, Davos, Switzerland, Feb. 7-13, 1998, Abstract in Schizophrenia Research. vol. 29. No. 1/02, Jan. 1998.
Belikov, Pharmaceutical Chemistry in Two Parts, 1/General Pharmaceutical Chemistry 43-47 (1993) (with English translation)(9 pages).
Belmaker et al., "Addition of Omega-3 Fatty Acid to Maintenance Medication Treatment for Recurrent Unipolar Depressive Disorder," Am. J. Psychiatry, 159:477-479 (Mar. 2002).
Belmaker, et al., "Omega-3 Eicosapentaenoic Acid in Bipolar Depression: Report of a Small Open-Label Study," J Clin Psychiatry; 66:726-729. (Jun. 2005).

Bender NK, Kraynak MA, Chiquette E, et al. Effects of marine fish oils on the anticoagulation status of patients receiving chronic warfarin therapy. J. Thromb. Thrombolysis Jul. 5, 1998 (3): 257-61.
Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (Oct. 1996).
Benn et al., Improving Prediction of Ischemic Cardiovascular Disease in the General Population Using Apolipoprotein B: The Copenhagen City Heart Study, 27 Arteriosclerosis, Thrombosis, & Ascular Biology 661 (Mar. 2007).
Bennett et al., "Treatment of IgA nephropathy with eicosapentanoic acid (EPA): a two-year prospective trial [Abstract Only]." Clin. Nephrol. 31(3):128-131 (Mar. 1989).
Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J.; 343(Pt 1):191-197. (Oct. 1999).
Berglund L, Brunzell JD, Goldberg AC, et al. Evaluation and treatment of hypertriglyceridemia: an endocrine society clinical practice guideline. J. Clin. Endocrinol. Metab. Sep. 2012 97 (9): 2969-89.
Berliner JA, Watson AD. A role for oxidized phospholipids in atherosclerosis. N. Engl. J. Med. Jul. 2005;353(1):9-11.
Bertelsen M, Anggard EE, Carrier MJ. Oxidative stress impairs insulin internalization in endothelial cells in vitro. Diabetologia. May 2001;44(5):605-613.
Betteridge, D.J., "Diabetic dyslipidaemia: past, present and future." Practical Diabetes Int, 21(2): 78-85. (Mar. 2004).
Bild et at., "Multi-Ethnic Study of Atherosclerosis: objectives and design," Am J Epidemiol 156(9):871-81 (Nov. 1, 2002).
Black et al., "Effect of intravenous eicosapentaenoic acid on cerebral blood flow, edema, and brain prostaglandins in ischemic gerbils", Prostaglandins, 28(4), pp. 545-546. (Oct. 1984).
Blankenhorn D.H. et al., "Beneficial effects of combined colestipol-niacin therapy on coronary atherosclerosis and coronary venous bypass grafts." JAMA 257: 3233-3240. (Jun. 1987).
Block, R. C., et al., "EPA and DHA in blood cell membranes from acute coronary syndrome patients and controls." Atherosclerosis, 197(2):821-828 (Apr. 2008).
Blumenthal, Advanced Studies in Medicine, 2:148-157 (2002).
Boden WE, Probstfield JL, Anderson T, Chaitman BR, Desvignes-Nickens P, Koprowicz K, IJ McBride R, Teo K, Weintraub W. and the Aim-High Investigators, "Niacin in patients with low hdl cholesterol levels receiving intensive statin therapy," N. Engl. J. Med. Dec. 2011;365:2255-2267.
Bonaa, KH et al., Docosahexaenoic and Eicosapentaenoic acids in plasma phospholipids are divergently associated with high density lipoprotein in humans, Arterioscler. Thromb. Vasc. Biol.;12;675-681 (Jun. 1992).
Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study," Clinical Therapeutics. 30(12):2298-2313 (Dec. 2008).
Borchman D, Lamba OP, Salmassi S, Lou M, Yapped MC. The dual effect of oxidation on lipid bilayer structure. Lipids. Apr. 1992;27(4):261-265.
Bordin et al., "Effects of fish oil supplementation on apolipoprotein B100 production and lipoprotein metabolism in normolipidaemic males," Eur. J. Clin. Nutr. 52: 104-9 (Feb. 1998).
Borow et al., "Biologic plausibility, cellular effects, and molecular mechanisms of eicosapentaenoic acid (EPA) in atherosclerosis," Atherosclerosis, 242(1):357-66 (Sep. 2015).
Borthwick et al., "The effects of an omega-3 ethyl ester concentrate on blood lipid concentrations in pateitns with hyperlipidemia," Clin. Drug Investig. (1998) 15(5): 397-404.
Bossaller C, Habib GB, Yamamoto H, Williams C, Wells S, Henry PD. Impaired muscarinic endothelium-dependent relaxation and cyclic guanosine 5'-monophosphate formation in atherosclerotic human coronary artery and rabbit aorta. J. Clin. Invest. Jan. 1987;79:170-174.

(56) References Cited

OTHER PUBLICATIONS

Bousserouel, S., et al., "Different effects of n-6 and n-3 polyunsaturated fatty acids on the activation of rat smooth muscle cells by interleukin-1 beta." J. Lipid Res. 44:601-611 (Mar. 2003).

Bousserouel, S., et al., "Modulation of cyclin D1 and early growth response factor-1 gene expression in interleukin-1beta-treated rat smooth muscle cells by n-6 and n-3 polyunsaturated fatty acids." Eur. J. Biochem. 271:4462-4473 (Nov. 2004).

Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(Jun. 2004).

Braeckman et al., "Abstract 18549: Effects of AMR101, a Pure Eicosapentaenoic Omega-3 Fatty Acid, on the Fatty Acid Profile in Plasma and Red Blood Cells in Statin-Treated Patients with Persistent High Triglycerides—Results from the ANCHOR study," Circulation 126(21S):A15071 (Nov. 20, 2012)(2 pages).

Braeckman et al., "Effect of Concomitant Icosapent Ethyl (Eicosapentaenoic Acid Ethyl Ester) on Pharmacokinetics of Atorvastatin," Clinical Drug Investigation. (Jan. 2015) (3)45-51.

Braeckman RA, Manku MS, Bays HE, Stirtan WG, Soni PN. Icosapent ethyl, a pure EPA omega-3 fatty acid: effects on plasma and red blood cell fatty acids in patients with very high triglyceride levels (results from the MARINE study). Prostaglandins Leukot Essent Fatty Acids. Sep. 2013;89(4):195-201.

Braeckman RA, Stirtan WG, Soni PN. Pharmacokinetics of eicosapentaenoic acid in plasma and red blood cells after multiple oral dosing with AMR101 (ethyleicosapentaenoic acid) in healthy subjects [abstract]. Presented at: Congress of the International Society for the Study of Fatty Acids and Lipids, Vancouver, Canada, May 26-30, 2012.

Braeckman RA, Stirtan WG, Soni PN. Pharmacokinetics of eicosapentaenoic acid in plasma and red blood cells after multiple oral dosing with icosapent ethyl in healthy subjects. Clin. Pharmacol. Drug Dev. 2013;3:101-108.

Braunersreuther V, Steffens S, Arnaud C, Pelli G, Burger F, Proudfoot A, Mach F. A novel rantes antagonist prevents progression of established atherosclerotic lesions in mice. Arterioscler. Thromb. Vasc. Biol. Jun. 2008;28:1090-1096.

Breslow, J., "n-3 Fatty acids and cardiovascular disease." Am J Clin Nutr., 83:1477S-82S (Jun. 2006).

Brinton EA, Ballantyne CM, Bays HE, Kastelein JJ, Braeckman RA, Soni PN. Effects of AMR101 on lipid and inflammatory parameters in patients with diabetes mellitus-2 and residual elevated triglycerides (200-500 mg/dl) on statin therapy at LDL-C goal: the ANCHOR study.[abstract 629-P] Diabetes. 2012;61(suppl 1):A159-A160.

Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (Oct. 1996).

Brouwer, I.A., et al., "Effect of fish oil on ventricular tachyarrhythmia and death in patients with implantable cardioverter defibrillators." JAMA. 295(22):2613-2619 (Jun. 2006).

Brovkovych V, Dobrucki LW, Brovkovych S, Dobrucki I, Do Nascimento CA, Burewicz A, Malinski T. Nitric oxide release from normal and dysfunctional endothelium. J. Physiol. Pharmacol. Dec. 1999;50:575-586.

Brown et al., Simvastatin and Niacin, Antioxidant Vitamins, or the Combination for the Prevention of Coronary Disease, N Engl J Med, vol. 345, No. 22, 1583-1592 (Nov. 29, 2001).

Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (Jan. 1999).

Brown, A. J., et al., "Persistent changes in the fatty acid composition of erythrocyte membranes after moderate intake of n-3 polyunsaturated fatty acids: study design and implications." Am.J. Clin. Nutri. 54:668-73(Oct. 1991).

Brown, G., et al., "Regression of coronary artery-disease as a result of intensive lipid-lowering therapy in men with high levels of apolipoprotein," B., N. Engl. J. Med. 323: 1289-1298. (Nov. 1990).

Brownlee M. Biochemistry and molecular cell biology of diabetic complications. Nature. Dec. 2001; 414(6865):813-820.

Bryhn, M., et al., "The bioavailability and pharmacodynamics of different concentrations of omega-3 acid ethyl esters." Prostaglandins, Leukotrienes and Essential Fatty Acids 75:19-24 (Jul. 2006).

Budavari, S., Editor, "The Merck Index", Merck & Co., Inc., p. 725 item 4511 and p. 279 and item 2417 (1989).

Budoff, "Triglycerides and Triglyceride-Rich Lipoproteins in the Causal Pathway of Cardiovascular Disease," Am. J. Cardiol., 118(1):138-45 (Jul. 1, 2016).

Bunting et al. "Depression in Parkinson's Disease". J Neurosci Nurs.; 23(3):158-164. (Abstract Only) (Jun. 1991).

Burdge, G.C., et al., "Eicosapentaenoic and docosapentaenoic acids are the principal products of a-linolenic acid metabolism in young men." British Journal of Nutrition 88:355-363 (Oct. 2002).

Burdge, G.C., et al., "Lack of effect of meal fatty acid composition on postprandial lipid, glucose and insulin responses in men and women aged 50-65 years consuming their habitual diets." British Journal of Nutrition, 96:489-500 (Sep. 2006).

Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (Jul. 2007).

Burr, M. L., et al., "Effects of changes in fat, fish and fibre intakes on death and myocardial reinfarction: Diet and reinfarction trial." The Lancet, 2(8666):757-61 (Sep. 1989).

Buse JB, Ginsberg HN, Bakris GL, et al. Primary prevention of cardiovascular diseases in people with diabetes mellitus: a scientific statement from the American Heart Association and the American Diabetes Association. Diabetes Care. 2007;30:162-172.

Calabresi, L., et al., "Omacor in familial combined hyperlipidemia: effects on lipids and low density lipoprotein subclasses." Atherosclerosis 148:387-396 (Feb. 2000).

Calder PC. The role of marine omega-3 (n-3) fatty acids in inflammatory processes, atherosclerosis and plaque stability. Mol. Nutr. Food Res. Jul. 2012;56(7)1073-1080.

Campos, H., et al., "Lowdensity lipoprotein size, pravastatin treatment, and coronary events." JAMA, 286:1468-1474 (Sep. 2001).

Canner P.L. et al., "Fifteen year mortality in Coronary Drug Project patients: long-term benefit with niacin," J. Am. Coll. Cardiol. 8. 1245-1255. (Dec. 1986).

Cao, et al., "Cloning, Expression, and Chromosomal Locatlization . . . ", Genomics, 49:327-331, (Apr. 15, 1998).

Cao, J., et al., "Incorporation and Clearance of Omega-3 Fatty Acids in Erythrocyte Membranes and Plasma Phospholipids." Clinical Chemistry 52(12):2265-2272 (Dec. 2006).

Capuzzi, DM et al., "Efficacy and safety of an extended-release niacin (Niaspan): a long-term study." Am. J. Cardiol. 82: 74U-81U. (Dec. 17, 1998).

Carlson, L.A. & Rosenhamer G., "Reduction of mortaility in the Stockholm Ischaemic Heart Disease Secondary Prevention Study by combined treatment with clofibrate and nicotinic acid." Acta Med. Scand. 223, 405-418 (1988).

Carlson, L.A., "Nicotinic acid: the broad spectrum lipid drug. A 50th Anniversary review", J. Int. Med., 258:94-114, (Aug. 2005).

Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390 (Feb. 2007).

Carrero, J.J. et al. "Efectos cardiovasculares de los acidos grasos omega-3 y alternativas para incrementar su ingesta," Nutricion Hospitalaria. (2005) (1) 63-69 [with English abstract].

Carroll, D. N., et al., "Evidence for the Cardioprotective Effects of Omega-3 Fatty Acids." Ann Pharmacother., 36:1950-6 (Dec. 2002).

Carulli et al., "Chenodeoxycholic acid and ursodeoxycholic acid effects in endogenous hypertriglyceridemias. A controlled double-blind trial." J. Clin. Pharmacol., 21(10):436-42 (Oct. 1981).

(56) References Cited

OTHER PUBLICATIONS

Cazzola, R., et al., "Age- and dose-dependent effects of an eicosapentaenoic acid-rich oil on cardiovascular risk factors in healthy male subjects." Atherosclerosis 193:159-167 (Jul. 2007).
Ceci et al., "The effects of oral 5-hydroxytryptophan administration on feeding behavior in obese adult female subjects," J Neural. Transm (1989) 76(2):109-117.
Cefali, E.A., et al., "Aspirin reduces cutaneous flushing after administration of an optimised extended-release niacin formulation", Int. J. Clin. Pharmacol. & Ther., 45(2):78-88, (Feb. 2007).
Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. (Accessed Jan. 26, 2012) (156 pages).
Center for Drug Evaluation and Research. Approval Package for Application No. 202057Orig1s000. Review—Vascepa (formerly AMR101), 373 pages (Jul. 26, 2012)(in two parts).
Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012. (54 pages).
Ceriello A, Motz E. Is oxidative stress the pathogenic mechanism underlying insulin resistance, diabetes, and cardiovascular disease? The common soil hypothesis revisited. Arterioscler. Thromb. Vasc. Biol. (May 2004);24(5):816-823.
Chait A, Brazg RL, Tribble DL, Krauss RM. Susceptibility of small, dense, low-density lipoproteins to oxidative modification in subjects with the atherogenic lipoprotein phenotype, pattern B. Am. J. Med. (Apr. 1993);94(4):350-356.
Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).
Chan et al., Factorial Study of the Effects of Atorvastatin and Fish Oil on Dyslipidaemia in Visceral Obesity, 32 Euro. J. Clinical Investigation. 32(6):429-36 (Jun. 2002).
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).
Chapman, M.J., et al., "Cholesteryl ester transfer protein: at the heart of the action of lipid-modulating therapy with statins, fibrates, niacin, and cholesteryl ester transfer protein inhibitors." Eur Heart J., 31(2):149-164 (Jan. 2010).
Chatterjee SN, Agarwal S. Liposomes as membrane model for study of lipid peroxidation. Free Radic. Biol. Med. 1988;4(1):51-72.
Chemical Book, Eicosapentaenoic acid ethyl ester, copyright 2010, printed Jun. 16, 2011 from www.chemicalbook.com. (2010).
Chen, H., et al., "Eicosapentanoic acid inhibits hypoxia-reoxygenation-induced injury by attenuating upregulation of MMP-1 in adult rat myocytes." Cardiovascular Research 59:7-13 (Jul. 2003).
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (Jul. 2003).
Chen, I.S., et al., "In vitro clearance of chylomicron triglycerides containing (ω-3) eicosapentaenoate." Atherosclerosis, 65:193-198 (1987).
Cheng et al., "Antagonism of the prostaglandin D2 receptor 1 suppresses nicotinic acid-induces vasodilation in mice and humans," PNAS 103(17):6682-7 (Apr. 25, 2006).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, (Oct. 1990).
Christensen, J. H., et al., "Effect of fish oil on heart rate variability in survivors of myocardial infarction: a double blind randomised controlled trial." BMJ, 312:677-678 (Mar. 16, 1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (Jan. 1995).
Classification of Hyperlipidaemias and Hyperlipoproteinaemias, Bulletin of the World Health Organization, 43(6): 891-915 (1970).
Cleland, L.G., et al., "A Biomarker of n-3 compliance in patients taking fish oil for rheumatoid arthritis." Lipids 38:419-424 (Apr. 2003).
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from the Internet: <http://clinicaltrials.gov/ct2/show/NCT01047501> (3 pages).
Cohen AW, Combs TP, Scherer PE, Lisanti MP. Role of caveolin and caveolae in insulin signaling and diabetes. American journal of physiology. Endocrinology and metabolism. (Dec. 2003);285(6):E1151-1160.
Cohen, J.D., et al., "30-year trends in serum lipids among United States adults: results from the National Health and Nutrition Examination Surveys II, III, and 1999-2006." Am J Cardiol., 106:969-975. (Dec. 15, 2010).
Cole et al., "Challenges and opportunities in the encapsulation of liquid and semi-solid formulations into capsules for oral administration," Advanced Drug Delivery Reviews, vol. 60, No. 6, pp. 747-756. (Mar. 17, 2007).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (Aug. 21-24, 2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (Dec. 2008).
Committee Roster for the Oct. 16, 2013 Meeting of the Endocrinologic and Metabolic Drugs Advisory Committee, 2 pages. (2013).
Conklin, S. M., et al., "Serum ω-3 fatty acids are associated with variation in mood, personality and behavior in hypercholesterolemic community volunteers." Psychiatry Research 152: 1-10 (Jul. 30, 2007).
Connor et al., "Seminars in thrombosis and hemostasis," 14:271-284. (1988).
Connor, W.E., "Importance of n-3 Fatty Acids in Health and Disease", Am. J. Clin. Nutr., 71(1(S)):171S-175S, (Jan. 2000).
Conquer, J.A., et al., "Effect of supplementation with different doses of DHA on the levels of circulating DHA as non-esterified fatty acid in subjects of Asian Indian background. J Lipid Res." 39:286-292. (Feb. 1998).
Conquer, J.A., et al., "Supplementation with an algae source of docosahexaenoic acid increases (n-3) fatty acid status and alters selected risk factors for heart disease in vegetarian subjects." J Nutr., 126: 3032-3039. (Dec. 1996).
Contacos et al. Effect of pravastatin and omega-3 fatty acids on plasma lipids and lipoproteins in patients with combined hyperlipidemia, pp. 1755-1762 (Dec. 1993).
Coronary Artery Bypass Grafting, NIH, published online Feb. 23, 2012 (12 pages).
Coumadin [package insert], Princeton, NJ: Bristol-Myers Squibb; 2011. (10 pages).
Cox PJ, Ryan DA, Hollis FJ, et al. Absorption, disposition, and metabolism of rosiglitazone, a potent thiazolidinedione insulin sensitizer, in humans. Drug Metab. Dispos. Jul. 2000;28:772-780.
Creager MA, Gallagher SJ, Girerd XJ, Coleman SM, Dzau VJ, Cooke JP. L-arginine improves endothelium-dependent vasodilation in hypercholesterolemic humans. J. Clin. Invest. Oct. 1992;90:1248-1253.
Crevel et al., "Allergenicity of Refined Vegetable Oils," Food and Chemical Toxicology, 38, pp. 385-393 (Apr. 2000).
Criqui, M., "Triglycerides and Coronary Heart Disease Revisited (AGAIN)," vol. 147 No. 6, pp. 425-427 (Sep. 18, 2007).

(56) References Cited

OTHER PUBLICATIONS

Cromwell et al., "LDL particle No. and risk of future cardiovascular disease in the Framingham Offspring Study—Implications for LDL Management," Journal of Lipidololgy. (Dec. 2007) 1, 583-592.
Crowe, F. L., et al., "Serum phospholipid n-3 long-chain polyunsaturated fatty acids and physical and mental health in a population-based survey of New Zealand adolescents and adults." Am J Clin Nutr 86:1278-85 (Nov. 2007).
Cruz et al., "The metabolic syndrome in children and adolescents," Curr. Diab. Rep., vol. 4(1):53-62 (Feb. 2004).
Culhane et al., "Rosuvastatin for the treatment of hypercholesterolemia," Pharmacotherapy, 25(7):990-1000 (Jul. 2005).
Daggy, B., et al., Dietary fish oil decreases VLDL production rates. Biochimica et Biophysics Acta 920: 293-300 (Aug. 15, 1987).
Dall et al., "Clinical utility of low-density lipoprotein particle measurement in management of cardiovascular disease: a case report," Research Reports in Clin. Cardiol., vol. 2, pp. 57-62 (2011).
Das, U.N., Essential fatty acids as possible mediators of the actions of statins. Prostaglandins, Leukotrienes and Essential FattyAcids 65(1):37-40, (Jul. 2001).
Davidson MH, Ballantyne CM, Jacobson TA, et al. Clinical utility of inflammatory markers and advanced lipoprotein testing: advice from an expert panel of lipid specialists. J. Clin. Lipidol. Sep./Oct. 2011;5:338-367.
Davidson MH, et al., Effects of prescription omega-3-acid ethyl esters on lipo protein particle concentrations, apolipoproteins AI and CIII, and lipoprotein-associated phospholipase $A_2$ mass in statin-treated subjects with hypertrigylceridemia, J.Clin. Lipid., vol. 3(5), pp. 332-340 (Oct. 2009).
Davidson MH, Rosenson RS, Maki KC, Nicholls SJ, Ballantyne CM, Mazzone T, Carlson DM, Williams LA, Kelly MT, Camp HS, Lele A, Stolzenbach JC. Effects of fenofibric acid on carotid intima-media thickness in patients with mixed dyslipidemia on atorvastatin therapy: Randomized, placebo-controlled study (first). Arterioscler. Thromb. Vasc. Biol. Jun. 2014;34:1298-1306.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther., 29:1354-1367. (2007).
Davidson MH., "Mechanisms for the hypotriglyceridemic effect of marine omega 3 fatty acids." Am J Cardiol 98(4A):27i-33i. (2006).
Davidson, M.H., et al., "Effects of docosahexaenoic acid on serum lipoproteins in patients with combined hyperlipidemia: a randomized, doubleblind, placebo-controlled trial." J Am Coll Nutr., 16:236-243. (1997).
Davies et al., "Rapid separation of LDL subclasses by iodixanol gradient ultracentrifugation," Clin. Chem., 49(11):1865-72. (Nov. 2003).
Davies-Tuck et al., "Total cholesterol and triglycerides are associated with development of new bone marrow lesions in asymptomatic middle-aged women—a prospective cohort study," Arthritis Research & Therapy. (2009) pp. 1-7.
De Caterina, R, et al., "Control of Endothelial Leukocyte Adhesion Molecules by Fatty Acids." Lipids, vol. 31:S57-S63 (1996).
De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).
De Graaf J, Hak-Lemmers HL, Hectors MP, Demacker PN, Hendriks JC, Stalenhoef AF. Enhanced V susceptibility to in vitro oxidation of the dense low density lipoprotein subfraction in healthy subjects. Arterioscler. Thromb. 1991;11(2):298-306.
De Morais et al., "Evaluation of lipid extraction and fatty acid composition of human plasma," Rev. Bras. Hematol. Hemoter. 32(6):439-443 (2010).
Deckelbaum,, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).
Defendants' Invalidity Contentions, 3:14-CV-02550-MLC-DEA (D.N.J.), 520 pages (Dec. 5, 2014).
Defendants' Joint Invalidity Contentions, 3:14-CV-02550-MLC-TJB (D.N.J.), 901 pages (Dec. 5, 2014).
Dewailly, E., et al., "n-3 Fatty acids and cardiovascular disease risk factors among the Inuit of Nunavik." Am J Clin Nutr 74:464-73 (2001).
Di Spirito, M., Morelli, G., Doyle, R.T., Johnson, J. & McKenney, J. Effect of omega-3-acid ethyl esters on steady-state plasma pharmacokinetics of atorvastatin in healthy adults. Expert Opin. Pharmacother. 9, 2939-2945 (2008).
Diagnostic and Statistical Manual of Mental Disorders, 4.Ed. Text revision, published by the American Psychiatric Assoc., pp. 154-163 and 369-381 (2000).
Diagnostic and Statistical Manual of Mental Disorders, 4.sup.th Ed., published by the American Psychiatric Assoc., pp. 285-286, (1994).
Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, (1996).
Dijk, J. M., et al., "Carotid intima-media thickness and the risk of new vascular events in patients with manifest atherosclerotic disease: the SMART study." European Heart Journal 27:1971-1978 (2006).
Din et al., "Omega 3 fatty acids and cardiovascular disease—fishing for a natural treatment," BMJ, vol. 327, No. 7430, pp. 30-35 (2004).
Dodin, S., et al., "Flaxseed on cardiovascular disease markers in healthy menopausal women: a randomized, double-blind, placebo-controlled trial." Nutrition 24:23-30 (2008).
Dolecek, "Epidemiological Evidence of Relationships Between Dietary Polyunsaturated Farry Acids and Morality in the Multiple Risk Factor Intervention Trial", Society of Experimental Biology and Medicine, 200(2):177-182, (1991).
Draft Agenda for the Oct. 16, 2013 Meeting of the Endocrinologic and Metabolic Drugs Advisory Committee, 2 pages.
Draft Meeting Roster for the Oct. 16, 2013 Meeting of the Endocrinologic and Metabolic Drugs Advisory Committee, 2 pages.
Draft Questions for the Oct. 16, 2013 Meeting of the Endocrinologic and Metabolic Drugs Advisory Committee, 1 page.
Drexler H, Zeiher AM, Meinzer K, Just H. Correction of endothelial dysfunction in coronary microcirculation of hypercholesterolaemic patients by !-arginine. Lancet. 1991;338:1546-1550.
Dullenmeijer, C., et al., "n-3 Fatty acid proportions in plasma and cognitive performance in older adults." Am J Clin Nutr 86:1479-85 (2007).
Duncan, R. E., et al., "Regulation of HMG-CoA reductase in MCF-7 cells by genistein, EPA, and DHA, alone and in combination with mevastatin." Cancer Letters 224:221-228 (2005).
Durrington PN et al. "An omega 3 poly unsaturated fatty acid concentrate administered for one year decreased triglycerides in simvastatin treated patients with coronary heart disease and persistent Hypertriglyceridemia," Heart, 85:544-48 (2001).
Dwyer, J. H., et al., "Arachidonate 5-Lipoxygenase Promoter Genotype, Dietary Arachidonic Acid, and Atherosclerosis." N. Engl. J. Med., 350:1 (2004).
Dyerberg, J., et al., "Marine Oils and Thrombogenesis." Prog. Lipid Res. 21:255-269 (1982).
Egert, S., et al., "Dietary alpha-linolenic acid, EPA, and DHA have differential effects on LDL fatty acid composition but similar effects on serum lipid profiles in normolipidemic humans." J Nutr., 139:861-868 (2009).
Ehara S, Ueda M, Naruko T, Haze K, Itoh A, Otsuka M, Komatsu R, Matsuo T, Itabe H, Takano T, Tsukamoto Y, Yoshiyama M, Takeuchi K, Yoshikawa J, Becker AE. Elevated levels of oxidized low density lipoprotein show a positive relationship with the severity of acute coronary syndromes. Circulation. 2001;103(15):1955-1960.
Eilat-Adar et al. "Association of Intentional Changes in Body Weight with Coronary Heart Disease Event Rates in Overweight Subjects who have an Additional Coronary Risk Factor," Amer. Journ. Epidemiol.161(4)pp. 352-358 (Sep. 9, 2004).

(56) References Cited

OTHER PUBLICATIONS

Eisenberg S, Bilheimer DW, Levy RI, Lindgren FT. "On the metabolic conversion of human plasma very low density lipoprotein to low density lipoprotein," Biochim Biophys Acta, 326:361-77 (1973).
Eisenberg S, Rachmilewitz D. "Metabolism of rat plasma very low density lipoprotein. I. Fate in circulation of the whole lipoprotein," Biochim Biophys Acta, 326:378-90 (1973).
El-Serag HB, Graham DY, Satia JA, et al. Obesity is an independent risk factor for GERD symptoms and erosive esophagitis. Am. J. Gastroenterol. Jun. 2005 100 (6): 1243-50.
Elam, M.B., et al., "Effect of niacin on lipid and lipoprotein levels and glycemic control in patients with diabetes and peripheral arterial disease study: a randomized trial", The ADMIT [Arterial Disease Multiple Intervention Trial] JAMA, 284:1263-1270, (2000).
El-Saadani M, Esterbauer H, El-Sayed M, Gober M, Nassar AY, Jurgens G. A spectrophotometric assay for lipid peroxides in serum lipoproteins using commercially available reagent. J. Lipid Res. 1989;30:627-630.
El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).
Emsley et al., "Randomized, Placebo-Controlled Study of Ethyl-Eicosapentaenoic Acid as Supplemental Treatment in Schizophrenia," Am. J. Psychiatry, 159:1596-1598 (2002).
Endo et al., "The Effects of Dietary Fatty Acids on Serum Lipids and Plasma Prostaglandin Levels in the Treatment of Obesity," Japanese Journal of Pediatric Gastroenterology and Nutrition 7(1):67-72 (Apr. 15, 1993) (with English translation)(22 pages).
ENews, "Cholesterol Crystals Induce Atherosclerosis-Associated Inflammation in Mice," 1-4 (Jun. 14, 2010)(4 pages).
Engler, et al., "Docosahexaenoic acid restores endothelial function in children with hyperlipidemia: results from the EARLY Study." International Journal of Clinical Pharmacology and Therapeutics, vol. 42—No. 12-2004 (672-679). (2004).
Engler, M.B., et al., "Mechanisms of vasorelaxation induced by eicosapentaenoic acid (20:5n-3) in WKY rat aorta." British Journal of Pharmacology 131:1793-1799 (2000).
Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).
Ennis JL, Cromwell WC. Clinical utility of low-density lipoprotein particles and apolipoprotein B in patients with cardiovascular risk. J. Fam. Pract. 2013;62:1-8.
Epadel—PubChem CID 9831415, Retrieved on Apr. 9, 2014 [Retrieved from the internet] <URL:http://pubchem.ncbi.nlm.nih.gov/compound/9831415> (19 pages).
Epadel 1990 and JELIS Study (4 pages).
Epadel Capsules 300, Japan Pharmaceutical Reference 369-371 (2nd ed.) (1991). (5 pages).
Epadel drug information brochure (2000), certified English translation(36 pages).
Epadel Package Insert 2007 (with Translation)(6 pages).
Epadel® [Complete prescribing information]. Update (Version 5). Tokyo, Japan: Mochida Pharmaceutical; Jan. 2007 (9 pages).
EPANOVA® (omega-3-carboxylic acids) capsules, for oral use, Prescribing information, 5 pgs., AstraZeneca Pharmaceuticals LP, (Revised: Mar. 2017)(5 pages).
Eritsland J, Arnesen H, Gronseth K, et al. Effect of dietary supplementation with n-3 fatty acids on coronary artery bypass graft patency. Am. J. Cardiol. Jan. 1996 77 (1): 31-6.
Eritsland J, Arnesen H, Seljeflot I, et al. Long-term effects of n-3 polyunsaturated fatty acids on haemostatic variables and bleeding episodes in patients with coronary artery disease. Blood Coagul. Fibrinolysis Feb. 1995 6 (1): 17-22.
Errata to the FDA Briefing Document Endocrinologic and Metabolic Drug Advisory Committee Meeting Oct. 16, 2013, 1 page.
Esposito, "Effect of a Mediterranean-Style Diet on Endothelial Dysfunction and Markers of Vascular Inflammation in the Metabolic Syndrome: A Randomized Trial", Journal of the American Medical Association, 2004, 292(12), 1440-1446.
Essentialis Inc. press release, "Essentialis Meets Primary Endpoint in Phase 2b Trial of DCCR for Treatement of Hypertriglyceridemia and is Granted Extensive Patent Coverage in the US," PR Newswire (May 17, 2009)( 2 pages).
Exhibit A to Defendants' Joint Invalidity Contentions, 3:14-CV-02550-MLC-TJB (D.N.J.), 48 pages (Dec. 5, 2014).
Exhibit B to Defendants' Joint Invalidity Contentions, 3:14-CV-02550-MLC-TJB (D.N.J.), 6 pages (Dec. 5, 2014).
Exhibit C to Defendants' Joint Invalidity Contentions, 3:14-CV-02550-MLC-TJB (D.N.J.), 14 pages (Dec. 5, 2014).
Exhibit D to Defendants' Joint Invalidity Contentions, 3:14-CV-02550-MLC-TJB (D.N.J.), 19 pages (Dec. 5, 2014).
Exhibit E to Defendants' Joint Invalidity Contentions, 3:14-CV-02550-MLC-TJB (D.N.J.), 6 pages (Dec. 5, 2014).
Exhibit F to Defendants' Joint Invalidity Contentions, 3:14-CV-02550-MLC-TJB (D.N.J.), 10 pages (Dec. 5, 2014).
Exhibit G to Defendants' Joint Invalidity Contentions, 3:14-CV-02550-MLC-TJB (D.N.J.), 21 pages (Dec. 5, 2014).
Exhibit H to Defendants' Joint Invalidity Contentions, 3:14-CV-02550-MLC-TJB (D.N.J.), 10 pages (Dec. 5, 2014).
Exhibit I to Defendants' Joint Invalidity Contentions, 3:14-CV-02550-MLC-TJB (D.N.J.), 14 pages (Dec. 5, 2014).
Exhibit J to Defendants' Joint Invalidity Contentions, 3:14-CV-02550-MLC-TJB (D.N.J.), 13 pages (Dec. 5, 2014).
Exhibit K to Defendants' Joint Invalidity Contentions, 3:14-CV-02550-MLC-TJB (D.N.J.), 5 pages (Dec. 5, 2014).
Exhibit L to Defendants' Joint Invalidity Contentions, 3:14-CV-02550-MLC-TJB (D.N.J.), 5 pages (Dec. 5, 2014).
Exhibit M to Defendants' Joint Invalidity Contentions, 3:14-CV-02550-MLC-TJB (D.N.J.), 7 pages (Dec. 5, 2014).
Exhibit N to Defendants' Joint Invalidity Contentions, 3:14-CV-02550-MLC-TJB (D.N.J.), 15 pages (Dec. 5, 2014).
Exhibit O to Defendants' Joint Invalidity Contentions, 3:14-CV-02550-MLC-TJB (D.N.J.), 6 pages (Dec. 5, 2014).
Exhibit P to Defendants' Joint Invalidity Contentions, 3:14-CV-02550-MLC-TJB (D.N.J.), 17 pages (Dec. 5, 2014).
Exhibit Q to Defendants' Joint Invalidity Contentions, 3:14-CV-02550-MLC-TJB (D.N.J.), 64 pages (Dec. 5, 2014).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).
FDA Briefing Document, Endocrinologic and Metaboloic Drugs Advisory Committee Meeting, dated Oct. 16, 2013, available publicly at least as of Oct. 16, 2013, 115 pages.
FDA News Release, "FDA approves new orphan drug Kynamro to treat inherited cholesterol disorder," U.S. Food and Drug Administration, Protecting and Promoting Your Health (Jan. 29, 2013)(2 pages).
Fer, M., et al., "Metabolism of eicosapentaenoic and docosahexaenoic acids by recombinant human cytochromes P450." Archives of Biochemistry and Biophysics 471:116-125 (2008).
Ferns, G., et al., "Investigation and management of hypertriglyceridaemia." J. Clin. Pathol. 61:1174-1183 (2008).
Feron O, Dessy C, Desager JP, Balligand JL. Hydroxy-methylgluataryl-coenzyme a reductase inhibition promotes endothelial nitric oxide synthase activation through a decrease in caveolin abundance. Circulation. 2001;103:113-118.
Final Agenda for the Oct. 16, 2013 Meeting of the Endocrinologic and Metabolic Drugs Advisory Committee, 2 pages.
Final Meeting Roster for the Oct. 16, 2013 Meeting of the Endocrinologic and Metabolic Drugs Advisory Committee, 2 pages.
Final Questions for the Oct. 16, 2013 Meeting of the Endocrinologic and Metabolic Drugs Advisory Committee, 1 page.
Finnen et al., "Purification and characterisation of phospholipase A2 from human epidermis,", Biochemical Society Trans,19(2):91S, 1991.
Fischer, R., et al., "Dietary n-3 polyunsaturated fatty acids and direct renin inhibition improve electrical remodeling in a model of high human renin hypertension." Hypertension 51:540-546 (2008).

(56) References Cited

OTHER PUBLICATIONS

Fisher et al., Journal of Biological Chemistry (2001) 276(3) 27855-27863.

Flaten, H., et al., "Fish-oil concentrate: effects on variables related to cardiovascular disease." Am. J. Clin. Nutr. 52:300-306 (1990).

Food and Drug Administration (FDA), (2005) *NIASPAN niacin extended release tablets*.

Food and Drug Administration (FDA), (2005) *Tablets ZOCOR® (SIMVASTATIN)*.

Ford, E.S. et al., "Hypertriglyceridemia and Its Pharmacologic Treatment Among US Adults." Arch, Intern. Med., 169(6): 572-78 (2009).

Frangou et al., "Efficacy of ethyl-eicosapentaenoic acid in bipolar depression: randomised double-blind placebo-controlled study," British Journ. Psychiatry, 188, 46-50 (2006).

Frey R, Muck W, Kirschbaum N, et al. Riociguat (BAY 63-2521) and warfarin: a pharmacodynamic and pharmacokinetic interaction study. J. Clin. Pharmacol. Jul. 2011 51 (7): 1051-60.

Frick, MH, et al., "Helsinki Heart Study. Primary prevention trial with gemfibrozil in middle-aged men with dyslipidaemia. Safety of treatment, changes in risk factors and incidence of coronary heart disease", N. Eng. J. Med., 317:1237-1245, (1987).

Friedewald, W.T., et al., "Estimation of the concentration of low-density lipoprotein cholesterol in plasma, without use of the preparative ultracentrifuge." Clin Chem.,18:499-502 (1972).

Friedman, A. N., et al., "Fish Consumption and Omega-3 Fatty Acid Status and Determinants in Long-Term Hemodialysis." Amer. J. Kidney Diseases, 47(6)1064-1071 (2006).

Frøyland et al., "Chronic administration of eicosapentaenoic acid and docosahexaenoic acid as ethyl esters reduced plasma cholesterol and changed the fatty acid composition in rat blood and organs." Lipids 31(2):169-78 (Feb. 1996).

Frøyland, L., et al., "Hypotriacylglycerolemic component of fish oil." Prostaglandins, Leukotrienes and Essential Fatty Acids 57 (4 & 5):387-388 (1997).

Furuta T, Shirai N, Sugimoto M, et al. Influence of CYP2C19 pharmacogenetic polymorphism on proton pump inhibitor-based therapies. Drug Metab. Pharmacokinet Jun. 2005 20 (3): 153-67.

Futata et al., "Effect of Eicosapentaenoic Acid (EPA) Formulation on Glucose Metabolism in Non-Insulin Dependent Diabetic Patients," Journal of Clinical and Experimental Medicine 169(8):889-890 (May 21, 1994)(English translation, 4 pages).

Galeano NF, Al-Haideri M, Keyserman F, Rumsey SC, Deckelbaum RJ. Small dense low density lipoprotein has increased affinity for LDL receptor-independent cell surface binding sites: a potential mechanism for increased atherogenicity. J. Lipid Res. 1998;39(6):1263-1273.

Gallagher et al., "Germline BRCA Mutations Denote a Clinicopathalogic Subset of Prostate Cancer," Amer. Assoc. Cancer Res. Clin Cancer Res., 16(7):2115-21 (2010).

Garber AJ, Abrahamson MJ, Barzilay JI, et al. American Association of Clinical Endocrinologists' comprehensive diabetes management algorithm 2013 consensus statement. Endocr. Pract. 2013;19(suppl 2):1-48.

Gardner CD, Fortmann SP, Krauss RM. Association of small low-density lipoprotein particles with the incidence of coronary artery disease in men and women. JAMA. 1996;276(11):875-881.

Garg, R., et al., "Niacin treatment increases plasma homocyst(e)ine levels", Am. Heart. J., 138:1082-1087, (1999).

Garnett, "Interactions with Hydroxymethylglutaryl-coenzyme A reductase inhibitors," Am J Health-Sys Pharm vol. 52, 1639-1645, (1995).

Genest, JJ, et al., "Familial lipoprotein disorders in patients with premature coronary artery disease", 85:2025-2033, (1992).

Geppert, et al. "Microalgal docosahexaenoic acid decreases plasma triacylglycerol in normolipidaemic vegetarians: a randomized trial." British Journal of Nutrition, 95, 779-786. (2006).

Gillies, et al. "Effect of a Novel Eicosapentaenoic Acid-Rich Oil on Serum Cholesterol in Man," DuPont 2010.

Ginsberg HN, Elam MB, Lovato LC, Crouse JR, 3rd, Leiter LA, Linz P, Friedewald WT, Buse JB, Gerstein HC, Probstfield J, Grimm RH, Ismail-Beigi F, Bigger JT, Goff DC, Jr., Cushman WC, Simons-Morton DG, Byington RP. Effects of combination lipid therapy in type 2 diabetes mellitus. N. Engl. J. Med. 2010;362:1563-1574.

Ginsberg HN. "Hypertriglyceridemia: new insights and new approaches to pharmacologic therapy," Am J Cardiol, 87:1174-1180 (2001).

Girotti A W. Lipid hydroperoxide generation, turnover, and effector action in biological systems. J. Lipid Res. 1998;39(8):1529-1542.

Gissi-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455, (Aug. 7, 1999).

Glod, "Recent Advances in the Pharmacotherapy of Major Depression", Arch. Psychiatr. Nurs., 10(6):355-364 (Dec. 1996).

Goldberg, A C: "Combination therapy of dyslipidemia," Current Treatment Options in Cardiovascular Medicine 200708 GB, vol. 9, No. 4, pp. 249-258 (2007).

Goodman & Gilman (Robert W. Mahley & Thomas P. Bersot) Drug Therapy for Hypercholesterolemia and Dyslipidemia, in Goodman & Gilman's The Pharmacological Basis fo Therapeutics 971 (Hardman et al., eds 10th ed. 2001)(32 pages).

Gordon, DJ. et al., High density lipoprotein cholesterol and cardiovascular disease: four prospective American studies. Circulation. 79: 8-15. (1989).

Gorriz JL et al., "Rhabdomyolysis and Acute Renal Failure Associated with Gemfibrozil Therapy," Nephron 74(2): 437-438 (1996).

Gorriz, JL, "Rhabdomyolysis and Acute Renal Failure Associated with Bezafibrate Treatment," Nephrol Dial Transplant 10(12):2371-2372 (1995).

Gosai, P. et al. Effect of omega-3-acid ethyl esters on the steady-state plasma pharmacokinetics of rosuvastatin in healthy adults. Expert Opin. Pharmacother. 9, 2947-2953 (2008).

Goto, Y., et al., "Clinical Pharmacological Trial of Ethyl Icosapentate (MND-21)-Dose Finding Study." Journal of Clinical Therapeutic & Medicines 8:1293-309 (1992).

Gould, A.L., et al., "Cholesterol reduction yields clinical benefit: impact of statin trials." Circulation, 97:946-952 (1998).

Greenblatt DJ, von Moltke LL. Interaction of warfarin with drugs, natural substances, and foods. J. Clin. Pharmacol. Feb. 2005 45 (2): 127-32.

Grenyer, Brin F.S., et al., "Fish Oil Supplementation in the Treatment of Major Depression: A Randomised Double-Blind Placebo-Controlled Trial", Progress in Neuro-Psychopharmacology & Biological Psychiatry, 31:1393-1396, (2007).

Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006).

Grimsgaard et al., "Effects of Highly Purified Eicosapentaenoic Acid and Docosahexaenoic Acid on Hemodynamics in Humans" American Society for Clinical Nutrition, 68:52-9, (1998).

Grimsgaard, Kaare H. Bonaa, John-Bjarne Hansen, and Arne Nordoy, "Highly purified eicosapentaenoic acid and docosahexaenoic acid in humans have similar triacylglycerol-lowering effects but divergent effects on serum fatty acids" Am J Clin Nutr, 66:649-659, (1997).

Grundy S.M et al., Efficacy, safety, and tolerability of once-daily niacin for the treatment of dyslipidemia associated with type 2 diabetes: results of the Assessment of Diabetes Control and Evaluation of the Efficacy of Niaspan Trial. Arch. Intern. Med. 162: 1568-1576 (2002).

Grundy SM, et al. Implications of Recent Clinical Trials for the National Cholesterol Education Prgram Adult Treatment Panel III Guidelines, Circulation. 2004; 110:227-39.

Grundy, Scott M., "Low-Density Lipoprotein, Non-High-Density Lipoprotein, and Apolipoprotein B as Targets of Lipid-Lowering Therapy" Circulation. 106:2526-2529 (2002).

Guallar, E., et al., "Omega-3 fatty acids in adipose tissue and risk of myocardial infarction—The EURAMIC study." Arterioscler. Thromb. Vasc. Biol., 19:1111-1118 (1999).

(56) References Cited

OTHER PUBLICATIONS

Guillot, et al., "Increasing intakes of the long-chain omega-3 docosahexaenoic acid: effects on platelet functions and redox status in healthy men," The FASEV Journal, vol. 23, pp. 2909-2916 (2009).

Guizy, M., et al., "ω-3 and ω-6 Polyunsaturated fatty acids block HERG channels." Am J Physiol Cell Physiol 289:C1251-C1260 (2005).

Gyarmathy, M., "Selection from the industrial manufacturing. 5th part: Gelatine capsules. 5/2 part: Soft gelatine capsules," Gyogyszereszet, vol. 38, No. 2, pp. 105-109 (1994) (with English summary).

Hakonarson, H., et al., "Effects of a 5-lipoxygenase-activating protein inhibitor on biomarkers associated with risk of myocardial infarction—a randomized trial." JAMA, 293(8):2245-56 (2005).

Hall, W. L., et al., "A high-fat meal enriched with eicosapentaenoic acid reduces postprandial arterial stiffness measured by digital volume pulse analysis in healthy men." J. Nutr. 138: 287-291 (2008).

Hamazaki et al., "Docosahexaenoic Acid-Rich Fish Oil Does Not Affect Serum Lipid Concentrations of Normolipidemic Young Adults", American Institute of Nutrition, 126(11):2784-2789, Nov. (1996).

Hamazaki et al., "Effects of Orally Administered Ethyl Ester of Eicosapentaenoic Acid (EPA: C20:5, omega-3) On PG12-Like Substance Production by Rat Aorta" Prostaglandins, vol. 23 No. 4, pp. 557-567 (1982).

Hamazaki T. et al., "Reduction of microalbuminuria in diabetics by Eicosapentaenoic acid ethyl ester" Lipids. 25 (9):542-5 (1990).

Hampel H, Abraham NS, El-Se rag HB. Meta-analysis: obesity and the risk for gastroesophageal reflux disease and its complications. Ann. Intern. Med. Aug. 2005 143 (3): 199-211.

Han, J. J., et al., "Enhancement of both reaction yield and rate of synthesis of structured triacylglycerol containing eicosapentaenoic acid under vacuum with water activity control." Lipids 34:989-995 (1999).

Hanasaki, K., et al., "Potent modification of low density lipoprotein by group X secretory phospholipase A2 is linked to macrophage foam cell formation." J. Biol. Chem. 277(32):29116-24 (2002).

Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. (Accessed Mar. 23, 2011)(573 pages).

Hannah, J., et al., "Effect of dietary fatty acids on LDL binding." Ann N Y Acad Sci., 683:178-182 (1993).

Hansen et al., "Comparative effects of prolonged intake of highly purified fish oils as ethyl ester or triglyceride on lipids, haemostasis and platelet function in normolipaemic men." Eur. J. Clin. Nutr. 47(7):497-507 (Jul. 1993).

Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).

Harris, "n-3 Fatty acids and lipoproteins: a comparison of results from human and animal studies," Lipids 31, 243-252 (1996).

Harris, W. S. et al. "Safety and efficacy of Omacor in severe hypertriglyceridemia," Journal of Cardiovascular Risk, 4:385-391 (1997).

Harris, W. S., "Fish oils and plasma lipid and lipoprotein metabolism in humans: a critical review." J Lipid Res. 30:785-807 (1989).

Harris, W. S., "The omega-3 index as a risk factor for coronary heart disease." Am J Clin Nutr 87:1997S-2002S (2008).

Harris, W. S., et al., "n-3 Fatty acids and urinary excretion of nitric oxide metabolites in humans." Am. J. Clin. Nutr., 65:459-64 (1997).

Harris, W. S., et al., "Influence of n-3 fatty acid supplementation on the endogenous activities of plasma lipases." Am. J. Clin. Nutr. 66:254-60 (1997).

Harris, W.S., "Expert opinion: omega-3 fatty acids and bleeding-cause for concern?" The American Journal of Cardiology 99(6A): 45C-46C (2007).

Harris, W.S., "n-3 Fatty acids and human lipoprotein metabolism: an update." Lipids 34:S257-S258 (1999).

Harris, W.S., "n-3 Fatty acids and serum lipoproteins: human studies." Am J Clin Nutr 65:1645S-54S (1997).

Harris, W.S., "Omega-3 fatty acids in cardiac biopsies from heart transplantation patients." Circulation 110;1645-1649 (2004).

Harris, W.S., et al., "Comparison of the effects of fish and fish-oil capsules on the n-3 fatty acid content of blood cells and plasma phospholipids." Am J Clin Nutr 86:1621-5 (2007).

Harris, W.S., et al., "Omega-3 fatty acids and coronary heart disease risk: Clinical and mechanistic perspectives." Atherosclerosis 197:12-24 (2008).

Harris, W.S., et al., "Stearidonic acid increases the red blood cell and heart eicosapentaenoic acid content in dogs." Lipids 42:325-333 (2007).

Harris, W.S., et al., "Tissue n-3 and n-6 fatty acids and risk for coronary heart disease events." Atherosclerosis 193:1-10 (2007).

Hartweg, J., et al., "Potential impact of omega-3 treatment on cardiovascular disease in type 2 diabetes." Curr Opin Lipidol., 20:30-38 (2009).

Hata et al, Geriatric Medicine, 30 (5), 799-852, 1992 (with English introduction).

Hawthorne, et al., "High dose eicosapentaenoic acid ethyl ester: effects on lipids and neutrophil leukotriene production in normal volunteers." Br. J. Clin. Pharmac., vol. 30, 187-194 (1990).

Hayashi et al., Decreases in Plasma Lipid Content and Thrombotic Activity by Ethyl Icosapentate Purified from Fish Oiles, Current Therapeutic Research, vol. 56, No. 1, pp. 24-31 (1995).

Herbette L, Marquardt J, Scarpa A, Blasie JK. A direct analysis of lamellar x-ray diffraction from hydrated oriented multilayers of fully functional sarcoplasmic reticulum. Biophys. J. 1977;20(2):245-272.

Hibbeln, J. R., et al., "Healthy intakes of n-3 and n-6 fatty acids: estimations considering worldwide diversity." Am J Clin Nutr. 83:1483S-93S (2006).

Higashihara et al. "Effects of Eicosapentaenoic Acid on Biochemical Failure after Radical Prostatectomy for Prostate Cancer," in vivo 24:561-566 (2010).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-1 beta induction of nitric oxide synthase through mechanism involving p44/42 MAPK activation in rat vascular smooth muscle cells." British Journal of Pharmacology 136:613-619 (2002).

Hirai, A., et al., "The effects of the oral administration of fish oil concentrate on the release and the metabolism of [14C ] arachidonic acid and [14C ] eicosapentaenoic acid by human platelets", Thromb. Res., 28:285-298, (1982).

Hirano T, Ito Y, Koba S, Toyoda M, Ikejiri A, Saegusa H, Yamazaki J, Yoshino G. Clinical significance of small dense low-density lipoprotein cholesterol levels determined by the simple precipitation method. Arterioscler. Thromb. Vase. Biol. 2004;24(3):558-563.

Hirano, R., et al., "Regulation by long-chain fatty acids of the expression of cholesteryl ester transfer protein in HepG2 cells." Lipids, 36:401-406 (2001).

Hofacer R, et al., Omega-3 fatty acid deficiency increases stearoyl-CoA desaturase expression and activity indices in rat liver: Positive association with non-fasting plasma triglyceride levels, Prostaglandins Leukot. Essent. Fatty Acids. 2012;86:71-7.

Hoffman, "Atherosclerosis: Prevention through the Ages," WebMD, https://www.webmed.com/heart/features/atherosclerosis-prevention-through-ages#1, (Dec. 4, 2007).

Hohenester, "Primary Biliary Cirrhosis," Semin Immunopathol. 31L:283-307, 285 (2009).

Holmeide, A. K., et al., "Oxidative degradation of eicosapentaenoic acid into polyunsaturated aldehydes." Tetrahedron 59:7157-7162 (2003).

Holub, B.J., PhD, "Fish Oils and Cardiovascular Disease", Canadian Medical Association Journal, 141(10):1063 (1989).

(56) References Cited

OTHER PUBLICATIONS

Holvoet P, Kritchevsky SB, Tracy RP, Mertens A, Rubin SM, Butler J, Goodpaster B, Harris TB. The metabolic syndrome, circulating oxidized LDL, and risk of myocardial infarction in wellfunctioning elderly people in the health, aging, and body composition cohort. Diabetes. 2004;53(4):1068-1073.
Hom et al., "Soft Gelatin Capsules II: Oxygen Permeability Study of Capsule Shells," J Pharm Sci. (1975) 64(5):851-857.
Hombeck, M., et al., "Biosynthesis of the algal pheromone fucoserratene by the freshwater diatom Asterionella formosa (Bacillariophyceae)." Tetrahedron 54:11033-11042 (1998).
Horrobin, D.F. The Phospholipid Concept of Psychiatric Disorders and its Relationship to the Neurodevelopmental Concept of Schizophrenia. In M. Peet (ed.) Phospholipid Spectrum Disorder in Psychiatry pp. 1-19 (1999).
Hoskins et al., "Combination use of statins and omega-3 fatty acids: an emerging therapy for combined hyperlipidemia," Abstract, 1(5): 579-591(13) (2006).
Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).
HPs2-thrive Collaborative Group, "Randomized placebo-controlled trial in 25 673 high-risk patients of er niacin/laroprant: Trial design, pre-specified muscle and liver outcomes, and reasons for stopping study treatment." Eur. Heart J. 2013;34:1279-1291.
Hruska MW, Amico JA, Langaee TY, Ferrell RE, Fitzgerald SM, Frye RF. The effect of trimethoprim on CYP2C8 mediated rosiglitazone metabolism in human liver microsomes and healthy subjects. Br. J. Clin. Pharmacol. 2005;59:70-79.
Hughes et al., "Fish oil produces an atherogenic lipid profile in hypertensive men," Atherosclerosis, 84, pp. 229-237 (1990).
Hulthe J, Hulten LM, Fagerberg B. Low adipocyte-derived plasma protein adiponectin CJ concentrations are associated with the metabolic syndrome and small dense low-density lipoprotein particles: atherosclerosis and insulin resistance study. Metab. Clin. Exp. 2003;52(12):1612-1614.
Huntington's Diesase Drug Works—The DHA Dilemma http://hddrugworks.org/index2.php?option=com_content&task=view&id=185&pop=1&pa . . . Printed on Aug. 22, 2008.(2 pages).
Ignarro LJ, Buga GM, Wood KS, Byrnes RE, Chaudhuri G. Endothelium-derived relaxing factor produced and released from artery and vein is nitric oxide. Proc. Natl. Acad. Sci. USA. 1987;84:9265-9269.
Illingworth, DR, et al., "Comparative effects of lovastatin and niacin in primary hypercholesterolemia: A prospective trial", Arch. Int. Med., 154:1586-1595, (1994).
Inoue, I., et al., "Expression of peroxisome proliferator-activated receptor α (PPARα) in primary cultures of human vascular endothelial cells." Biochem. Biophys. Res. Comm., 246, 370-374 (1998).
Ishida, Y., et al., "α-Lipoic Acid and Insulin Autoimmune Syndrome." Diabeters Care, 30(9): 2240-41 (2007).
Isley, et al., "Pilot study of combined therapy with ω-3 fatty acids and niacin in atherogenic dyslipidemia," Journal of Clinical Lipidology, 1, 211-217 (2007).
Itoh et al., "Increased adinponectin secretion by highly purified eicosapentaenoic acid in rodent models of obesity and human obeses subjects," Arterioscler. Thromb. Vasc. Biol., pp. 1918-1925 (together with online Supplements 1-15) (2007).
Jacob RF, Mason RP. Lipid peroxidation induces cholesterol domain formation in model membranes. J. Biol. Chem. 2005;280(47):39380-39387.
Jacob RF, Walter MF, Self-Medlin Y, Mason RP. Atorvastatin active metabolite inhibits oxidative modification of small dense low-density lipoprotein. J. Cardiovasc. Pharmacol. 2013;62(2):160-166.
Jacobson et al. "Hypertriglyceridemia and Cardiovascular Risk Reduction", Clinical Therapeutics, vol. 29 pp. 763-777 (2007).
Jacobson TA. Opening a new lipid "apo-thecary": incorporating apolipoproteins as potential risk factors and treatment targets to reduce cardiovascular risk. Mayo Clin. Proc. 2011;86:762-780.
Jacobson, T. Secondary Prevention of Coronary Artery Disease with Omega-3 Fatty Acids. Am J Cardiol; 98 [suppl]: 61i-70i (2006).
Jacobson, T.A., "Role of n-3 fatty acids in the treatment of hypertriglyceridemia and cardiovascular disease." Am J Clin Nutr 87:1981S-90S (2008).
Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).
Jakus V, Rietbrock N. Advanced glycation end-products and the progress of diabetic vascular complications. Physiol. Res. 2004;53(2): 131-142.
Jenner, "Presymptomatic Detection of Parkinson's Disease". J Neural Transm Suppl., 40:23-36. (Abstract only) (1993).
Jialal I, Devaraj S. Antioxidants and atherosclerosis: Don't throw out the baby with the bath water. Circulation. 2003;107:926-928.
Jialal, I., "Editorial: Remnant lipoproteins: measurement and clinical significance." Clinical Chemistry 48(2):217-219 (2002).
Jong et al., "Role of ApoCs in Lipoprotein Metabolism: Function Differences Between ApoC1, ApoC2, and ApoC3," Arteriosclerosis, Thrombosis and Vascular Biology. (1999) 19(3):472-484.
Journal of Practical Pharmacy, "Hyperlipidemia Drug," 58(4):1303-1324 (2007) (with English abstract).
Journal of the Japan Diabetes Society, "The Relationship Between Postprandial ApoB48 Increase and Insulin Resistance in Type-2 Diabetes," 55(Suppl. 1):S310 (Apr. 2012) (with English Translation)(5 pages).
Journal of the Japanese Diabetes Society, "A Case of Familial Combined Hyperlipidemia Associated with Obesity, Type 2 Diabetes Mellitus and Severe Hypertriglyceridemia," 51(3), pp. 233-237 (Mar. 30, 2008) (with English abstract).
Jung, U.J., et al., "n-3 Fatty acids and cardiovascular disease: mechanisms underlying beneficial effects." Am J Clin Nutr 87: 2003S-9S (2008).
Kamanna et al., "Mechanism of Action of Niacin," The American Journal of Cardiology (Apr. 17, 2008), 101(8), S20-S26.
Kamido et al., Lipid Composition of Platelets from Patients with Atherosclerosis:Effect of Purified Eicosapentaenoic Acid Ethyl Ester Administration, 1988, Lipids, 23, pp. 917-923 [Abstract only] (7 pages).
Kaminski WE, Jendraschak E, Kiefl R, et al. Dietary omega-3 fatty acids lower levels of platelet-derived growth factor mRNA in human mononuclear cells. Blood Apr. 1993 81 (7): 1871-9.
Kanayasu, T., et al., "Eicosapentaenoic acid inhibits tube formation of vascular endothelial cells in vitro." Lipids 26:271-276 (1991).
Kastelein et al., Omega-3 Free Fatty Acids for the Treatment of Severe Hypertriglyceridemia: The EpanoVa for Lowering Very High Triglycerides (EVOLVE) Trial, J. Clin. Lipidol. (JACL 597) 2013 (54 pages).
Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).
Katayama et al., "Efficacy and Safety of Ethyl Icosapentate (Epadel) Given for a Long Term Against Hyperlipidemia," Prog. Med., 21:457-467 (2001) (with English translation).
Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).
Kawamura et al., "Effects of 4 weeks' intake of polyunsaturated fatty acid ethylester rich in eicosapentaenoic acid (ethylester) on plasma lipids, plasma and platelet phsopholipid fatty acid composition and platelet aggregation; a double blind study," Nihon Naika Gakkai Zasshi, 72(1):18-24 (1983).
Kawano, H., et al., "Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid", J. Atheroscler. Thromb., 9:170-177, (2002).
Kawashima, H., et al., "Oral Administration of Dihomo-y-Linolenic Acid Prevents Development of Atopic Dermatitis in NC/Nga Mice." Lipids 43:37-43 (2008).

(56) References Cited

OTHER PUBLICATIONS

Keech A, Simes RJ, Barter P, Best J, Scott R, Taskinen MR, Forder P, Pillai A, Davis T, Glasziou P, Drury P, Kesaniemi Y A, Sullivan D, Hunt D, Colman P, d'Emden M, Whiting M, Ehnholm C, Laakso M. Effects of long-term fenofibrate therapy on cardiovascular events in 9795 people with type 2 diabetes mellitus (the FIELD study): Randomised controlled trial. Lancet. 2005;366:1849-1861.
Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).
Kelley, et al., "Docosahexaenoic acid supplementation improves fasting and postprandial lip profiles in hypertriglyceridemic men." The American Journal of Clinical Nutrition, 86: 324-333 (2007).
Kellner-Weibel G, Yancey PG, Jerome WG, Walser T, Mason RP, Phillips MC, Rothblat GH. Crystallization of free cholesterol in model macrophage foam cells. Arterioscler. Thromb. Vasc. Biol. 1999;19(8):1891-1898.
Kendall BJ, Macdonald GA, Hayward NK, et al. The risk of Barrett's esophagus associated with abdominal obesity in males and females. Int. J. Cancer May 2013 132(9): 2192-9.
Kerr, S., Brosnan MJ, Mcintyre M, Reid JL, Dominiczak AF, Hamilton CA. Superoxide anion production is increased in a model of genetic hypertension role of the endothelium. Hypertension. 1999;33:1353-1358.
Kew, S., et al., "Effects of oils rich in eicosapentaenoic and docosahexaenoic acids on immune cell composition and function in healthy humans." Am J Clin Nutr 79:674-81 (2004).
Kholodov et al., "Clinical Pharmacokinetics," M. Medicine. (1985) pp. 89-98, 134-138, 160, 378-380 [with English Summary](27 pages).
Kim F, Tysseling KA, Rice J, Gallis B, Haji L, Giachelli CM, Raines EW, Corson MA, Schwartz MW. Activation of IKKbeta by glucose is necessary and sufficient to impair insulin signaling and nitric oxide production in endothelial cells. J. Mol. Cell. Cardiol. 2005;39(2):327-334.
Kim KA, Park PW, Kim HK, Ha JM, Park JY. Effect of quercetin on the pharmacokinetics of rosiglitazone, a CYP2C8 substrate, in healthy subjects. J. Clin. Pharmacol. 2005;45:941-946.
Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).
Kinoshita, "Anti-hyperlipidemic agents," Nihon Rinsho, 60(5):968-74 (May 2002) (with English Abstract)(11 pages).
Kinsella, J.E., et al., "Dietary n-3 polyunsaturated fatty acids and amelioration of cardiovascular disease: possible mechanisms." Am J Clin Nutr 52:1-28 (1990).
Kitada, 9th Diabetes Drug and Drug Related Seminar Diabetes Q&A, Kanazawa Medical University, Diabetes and Endocrine Internal Medicine (http://plaza.umin.ac.jp/iby/etcdata/yakuyaku110410.pdf)(Apr. 10, 2011) (with English translation)(105 pages).
Knapp HR. Dietary fatty acids in human thrombosis and hemostasis. Am. J. Clin. Nutr. May 1997 65 (5 Suppl): 1687S-98S.
Knopp, R.H., et al., "Contrasting effects of unmodified and time-release forms of niacin on lipoproteins in hyperlipidemic subjects: clues to mechanism of action of niacin", Metabolism, 34:642-650, (1985).
Koba S, Hirano T, Ito Y, Tsunoda F, Yokota Y, Ban Y, Iso Y, Suzuki H, Katagiri T. Significance of small dense low-density lipoprotein-cholesterol concentrations in relation to the severity of coronary heart diseases. Atherosclerosis. 2006;189(1):206-214.
Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).
Kojda G, Harrison DG. Interactions between no and reactive oxygen species: Pathophysiological importance in atherosclerosis, hypertension, diabetes and heart failure. Cardiovasc. Res. 1999;43:562-571.
Kojima, T, et al., "Long-term administration of highly purified eicosapentaenoic acid provides improvement of psoriasis." Dermatologica, 182:225-230 (1991).
Koroshetz, W.J. Huntington's Disease. In Samuels, M. (ed.) Office Practice of Neurology, pp. 654-661 (1996).
Kosonen, O., et al., "Inhibition by nitric oxide-releasing compounds of E-selectin expression in and neutrophil adhesion to human endothelial cells." European Journal of Pharmacology 394:149-156 (2000).
Koyama et al., Plague Reduction and Stabilization Observed in Borderline Diabetes Using Coronary CT Angiogram During Administration of Purified Eicosapentaenoic Acid (EPA) Ther. Res. 31(2):219-225 (Feb. 2010) (with English translation)(20 pages).
Krauss RM. Heterogeneity of plasma low-density lipoproteins and atherosclerosis risk. Curr. Opin. Lipidol. 1994;5(5):339-349.
Kris-Etherton, et al., "Fish Consumption, Fish Oil, Omega-3 Fatty Acids, and Cardiovascular Disease" Circulation, 106:2747-2757 (2002).
Kris-Etherton, P. M., et al., "Omega-3 Fatty Acids and Cardiovascular Disease—New Recommendations From the American Heart Association." Arterioscler Thromb Vasc Biol. 23:151-152 (2003).
Krzynowek et al., "Purification of Omega-3 Fatty Acids from Fish Oils Using HPLC: An Overview," National Marine Fisheries—Proceedings of the first joint conference of the Tropical and Subtropical Fisheries Technological Soceity of the Americas with the Atlantic Fisheries Technological Society, pp. 74-77 (1988).
Ku, K., et al., "Beneficial Effects of to-3 Fatty Acid Treatment on the Recovery of Cardiac Function After Cold Storage of Hyperlipidemic Rats." Metabolism, 48(10):123-1209 (1999).
Kunimoto M, Inoue K, Nojima S. Effect of ferrous ion and ascorbate-induced lipid peroxidation on liposomal membranes. Biochem. Biophys.Acta. 1981;646(1):169-178.
Kurabayashi, T., et al., "Eicosapentaenoic acid effect on hyperlipidemia in menopausal Japanese women." Obstet Gynecol 96:521-8 (2000).
Labor Diagnostik Karlsruhe, "Target Values of Lipid Metabolism [Recommendation for lipid plasma levels in Germany]," (exact publication date unknown; circa 2006) (with English abstract)(4 pages).
Lada et al., "Associations of Low Density Lipoprotein Particle Compositions with Atherogenicity," Curr. Opin. Lipidol. (2004) 15(1):19-24.
Lai, E., et al., "Suppression of niacin-induced vasodilation with an antagonist to prostaglandin D2 receptor subtype 1", Clin. Pharm. & Ther., 81:849-857, (2007).
Laidlaw, M., et al., "Effects of supplementation with fish oil-derived n-3 fatty acids and y-linolenic acid on circulating plasma lipids and fatty acid profiles in women." Am J Clin Nutr 77:37-42 (2003).
Lamb RE, Goldstein BJ. Modulating an Oxidative-Inflammatory Cascade: Potential New Treatment Strategy for Improving Glucose Metabolism, Insulin Resistance, and Vascular Function. Int. J. Clin. Pract. 2008;62(7): 1087-1095.
Lamharzi N, Renard CB, Kramer F, Pennathur S, Heinecke JW, Chait A, Bomfeldt KE. Hyperlipidemia in concert with hyperglycemia stimulates the proliferation of macrophages in atherosclerotic lesions: potential role of glucose-oxidized LDL. Diabetes. 2004;53(12):3217-3225.
Landmesser U, Dikalov S, Price SR, McCann L, Fukai T, Holland SM, Mitch WE, Harrison DG. Oxidation of tetrahydrobiopterin leads to uncoupling of endothelial cell nitric oxide synthase in hypertension. J. Clin. Invest. 2003;111:1201-1209.
Larsen, L.N., et al., "Heneicosapentaenoate (21:5n-3): Its incorporation into lipids and its effects on arachidonic acid and eicosanoid Synthesis." Lipids 32:707-714 (1997).
Laufs et al., "Upregulation of endothelial nitric oxide synthase by hmg coa reductase inhibitors," Circulation (1998) 97:1129-1135.
Law, M.R., et al., "Quantifying effect of statins on low density lipoprotein cholesterol, ischaemic heart disease, and stroke: systematic review and meta-analysis." Br Med J., 326:1423-1427 (2003).
Lawson et al., "Human absorption of fish oil fatty acids as triacylglycerols, free acids or ethyl esters," Biochemical and Biophysical Research Communications 152(1):328-335 (Apr. 15, 1988).

(56) References Cited

OTHER PUBLICATIONS

Leaf, "Hypertriglyceridemia: A Guide to Assessment and Treatment," Hospital Physician 17-23 (Sep. 2008).
Leaf, A., "Historical overview of n3 fatty acids and coronary heart disease." Am J Clin Nutr 87:1978S-80S. (2008).
Lee and G.Y.H. Lip, "The Role of Omega-3 Fatty Acids in the Secondary Prevention of Cardiovascular Disease", Q J Med, 96:465-480, (2003).
Lee C, Sigari F, Segrado T, Horkko S, Hama S, Subbaiah PV, Miwa M, Navab M, Witztum JL, Reaven PD. All ApoB-containing lipoproteins induce monocyte chemotaxis and adhesion when minimally modified. Modulation of lipoprotein bioactivity by platelet-activating factor acetylhydrolase. Arterioscler. Thromb. Vase. Biol. 1999; 19(6): 1437-1446.
Lee, J.H., et al., "Omega-3 fatty acids for cardioprotection." Mayo Clin Proc., 83(3):324-332 (2008).
Leigh-Firbank et al., "Eicosapentaenoic acid and docosahexanoic acid from fish oils: differential associations with lipid responses," Br. J. Nutr. 87:435-445 (2002).
Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).
Leonard, Brian E., "Neurological Aspects", Fundamentals of Psychopharmacology,186-187, (1997).
Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68, (1999).
Li, D., et al., "Effect of dietary a-linolenic acid on thrombotic risk factors in vegetarian men." Am J Clin Nutr 69:872-82 (1999).
Li, H., et al., "EPA and DHA reduce LPS-induced inflammation responses in HK-2 cells: Evidence for a PPAR-γ-dependent mechanism." Kidney Int'l. 67:867-74 (2005).
Libby, "Inflammation and atherosclerosis," Nature (2002) 420(6917):868-874.
Lichtman et al., "Depression and Coronary Heart Disease, Recommendations for Screening, Referral and Treatment," AHA Science Advisory, Circulation 118:1768-1775 (Sep. 29, 2008).
Lien, E.L., "Toxicology and safety of DHA." Prostaglandins Leukot Essent Fatty Acids., 81:125-132 (2009).
Lin, Pao-Yen, M.D., et al., "A Meta-Analytic Review of Double-Blind, Placebo-Controlled Trials of Antidepressant Efficacy of Omega-3 Fatty Acids", Psychiatry, 1056-1061 (Jul. 2007).
Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).
Lindsey, S., et al., "Low density lipoprotein from humans supplemented with n-3 fatty acids depresses both LDL receptor activity and LDLr mRNA abundance in HepG2 cells." J Lipid Res., 33:647-658 (1992).
Lipitor [package insert]. New York, NY: Parke-Davis (2012). (22 pages).
Lipitor [product information] Dublin, Ireland: Pfizer Inc. ( 2007). (18 pages).
Liu et al., "Effects of stable fish oil and simvastatin on plasma lipoproteinc in patients with hyperlipidemia," Nutrion Res. , vol. 23, pp. 1027-1034 (2003).
Liu X, et al., Stearoyl CoA Desaturase 1: Role in Cellular Inflammation and Stress, Adv. Nutr. 2011;2:15-22.
Lohmussaar, E., et al., "ALOX5AP Gene and the PDE4D Gene in a Central European Population of Stroke Patients." Stroke, 36:731-736 (2005).
Lovaza (omega-3-acid ethyl esters) Capsules, Prescribing information, GlaxoSmithKline (Nov. 2008).(9 pages).
Lovaza [package insert]. Research Triangle Park, NC: GlaxoSmithKline (2012). (14 pages).
Lovaza Side Effects, web archived webpage, archived from Drugs. com website on (Jul. 31, 2010), Retrieved from URL <https://web.archive.org/web/20100731021902/https://www.drugs.com/sfx/lovaza-side-effects.html> (4 pages)(Jul. 2010).
Lovaza, (omega-3-acid ethyl esters) Capsules, Prescribing information Smith Kline Beechum (Jul. 2009).(17 pages).
Lovaza, GlaxoSmithKline, Lovaza Prescribing Information, Jun. 2008 [retrieved from the internet Jun. 6, 2012 <https://web.archive.org/web/20090206170311/http://us.gsk.com/products/assets/us_lovaza.pdf>]; Table 3, p. 1, section entitled 'Description;' p. 3, section entitled 'Very High Triglycerides: Monotherapy;' p. 4 section entitled 'Indications and Usage' and 'Information for Patients.' (12 pages).
LOVAZA® (omega-3-acid ethyl esters) Capsules, Prescribing information, GlaxoSmithKline, (Dec. 2010)(12 pages).
Lovaza®, Physicians' Desk Reference 2699-2701 (62d ed., 2008). (4 pages).
Lovegrove et al., "Moderate fish-oil supplementation reverses low-platelet, long chain n-3 polyunsaturated fatty acid status and reduced plasma triacylglycerol concentrations in British Indo-Asians," Am. J. Clin. Nutr., 79:974-982 (2004).
Lu, G., et al., "Omega-3 fatty acids alter lipoprotein subfraction distributions and the in vitro conversion of very low density lipoproteins to lowdensity lipoproteins." J Nutr Biochem., 10:151-158 (1999).
Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).
Luria, MH, "Effect of low-dose niacin on high-density lipoprotein cholesterol and total cholesterol/high density lipoprotein cholesterol ratio", Arch. Int. Med., 148:2493-2495, (1998).
Lvovich V, Scheeline A. Amperometric sensors for simultaneous superoxide and hydrogen peroxide detection. Anal. Chem. 1997;69:454-462.
Madhavi et al., "Effect of n-6 and n-3 fatty acids on the survival of vincristine sensitive and resistant human cervical carcinoma cells in vitro", Cancer Letters, vol. 84. No. 1, pp. 31-41 (1994).
Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).
Mak IT, Weglicki WB. Antioxidant properties of calcium channel blocking drugs. Methods Enzymol. 1994;234:620-630.
Maki, K.C., et al., "Baseline lipoprotein lipids and low-density lipoprotein cholesterol response to prescription omega-3 acid ethyl ester added to simvastatin therapy." Am J Cardiol., 105:1409-1412 (2010).
Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).
Malinowski et al., "Elevation of Low-Density Lipoprotein Cholesterol Concentration with Over-the-Counter Fish Oil Supplementation." Annals of Pharmacotherapy 41:1296-1300 (Jul./Aug. 2007).
Malinski T, Taha Z. Nitric oxide release from a single cell measured in situ by a porphyrinic-based microsensor. Nature. 1992;358:676-678.
Mallat, Z., et al., "Apoptosis in the vasculature: mechanisms and functional importance." British Journal of Pharmacology 130:947-962 (2000).
Mallat, Z., et al., "Protective role of interleukin-10 in atherosclerosis." Circ. Res. 85:e17-e24 (1999).
Marangell, Lauren B., M.D., et al., "A Double-Blind, Placebo-Controlled Stury of the Omega-3 Fatty Acid Docosahexaenoic Acid in the Treatment of Major Depression", Am. J. Psychiatry, 160(5):996-998, (May 2003).
Marckmann, P., "Fishing for heart protection." Am J Clin Nutr, 78:1-2 (2003).
Marder, "An Approach to Treatment Resistance in Schizophrenia," British Journ. Psychiatry, 37:19-22 (1999).
Margolis, Simeon "What is Hyperlipidemia?" (http:www.healthcommunities.com/highcholesterol/whatishyperlipidemia.shtml, accessed Oct. 20, 2015, published Aug. 25, 2011)(4 pages).

(56) References Cited

OTHER PUBLICATIONS

Martinez-Gonzalez J, Raposo B, Rodriguez C, Badimon L. 3-hydroxy-3-methylglutaryl coenzyme a reductase inhibition prevents endothelial no synthase downregulation by atherogenic levels of native ldls: Balance between transcriptional and posttranscriptional regulation. Arterioscler. Thromb. Vasc. Biol. 2001;21:804-809.
Martinez-Gonzalez, Jose et al., "Estatinas y acidos grasos omega-3. Disminucion de la mortalidad cardiovascular dependiente e independiente de la reduccion de la colesterolemia," (2006) Rev Esp Cardiol Suppl., 6(D):20D-30D [with English abstract].
Martin-Jadraque, R. et al., Effectiveness of low dose crystalline nicotinic acid in men with low density lipoprotein cholesterol levels. Arch. Int. Med. 156: 1081-1088. (1996).
Martz, "Moving Upstream in Huntington's," Science-Business eXchange, 2 pgs., 2008.
Mason et al., "Comparative lipid antioxidant effects of omega-3 fatty acids in combination with HMG-CoA reductase inhibitors," Journ. Clin. Lipidology (2011) 5(3):20.
Mason et al., "Direct evidence for cholesterol crystalline domains in biological membranes: role in human pathobiology," Biochimica et Biophysica Acta 198-207 (Mar. 10, 2003).
Mason et al., "Eicosapentaenoic Acid (EPA) inhibits the formation of membrane cholesterol crystalline domains by a potent antioxidant mechanism," Journ. Clin. Lipid., 7(3): 272-273 (2013) [Abstract only].
Mason et al., "Eicosapentaenoic acid inhibits glucose-induced membrane cholesterol crystalline domain formation through a potent antioxidant mechanism," Biochim. Biophy. Acta., 1848(2):502-9, (Feb. 2015).
Mason et al., "Eicosapentaenoic Acid Inhibits Oxidation of ApoB-containing Lipoprotein Particles of Different Size In Vitro When Administered Alone or in Combination With Atorvastatin Active Metabolite Compared With Other Triglyceride-lowering Agents," J. Cardiovasc. Pharmacol., 68(1):33-40 (Jul. 2016).
Mason et al., "Eicosapentaenoic acid reduces membrane fluidity, inhibits cholesterol domain formation, and normalizes bilayer width in atherosclerotic-like model membranes," Biochim. Biophy. Acta., 1858(12):3131-3140 (Dec. 2016).
Mason RP, Gonye GE, Chester DW, Herbette LG. Partitioning and location of Bay K 8644, 1,4-dihydropyridine calcium channel agonist, in model and biological membranes. Biophys. J. 1989;55(4):769-778.
Mason RP, Jacob RF, Kubant R, Walter MF, Bellamine A, Jacoby A, Mizuno Y, Malinski T. Effect of enhanced glycemic control with saxagliptin on endothelial nitric oxide release and CD40 levels in obese rats. J. Atheroscler. Thromb. 2011;18:774-783.
Mason RP, Jacob RF. Membrane microdomains and vascular biology: Emerging role in atherogenesis. Circulation. May 6, 2003; 107:2270-2273.
Mason RP, Kalinowski L, Jacob RF, Jacoby AM, Malinski T. Nebivolol reduces nitroxidative stress and restores nitric oxide bioavailability in endothelium of black americans. Circulation. 2005;112:3795-3801.
Mason RP, Kubant R, Heeba G, Jacob RF, Day CA, Medlin YS, Funovics P, Malinski T. Synergistic effect of amlodipine and atorvastatin in reversing ldl-induced endothelial dysfunction. Pharm. Res. 2008;25:1798-1806.
Mason RP, Walter MF, Day CA, Jacob RF. Active metabolite of atorvastatin inhibits membrane cholesterol domain formation by an antioxidant mechanism. J. Biol. Chem. 2006;281(14):9337-9345.
Mason RP, Walter MF, Day CA, Jacob RF. Intermolecular differences for HMG-CoA reductase inhibitors contribute to distinct pharmacologic and pleiotropic actions. Am. J Cardiol. 2005;96(5A):11F-23F.
Mason RP, Walter MF, Jacob RF. Effects of hmg-coa reductase inhibitors on endothelial function: Role of microdomains and oxidative stress. Circulation. 2004;109:II34-II41.
Mason RP, Walter MF, Mason PE. Effect of oxidative stress on membrane structure: Small angle x-ray diffraction analysis. Free Radic. Biol. Med. 1997;23(3):419-425.
Mason RP. Molecular basis of differences among statins and a comparison with antioxidant vitamins. Am. J. Cardiol. 2006;98:34P-41P.
Mataki et al., "Effect of Eicosapentaenoic Acid in Combination with HMG-CoA Reductase Inhibitor on Lipid Metabolism," Int. Med. J. 5(1):35-36 (Mar. 1998).
Mater, M.K., et al., "Arachidonic acid inhibits lipogenic gene expression in 3T3-L1 adipocytes through a prostanoid pathway." J. Lipid Res. 39:1327-1334 (1998).
Matsumoto, M., et al., "Orally administered eicosapentaenoic acid reduces and stabilizes atherosclerotic lesions in ApoE-deficient mice." Atherosclerosis, 197(2):524-533 (2008).
Matsuzaki et al., "Incremental Effects of Eicosapentaenoic Acid on Cardiovascular Events in Statin-Treated Patients with Coronary Artery Disease," Circ. J. 73:1283-1290 (2009).
Matsuzawa, Y., et al., "Effect of Long-Term Administration of Ethyl Icosapentate (MND-21) in Hyperlipaemic Patients," J. Clin Therapeutic & Medicines, 7: 1801-16 (1991).
Mattson MP. Modification of ion homeostasis by lipid peroxidation: roles in neuronal degeneration and adaptive plasticity. Trends Neurosci. 1998;21(2):53-57.
Mayatepek, E., et al., The Lancet, vol. 352, Leukotriene C4-synthesis deficiency: a new inborn error of metabolism linked to a fatal developmental syndrome, pp. 1514-1517 (1998).
Mayo Clinic at http://www.mayoclinic.org.diseases-conditions/high-blood-cholesterol/in-depth/cholesterol (2014)(5 pages).
McElroy, S.L., et al., "Clozapine in the Treatment of Psychotic Mood Disorders, Schizoaffective Disorder, and Schizophrenia", Journal of Clinical Psychiatry, vol. 52, No. 10, pp. 411-414 (1991).
McIntyre M, Hamilton CA, Rees DD, Reid JL, Dominiczak AF. Sex differences in the abundance of endothelial nitric oxide in a model of genetic hypertension. Hypertension. 1997;30:1517-1524.
McKenney et al., "Prescription omega-3 fatty acids for the treatment of hypertriglyceridemia," Am. J. Health Syst. Pharm., 64(6):595-605 (2007).
McKenney et al., CMRO, "Comparison of the efficacy of rosuvastatin versus atorvastatin, simvastatin and pravastatin in achieving lipid goals: results from the STELLAR trial", 689-98 (2003).
McKenney, J., "Niacin for dyslipidemia: considerations in product selection", Am. J. Health Syst. Pharm., 60:995-1005, (2003).
McKenney, J.M. et al. Study of the pharmacokinetic interaction between simvastatin and prescription omega-3-acid ethyl esters. J. Clin. Pharmacol. 46, 785-791 (2006).
McKenney, James et al., "Role of prescription omega-3 fatty acids in the treatment of Hypertriglyceridemia," Pharmacotherapy, LNKD—Pubmed: 17461707, vol. 27, No. 5, pp. 715-728 (2007).
McKeone et al., "Alterations in serum phosphatidylcholine fatty acyl species by eicosapentaenoic and docosahexaenoic ethyl esters in patients with severe hypertriglyceridemia." J. Lipid Res. 38:429-436 (1997).
McMurchie, E.J., et al., "Incorporation and effects of dietary eicosapentaenoate (20 : 5(n-3)) on plasma and erythrocyte lipids of the marmoset following dietary supplementation with differing levels of linoleic acid." Biochimica et Biophysics Acta, 1045:164-173 (1990).
McNamara Jr, et al., Remnant-like particle (RLP) Cholesterol is an independent cardiovascular disease risk factor in women: results from the Framingham Heart Study, Atherosclerosis, vol. 154(1), pp. 229-36 (2001).
MedlinePlus. "Coronary heart disease," Available at: https://medlineplus.gov/ency/article/007115.htm (review date Jul. 14, 2015)(accessed Sep. 2, 2016)(5 pages).
Menuet, R. et al., "Importance and management of dyslipidemia in the metabolic syndrome," American Journal of the Medical Sciences 200512 US, vol. 33, No. 6, pp. 295-302 (2005).
Merched, A.J., et al., "Atherosclerosis: evidence for impairment of resolution of vascular inflammation governed by specific lipid mediators." FASEB J. 22:3595-3606 (2008).
Merkl et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," Circulation, vol. 118, pp. 743-753 (2008).

(56) References Cited

OTHER PUBLICATIONS

Mesa, M., "Effects of oils rich in Eicosapentaenoic and docosahexaenoic acids on the oxidizability and thrombogenicity of low-density lipoprotein," Artherosclerosis 175, pp. 333-343 (2004).
Metcalf, R.G. et al., "Effect of dietary n-3 polyunsaturated fatty acids on the inducibility of ventricular tachycardia in patients with ischemic cardiomyopathy." Am J Cardiol 101:758-761 (2008).
Metcalf, R.G., et al., "Effects of fish-oil supplementation on myocardial fatty acids in humans." Am J Clin Nutr 85:1222-28 (2007).
Meyer, et al., "Dose-Dependent Effects of Docosahexaenoic Acid Supplementation on Blood Lipids in Statin-Treated Hyperlipidaemic Subjects." Lipids, 42:109-115 (2007).
Meyers, et al., "Nicotinic acid induces secretion of prostaglandin D2 in human macrophages: An in vitro model of the niacin-flush", Atherosclerosis, 192:253-258, (2007).
Micheletta F, Natoli S, Misuraca M, Sbarigia E, Diczfalusy U, Iuliano L. Vitamin E supplementation in patients with carotid atherosclerosis: Reversal of altered oxidative stress in plasma but not in plaque. Arterioscler. Thromb. Vasc. Biol. 2004;24:136-140.
Michos et al., "Niacin and Statin Combination Therapy for Atherosclerosis Regression and Prevention of Cardiovascular Disease Events," Journ. Amer. Coll. Cardiol., vol. 59, No. 23:2058-2064 (2012).
Mii, S., et al., "Perioperative use of eicosapentaenoic acid and patency of infrainguinal vein bypass: a retrospective chart review." Curr Ther Res Clin Exp. 68:161-174 (2007).
Miles, et al., "Effect of orlistat in overweight and obese patients with type 2 diabetes treated with metformin," Diabetes Care, 25(7):1123-1128 (2002).
Miller AK, DiCicco RA, Freed MI. The effect of ranitidine on the pharmacokinetics of rosiglitazone in healthy adult male volunteers. Clin. Ther. 2002;24:1062-1071.
Miller AK, Inglis AM, Culkin KT, Jorkasky DK, Freed MI. The effect of acarbose on the pharmacokinetics of rosiglitazone. Eur. J. Clin. Pharmacol. 2001;57:105-109.
Miller M, Stone NJ, Ballantyne C, et al. Triglycerides and cardiovascular disease: a scientific statement from the American Heart Association. Circulation. 2011;123:2292-2333.
Miller, M., et al., "Impact of lowering triglycerides on raising HDL-C in hypertriglyceridemic and non-hypertriglyceridemic subjects." International Journal of Cardiology 119:192-195 (2007).
Minihane, A.M., et al., "ApoE polymorphism and fish oil supplementation in subjects with an atherogenic lipoprotein phenotype." Arterioscler. Thromb. Vasc. Biol. 20:1990-1997 (2000).
Mishra, A., et al., "Oxidized omega-3 fatty acids inhibit NF-κB activation via a PPARα-Dependent Pathway." Arterioscler Thromb Vasc Biol. 24:1621-1627 (2004).
Missouri DUReport, Statin Therapy (Oct./Nov. 2003) Drug Use Review Newsletter 8(6):1-9.
Mita, T. et al., Eicosapentaenoic acid reduces the progression of carotid intima-media thickness in patients with type 2 diabetes, Atherosclerosis 191:162-167 (2007).
Mizota M, Katsuki Y, Mizuguchi K, Endo S, Miyata H, Kojima M, Kanehiro H et al. "Pharmacological studies of eicosapentaenoic acid ethylester (EPA E) on high cholesterol diet-fed rabbits," Nippon Yakurigaku Zasshi, 91:255-66 (1988) (with English abstract).
Mizota M, Katsuki Y, Mizuguchi K, Endo S, Miyata H, Kojima M, Kanehiro H et al. "The effects of eicosapentaenoic acid ethylester (EPA E) on arterial thrombosis in rabbits and vascular lesions in rats," Nippon Yakurigaku Zasshi, 91:81-9 (1988)(with English abstract).
Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol., 59:3307-12 (1992).
Mizuguchi, K., et al., "Ethyl all-cis-5,8,11,14,17-icosapentaenoate modifies the biochemical properties of rat very low-density lipoprotein." European Journal of Pharmacology, 231:221-227 (1993).
Mizuguchi, K., et al., "Mechanism of the lipid-lowering effect of ethyl all-cis-5,8,11,14,17-icosapentaenoate." European Journal of Pharmacology, 231:121-127 (1993).
Mochida Press Release, Pharmaceutical Col., Ltd.: Conclusion of Distributorship Agreement Concerning Switch-OTC Drug for Hyperlipidemia Treatment, Epadel, (2009)(1 page).
Mochida, Announcement, "Mochida Announces Completion of "JELIS" Major Clinical Trial for Epadel," Mar. 22, 2005 (2 pages).
Mochida's Epadel Reduces Risk of Stroke Recurrence—New Results of JELIS Major Clinical Trial, JCNNetwork Newswire Nov. 13, 2006 (2 pages).
Mora, S., et al., "LDL particle subclasses, LDL particle size, and carotid atherosclerosis in the Multi-Ethnic Study of Atherosclerosis (MESA)." Atherosclerosis. 2007;192:211-217 (2007).
Mori et al., "Differential Effects of Eicosapentaenoic Acid and Docosahexaenoic Acid on Vascular Reactivity of the Forearm Microcirculation in Hyperlipidemic, Overweight Men," Circulation, 102:1264-1269 (2000).
Mori TA, Woodman RJ. "The independent effects of eicosapentaenoic acid and docosahexaenoic acid on cardiovascular risk factors in humans," Curr Opin Clin Nutr Metab Care 2006; 9:95-104 (2006).
Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 71:1085-1094 (2000).
Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781 (2003).
Mori, Trevor A., et al., "Docosahexaenoic Acid but Not Eicosapentaenoic Acid Lowers Ambulatory Blood Pressure and Heart Rate in Humans", Hypertension, 34(2):253-60 (Aug. 1999).
Morita, I., et al., "Effects of purified eicosapentaenoic acid on arachidonic acid metabolism in cultured murine aortic smooth muscle cells, vessel walls and platelets." Lipids 18:42-490 (1983).
Morrow, JD, "Release of markedly increased quantities of prostaglandin D2 in vivo in humans following the administration of nicotinic acid", Prostaglandins, 38:263-274, (1989).
Morton, R.E., "Specificity of lipid transfer protein for molecular species of cholesteryl ester." J Lipid Res., 27:523-529 (1986).
Mosher LR et al., "Nicotinic Acid Side Effects and Toxicity: A review," Am J Psychiat., 126: 1290-1296 (1970).
Mostad et al., "Effects of Marine N-3 Fatty Acid Supplementation on Lipoprotein Subclasses Measured by Nuclear Magnetic Resonance in Subjects with Type II Diabetes," European Journ. Clin. Nutr., 62(3):419-429 (2007).
Mostad, I.L, et al., "Effects of n-3 fatty acids in subjects with type 2 diabetes: reduction of insulin sensitivity and time-dependent alteration from carbohydrate to fat oxidation." Am J Clin Nutr 84:540-50 (2006).
Mozaffarian et al., "Omega-3 fatty acids and cardiovascular disease: effects on risk factors, molecular pathways and clinical events," J. Am. Coll. Cardiol. (2011) 58(2):2047-2067.
Mozaffarian, "JELIS, fish oil, and cardiac events," www.thelancet. com vol. 369, pp. 1062-1063 (2007).
Mozaffarian, D., "Fish and n-3 fatty acids for the prevention of fatal coronary heart disease and sudden cardiac death." Am J Clin Nutr, 87:1991S-6S (2008).
Mozaffarian, D., et al., "Dietary fish and ω-3 fatty acid consumption and heart rate variability in US adults." Circulation, 117:1130-1137 (2008).
Naba, H., et al., "Improving effect of ethyl eicosapentanoate on statin-induced rhabdomyolysis in Eisai hyperbilirubinemic rats." Biochemical and Biophysical Research Communications, 340:215-220 (2006).
Nagakawa et al., Effect of [EPA] on the Platelet Aggregation and Composition of Fatty Acid in Man: A Double Blind Study, Atherosclerosis 47(1):71-75 (1983).
Naik H, Wu JT, Palmer R, McLean L. The effects of febuxostat on the pharmacokinetic parameters of rosiglitazone, a CYP2C8 substrate. Br. J. Clin. Pharmacol. Jan. 13, 2012;74:327-335.

(56) References Cited

OTHER PUBLICATIONS

Nakamura et al., Remnant lipoproteniemia is a risk factor for endothelial vasomotor dysfuction and coronary artery disease in metabolic syndrome, Atherosclerosis, vol. 181(2), pp. 321-327 (2005).
Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).
Nakamura, H., et al., "Evaluation of ethyl icosapentate in the treatment of hypercholesterolemia in kidney transplant recipients." Transplantation Proceedings, 30:3047-3048 (1998).
Nakamura, N. et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, pp. 22-25 (1999).
Nambi, V., et al., "Combination therapy with statins and omega-3 fatty acids." Am J Cardiol 98:34i-38i (2006).
Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).
Natsuno et al., "Clinical Effects of Eicosapentaenoic Acid on Type-2 Diabetes Effects on Serum Lipids, Pulse Wave Speed, and Ankle-Brachial Blood Pressure Index," Diagnosis and Treatment 93(12):133-137 (2005)(16 pages).
Nattel, S., et al., "Atrial remodeling and atrial fibrillation: Mechanisms and implications." Circ Arrhythmia Electrophysiol, 1:62-73 (2008).
Negre-Salvayre, A., et al., "Advanced lipid peroxidation end products in oxidative damage to proteins. Potential role in diseases and therapeutic prospects for the inhibitors." British Journal of Pharmacology 153:6-20 (2008).
Nelson, G.J., et al., "The Effect of Dietary Docosahexaenoic Acid on Plasma Lipoproteins and Tissue Fatty Acid Composition in Humans", Lipids, 32(11):1137-1146, (1997).
Nemets, Boris, M.D., "Addition of Omega-3 Fatty Acid to Maintenance Medication Treatment for Recurrent Unipolar Depressive Disorder", Am. J. Psychiatry, 159(3):477-479, (Mar. 2002).
Nemoto et al., "Ethyl-eicosapentaenoic Acid Reduces Liver Lipids and Lowers Plasma Levels of Lipids in Mice Fed a High-Fat Diet, in vivo," 23:685-690 2009).
Nenseter, MS et al., "Effect of dietary supplementation with n-3 polyunsaturated fatty acids on physical properties and metabolism of low density lipoprotein in humans," Arterioscler. Thromb. Vasc. Biol., 12;369-379 (1992).
Nestel, et al., "The n-3 fatty acids eicosapentaenoic acid and docosahexaenoic acid increase systemic arterial compliance in humans," Am J Clin Nutr., 76:326-30 (2002).
Nestel, P.J., "Effects of N-3 fatty acids on lipid metabolism." Ann Rev Nutr., 10:149-167 (1990).
Niemi M, Backman JT, Grantors M, Laitila J, Neuvonen M, Neuvonen PJ. Gemfibrozil considerably increases the plasma concentrations of rosiglitazone. Diabetologia. 2003;46: 1319-1323.
Niemi M, Backman JT, Neuvonen PJ. Effects of trimethoprim and rifampin on the pharmacokinetics of the cytochrome P450 2C8 substrate rosiglitazone. Clin. Pharmacol. Ther. 2004;76:239-249.
Nigon F, Lesnik P, Rouis M, Chapman MJ. Discrete subspecies of human low density lipoproteins are heterogeneous in their interaction with the cellular LDL receptor. J. Lipid Res. 1991;32(11):1741-1753.
Nishikawa M. et al., "Effects of Eicosapentaenoic acid (EPA) on prostacyclin production in diabetics. GC/MS analysis of PG12 and PG13 levels" Methods Find Exp Clin Pharmacol. 19(6):429-33 (1997).
Nobukata, H., et al., "Age-related changes in coagulation, fibrinolysis, and platelet aggregation in male WBN/Kob rats." Thrombosis Research 98: 507-516 (2000).
Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).
Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).
Noguchi et al., "Chemoprevention of DMBA-induced mammary carcinogenesis in rats by low-dose EPA and DHA." Br. J. Cancer 75(3): 348-353 (1997).
Nomura et al., "The effects of pitavastatin, eicosapentaenoic acid and combined therapy on platelet-derived microparticles and adiponectin in hyperlipidemic, diabetic patients." Platelets, 20(1):16-22 (2009).
Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).
Nozaki S. et al., "Effects of purified Eicosapentaenoic acid ethyl ester on plasma lipoproteins in primary hypercholesterolemia" Int J Vitam Nutr Res. 62(3):256-260 (1992).
Obata, et al., "Eicosapentaenoic acid inhibits prostaglandin D2 generation by inhibiting cyclo-oxygenase in cultured human mast cells", Clin. & Experimental Allergy, 29:1129-1135, (1999).
O'Donnell, C.J., et al., "Leukocyte telomere length and carotid artery intimal medial thickness—the Framingham heart study." Arteriosclerosis, Thrombosis, and Vascular Biology.28:1165-1171 (2008).
Oemar BS, Tschudi MR, Godoy N, Brovkovich V, Malinski T, Luscher TF. Reduced endothelial nitric oxide synthase expression and production in human atherosclerosis. Circulation. 1998;97:2494-2498.
Oh, Robert C et al., Management of Hypertriglyceridemia, American Family Physician, LNKD-PUBMED: 17508532, vol. 75, No. 9, pp. 1365-1371 (2007).
Ohara Y, Peterson TE, Harrison DG. Hypercholesterolemia increases endothelial superoxide anion production. J. Clin. Invest. 1993;91:2546-2551.
Okuda, Y. et al., Eicosapentaenoic acid enhances nitric oxide production by cultured human endothelial cells. Biochem. Biophys. Res. Commun. 232: 487-491 (1997).
Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).
Okumura, T., et al., "Eicosapentaenoic acid improves endothelial function in hypertriglyceridemic subjects despite increased lipid oxidizability." Am J Med Sci 324(5):247-253 (2002).
Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126, 261-268 (1992).
Olofsson et al., "Apolipoprotein B: a clinically important apolipoprotein which assembles atherogenic lipoproteins and promotes the development of atherosclerosis" Journal of Internal Medicine, 258: 395-410 (2005).
OMACOR® Prescribing Information (Omega-3-acid ethyl esters, capsules) (2004). (9 pages).
Omacor®, Physicians' Desk Reference 2735 (60th ed. 2006)(3 pages).
Ona, V.O., et al., Nature, vol. 399, Inhibition of caspase-1 slows disease progression in a mouse model of Huntington's disease, pp. 263-267 (1999).
Ooi EM, Apolipoprotein C-III: Understanding an emerging cardiovascular risk factor, Clin.Sci. (London), vol. 114, pp. 611-624 (2008).
Opalinska et al., "Increasing Level of Prostate-Specific Antigen and Prostate Cancer Risk Factors Among 193 Men Examined in Screening Procedure," Ann. Univ. Curie Sklowoska Med., 58(2):57-63 (Abstract Only)(2003)(2 pages).

(56) References Cited

OTHER PUBLICATIONS

O'Riordan, "DHA and EPA have differential effects on LDL-cholsterol," May 24, 2011 [online][Retrieved on Aug. 21, 2015] Retrieved from website: http://www.medscape.com/viewarticle/743305 (2 pages).
Osher et al., "Omega-3 Eicosapentaenoic Acid in Bipolar Depression: Report of a Small Open-Label Study," J. Clin. Psych. 66:726-729 (2005).
Ou Z, Ou J, Ackerman AW, Oldham KT, Pritchard KA, Jr. L-4f, an apolipoprotein a-1 mimetic, restores nitric oxide and superoxide anion balance in low-density lipoprotein-treated endothelial cells. Circulation. 2003;107:1520-1524.
Ozaki M, Kawashima S, Yamashita T, Hirase T, Namiki M, Inoue N, Hirata K, Yasui H, Sakurai H, Yoshida Y, Masada M, Yokoyama M. Overexpression of endothelial nitric oxide synthase accelerates atherosclerotic lesion formation in apoe-deficient mice. J. Clin. Invest. 2002; 110:331-340.
Ozawa, Akio, Nakamura E, Jinbo H. Fujita T, Hirai A, Terano T, Hamazaki T et al., "Determination of highger fatty acids in various lipid fractions of human plasma, platelets, and erythrocyte membrane using thin layer chromatography and gas chromatography," Bunseki Kagaku, 32:174-8 (1982) (with English abstract).
Padgett et al., "Phylogenetic and immunological definition of four lipoylated proteins from *Novosphingobium aromaticivorans*, implications for primary biliary cirrhosis," Journ. Autoimmunity 24:209-219 (May 2005)(available online Feb. 24, 2005).
Park JH, Park DI, Kim HJ, et al. Metabolic syndrome is associated with erosive esophagitis. World J. Gastroenterol. Sep. 14, 2008 (35): 5442-7.
Park JY, Kim KA, Kang MH, Kim SL, Shin JG. Effect of rifampin on the pharmacokinetics of rosiglitazone in healthy subjects. Clin. Pharmacol. Ther. 2004;75:157-162.
Park, Y., et al., "Omega-3 fatty acid supplementation accelerates chylomicron triglyceride clearance." J. Lipid Res. 44:455-463 (2003).
Patel et al., "Rosiglitazone monotherapy improves glycaemic control in patients with type 2 diabetes: a twelve-week, randomized, placebo-controlled study," Diabetes, Obesity and Metabolism, vol. 1, pp. 165-172 (1999).
Paton, CM, Ntambi, JM., Biochemical and physiological function of stearoyl-CoA desaturase, AM. J. Physiol. Endocrinol. Metab. 2009;297:E28-E37.
PCT/GB00/00164 International Search Report dated Oct. 20, 2000 (8 pages).
PCT/US2011/062247 International Search Report and Written Opinion dated Jun. 14, 2012 (12 pages).
PCT/US2013/020526 International Search Report dated Mar. 29, 2013 (2 pages).
PCT/US2013/048241 International Search Report dated Dec. 13, 2013 (3 pages).
PCT/US2013/048516 International Search Report dated Dec. 20, 2013 (3 pages).
PCT/US2013/048559 International Search Report dated Dec. 13, 2013 (3 pages).
PCT/US2013/068647 International Search Report and Written Opinion dated May 13, 2014 (18 pages).
PCT/US2014/019454 International Search Report and Written Opinion dated Jun. 3, 2014 (12 pages).
Pedersen RS, Damkier P, Brosen K. The effects of human CYP2C8 genotype and fluvoxamine on the pharmacokinetics of rosiglitazone in healthy subjects. Br. J. Clin. Pharmacol. 2006;62:682-689.
Pedersen, T., et al., "Randomised trial of cholesterol lowering in 4444 patients with coronary heart disease: the Scandinavian Simvastation Survival Study (4S)", The Lancet, No. 19, vol. 344, 8934, p. 1383-1389 (1994).
Peet et al., "A Dose-Ranging Study of the Effects of Ethyl-Eicosapentaenoate in Patients with Ongoing Depression Despite Apparently Adequate Treatment with Standard Drugs", Arch. Gen. Psychiatry, 59:913-919, (2002).
Peet, M., et al., Phospholipid Spectrum Disorder in Psychiatry pp. 1-19, (1999).

Pejic et al., "Hypertriglyceridimia," Journ. Amer. Board Fam. Med., vol. 19(3):310-316 (2006).
Pennathur S, Heinecke JW. Mechanisms for oxidative stress in diabetic cardiovascular disease. Antioxid. Redox Signal. 2007;9(7):955-969.
Piccini, Monica, et al., Genomics, vol. 47, "FACL4, a new gene encoding long-chain acyl-CoA synthetase 4, is deleted in a family with Alport syndrome, elliptocytosis, and mental retardation," pp. 350-358 (1998).
Piche, "Tumor Necrosis Factor-Alpha, and Fibrinogen to Abdominal Adipose Tissue, Blood Pressure, and Cholesterol and Triglyceride Levels in Healthy Postmenopausal Women", American Journal of Cardiology, 2005, 96(1), 92-97.
Pike, NB, "Flushing out the role of GPR109A (HM74V) in the clinical efficacy of nicotinic acid", J. Clin. Invest., 115:3400-3403, (2005).
PLUSEPA® Product brochure "Super Critically Different from Other Omega-3 Fish Oil Supplements for Depression and ADHD," by Minami Nutrition (Apr. 2009, pp. 1-6).
Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).
Press Release: Amarin Corporation Says Huntington's Diease Drug Failed in Trials, http://www.fiercebiotech.com/node/6607/print (Apr. 24, 2007) (Printed on Aug. 22, 2008)(2 pages).
Pritchard KA, Ackerman AW, Ou J, Curtis M, Smalley DM, Fontana JT, Stemerman MB, Sessa WC. Native low-density lipoprotein induces endothelial nitric oxide synthase dysfunction: Role of heat shock protein 90 and caveolin-1. Free Radic. Biol. Med. 2002;33:52-62.
Pritchard KA, Jr., Groszek L, Smalley DM, Sessa WC, Wu M, Villalon P, Wolin MS, Stemerman MB. Native low-density lipoprotein increases endothelial cell nitric oxide synthase generation of superoxide anion. Circ. Res. 1995;77:510-518.
Puri et al., "Reduction in Cerebral Atrophy Associated with Ethyl-eicosapentaenoic Acid Treatment in Patients with Huntington's Disease," Journ. Int'l. Med. Research, 36:896-905 (Oct. 1, 2008).
Puri, B., et al., "Eicosapentaenoic Acid in Treatment-Resistant Depression Associated with Symptom Remission, Structural Brain Changes and Reduced Neuronal Phospholipid Turnover," Int J Clinical Practice, 55:560-563 (2001).
Puri, B., et al., Archives of General Psychiatry, No. 55, "Sustained remission of positive and negative symptoms of schizophrenia following treatment with eicosapentaenoic acid," pp. 188-189, (1998).
Puri, B.K., et al., "Ethyl-EPA in Huntington Disease: A Double-Blind, Randomized, Placebo-Controlled Trial", Neurology, 65:286-292, (2005).
Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).
Rader, Lipid Disorders, in Eric J. Topol (ed.)Textbook of Cardiovascular Medicine pp. 55-75 (2007).
Rahimy M, Hallen B, Narang P. Effect of tolterodine on the anticoagulant actions and pharmacokinetics of single-dose warfarin in healthy volunteers. Arzneimittelforschung 2002 52 (12): 890-5.
Raitt, M.H., et al., "Fish oil supplementation and risk of ventricular tachycardia and ventricular fibrillation in patients with implantable defibrillators—a randomized controlled trial." JAMA. 293(23):2884-2891 (2005).
Rambjor, Gro S., et al., "Eicosapentaenoic Acid is Primarily Responsible for Hypotrigylceridemic Effect of Fish Oil in Humans", Fatty Acids and Lipids from Cell Biology to Human Disease: Proceedings of the 2nd international Congress of the ISSFAL (International Society for the Study of Fatty Acids and Lipids, AOCS Press, 31:S-45-S-49, (1996).
Randomised trial of cholesterol lowering in 4444 patients with coronary heart disease. The Scandinavian Simvastatin Survival Study, Lancet. 344: 1383-1389 (1994).

(56) References Cited

OTHER PUBLICATIONS

Rao MN, Mullangi R, Katneni K, et al. Lack of effect of sucralfate on the absorption and pharmacokinetics of rosiglitazone. J. Clin. Pharmacol. 2002;42:670-675.
Rees DD, Palmer RM, Moncada S. The role of endothelium-derived nitric oxide in the regulation of blood pressure. Proc. Natl. Acad. Sci. USA. 1989;86:3375-3378.
Reich, "Formulation and physical properties of soft capsules," Pharmaceutical capsules. (2004) Chapter 11:201-212.
Reiffel, J.A., et al., "Antiarrhythmic effects of omega-3 fatty acids." Am J Cardiol 98:50i-60i (2006).
Reiner Z, Catapano AL, De BG, et al. ESC/EAS Guidelines for the management of dyslipidaemias: the Task Force for the management of dyslipidaemias of the European Society of Cardiology (ESC) and the European Atherosclerosis Society (EAS). Eur. Heart J. 2011;32:1769-1818.
Richter, Werner O., "Hypertriglyceridamie: Ein klinischer•Leitfaden," Wissenschaftliche Verlagsgesellschaft mbH Stuttgart, front page to p. V, pp. 2 to 55, 64 to 85, 90 to 97 (2008) (with English Summary).
Ridker, "C-Reactive Protein : A Simple Test to Help Predict Risk of Heart Attack and Stroke", Circulation: Journal of the American Heart Association, 2003, 108, e81-e85.
Riediger, N.D., et al., "A systemic review of the roles of n-3 fatty acids in health and disease." J Am Diet Assoc. 109:668-679. (2009).
Rifai, "High-Sensitivity C-Reactive Protein: A Novel and Promising Marker of Coronary Heart Disease", Clinical Chemistry, 2001, 47(3), 403-411.
Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).
Rissanen et al., "Fish Oil-Derived Fatty Acids, Docosahexaenoic Acid and Docosapentaenoic Acid, and the Risk of Acute Coronary Events The Kuopio Ischaemic Heart Disease Risk Factor Study," Circulation. (Nov. 28, 2000)(102):2677-2679 doi:10.1161/01.CIR.102.22.2677.
Rizzo M, Bemeis K. Low-density lipoprotein size and cardiovascular risk assessment. Q. J. Med. 2006;99(1): 1-14.
Roach, P.D., et al., "The effects of dietary fish oil on hepatic high density and low density lipoprotein receptor activities in the rat." FEBS Lett., 222: 159-162 (1987).
Robinson, J.G., et al., "Meta-analysis of the relationship between non-high-density lipoprotein cholesterol reduction and coronary heart risk." J Am Coll Cardiol., 53: 316-322 (2009).
Roche, H.M., et al., "Effect of long-chain n-3 polyunsaturated fatty acids on fasting and postprandial triacylglycerol metabolism." Am J Clin Nutr 71:232S-7S (2000).
Roche, H.M., et al., "Long-chain n-3 polyunsaturated fatty acids and triacylglycerol metabolism in the postprandial state." Lipids 34: S259-S265 (1999).
Rodriguez, Y., et al., "Long-chain ω6 polyunsaturated fatty acids in erythrocyte phospholipids are associated with insulin resistance in non-obese type 2 diabetics." Clinica Chimica Acta 354:195-199 (2005).
Rogers, P. J., "No effect of n-3 long-chain polyunsaturated fatty acid (EPA and DHA) supplementation on depressed mood and cognitive function: a randomised controlled trial" British Journal of Nutrition, 99:421-431, (2008).
Rost KL, Roots I. Nonlinear kinetics after high-dose omeprazole caused by saturation of genetically variable CYP2C19. Hepatology Jun. 23, 1996 (6): 1491-7.
Rubins, HB, et al., "Distribution of lipids in 8,500 men with coronary artery disease: Department of Veterans Affairs HDL Intervention Trial Study Group," Am. J. Cardiol, 75:1196-1201, (1995).
Rubins, HB, et al., "Gemfibrozil for the prevention of coronary heart disease in men with low levels of high-density lipoprotein cholesterol: Veterans Affairs HDL-C Intervention Trial Study Group", N. Eng. J. Med., 341:410-418, (1999).
Ruiz-Narváez, E.A., et al., "Abdominal obesity and hyperglycemia mask the effect of a common APOC3 haplotype on the risk of myocardial infarction." Am J Clin Nutr 87:1932-8 (2008).
Ruocco MJ, Shipley GG. Interaction of cholesterol with galactocerebroside and galactocerebroside phosphatidylcholine bilayer membranes. Biophys. J. 1984;46:695-707.
Rustan, A.C., et al., "Eicosapentaenoic acid inhibits cholesterol esterification in cultured parenchymal cells and isolated microsomes from rat liver." J. Bio. Chem. 263(17):8126-32 (1988).
Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).
Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).
Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).
Ryan, A.S., et al., "Clinical overview of algal-docosahexaenoic acid: effects on triglyceride levels and other cardiovascular risk factors." Am J Ther., 16:183-192 (2009).
Sacks, Frank M., "The apolipoprotein story," Atherosclerosis Supplements, 23-27 (2006).
Saito et al., "Effects of EPA on coronary artery disease in hypercholesterolemic patients with multiple risk factors: Sub-analysis of primary prevention cases from the Japan EPA Lipid Intervention Study (JELIS)," Atherosclerosis, 200:135-140 (2008).
Saito et al., "Results of Clinical Usage of Improved Formulation (MND-21S) Epadel Capsule 300 with Respect to Hyperlipidemia," 26(12) Jpn. Pharmacol. Ther. 2047-62 (1998) (with English abstract).
Saito, J., et al., "Mechanisms of enhanced production of PGI2 in cultured rat vascular smooth muscle cells enriched with eicosapentaenoic acid." Atherosclerosis 131: 219-228 (1997).
Sampath H, Ntambi JM., Role of stearoyl-CoA desaturase in human metabolic disease, Future Lipidol. 2008;3.163-73.
Sampath H, Ntambi JM., The Role of stearoyl-CoA desaturase in obesity, insulin resistance, and inflammation, Ann. NY. Acad. Sci. 2011; 1243:4 7-53.
Samuels, Martin A., M. D., et al., "Huntington's Disease", Office Practice of Neurology, (122):654-655, (1996).
Sanders, A. Hinds and C.C. Pereira, "Influence of n-3 fatty acids on blood lipids in normal subjects" Journal of Internal Medicine. 225:99-104,(1989).
Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition, 95, 525-531 (2006).
Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).
Sanders, T.A., et al., "Triglyceride-lowering effect of marine polyunsaturates in patients with hypertriglyceridemia." Arterioscler. Thromb. Vasc. Biol. 5:459-465 (1985).
Sasaki J, Miwa T, Odawara M. Administration of highly purified eicosapentaenoic acid to stain-treated diabetic patients further improves vascular function. Endocrine J. 2012; 59(4):297-304.
Sasaki J, Yokoyama M, Matsuzaki M, et al. Relationship between coronary artery disease and non-HDL-C, and effect of highly purified EPA on the risk of coronary artery disease in hypercholesterolemic patients treated with statins: sub-analysis of the Japan EPA Lipid Intervention Study (JELIS). J. Atheroscler. Thromb. 2012;19:194-204.
Sasaki, Y.F., et al., "Bio-anticlastogenic effects of unsaturated fatty acids included in fish oil—docosahexaenoic acid, docosapentaenoic acid, and eicosapentaenoic acid—in cultured Chinese hamster cells." Mutation Research, 320: 9-22 (1994).

(56) References Cited

OTHER PUBLICATIONS

Sato et al., "General Pharmacological Studies on 5 8 11 14 17 Eicosapentaenoic Acid Ethyl Ester EPA-E", Folia Pharmacol JPN, 94 (1), 35-47. (1989) (with English abstract).
Sato, "Effects of Highly Purified Ethyl All-cis-5,8,11,14,17-icosapentaenoate (EPA-E) on Rabbit Platelets," Biol. Pharm. Bull., 16(4)362-367 (1993).
Satoh et al., "Highly purified eicosapentaenoic acid reduces cardio-ankle vascular index in association with decreased serum amyloid A-LDL in metabolic syndrome," Hypertension Research (2009) (32):1004-1008.
Satoh, N., et al., "Purified eicosapentaenoic acid reduces small dense LDL, remnant lipoprotein particles, and C-reactive protein in metabolic syndrome." Diabetes Care, 30(1): 144-146 (2007).
Satoh-Asahara N, Shimatsu A, Sasaki Y, Nakaoka H, Himeno A, Tochiya M, Kono S, Takaya T, Ono K, Wada H, Suganami T, Hasegawa K, Ogawa Y., "Highly purified eicosapentaenoic acid increases interleukia-10 levels of peripheral blood monocytes in obese patients with dyslipidemia." Diabetes Care. 2012;35(12):2631-2639.
Schaefer, E.J., et al., "Effects of eicosapentaenoic acid, docosahexaenoic acid, and olive oil on cardiovascular disease risk factors [abstract 20007]." Circulation, 122:A20007 (2010) (Abstract only).
Schectman, G. & Hiatt, J., "Drug therapy for hypercholesterolemia in patients with cardiovascular disease: factors limiting achievement of lipid goals", Am. J. Med., 100:197-204, (1996).
Schectman, G., et al., "Dietary fish oil decreases low-density-lipoprotein clearance in nonhuman primates." Am J Clin Nutr., 64:215-221 (1996).
Schectman, G., et al., "Heterogeneity of Low Density Lipoprotein Responses to Fish-Oil Supplementation in Hypertriglyceridemic Subjects." Arterioscler. Thromb. Vasc. Biol. 9:345-354 (1989).
Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).
Schmitz PG, McCloud LK, Reikes ST, et al. Prophylaxis of hemodialysis graft thrombosis with fish oil: double-blind, randomized, prospective trial. J. Am. Soc. Nephrol. Jan. 13, 2002 (1): 184-90.
Schmitz, G., et al., "The opposing effects of n-3 and n-6 fatty acids." Progress in Lipid Research, 47:147-155 (2008).
Schreiner et al., Lipoprotein[a] as a Risk Factor for Preclinical Atherosclerosis, 13 Atherosclerosis, Thrombosis & Vascular Biology 826, 826 (1993).
Schuirmann, D.J. A comparison of the two one-sided tests procedure and the power approach for assessing the equivalence of average bioavailability. J. Pharmacokinet. Biopharm. 15, 657-680 (1987).
Schwarz, S., et al., "Lycopene inhibits disease progression in patients with benign prostate hyperplasia." J. Nutr. 138: 49-53 (2008).
Schwellenbach et al., "The Triglyceride-Lowering Effects of a Modest Dose of Docosahexaenoic Acid Alone Versus in Combination with Low Dose Eicosapentaenoic Acid in Patients with Coronary Artery Disease and Elevated Triglycerides." J. Am. Coll. Nutr. 25(6):480-485 (2006).
Segrest et al., Structure of Apolipoprotein B-100 in Low Density Lipoproteins, J. Lipid Res. 42(9):1346-1367 (2001).
Self-Medlin Y, Byun J, Jacob RF, Mizuno Y, Mason RP. Glucose promotes membrane cholesterol crystalline domain formation by lipid peroxidation. Biochim. Biophys. Acta. 2009; 1788(6): 1398-1403.
Serhan, C.N., et al., "Resolvins: A family of bioactive products of omega-3 fatty acid transformation circuits initiated by aspirin treatment that counter proinflammation signals." J. Exp. Med. 196:1025-1037 (2002).
Sevanian A, Ursini F. Lipid peroxidation in membranes and low-density lipoproteins: similarities and differences. Free Radic. Biol. Med. 2000;29(3-4):306-311.

Shah, S., et al., "Eicosapentaenoic Acid (EPA) as an Adjunct in the Treatment of Schizophrenia", Schizophrenia Research, vol. 29, No. 1/02 (1998).
Shan, Z., et al., "A combination study of spin-trapping, LC/ESR and LC/MS on carbon-centred radicals formed from lipoxygenase-catalysed peroxidation of eicosapentaenoic acid." Free Radical Research, 43(1):13-27 (2009).
Shimizu et al., "Effects of Highly Purified Eicosapentaenoic Acid on Erythrocyte Fatty Acid Composition and Leukocyte and Colonic Mucosa Leukotriene B4 Production in Children with Ulcerative Colitis," J. Pediatr. Gastroenterol. Nutr., vol. 37, No. 5, pp. 581-585 (2003).
Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).
Shimokawa H, Flavahan NA, Vanhoutte PM. Loss of endothelial pertussis toxin-sensitive g protein function in atherosclerotic porcine coronary arteries. Circulation. 1991;83:652-660.
Shinozaki K. et al., "The long-term effect of Eicosapentaenoic acid on serum levels of lipoprotein (a) and lipids in patients with vasciular disease" J Atheroscler Thromb. 2(2):207-9 (1996).
Shishehbor MH, Brenna ML, Aviles RJ, Fu X, Penn MS, Sprecher DL, Hazen SL. Statins promote potent systemic antioxidant effects through specific inflammatory pathways. Circulation. 2003;108(4):426-431.
Sicherer et al., "Prevalence of seafood allergy in the United States determined by a random telephone survey," J. Allergy Clin. Immunol., 114(1):159-165 (Jul. 2004).
Sierra, S., et al., "Dietary eicosapentaenoic acid and docosahexaenoic acid equally incorporate as decosahexaenoic acid but differ in inflammatory effects." Nutrition 24: 245-254 (2008).
Silvers, Karen M., et al., "Randomised double-blind placebo-controlled trial of fish oil in the treatment of depression", Prostagandins, Leukotrienes and Essential Fatty Acids, 72:211-218, (2005).
Simoens, C.M., et al., "Inclusion of 10% fish oil in mixed medium-chain triacylglycerol-long chain triacylglycerol emulsions increases plasma triacylglycerol clearance and induces rapid eicosapentaenoic acid (20:5n-3) incorporation into blood cell phospholipids." Am J Clin Nutr 88: 282-8 (2008).
Simon, Joel A., et al., "Serum Fatty Acids and the Risk of Coronary Heart Disease", American Journal of Epidemiology, 142(5):469-476, (1995).
Simopolous, The Importance of the Omega-6/Omega-3 Fatty Acid Ratio in Cardiovascular Disease and Other Chronic Diseases, Exp. Biol. Med, 233:674-688 (Jun. 1, 2008)(available online Jun. 1, 2008).
Simopoulos, "Omega-3 fatty acids in health and disease and in growth and development," Am. J. Clin. Nutr. 54:438-63 (1991).
Singer, Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (2005).
Singh, R.B., et al., "Randomized, double-blind, placebo-controlled trial of fish oil and mustard oil in patients with suspected acute myocardial infarction: the Indian experiment of infarct survival—4." Cardiovascular Drugs and Therapy 11:485-491 (1997).
Sirtori, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).
Skinner JS, Cooper A, & Feder GS and on behalf of the Guideline Development Group. "Secondary prevention for patients following a myocardial infarction; summary of NICE guidance," Heart, 93:862-864 (2007).
Slides for the Oct. 16, 2013 Meeting of the Endocrinologic and Metabolic Drugs Advisory Committee, (158 pages).
Smith et al., Pharmacokinetics and Pharmacodynamics of Epoetin Delta in Two Studies in Health Volunteers and Two Studies in Patients with Chronic Kidney Disease, Clinical Therapeutics/vol. 29, pp. 1368-1380 (2007).
Sniderman A, Kwiterovich PO. Update on the detection and treatment of atherogenic low-density lipoproteins. Curr. Opin. Endocrinol. Diabetes Obes. Apr. 20, 2013;20:140-147.

(56) References Cited

OTHER PUBLICATIONS

Sohma, R., et al., "Protective effect of n-3 polyunsaturated fatty acid on primary culture of rat hepatocytes without glycemic alterations." Journal of Gastroenterology and Hepatology 22: 1965-1970 (2007).
Spector, A.A., "Arachidonic acid cytochrome P450 epoxygenase pathway." Journal of Lipid Research, 50: S52-S56 (2009) (published online on Oct. 23, 2008.).
Spector, A.A., et al., "Epoxyeicosatrienoic acids (EETs): metabolism and biochemical function." Progress in Lipid Research 43: 55-90 (2004).
Springer, T.A., "Traffic signals for lymphocyte recirculation and leukocyte emigration: The multistep paradigm." Cell, 76: 301-314 (1994).
Squires, RW, et al., "Low-dose, time release nicotinic acid: effects in selected patients with low concentrations of high density lipoprotein cholesterol", Mayo Clinic Proc., 67:855-860, (1992).
Srinivas, et al., "Controlled release of lysozyme from succinylated gelatin microspheres," J. Biomater. Sci., Polymer Ed., vol. 12(2):137-148 (2001).
Stalenhoef, A.F.H., et al., "The effect of concentrated n-3 fatty acids versus gemfibrozil on plasma lipoproteins, low density lipoprotein heterogeneity and oxidizability in patients with hypertriglyceridemia." Atherosclerosis 153: 129-138 (2000).
Stampfer MJ, Krauss RM, Ma J, et al. A prospective study of triglyceride level, lowdensity lipoprotein particle diameter, and risk of myocardial infarction. JAMA. 1996;276:882-888.
Stancu et al., "Statins: Mechanism of Action and Effects," *Journal of Cellular and Molecular Medicine* (2001), 5(4), 378-387.
Stark, K.D. & Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-773 (2004).
Stark, K.D., "The percentage of n-3 highly unsaturated fatty acids in total HUFA as a biomarker for omega-3 fatty acid status in tissues." Lipids 43:45-53 (2008).
Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).
Stein et al., "Effect of Statin Therapy on Remnant Lipoprotein Cholesterol Levels in Patients with Combined Hyperlipidemia," Arteriosclerosis, Thrombosis and Vascular Biology, vol. 21, pp. 2026-2031(Dec. 1, 2001).
Steinberg D, Witztum JL. Is the oxidative modification hypothesis relevant to human atherosclerosis? Do the antioxidant trials conducted to date refute the hypothesis? Circulation. 2002;105:2107-2111.
Steinberg D. Lewis A. Conner Memorial Lecture: Oxidative modification of LDL and atherogenesis. Circulation. 1997;95(4):1062-1071.
Stepp DW, Ou J, Ackerman AW, Welak S, Klick D, Pritchard KA, Jr. Native ldl and minimally oxidized ldl differentially regulate superoxide anion in vascular endothelium in situ. Am. J. Physiol. 2002;283:H750-H759.
Sternbach "The Glasgow Coma Scale." The Journal of Emergency Medicine, 19(1):67-71 (Feb. 8, 2000).
Stiles, FDA approves EPA-only omega-3 PUFA capsule for high TG, http://www.medscape.com/viewarticle/791268, accessed Dec. 17, 2014 (1 page).
Stojancevic et al., "The impact of farnesoid X receptor activation on intestinal permeability in inflammatory bowel disease," Can. J Gastroenterol. 26(9):631-637 (2012).
Stoll, Andrew L. et al., "Omega 3 Fatty Acids in Bipolar Disorder", Arch. Gen. Psychiatry, 56:407-412, (May 1999).
Su, Kuan-Pin, et al., "Omega-3 Fatty Acids in Major Depressive Disorder a Preliminary Double-Blind, Placebo-Controlled Trial", European Neuropsychopharmacology, 13:267-271, (2003).
Sugiyama et al., "A Comparison of the Hypotensive Effects of Eicosapentaenoic Acid Ethyl (EPA) on Three Diseases (Occluded Arteriosclerosis, Hyperlipidemia, and These Two Diseases Combined) P2-504 Abstract," Annual Meeting of the Japanese Society of Pharmaceutical Health Care and Sciences 20:473 (Nov. 2010) (with English translation)(3 pages).
Sugiyama, E., et al., "Eicosapentaenoic acid lowers plasma and liver cholesterol levels in the presence of peroxisome proliferators-activated receptor alpha." Life Sciences, 83:19-28 (2008).
Superko et al., "Lipid Management to Reduce Cardiovascular Risk: A New Strategy is Required," Circulation, 117:560-568 (2008).
Surette, M.E., et al., "Dependence on dietary cholesterol for n-3 polyunsaturated fatty acid induced changes in plasma cholesterol in the Syrian hamster." J Lipid Res., 33:263-271 (1992).
Surette, M.E., et al., "Evidence for mechanisms of the hypotriglyceridemic effect of n-3 polyunsaturated fatty, acids." Biochimica et Biophysic Acta, 1126: 199-205 (1992).
Takaki A, Umemoto S, Ono K, Seki K, Ryoke T, Fujii A, Itagaki T, Harada M, Tanaka M, Yonezawa T, Ogawa H, Matsuzaki M. Add-on therapy of epa reduces oxidative stress and inhibits the progression of aortic stiffness in patients with coronary artery disease and statin therapy: A randomized controlled study. J. Atheroscler. Thromb. 2011;18:857-866.
Takaku et al., Study on the Efficacy and Safety of Ethyl Icosapentate (MND-21) in Treatment of Hyperlipidemia Based on a Long-Term Administration Test, 7 J. Clin. Ther. Med. 191 (1991) (with English Translation)(27 pages).
Talayero BG, Sacks FM. The role of triglycerides in atherosclerosis. Curr. Cardiol. Rep. 2011;13:544-552.
Tamura, et al., "Study of the Clinical Usefulness of Ethyl Icosapentate (MND-21) in Long-Term Treatment of Hyperlipaemic Patients." J Clin Thera & Medicines, 7:1817-1834 (1991).
Tanaka et al., "Genome-Wide Association Study of Plasma Polyunsaturated Fatty Acids in the InCHIANTI Study." PLoS Genetics 5(1):1-8 (Jan. 2009).
Tanaka et al., "Suppression of prostaglandin synthesis by arachidonic acid or eicosapentaenoic acid in a macrophage-like cell line, RAW 264.7, treated with LPS," Biol. Pharm. Bull., 22(10):1057-7 (1999).
Tanaka et al., "Administration of high dose eicosapentaenoic acid enhances anti-inflammatory properties of high-density lipoprotein in Japanese patients with dyslipidemia," Atherosclerosis, 237(2):577-83 (Dec. 2014).
Tanaka et al., "Eicosapentaenoic Acid-Enriched High-Density Lipoproteins Exhibit Anti-Atherogenic Properties," Circ. J., doi: 10.1253/circj.CJ-17-0294. [Epub ahead of print] (Jun. 23, 2017)(6 pages).
Tanaka, K.T., et al., "Reduction in the recurrence of stroke by eicosapentaenoic acid for hypercholesterolemic patients—Subanalysis of the JELIS trial." Stroke, 39(7):2052-8 (2008).
Tatarczyk, et al., "Analysis of long-chain ω-3 fatty acid content in fish-oil supplements," Wien Klin Wochenschr, 119/13-14: 417-422 (2007).
Tatsuno et al., Efficacy and safety of TAK-085 compared with eicosapentaenoic acid in Japanese subjects with hypertriglyceridemia undergoing lifestyle modification: The omega-3 fatty acids randomized double-blind (ORL) study, J. Clin. Lipid; vol. 7(6), pp. 615-625 (Sep. 12, 2013).
Taylor et al., "Fish allergy: fish and products thereof," Journal Food Science (2004) 69.8 R175-R180.
Taylor, A.J., et al., "Arterial Biology for the Investigation of the Treatment Effects of Reducing Cholesterol (ARBITER) 2: a double-blind, placebo-controlled study of extended-release niacin on atherosclerosis progression in secondary prevention patients treated with statins", Circulation, 110:3512-3517, (2004).
Tedgui, A., et al., "Anti-inflammatory mechanisms in the vascular wall." Circ. Res. 88:877-887 (2001).
Teissier E, Nohara A, Chinetti G, Paumelle R, Cariou B, Fruchart JC, Brandes RP, Shah A, Steels B. Peroxisome proliferator-activated receptor alpha induces NADPH oxidase activity in macrophages, leading to the generation of LDL with PPAR-alpha activation properties. Circ. Res. 2004;95(12):1174-1182.
Terano, et al., "Effect of Oral Administration of Highly Purified Eicosapentaenoic Acid on Platelet Function, Blood Viscosity and Red Cell Deformability in Healthy Human Subjects," Atherosclerosis, 46, 321-331 (1983).

(56) References Cited

OTHER PUBLICATIONS

Theilla, M., et al., "A diet enriched in eicosapentaenoic acid, gamma-linolenic acid and antioxidants in the prevention of new pressure ulcer formation in critically ill patients with acute lung injury: A randomized, prospective, controlled study." Clinical Nutrition 26: 752-757 (2007).
Theobald et al., "LDL Cholesterol-Raising Effect of Low-Dose Docosahexaenoic Acid in Middle-Aged Men and Women," Am. J. Clin. Nutr. 79:558-63 (2004).
Thies, F., et al., "Association of n-3 polyunsaturated fatty acids with stability of atherosclerotic plaques: a randomised controlled trial." Lancet 361: 477-85 (2003).
Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).
Third Report of the NCEP Expert Panel on Detection, Evaluation, and Treatment of High Blood Cholesterol in Adults (Adult Treatment Panel III) Final Report, NIH Publication No. 02-5215 Sep. 2002 (220 pages in three parts).
Thorwest M, Balling E, Kristensen SD, et al. Dietary fish oil reduces microvascular thrombosis in a porcine experimental model. Thromb. Res. Jul. 2000 99 (2): 203-8.
Tilg H, Moschen AR. Inflammatory Mechanisms in the Regulation of Insulin Resistance. Mol. Med. 2008;14(3-4):222-231.
Tirosh et al., "Changes in Triglyceride Levels and Risk for Coronary Heart Disease in Young Men," American College of Physicians, pp. 377-385 (2007).
Torrejon, C. et al., "n-3 Fatty acids and cardiovascular disease: Actions and molecular mechanisms," Prostaglandins Leukotrienes & Essent. Fatty Acids, doi:10.1016/j.plefa.2007.10.014 (2007).
Transcript from Oct. 16, 2013 Meeting of the Endocrinologic and Metabolic Drugs Advisory Committee, 76 pages.
TREND-HD Investigators, Randomized controlled trial of ethyl-eicosapentaenoic acid in Huntington disease: the TREND-HD study, Arch Neurol., vol. 65(12): 1582-9 (2008).
Tribble DL, Holl LG, Wood PD, Krauss RM. Variations in oxidative susceptibility among six low density lipoprotein subfractions of differing density and particle size. Atherosclerosis. 1992;93(3):189-199.
Tribble DL, Rizzo M, Chait A, Lewis DM, Blanche PJ, Krauss RM. Enhanced oxidative susceptibility and reduced antioxidant content of metabolic precursors of small, dense low-density lipoproteins. Am. J. Med. 2001;110(2):103-110.
Trilipix Package Insert (Sep. 2010)(10 pages).
Tsimikas S, Witztum JL, Miller ER, Sasiela WJ, Szarek M, Olsson AG, Schwartz GG. High-dose atorvastatin reduces total plasma levels of oxidized phospholipids and immune complexes present on apolipoprotein B-1 00 in patients with acute coronary syndromes in the MIRACL trial. Circulation. 2004;110(11):1406-1412.
Tsuruta K., et al.,"Effects of purified eicosapentaenoate ethyl ester on fibriolytic capacity in patients with stable coronary artery disease and lower extremity ischaemia" Coron Artery Dis. 7(11):837-42 (Nov. 1996).
Tulenko TN, Chen M, Mason PE, Mason RP. Physical effects of cholesterol on arterial smooth muscle membranes: Evidence of immiscible cholesterol domains and alterations in bilayer width C during atherogenesis. J. Lipid Res. 1998;39:947-956.
Tungsiripat, et al., "Dyslipidemia in HIV patients," Cleveland Clinic Journal of Medicine, v. 72, No. 12 (2005).
Turini et al., "Short-term fish oil supplementation improved innate immunity, but increased ex vivo oxidation of LDL in man—a pilot study." Eur. J. Nutr. 40:56-65 (2001).
U.S. Appl. No. 14/245,499, filed Apr. 4, 2014 (now abandoned)(43 pages).
Ullian, M.E., "Fatty acid inhibition of angiotensin II-stimulated inositol phosphates in smooth muscle cells." Am J Physiol Heart Circ Physiol (1996).
Urakaze, Masaharu, et al., "Infusion of emulsified trieicosapentaenoylglycerol into rabbits. The effects on platelet aggregation, polymorphonuclear leukocyte adhesion, and fatty acid composition in plasma and platelet phospholipids", Thromb. Res., 44(5):673-682 (1986).
Urquhart et al., "Profile of eicosanoids produced by human saphenous vein endothelial cells and the effect of dietary fatty acids," Prostaglandins Leukot. Essent. Fatty Acid, 65(1):15-22 (2001).
US Food and Drug Administration and Dept of Health and Human Services. Substances affirmed as generally recognized as safe: Menhaden Oil. Fed Register, 62:30751-30757 (1997).
Vaagenes et al., "The Hypolipidaemic Effect of EPA is Potentiated by 2- and 3-Methylation." In P. Quant & S. Eaton (eds.) Current Views of Fatty Acid Oxidation and Ketogenesis from Organelles to Point Mutations; Advances in Experimental Medicine and Biology, vol. 466 , pp. 221-226 (1999).
Vaddadi, K.S., et al., "A Randomised, Placebo-Controlled, Double-Blind Study of Treatment of Huntington's Disease with Unsaturated Fatty Acids", Clinical Neuroscience and Neuropathology, 13(1):29-33, (Jan. 2002).
Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).
Van Do et al., "Allergy to fish parvalbumins: Studies on the cross-reactivity of allergens from 9 commonly consumed fish," Journ. Allergy & Clin. Immunol., 16(6):1314-1320 (Dec. 1, 2005).
Van Wijk et al. Rosiglitazone improves postprandial triglyceride and free fatty acid metabolism in type 2 diabetes. Diabetes Care, vol. 28, No. 4, (2005) pp. 844-849.
Varbo et al., Remnant Cholesterol as a Causal Risk Factor for Ischemic Heart Disease, J. Am. Coll. Cardiol., vol. 61(4), pp. 427-436 (2013).
Varbo et al., Remnant cholesterol as a cause of ischemic heart disease: Evidence, definition, measurement, atherogenicity, high risk patients, and present and future treatment, Pharmacol. Ther., vol. 141(3), pp. 358-367 (2014).
Vascepa [package insert], Bedminster, NJ: Amarin Pharma Inc.; Jul. 2012. (12 pages).
Vascepa [package insert]. Bedminster, NJ: Amarin Pharma Inc.; Nov. 2013. (11 pages).
Vasudevan et al., "Effective Use of Combination of Lipid Therapy", Curr. Atheroscl. Rep., vol. 8, pp. 76-84 (2006).
Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).
Velliquette et al., "Regulation of human stearoyl-CoA desaturase by omega-3 and omega-6 fatty acids: Implications for the dietary management of elevated serum triglycerides," Journal of Clinical Lipidology. (2009) 3:281-288.
Vergnani L, Hatrik S, Ricci F, Passaro A, Manzoli N, Zuliani G, Brovkovych V, Fellin R, Malinski T. Effect of native and oxidized low-density lipoprotein on endothelial nitric oxide and superoxide production : Key role of 1-arginine availability. Circulation. 2000;101:1261-1266.
Vidal F, Colome C, Martinez-Gonzalez J, Badimon L. Atherogenic concentrations of native low density lipoproteins down-regulate nitric-oxide-synthase mma and protein levels in endothelial cells. Eur. J. Biochem. 1998;252:378-384.
Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).
Virani et al., "The Role of Lipoprotein-associated Phospholipase A2 as a marker for atherosclerosis" Curr. Atheroscler. Rep. 9[2]: 97-103 (2007).
Volcik, K.A., et al., "Peroxisome proliferator-activated receptor agenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).

(56) References Cited

OTHER PUBLICATIONS

Von Schacky C, Baumann K, Angerer P. The effect of n-3 fatty acids on coronary atherosclerosis: results from SCIMO, an angiographic study, background and implications. Lipids 2001 36 Suppl: S99-102.
Von Schacky, C., "A review of omega-3 ethyl esters for cardiovascular prevention and treatment of increased blood triglyceride levels." Vascular Health and Risk Management 2(3): 251-262 (2006).
Von Schacky, C., et al., "The Effect of Dietary ω-3 Fatty Acids on Cornoray Atherosclerosis: A Randomized, Double-Blind, Placebo-Controlled Trial", American College of Physicians-American Society of Internal Medicine, 130(7):554-562, (1999).
Wada, M., et al., "Enzymes and receptors of prostaglandin pathways with arachidonic acid-derived versus eicosapentaenoic acid-derived substrates and products." J. Biol. Chem. 282(31): 22254-22266 (2007).
Wagner AH, Kohler T, Ruckschloss U, Just I, Hecker M. Improvement of nitric oxide-dependent vasodilation by hmg-coa reductase inhibitors through attenuation of endothelial superoxide anion formation. Arterioscler. Thromb. Vasc. Biol. 2000;20:61-69.
Walker G, Mandagere A, Dufton C, et al. The pharmacokinetics and pharmacodynamics of warfarin in combination with ambrisentan in healthy volunteers. Br. J. Clin. Pharmacol. May 2009 67 (5): 527-34.
Walldius, G., et al., "Editorial: Rationale for using apolipoprotein B and apolipoprotein A-I as indicators of cardiac risk and as targets for lipid-lowering therapy." European Heart Journal 26, 210-212 (2005).
Walter MF, Jacob RF, Bjork RE, Jeffers B, Buch J, Mizuno Y, Mason RP. Circulating lipid hydroperoxides predict cardiovascular events in patients with stable coronary artery disease: the PREVENT study. J. Am. Coll. Cardiol. 2008;51(12):1196-1202.
Walter MF, Jacob RF, Jeffers B, Ghadanfar MM, Preston GM, Buch J, Mason RP. Serum levels of TBARS predict cardiovascular events in patients with stable coronary artery disease: A longitudinal analysis of the PREVENT study. J. Am. Coll. Cardiol. 2004;44(10):1996-2002.
Wander, R.C., et al., "Influence of long.chain polyunsaturated fatty acids on oxidation of low density lipoprotein." Prostaglandins, Leukotrienes and Essential Fatty Acids 59(2):143-151 (1998).
Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).
Wang, L., et al., "Triglyceride-rich lipoprotein lipolysis releases neutral and oxidized FFAs that induce endothelial cell inflammation." J. Lipid Res. 50:204-213 (2009).
Warren, Stephen T., "The Expanding World of Trinucleotide Repeats", Science, 271:1374-1375, (1996).
Wassmann S, Laufs U, Muller K, Konkol C, Ahlbory K, Baumer AT, Linz W, Bohm M, Nickenig G. Cellular antioxidant effects of atorvastatin in vitro and in vivo. Arterioscler. Thromb. Vasc. Biol. 2002;22:300-305.
Watanabe et al., "Bile acids lower triglyceride levels via a pathway involving FXR, SHP, and SREBP-1c," J Clin Invest. 113(10): 1408-1418 (May 2004).
Watanabe, Ikuyoshi, et al., "Usefulness of EPA-E (eicosapentaenoic acid ethyl ester) in preventing neointimal formation after vascular injury", Kokyu to Junkan, 42(7):673-677 (1994) (with English summary).
Weaver, K.L., et al., "Effect of Dietary Fatty Acids on Inflammatory Gene Expression in Healthy Humans." J. Biol. Chem., 284(23): 15400-15407 (2009) (published online Apr. 9, 2009).
Webcast Information for the Oct. 16, 2013 Meeting of the Endocrinologic and Metabolic Drugs Advisory Committee, (1 page).
Weber, P., "Triglyceride-lowering effect of n-3 long chain polyunsaturated fatty acid: eicosapentaenoic acid vs. docosahexaenoic acid." Lipids 34: S269 (1999).

Wei et al., Effects of [EPA] Versus [DHA] on Serum Lipids: A Systematic Review and Meta-Analysis, 13 Current Atherosclerosis Rep. 13(6):474-483 (2011).
Westerveld H.T. et al., "Effects of low-dose EPA-Eon glycemic control, lipid profile, lipoprotein(a), platelet aggretation, viscosity, and platelet and vessel wall interaction in NIDDM" Diabetes Care 16(5):683-8 (May 1993).
Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-20 (2000).
Whelan, J., et al., "Evidence that dietary arachidonic acid increases circulating triglycerides." Lipids 30, 425-429 (1995).
Wierzbicki, A.S., "Editorial: Newer, lower, better? Lipid drugs and cardiovascular disease—the continuing story." Int J Clin Pract, 61(7):1064-1067 (2007).
Wierzbicki, A.S., "Editorial: Raising HDL-C: back to the future?" Int J Clin Pract, 61(7): 1069-1071 (2007).
Williams et al., "NADPH Oxidase Inhibitors New Antihypertensive Agents?" J. Cardiovasc Pharmacol 50(1):9-16 (Jul. 1, 2007).
Willumsen, N. et al., Biochimica et Biophysica Acta. vol. 1369, "On the effect of 2-deuterium- and 2-methyl-eicosapentaenoic acid derivatives on triglycerides, peroxisomal beta-oxidation and platelet aggregation in rats," pp. 193-203, (1998).
Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).
Wilson Omega 3 fish oil: EPA versus DHA (Dietivity.com, 1-16) (2006).
Wilt, VM & Gumm, JG, "Isolated low high-density lipoprotein cholesterol", Ann. Pharmacol., 31:89-97, (1997).
Wink, J., et al., "Effect of very-low-dose niacin on high-density lipoprotein in patients undergoing long-term statin therapy", Am. Heart J., 143:514-518, (2002).
Witztum JL. The oxidation hypothesis of atherosclerosis. Lancet. 1994;344(8925):793-795.
Wojenski, C.M., et al., "Eicosapentaenoic acid ethyl ester as an antithrombotic agent: comparison to an extract of fish oil." Biochimica et Biophysica Acta. 1081:33-38 (1991).
Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).
Wood et al., "Carbohydrate Restriction Alters Lipoprotein Metabolism by Modifying VLDL, LDL and HDL Subraction Distribution and Size in Overweight Men," Journ. of Nutrition, 136(2):384-9 (2006).
Woodman et al., "Effects of Purified Eicosapentaenoic and Docosahexaenoic Acids on Glycemic Control, Blood Pressure, and Serum Lipids in Type 2 Diabetic Patients with Treated Hypertension", The American Journal of Clinical Nutrition: Official Journal of the American Society for Clinical Nutrition, Inc., 76(5):1007-1015 (2002).
Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).
Wu et al., "Diabetic dyslipidemia," Metabolism Clinical and Experimental, 63:1469-1479 (Dec. 2014)(available online Aug. 29, 2014).
Wu, W.H., et al., "Effects of docosahexaenoic acid supplementation on blood lipids, estrogen metabolism, and in vivo oxidative stress in postmenopausal vegetarian women." Eur J Clin Nutr., 60:386-392 (2006).
Xiao, Y.F., et al., "Inhibitory effect of n-3 fish oil fatty acids on cardiac Na+/Ca2+ exchange currents in HEK293t cells." Biochemical and Biophysical Research Communications 321: 116-123 (2004).
Xiao, Y-F., et al., "Blocking effects of polyunsaturated fatty acids on Na+ channels of neonatal rat ventricular myocytes." Proc. Natl. Acad. Sci. 92: 11000-11004 (1995).
Xiao, Y-F., et al., "Fatty acids suppress voltage-gated Na+ currents in HEK293t cells transfected with the a-subunit of the human cardiac Na+ channel." Proc. Natl. Acad. Sci. 95: 2680-2685 (1998).

(56) References Cited

OTHER PUBLICATIONS

Xydakis, A M et al., "Combination therapy for combined dyslipidemia," American Journal of Cardiology, Nov. 20, 2002 US, vol. 90, No. 10 Suppl. 2, p. 21 K-29K (2002).
Yacyshyn BR, Thomson AB. The clinical importance of proton pump inhibitor pharmacokinetics. Digestion 2002 66 (2): 67-78.
Yagi K. Assay for blood plasma or serum. Methods Enzymol. 1984;105:328-331.
Yamamoto, H. et al., Improvement of coronary vasomotion with Eicosapentaenoic acid does not inhibit acetylcholine-induced coronary vasospasm in patients with variant angina: Jpn Cir J. 59(9):608-16 (1995).
Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).
Yamashita et al., J. Biochem., vol. 122, No. 1, "Acyl-transferases and Transaclyases Involved in Fatty Acid Remoding of Phospholipids and Metabolism of Bioactive Lipids in Mammalian Cells", pp. 1-16 (1997).
Yamashita, N., et al., "Inhibition of natural killer cell activity of human lymphocytes by eicosapentaenoic acid." Biochem. Biophys. Res. Comm. 138(3): 1058-1067 (1986).
Yamazaki et al., "Changes in fatty acid composition in rat blood and organs after infusion of eicosapentaenoic acid ethyl ester", Biochim. Biophys. ACTA, 1128(1):3543, (1992).
Yamazaki, et. al., "Dissolution tests by RDC method for soft gelatin capsules containing ethyl icosapentate,", Pharm. Tech. Japan, vol. 15, No. 4, pp. 595-603 Abstract (1999) (with English abstract).
Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).
Yano T, Mizuguchi K, Takasugi K, Tanaka Y, Sato M. "Effects of ethyl all-cis-5,8,11,14,17-icosapentaenoate on low density lipoprotein in rabbits," Yakugaku Zasshi, 115:843-51 (1995).
Yano, T., et al., "Effects of ethyl-all-cis-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).
Yates RA, Wong J, Seiberling M, et al. The effect of anastrozole on the single-dose pharmacokinetics and anticoagulant activity of warfarin in healthy volunteers. Br. J. Clin. Pharmacol. May 2001 51 (5): 429-35.
Yerram, N.R., et al., "Eicosapentaenoic acid metabolism in brain microvessel endothelium: effect on prostaglandin formation." J. Lipid Res.30:1747-1757 (1989).
Yokoyama et al., "Effects of eicosapentaenoic acid on cardiovascular events in Japanese patients with hypercholeterolemia: Rationale, design, and baseline characteristics of the Japan EPA Lipid Intervention Study (JELIS)," Amer. Heart Journal 146(4):613-620 (2003).
Yokoyama et al., "Effects of eicosapentaenoic acid on major coronary events in hypercholesterolaemic patients (JELIS): a randomized open-label, blinded endpoint analysis", Lancet, vol. 369, pp. 1090-1098 (2007).
Yorioka, N, "Lipid-lowering therapy and coagulation/fibrinolysis parameters in patients on peritoneal dialysis," The International Journal of Artificial Organs, vol. 23(1):27-32 2000.
Yoshimura et al., "Effects of highly purified eicosapentaenoic acid on plasma beta thromboglobulin level and vascular reactivity to angiotensin II", Artery, 14(5):295-303 (1987).
Zaima, N., et al., "Trans geometric isomers of EPA decrease LXRa-induced cellular triacylglycerol via suppression of SREBP-1c and PGC-1β," J. Lipid Res. 47: 2712-2717 (2006).
Zalewski et al., Role of Lipoprotein-Associated Phospholipase A2 in Atherosclerosis: Biology, Epidemiology, and Possible Therapeutic Target, Arteriosclerosis, Thrombosis, & Vascular Biology 25(5):923-931 (2005).
Zanarini, et al., "Omega-3 Fatty Acid Treatment of Women with Borderline Personality Disorder: A Double-Blind, Placebo-Controlled Pilot Study," Am J Psychiatry, 160:167-169 (2003).
Zhan, S. et. al. "Meta-analysis of the effects of soy protein containing isoflavones on the lipid profile," Am. J. Clin. Nutr. (Feb. 2005), 81, p. 397-408.
Zhang, M., et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (2006).
Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).
Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).
Zhao et al., "Polyunsaturated Fatty Acids are FXR Ligands and Differentially Regulate Expression of FXR Targets," DNA and Cell Biology, 23(8):519-526 (Aug. 25, 2004).
Zhao, G. et al., "Dietary α-linolenic acid inhibits proinflammatory cytokine production by peripheral blood mononuclear cells in hypercholesterolemic subjects." Am J Clin Nutr 85:385-91 (2007).
Zhao, G., et al., "Dietary α-linolenic acid reduces inflammatory and lipid cardiovascular risk factors in hypercholesterolemic men and women." J. Nutr. 134: 2991-2997 (2004).
Ziegler, D., et al., "Treatment of symptomatic diabetic polyneuropathy with the antioxidant α-lipoic acid: A 7-month multicenter randomized controlled trial (ALADIN III Study)." Diabetes Care 22:1296-1301 (1999).
Zimmerman JJ, Raible DG, Harper DM, et al. Evaluation of a potential tigecycline-warfarin drug interaction. Pharmacotherapy Jul. 2008 28 (7): 895-905.
Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, pp. 89-100 (2000).
Zuijdgeest-van Leeuwen, S.D., et al., "Incorporation and washout of orally administered n-3 fatty acid ethyl esters in different plasma lipid fractions." British Journal of Nutrition 82:481-488 (1999).
Zuijdgeest-van Leeuwen, SD, et al., "Eicosapentaenoic acid inhibits lipolysis in weight-losing cancer patients as well as in healthy volunteers," Eur J Gastroenterol & Hepatol., 10(12):A67 (1998).
Zvyaga T, Chang SY, Chen C, et al. Evaluation of six proton pump inhibitors as inhibitors of various human cytochromes P450: focus on cytochrome P450 2C19. Drug Metab. Dispos. Sep. 2012 40 (9): 1698-711.
Aarsetoey H, Gurndt H, Nygaard O. The Role of Long-Chained Marine N-3 Polyunsaturated Fatty Acids in Cardiovascular Disease. Cardiol Res Pract. 2012. Epub Dec. 13, 2012.
Albert CM, Campos H, Stampfer MJ, et al. Blood Levels of Long-Chain n-3 Fatty Acids and the Risk of Sudden Death. N Engl J Med 346(15):1113-1138, 2002.
Alberti K, et. al. Harmonizing the Metabolic Syndrome: A Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity. Circulation. 120:1640-1645; 2009.
Amarin Corporation, Globe Newsire press release, "Reduce-It™ Cardiovascular Outcomes Study of Vascepa® (icosapent ethyl) Capsules Met Primary Endpoint," Sep. 24, 2018 (4 pages).
Amarin, Next Generation Lipid Modification in Cardiovascular Disease, Investor Meetings, Nov. 2010, (http://files.shareholder.com/downloads/AMRN/0x0x417754/AA72705F-1D67-4E1D-A989-5805E5CF0244/Investor_Presentation_2010_Nov_10.pdf, accessed Jan. 6, 2015.
American Heart Association. Heart Disease and Stroke Statistics—2010 Update. Dallas, Texas: American Heart Association; 2010.

(56) References Cited

OTHER PUBLICATIONS

Anand RG, Alkadri M, Lavie CJ, Milani RV. The Role of Fish Oil in Arrhythmia Prevention. J Cardioplin Rehabil Preven. 2008;28:92-98.
Anderson JL, Adams CD, Antman EM, et al. ACC/AHA 2007 guidelines for the management of patients with unstable angina/non-ST-elevation myocardial infarction—executive summary. A report of the American College of Cardiology/American Heart Association Task Force on Practice Guidelines (Writing Committee to Revise the 2002 Guidelines for the Management of Patients With Unstable Angina/Non-ST-Elevation Myocardial Infarction) developed in Collaboration with the American College of Emergency Physicians, the Society for Cardiovascular Angiography and Interventions, and the Society of Thoracic Surgeons Endorsed by the American Association of Cardiovascular and Pulmonary Rehabilitation and the Society for Academic Emergency Medicine. J Am Coll Cardiol 50:652-726, 2007.
Antman E, Anbe D, Armstrong P, et al. ACC/AHA guidelines for the management of patients with ST-elevation myocardial infarction—executive summary. A report of the American College of Cardiology/American Heart Association Task Force on Practice Guidelines (Writing Committee to revise the 1999 guidelines for the management of patients with acute myocardial infarction). J Am Coll Cardiol 44:671-719, 2004.
Armaganijan L, Lopes RD, Healey JS, Piccini JP, Nair GN, Morillo CA. Do Omega-3 fatty acids prevent atrial fibrillation after open heart surgery? A meta-analysis of randomized controlled trials. Clinics. 2011;66(11):1923-1928.
Ascend Study Collaborative Group. Effects of n-3 fatty acid supplements in diabetes mellitus. N Engl J Med, 379(16):1540-1550 (publication date Oct. 18, 2018; epublication date Aug. 26, 2018).
Astarita et al., "Targeted lipidomics strategies for oxygenated metabolites of polyunsaturated fatty acids," Biochim Biophys Acta, 1851(4):456-168 (Apr. 2015).
Aung T, Halsey J, Kromhout D, et al. Associations of omega-3 fatty acid supplement use with cardiovascular disease risks: Meta-analysis of 10 trials involving 77917 individuals. JAMA Cardiol 3:225-34 (publication date Mar. 1, 2018; epublication date Jan. 31, 2018).
Becker LB, Aufderheide TP, Geocadin RG, Callaway CW, Lazar RM, Donnino MW, Nadkarni VM, Abella BS, Adrie C, Berg RA, Merchant RM, O'Connor RE, Meltzer DO, Holm MB, Longstreth WT, Halperin HR. AHA Consensus Statement: Primary Outcomes for Resuscitation Science Studies: A Consensus Statement From the American Heart Association. *Circulation* 2011; CIR. 0b013e3182340239 published online before print Oct. 3, 2011, doi:10.1161/CIR.0b013e3182340239.
Bhatt DL, Eagle KA, Ohman EM, et al. Comparative determinants of 4-year cardiovascular event rates in stable outpatients at risk of or with atherothrombosis. JAMA 304(12):1350-7 (publication date Sep. 22, 2010; epublication date Aug. 30, 2010).
Bhatt DL, Fox KAA, Hacke W, et al; CHARISMA Investigators. Clopidogrel and aspirin versus aspirin alone for the prevention of atherothrombotic events. N Engl J Med. 354(16):1706-1717 (publication date Apr. 20, 2006; epublication date Mar. 12, 2006).
Bhatt DL, Hulot JS, Moliterno DJ, Harrington RA. Antiplatelet and anticoagulation therapy for acute coronary syndromes. Circ Res 114(12):1929-43 (publication date Jun. 6, 2014).
Bhatt DL, Steg PG, Brinton EA, et al. Rationale and design of REDUCE-IT: Reduction of Cardiovascular Events with Icosapent Ethyl-Intervention Trial. Clin Cardiol 40:138-48 (publication date Mar. 2017; epublication date Mar. 15, 2017).
Bhatt DL, Steg PG, Ohman EM, et al; Reach Registry Investigators. International prevalence, recognition and treatment of cardiovascular risk factors in outpatients with atherothrombosis. *JAMA*. 295(2)1 80-189 (publication date Jan. 11, 2006).
Bhatt et al., "Cardiovascular Risk Reduction with Icosapent Ethyl for Hypertiglyceridemia," N. Eng. J. Med., Nov. 10, 2018 (epub ahead of print)(12 pages)(downloaded from nejm.org on Nov. 13, 2018 at https://www.nejm.org/doi/full/10.1056/NEJMoa1812792).

Burr ML, Sweetham PM, Fehily AM. Diet and reinfarction. Eur Heart J 15:1152-1153, 1994.
Calder PC. Omega-3 Fatty Acids and Inflammatory Processes. Nutrients 2(3):355-374, 2010.
Cannon CP, Blazing MA, Giugliano RP, et al; IMPROVE-IT Investigators. Ezetimibe added to statin therapy after acute coronary syndromes. *N Engl J Med.* 372:2387-2397.
Cannon CP, Braunwald E, McCabe CH, et al. Intensive versus moderate lipid lowering with statins after acute coronary syndromes. N Engl J Med 350(15):1495-1504 (publication date Apr. 8, 2004; epublication date Mar. 8, 2004).
Cao H, Wang X, Huang H, Ying SZ, Guy W, Wang T, Huang CX. Omega-3 Fatty Acids in the Prevention of Atrial Fibrillation Recurrences after Cardioversion: A Meta-analysis of Randomized Controlled Trials. Int Med. 2012;51:2503-2508.
Caughey GE, Mantzioris E, Gibson RA, Cleland LG, James MJ. The effect on human tumor necrosis factor $\alpha$ and interleukin 1$\beta$ production of diets enriched in n-3 fatty acids from vegetable oil or fish oil. Am J Clin Nutr. 1996;63:116-122.
Cavender MA, Steg PG, Smith SC, et al; REACH Registry Investigators. Impact of diabetes mellitus on hospitalization for heart failure, cardiovascular events, and death: outcomes at 4 years from the reduction of atherothrombosis for continued health (REACH) registry. *Circulation.* 132(10):923-931 (publication date Sep. 8, 2015; epublication date Jul. 7, 2015).
Cawood AL, Ding R, Napper FL, et al. Eicosapentaenoic acid (EPA) from highly concentrated n-3 fatty acid ethyl esters is incorporated into advanced atherosclerotic plaques and higher plaque EPA is associated with decreased plaque inflammation and increased stability. Atherosclerosis. 2010;212:252-259.
Chang CL, Seo T, Du CB, Accili D, Deckelbaum RJ. n-3 Fatty Acids Decrease Arterial Low-Density Lipoprotein Cholesterol Delivery and Lipoprotein Lipase Levels in Insulin-Resistant Mice. Arterioscler Thromb Vasc Biol. 2010;30(12):2510-2517.
Citizen Petition, Pronova BioPharma Norge AS, Docket No. FDA-2009-P-0398-0001 (Aug. 4, 2009), at ii (Appendix), available at www.regulations.gov.
Costanzo S, di Niro V, Castelnuovo AD, et al. Prevention of postoperative atrial fibrillation in open heart surgery patients by preoperative supplementation of n-3 polyunsaturated fatty acids: an updated meta-analysis. Periop Manga. 2013; Apr. 12 epub.
DeMets DL, Lan KK. Interim Analysis: the Alpha Spending Function Approach. Stat Med 1994;13(13-14):1341-52.
Dewey FE, Gusarova V, O'Dushlaine C, et al. Supplement to: Inactivating variants in ANGPTL4 and risk of coronary artery disease. N Engl J Med. DOI: 10.1056/NEJMoa1510926; 2016.
Djousse L, Akinkuolie AO, Wu JHY, Ding EL, Gaziano JM. Fish consumption, omega-3 fatty acids and risk of heart failure: A meta-analysis. Clin Nutr. 2012;31:846-853.
Do R, Stitziel NO, Won HH, et. al. Exome sequencing identifies rare LDLR and APOA5 alleles conferring risk for myocardial infarction. Nature. 2015;518(7537):102-106.
Do R, Willer CJ, Schmidt EM, et al. Common variants associated with plasma triglycerides and risk for coronary artery disease. Nat Genet 2013;45(11):1345-52.
Doi M, Nosaka K, Miyoshi T, et al. Early eicosapentaenoic acid treatment after percutaneous coronary intervention reduced acute inflammatory responses and ventricular arrhythmias in patients with acute myocardial infarction: A randomized controlled study. Int J Cardiol., 176(3):577-82 (publication date Oct. 20, 2014; epublication date Aug. 19, 2014).
Epadel Summary of Product Characteristics (SPC), Mochida Pharmaceutical Co., Ltd. Tokyo, Japan, Oct. 2013.
Fraker TD, Fihn SD. Writing on behalf of the 2002 Chronic Stable Angina Writing Committee. 2007 chronic angina focused update of the ACC/AHA guidelines for the management of patients with chronic stable angina. A Report of the ACC/AHA Task Force on Practice Guidelines. Circulation 50:2264-2274, 2007.
Galan P, Kesse-Guyot E, Czernichow S, et al. Effects of B vitamins and omega 3 fatty acids on cardiovascular diseases: a randomised placebo controlled trial. Br Med J. 2010;341:c6273.

(56) References Cited

OTHER PUBLICATIONS

Ganda OP, Bhatt DL, Mason RP, Miller M, Boden WE. Unmet need for adjunctive dyslipidemia therapy in hypertriglyceridemia management. J Am Coll Cardiol 72(3):330-43 (publication date Jul. 17, 2018).

Geleijnse JM, Giltay EJ, Grobbee DE, Donders ART, Kok FJ. Blood pressure response to fish oil supplementation: metaregression analysis of randomized trials. J Hypertens. 2002;20(8):1493-1499.

Gillet L, Roger S, Bougnoux P, Le Guennec JY, Besson P. Beneficial effects of omega-3 long-chain fatty acids in breast cancer and cardiovascular diseases: voltage-gated sodium channels as a common feature? Biochimi. 2011;93:4-6.

Ginsberg HN, Elam MB, Lovato LC, et al, for the ACCORD Study Group. Effects of combination lipid therapy in Type 2 diabetes mellitus. N Engl J Med 362:1563-1574, 2010.

GISSI-HF Investigators. Effect of n-3 polyunsaturated fatty acids in patients with chronic heart failure (the GISSI-HF trial): a randomised, double-blind, placebo-controlled trial. Lancet. 2008;372(9645):1223-1230.

Goff DC, Lloyd-Jones DM, Bennett G, et al. ACC/AHA Prevention Guideline: 2013 ACC/AHA Guideline on the Assessment of Cardiovascular Risk: A Report of the American College of Cardiology/American Heart Association Task Force on Practice Guidelines. Circulation. 2014;129:S74-S75.

Harada-Shiba et al., Journal of Clinical and Experimental Medicine, Jun. 30, 2007, vol. 221, No. 13, pp. 1068-1073 (with English translation).

Harris WS. International recommendations for consumption of long-chain omega-3 fatty acids. J Cardiovasc Med (Hagerstown) 8(suppl 1):S50-S52, 2007.

Hong KN, Fuster V, Rosenson RS, Rosendorff C, Bhatt DL. How low to go with glucose, cholesterol, and blood pressure in primary prevention of CVD. J Am Coll Cardiol 70(17):2171-85 (publication date Oct. 24, 2017; epublication date Oct. 16, 2017).

Hoogeveen EK, Geleijnse JM, Kromhout D, et al. No effect of n-3 fatty acids supplementation on NT-proBNP after myocardial infarction: the Alpha Omega Trial. Eur J Prev Cardiol. May 2015;22:648-55.

HPS2-Thrive Collaborative Group, Landray MJ, Haynes R, et al. Effects of extended-release niacin with laropiprant in high-risk patients. N Engl J Med. 2014;371(3):203-12.

Inzucchi et al., "Diagnosis of Diabetes," New Engl. Journ of Med., 367(6):541-550 (2012).

Jinno Y, Nakakuki M, Kawano H, Notsu T, Mizuguchi K, Imada K. Eicosapentaenoic acid administration attenuates the pro-inflammatory properties of VLDL by decreasing its susceptibility to lipoprotein lipase in macrophages. Atheroscler. 2011;219:566-572.

Jørgensen AB, Frikke-Schmidt R, Nordestgaard BG, Tybjwrg-Hansen A. Loss-of-function mutations in APOC3 and risk of ischemic vascular disease. N Engl J Med. 2014; 371(1):32-41.

Jun M, Foote C, Lv J, et al. Effects of fibrates on cardiovascular outcomes: a systematic review and meta-analysis. Lancet 375 (9729):1875-1884, 2010.

Katayama et al., Effect of long-term administration of ethyl eicosapentate (EPA-E) on local cerebral blood flow and glucose utilization in stroke-prone spontaneously hypertensive rats (SHRSP), Brain Research, vol. 761, pp. 300-305 (Dec. 31, 1997).

Khoueiry G, Rafeh NA, Sullivan E, et al. Do omega-3 polyunsaturated fatty acids reduce risk of sudden cardiac death and ventricular arrhythmias? A meta-analysis of randomized trials. Heart and Lung. 2013;42:251-256.

Klempfner R, Erez A, Sagit BZ, et al. Elevated triglyceride level is independently associated with increased all-cause mortality in patients with established coronary heart disease: Twenty-two-year follow-up of the Bezafibrate Infarction Prevention Study and Registry. Circ Cardiovasc Qual Outcomes 9(2):100-8 (publication date Mar. 8, 2016).

LaRosa JC. Understanding risk in hypercholesterolemia. Clin Cardiol 26(Suppl 1):3-6, 2003.

Law TK, Yan AT, Gupta A, et al. Primary prevention of cardiovascular disease: global cardiovascular risk assessment and management in clinical practice. Eur Heart J Qual Care Clin Outcomes. 1(1):31-36 (publication date Jul. 2, 2015; epublication date Jul. 1, 2015).

Leaf A, Albert CM, Josephson M, et al. for the Fatty Acid Antiarrhythmia Trial Investigators. Prevention of Fatal Arrhythmias in High-Risk Subjects by Fish Oil n-3 Fatty Acid Intake. Circ. 2005;112:2762-2768.

Leaf A, Kang JX. Prevention of cardiac sudden death by N-3 fatty acids: a review of the evidence. J Intern Med 240:5-12, 1996.

Levey A, at. al. A New Equation to Estimate Glomerular Filtration Rate. Ann Intern Med. 150:604-612; 2009.

Libby P. Triglycerides on the rise: should we swap seats on the seesaw? Eur Heart J. 36(13):774-776 (publication date Apr. 1, 2015; epublication date Dec. 29, 2014).

Lovaza United States Prescribing Information, GlaxoSmithKline. Research Triangle Park, USA, May 2014.

Maki et al., "Effects of Adding Prescription Omega-3 Acid Ethyl Esters to Simvastatin (20 mg/day) on Lipids and Lipoprotein Particles in Men and Women with Mixed Dyslipidemia," Am. J. Cardiol., 102:429-433 (Aug. 15, 2008)(Epub May 22, 2008).

Manninen V, Tenkanen L, Koskinen P, et al. Joint effects of serum triglyceride and LDL cholesterol and HDL cholesterol concentrations on coronary heart disease risk in the Helsinki Heart Study. Implications for treatment. Circulation 85:37-45, 1992.

Marchioli R, Barzi F, Bomba E, et al, GISSI-Prevenzione Investigators. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. Circulation. 105(16)1897-1903, 2002.

Marcoux et al., "Plasma remnant-like particle lipid and apolipoprotein levels in normolipidemic and hyperlipidemic subjects," Atherosclerosis, vol. 139, pp. 161-171 (Jul. 1998).

Martin SS, Blaha MJ, Elshazly MB, et al. Comparison of a novel method vs the Friedewald equation for estimating low-density lipoprotein cholesterol levels from the standard lipid profile. JAMA. 2013;310:2061-8.

Miller M, Cannon CP, Murphy SA, et al. Impact of triglyceride levels beyond low-density lipoprotein cholesterol after acute coronary syndrome in the PROVE IT-TIMI 22 trial. J Am Coll Cardiol 51:724-730, 2008.

Miller M. Current perspectives on the management of hypertriglyceridemia. Am Heart J 140:232-40, 2000.

Mori TA. Omega-3 fatty acids and blood pressure. Cell Mol Biol. 2010; Feb. 25;56(1):83-92.

Morris M, Sacks F, Rosner B. Does fish oil lower blood pressure? A meta-analysis of controlled trials. Circ. 1993;88:523-533.

Mozaffarian D, Benjamin EJ, Go AS, Arnett DK, Blaha MJ, et al.; on behalf of the American Heart Association Statistics Committee and Stroke Statistics Subcommittee. Heart disease and stroke statistics—2016 update: a report from the American Heart Association [published online ahead of print Dec. 16, 2015]. Circulation. doi: 10.1161/CIR.0000000000000350.

Mozaffarian D, Geelen A, Brouwer I, Geleijnse J, Zock P, Katan M. Effect of Fish Oil on Heart Rate in Humans A Meta-Analysis of Randomized Controlled Trials. Circ.2005; 112:1945-1952.

Mozaffarian D, Marchioli R, Macchia A, et al. Fish Oil and Postoperative Atrial Fibrillation The Omega-3 Fatty Acids for Prevention of Post-operative Atrial Fibrillation (OPERA) Randomized Trial. JAMA. Nov. 21, 2012;308(19):2001-11.

Mozaffarian D, Psaty B, Rimm E, Lemaitre R, Burke G, Lyles M, Lefkowitz D, Siscovick D. Fish Intake and Risk of Incident Atrial Fibrillation. Circ.2004; 110:368-373.

Murphy SA, Cannon CP, Blazing MA, et al. Reduction in total cardiovascular events with ezetimibe/simvastatin post-acute coronary syndrome. J Am Coll Cardiol. 67(4):353-361 (publication date Feb. 2, 2016; epublication date Jan. 25, 2016).

Nambi V, Bhatt DL. Primary prevention of atherosclerosis: Time to take a selfie? J Am Coll Cardiol 2017;70(24):2992-4 (publication date Dec. 19, 2017; epublication date Dec. 11, 2017).

(56) References Cited

OTHER PUBLICATIONS

National Kidney Foundation, "Glomerular Filtration Rate (GFR)," Jan. 30, 2017 (Jan. 30, 2017), retrieved on Jul. 30, 2018 from https://web/archive.org/web/20170130183218/https://www.kidney.org/atoz/content/gfr; entire document, especially p. 1 paragraph 1 and p. 3, paragraph 2.

National Kidney Foundation, "The Heart and Kidney Connection," Apr. 17, 2017 (Apr. 17, 2017), retrieved on Jul. 30, 2018 from https://web.archive.org/web/20170417004l6/https://www.kidney.org/atoz/content/heart-and-kidney-connection; entire document, especially p. 2, paragraph 1.

Needleman P, Raz A, Minkes MS, Ferrendelli JA, Sprecher H. Triene prostaglandins: prostacyclin and thromboxane biosynthesis and unique biological properties. Proc Natl Acad Sci USA. 1979;76:944-948.

Nelson JR, Wani O, May HT, Budoff M. Potential benefits of eicosapentaenoic acid on atherosclerotic plaques. Vascul Pharmacol. 91:1-9 (publication date Apr. 2017; epublication date Mar. 2, 2017).

Nichols GA, Philip S, Reynolds K, Granowitz CB, Fazio S. Increased cardiovascular risk in hypertriglyceridemic patients with statin-controlled LDL cholesterol. J Clin Endocrinol Metab 103(8):3019-27 (publication date Aug. 1, 2018; epublication date May 29, 2018).

Nichols GA, Philip S, Reynolds K, Granowitz CB, Fazio S. Increased residual cardiovascular risk in patients with diabetes and high vs. normal triglycerides despite statin-controlled LDL Cholesterol. Diabetes Obes Metab (publication date Sep. 17, 2018; epublication date Sep. 17, 2018).

Nippon Rinsho, Metabolic Syndrome 2nd Edition—Basics and New Clinical Findings, Jan. 20, 2011, Special Issue 1 (vol. 992), pp. 503-506 (with English translation).

Nomura S, Shouzu A, Omoto S, et al. Effects of eicosapentaenoic acid on endothelial cell-derived microparticles, angiopoietins and adiponectin in patients with type 2 diabetes. J Atheroscler Throm. 2009;16:83-90.

Ohashi, Journal of Clinical and Experimental Medicine, Feb. 14, 2009, vol. 228, No. 7, pp. 795-805 (with English translation).

Omacor Summary of Product Characteristics, Pronova BioPharma Norge AS. Lysaker, Norway, Mar. 2015.

Origin Trial Investigators (The). n-3 fatty acids and cardiovascular outcomes in patients with dysglycemia. N Engl J Med 2012;367:309-318.

Otvos et al., "Clinical Implications of Discordance Between LDL Cholesterol and LDL Particle Number," J. Clin. Lipidol, 5(2):105-113 (Mar.-Apr. 2011)(available online Mar. 1, 2011).

Pase M, Grima N, Sarris J. Do long-chain n-3 fatty acids reduce arterial stiffness? A meta-analysis of randomized controlled trials.Br J Nutr.2011; 106:974-980.

Pollin TI, Damcott CM, Shen H, et al. A null mutation in human APOC3 confers a favorable plasma lipid profile and apparent cardioprotection. Science. 2008;322(5908):1702-1705.

Rauch B, Rudolf R, Schneider S, et al. OMEGA, a randomized, placebo-controlled trial to test the effect of highly purified omega-3 fatty acids on top of modern guideline-adjusted therapy after myocardial infarction. Circulation. 2010;122:2152-2159.

Ridker PM, Everett BM, Thuren T, et al. Antiinflammatory Therapy with canakinumab for atherosclerotic disease. N Engl J Med 377(12):1119-31 (publication date Sep. 21, 2017; epublication date Aug. 27, 2017).

Risk and Prevention Study Collaborative Group, Roncaglioni MC, Tombesi M, et al. n-3 fatty acids in patients with multiple cardiovascular risk factors. N Engl J Med. 2013;368(19):1800-8.

Roe MT, Armstrong PW, Fox KAA, et al; TRILOGY ACS Investigators. Prasugrel versus clopidogrel for acute coronary syndromes without revascularization. *N Engl J Med*. 367(14):1297-1309 (publication date Oct. 4, 2012; epublication Aug. 25, 2012).

Rupp, "Omega-3-Fettsauren in der Sekundarpravention nach Myokardinfarkt," Clin. Res. Cardiol., vol. 95:Suppl. 6, Vi/12/-V1-16 (2006)(with English summary).

Sarwar N, Danesh J, Eiriksdottir G, et al. Triglycerides and the risk of coronary heart disease: 10,158 incident cases among 262,525 participants in 29 Western prospective studies. Circulation 115:450-458, 2007.

Schunkert H, König IR, Kathiresan S, et al. Large-scale association analysis identifies 13 new susceptibility loci for coronary artery disease. Nat Genet. 2011;43(4):333-8.

Schwartz GG, Bessac L, Berdan LG, et al. Effect of alirocumab, a monoclonal antibody to PCSK9, on long-term cardiovascular outcomes following acute coronary syndromes: rationale and design of the ODYSSEY outcomes trial. Am Heart J 168(5):682-9 (publication date Nov. 2014, epublication date Aug. 7, 2017).

Serhan C, Chiang N, Van Dyke T. Resolving inflammation: dual anti-inflammatory and pro-resolution lipid mediators. Nat Rev Immunol. 2008; 8:3449-361.

Sherratt SCR, Mason RP. Eicosapentaenoic acid and docosahexaenoic acid have distinct membrane locations and lipid interactions as determined by X-ray diffraction. Chem Phys Lipids 212:73-9 (publication date May 2018, epublication date Jan. 31, 2018).

Steg PG, Bhatt DL, Wilson PWF, et al; REACH Registry Investigators. One-year cardiovascular event rates in outpatients with atherothrombosis. *JAMA*. 297(11):1197-1206 (publication date May 21, 2007).

Stitziel N, Stirrups K, Masca N, et al. Supplement to: Coding variation in ANGPTL4, LPL, and SVEP1 and the risk of coronary disease. N Engl J Med. DOI: 10.1056/NEJMoa1507652; 2016.

Stone NJ, Robinson J, Lichtenstein AH, et al. ACC/AHA Prevention Guideline: 2013 ACC/AHA Guideline on the Treatment of Blood Cholesterol to Reduce Atherosclerotic Cardiovascular Risk in Adults: A Report of the American College of Cardiology/American Heart Association Task Force on Practice Guidelines. Circulation. 2014;129:S46-S48.

Tagawa H, Shimokawa H, Tagawa T, et al. Long-term treatment with eicosapentaenoic acid augments both nitric oxide-mediated and non-nitric oxide-mediated endothelium-dependent forearm vasodilatation in patients with coronary artery disease. J Cardiovasc Pharmacol 33(4):633-40, 1999.

Teramoto T, Sasaki J, Ishibashi S, et al. Diagnosis of atherosclerosis. Executive Summary of the Japan Atherosclerosis Society (JAS) Guidelines for the Diagnosis and Prevention of Atherosclerotic Cardiovascular Diseases in Japan—2012 Version. J Atheroscler Thromb. 2014;21(4):296-8. Electronic publication Dec. 10, 2013.

The TG and HDL Working Group of the Exome Sequencing Project, National Heart, Lung, and Blood Institute. Loss-of-function mutations in APOC3, triglycerides, and coronary disease. N Engl J Med. 2014;371(1):22-31.

Thygesen K., Alpert J., Jaffe A., et al. Third Universal Definition of Myocardial Infarction. *J Am Coll Cardiol*. 2012;60(16):1581-1598.

Toth PP, Granowitz C, Hull M, Liassou D, Anderson A, Philip S. High Triglycerides are associated with increased cardiovascular events, medical costs, and resource use: A real-world administrative claims analysis of statin-treated patients with high residual cardiovascular risk. Journal of the American Heart Association, 7(15):e008740 (publication date Jul. 25, 2018; epublication Aug. 7, 2018).

Vaduganathan M, Venkataramani AS, Bhatt DL. Moving toward global primordial prevention in cardiovascular disease: The heart of the matter. J Am Coll Cardiol 2015;66(14):1535-7.

Varbo A, Benn M, Tybjærg-Hansen A, Nordestgaard BG. Reply to letters regarding article, "Elevated remnant cholesterol causes both low-grade inflammation and ischemic heart disease, whereas elevated low-density lipoprotein cholesterol causes ischemic heart disease without inflammation". Circulation. 2014;129:e656.

Verma S, Leiter LA, Bhatt DL. CANTOS ushers in a new calculus of inflammasome targeting for vascular protection-and maybe more. Cell Metab 26(5):703-5 (publication date Nov. 7, 2017; epublication date Oct. 19, 2017).

Wall R, Ross RP, Fitzgerald G, Stanton C. Fatty acids from fish: the anti-inflammatory potential of long-chain omega-3 fatty acids. Nutr Rev. 2010; 68:280-289.

Wang Q, Liang X, Wang L, Lu X, Huang J, Cao J, Li H, Gu D. Effect of omega-3 fatty acids supplementation on endothelial function: a meta-analysis of randomized controlled trials. Atherosc. 2012; 221:563-543.

(56) References Cited

OTHER PUBLICATIONS

Watanabe T, Ando K, Daidoji H, et al. A randomized controlled trial of eicosapentaenoic acid in patients with coronary heart disease on statins. J Cardiol 70(6):537-44 (publication date Dec. 2017; epublication date Aug. 31, 2017).
Wei LJ, Lin DY, Weissfeld L. Regression analysis of multivariate incomplete failure time data by modeling marginal distributions. *J Am Stat Assoc.* 84(408):1065-1073 (publication date Dec. 1989).
Wikipedia, "Diabetes mellitus," Dec. 12, 2016 (Dec. 12, 2016), retrieved on Jul. 30, 2018 from https://en.wikipedia.org/w/index.php?title=Diabetes_mellitus&oldid=754431573; entire document, especially p. 1, paragraph 1.
Wikipedia, "Ethyl eicosapentaenoic acid," Apr. 1, 2016 (Apr. 1, 2016); retrieved on Jul. 27, 2018 from https://en.wikipedia.org/w/index.php?title=Ehtyl_eicosapentaenoic_acid&oldid=713086755; entire document, especially p. 1, col. 2 and p. 3, paragraph 2.
Wittrup HH, Tybjærg-Hansen A, Nordestgaard BG. Lipoprotein lipase mutations, plasma lipids and lipoproteins, and risk of ischemic heart disease: a meta-analysis. Circulation. 1999;99:2901-2907.
Wojczynski et al., "High-fat meal effect on LDL, HDL and VLDL particle size and number in the Genetics of Lipid-Lowering Drugs and Diet Network (GOLDN): an interventional study," Lipids in Health and Disease 10:181, pp. 1-11 (Oct. 18, 2011).
Yadav D, Pitchumoni CS. Issues in Hyperlipidemic Pancreatitis. J Clin Gastroenterol 236(1):54-62, 2003.
Yamagishi K, Nettleton J, Folsom A. Plasma fatty acid composition and incident heart failure in middle-aged adults: The Atherosclerosis Risk in Communities (ARIC) Study. Am Heart J.2008; 156:965-974.
Yamakawa K, Shimabukuro M, Higa N, Asahi T, Ohba K, Arasaki O, Higa M, Oshiro Y, Yoshida H, Higa T, Saito T, Ueda S, Masuzaki H, Sata M. Eicosapentaenoic Acid Supplementation Changes Fatty Acid Composition and Corrects Endothelial Dysfunction in Hyperlipidemic Patients. Cardiol Res Practice. 2012; epub Article ID 754181.
Yamano T, Kubo T, Shiono Y, et al. Impact of eicosapentaenoic acid treatment on the fibrous cap thickness in patients with coronary atherosclerotic plaque: an optical coherence tomography study. J Atheroscler Thromb. 2015;22:52-61.
Zheng et al., "Function of ω-3 long chain unsaturated fatty acid in metabolic syndrome," Chinese Journal of Endocrinology and Metabolism, vol. 27, No. 9, pp. 787-790 (Sep. 30, 2011)(with English translation).
Balfour et al., "Rosiglitazone," Drugs, 57(6):921-930 (Jun. 1999).
Laird et al., "Relationship of early hyperglcemia to mortality in trauma patients," J. Trauma, 56(5):1058-1062 (May 2004).
Mayo Clinic, Diabetes Diagnosis and Treatment, 1998, http://www.mayoclinic.org/diseases-conditions/diabetes/diagnosis-treatment/drc-20371451 (1998-2018).
Meyer et al., "Comparison of Seal Oil to Tuna Oil on Plasma Lipid Levels and Blood Pressure in Hypertiglyceridaemic Subjects," Lipids, 44:827-835 (2009).
Murck et al., "Ethyl-EPA in Huntington disease—Potentially relevant mechanism of action," Brain Research Bulletin, 72:159-164 (2007) (available online Nov. 15, 2006).
Otvos et al., "Clinical Implications of Discordance Between LDL Cholesterol and LDL Particle Number," J. Clin. Lipid., 5(2):105-113(Mar./Apr. 2011)(avail. online Mar. 1, 2011).
Brinton et al., "Effects of icosapent ethyl on lipid and inflammatory parameters in patients with diabetes mellitus-2, residual elevated triglycerides (200-500 mg/dL), and on statin therapy at LDL-C goal: the ANCHOR study," Cardiovasc. Diabetol. Jul. 9, 2013;12:100. doi: 10.1186/1475-2840-12-100.
Daniel et al., "The Effect of Elevated Triglycerides on the Onset and Progression of Coronary Artery Disease: A Retrospective Chart Review," Cholesterol, vol. 2015, Article ID 292935, 5 pages (epub Nov. 4, 2015).
Hamazaki et al., "Effects of fish oil rich in eicosapentaenoic acid on serum lipid in hyperlipidemic hemodialysis patients," Kidney Int'l., 26:81-84 (Jul. 1984).
Lovaza TM (omega-3-acid ethyl esters) Capsules, Aug. 2007 (Aug. 1, 2007)m oaget 1-2, XP055589332.
Nelson et al. "Icosapent Ethyl for Treatment of Elevated Triglyceide Levels," Annals of Pharmacotheraphy, 47(11):1517-1523 (Nov. 2013/epub Nov. 5, 2013).
Poirier, "Obesity and Cardiovasculr Disease: Pathophysiology, Evaluation, and Effect of Weight Loss", Circulation, Feb. 14, 2006;113(6):898-918. Epub Dec. 27, 2005.
Shearer et al., "Red Blood Cell Fatty Acid Patters and Acute Coronary Syndrome," PLoS One 4(5): e5444, publ. May 6, 2009 (doi:10.1371/journal/pone.0005444).
Stielow et al., "Novel Nox Inhibitor of oxLDL-Induced Reactive Oxygen Species Formation in Human Endothelial Cells," Biochem. Biophys. Res. Comm., 344:200-205 (May 26, 2006/epub Mar. 26, 2006).
Third Report of the National Cholesterol Education Program (NCEPP) Expert Panel on Detection, Evaluation, and Treatment of High blood Cholesterol in Adults (Adult Treatment Panellll) May 2001.
Thomas et al., "Renal Failure—Measuring the Glomerular Filtration Rate," Dtsch Arztebl Int., Dec. 18, 2009, 106(51-52); 849-54.
Yao et al., "Oxidized high density lipoprotein induces macrophage apoptosis via toll-like receptor 4-dependent CHOIP pathway," Journ. Lipid Res., 58:164-177 (Jan. 2017)(First published Nov. 28, 2016).
Zimmer et al., "Danger signaling in Atherosclerosis," Circ. Res., 2015; 116:323-340.

\* cited by examiner

*p<0.01 and **p<0.001 versus control; †p<0.001 versus glucose treatment (Student-Newman-Keuls multiple comparisons test).

*$p<0.001$ versus glucose-treated control (Student-Newman-Keuls multiple comparisons test;
†$p=0.0002$ versus 1.0 µM EPA treatment (unpaired, two-tailed Student's t-test).

*p<0.05 versus control; †p<0.05 versus vitamin E treatment (Student-Newman-Keuls multiple comparisons test).

*p<0.05 and p<0.01 versus control and vitamin E treatments, respectively (Student-Newman-Keuls multiple comparisons test).

*$p<0.001$ versus cognate treatment effects in LDL (Student-Newman-Keuls multiple comparisons test; overall ANOVA: $p<0.0001$, $F=430.99$).

Glucose Increased sdLDL Oxidation Glucose was tested at 200 mg/dL. Values are mean ± S.D. (N=3). *p=0.0005 (unpaired, two-tailed Student's t-test).

METHODS OF REDUCING OR PREVENTING OXIDATION OF SMALL DENSE LDL OR MEMBRANE POLYUNSATURATED FATTY ACIDS

RELATED APPLICATIONS

This application is a continuation of U.S. patent application Ser. No. 15/415,667 filed Jan. 25, 2017, which claims priority to U.S. Provisional Patent Application Ser. No. 62/308,525 filed Mar. 15, 2016, the contents of which are hereby incorporated by reference in its entirety.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dyslipidemia, congestive heart failure and stroke. A need exists for improved treatments for cardiovascular diseases and disorders.

SUMMARY

In one embodiment, the present disclosure provides a method of treating or preventing atherosclerosis in a subject having a high baseline serum glucose level, the method comprising administering to the subject a pharmaceutical composition comprising eicosapentaenoic acid or a derivative thereof such as ethyl eicosapentaenoate.

In one embodiment, the present disclosure provides a method of reducing or preventing membrane cholesterol domain formation in a subject in need thereof, the method comprising administering to the subject a pharmaceutical composition comprising eicosapentaenoic acid or a derivative thereof.

In another embodiment, the present disclosure provides a method of reducing or preventing sdLDL oxidation in a subject in need thereof, the method comprising administering to the subject a pharmaceutical composition comprising eicosapentaenoic acid or a derivative thereof.

In another embodiment, the present disclosure provides a method of reducing or preventing membrane cholesterol domain formation in a subject in need thereof, the method comprising administering to the subject a pharmaceutical composition comprising eicosapentaenoic acid or a derivative thereof.

In another embodiment, the present disclosure provides a method of reducing or preventing oxidative modification of membrane polyunsaturated fatty acids in a subject in need thereof, the method comprising administering to the subject a pharmaceutical composition comprising eicosapentaenoic acid or a derivative thereof.

These and other embodiments of the present disclosure will be disclosed in further detail herein below.

Values are mean+/−S.D. (N=3-7). *p<0.05 versus vehicle alone (no oxLDL); †p<0.05 versus oxLDL+vehicle (Student-Newman-Keuls multiple comparisons test; overall ANOVA: p=0.0188, F=4.236).

Figure 31:
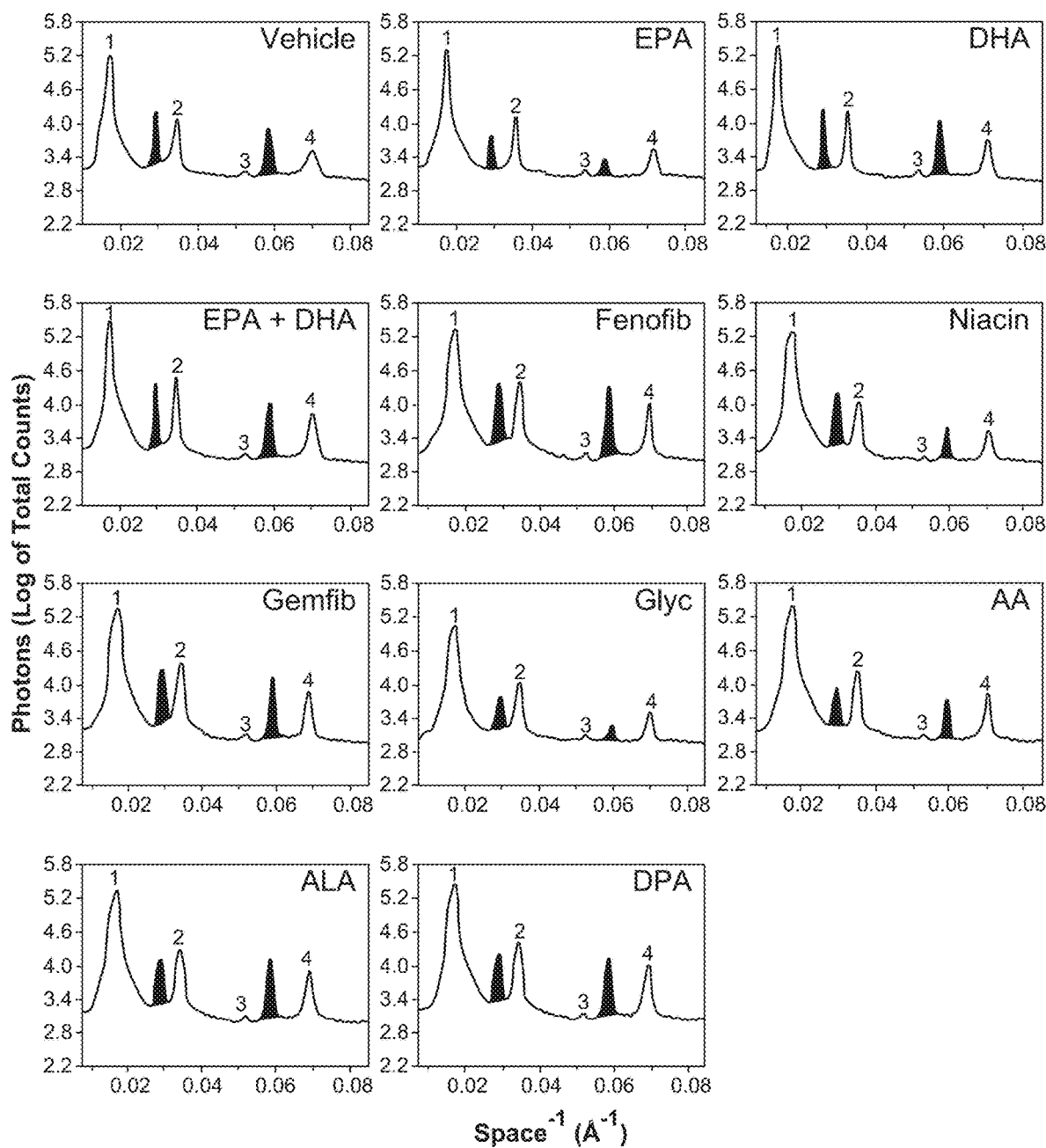

FIG. 31 shows representative x-ray diffraction patterns collected from cholesterol-enriched model membranes treated with vehicle (control), eicosapentaenoic acid (EPA), docosahexaenoic acid (DHA), EPA-DHA combination treatment, fenofibrate (Fenofib), nicotinic acid (Niacin), gemfibrozil (Gemfib), glycyrrhizin (Glyc), arachidonic acid (AA), α-linolenic acid (ALA), or docosapentaenoic acid (DPA).

Figure 32:
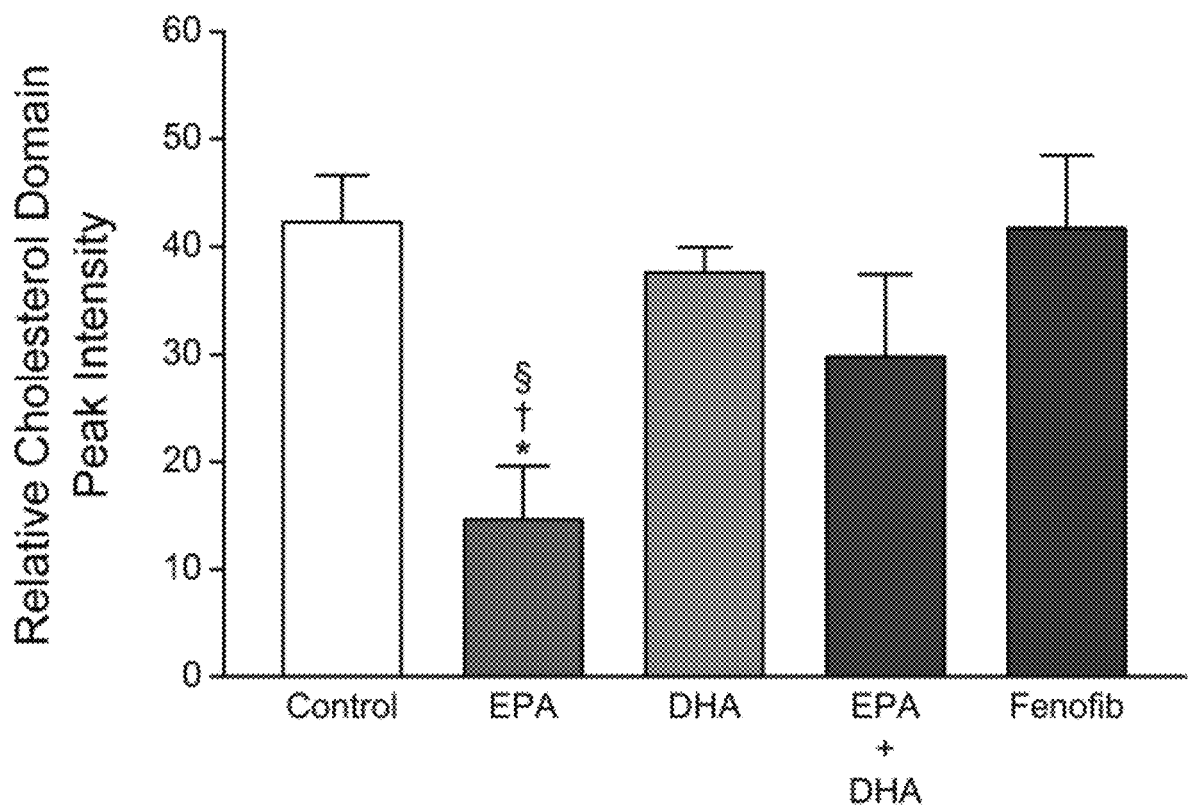

FIG. 32 shows the comparative effects of EPA, DHA, EPA-DHA combination treatment, and fenofibrate on membrane cholesterol domain structural integrity.

Figure 33:
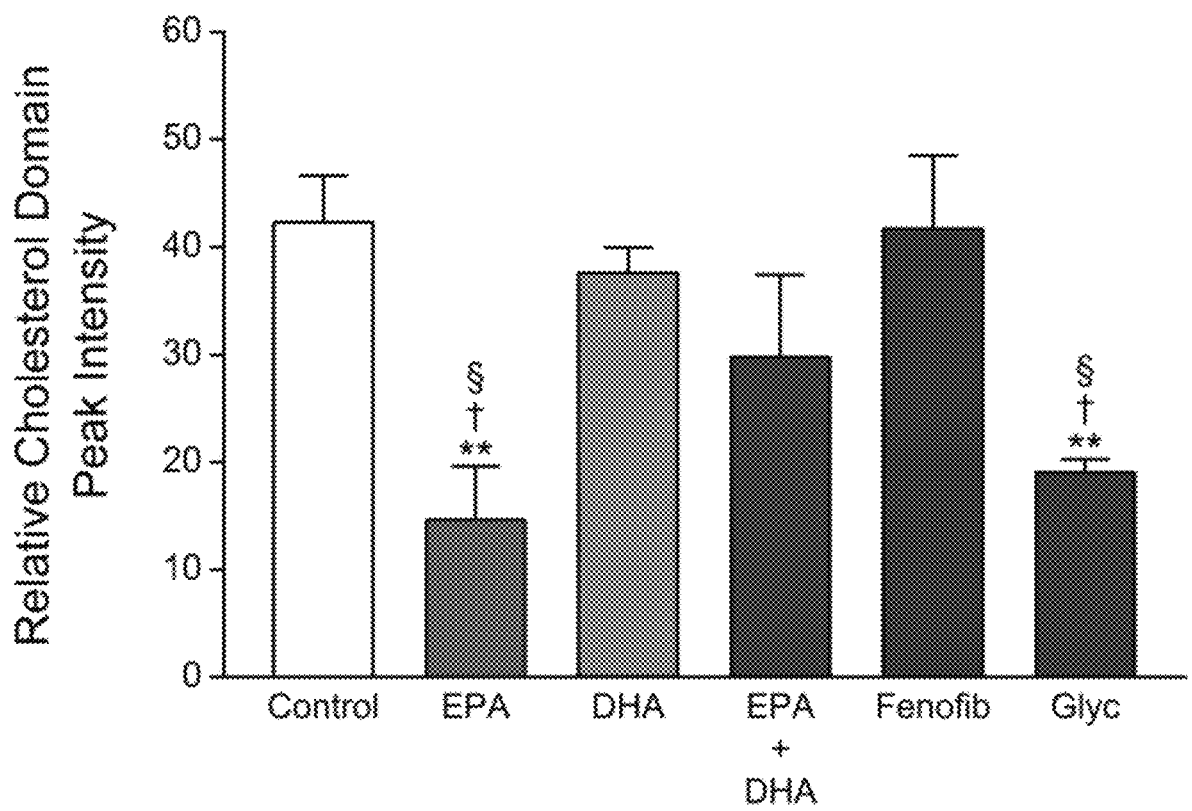

FIG. 33 shows the comparative effects of EPA, DHA, EPA-DHA combination treatment, fenofibrate and glycyrrhizin (Glyc) on membrane cholesterol domain structural integrity.

Figure 34:
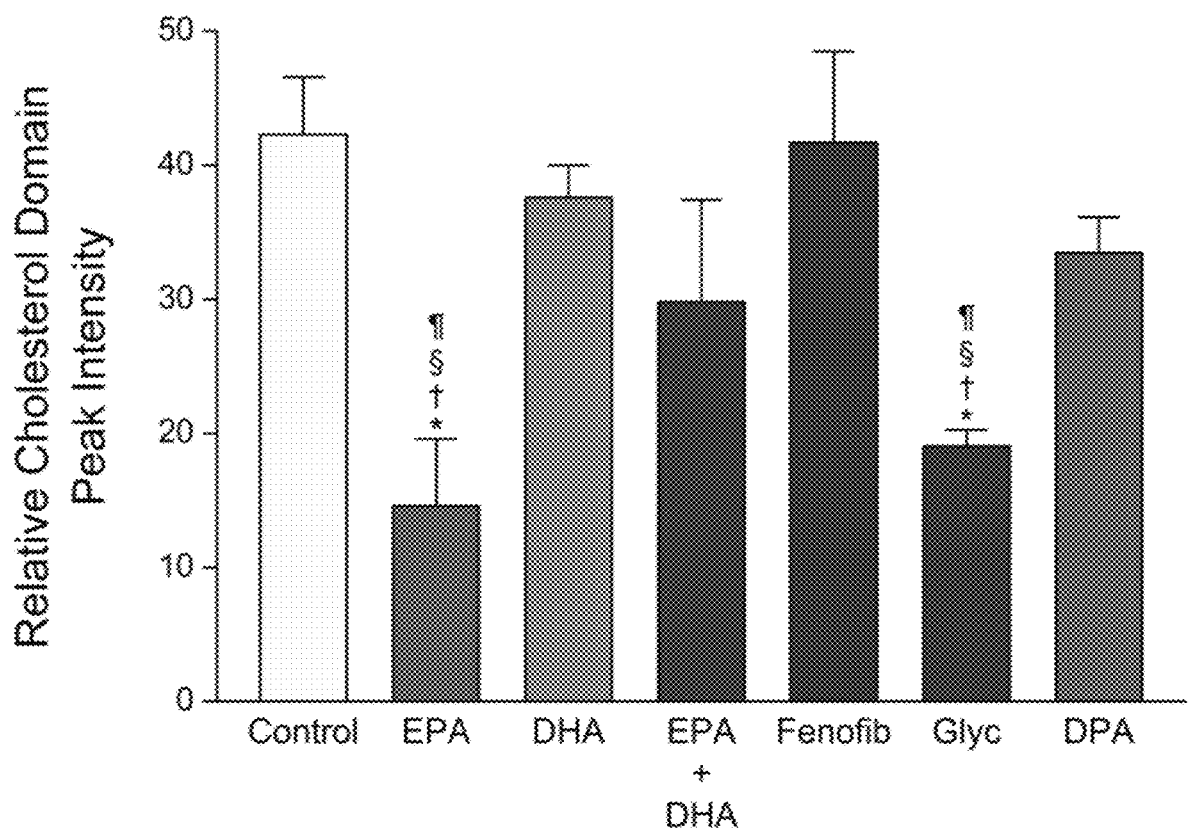

FIG. 34 shows the comparative effects of EPA, DHA, EPA-DHA combination treatment, fenofibrate, glycyrrhizin (Glyc), and docosapentaenoic acid (DPA) on membrane cholesterol domain structural integrity. Each agent was tested at D/P mole ratio of 1:30 and treated immediately with the different agents. Values are mean SEM (N=3-6). *p<0.01 versus control; †p<0.05 versus DHA; § p<0.01 versus Fenofib; ¶p<0.05 versus DPA (Student-Newman-Keuls multiple comparisons test; overall ANOVA: p=0.0946, F=1.864).

Figure 35:
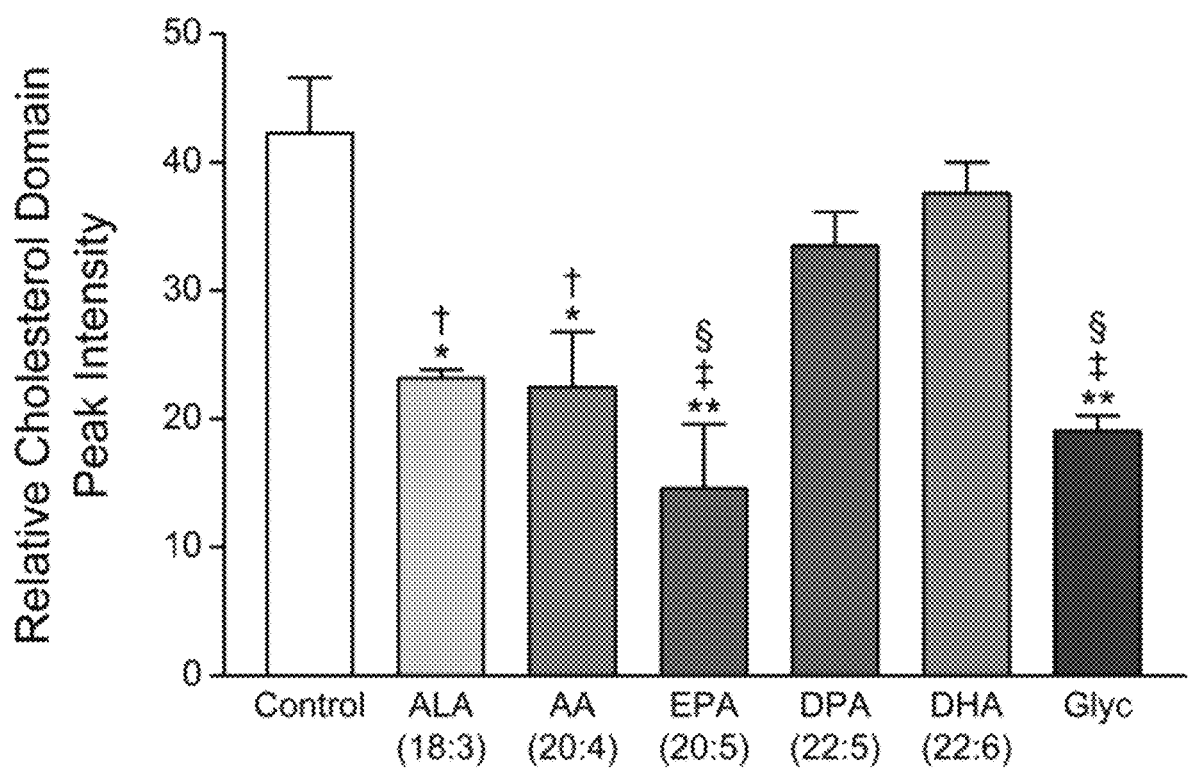

FIG. 35 shows the comparative effects of α-linolenic acid (ALA), arachidonic acid (AA), eicosapentaenoic acid (EPA), docosapentaenoic acid (DPA), docosahexaenoic acid (DHA), and glycyrrhizin (Glyc) on membrane cholesterol domain structural integrity. Each agent was tested at D/P mole ratio of 1:30. Values are mean±SEM (N=3-6). *p<0.01 and **p<0.001 versus control; †p<0.05 and ‡p<0.001 versus DHA; § p<0.01 versus DPA (Student-Newman-Keuls multiple comparisons analysis; overall ANOVA: p<0.0001, F=12.021).

Figure 36:
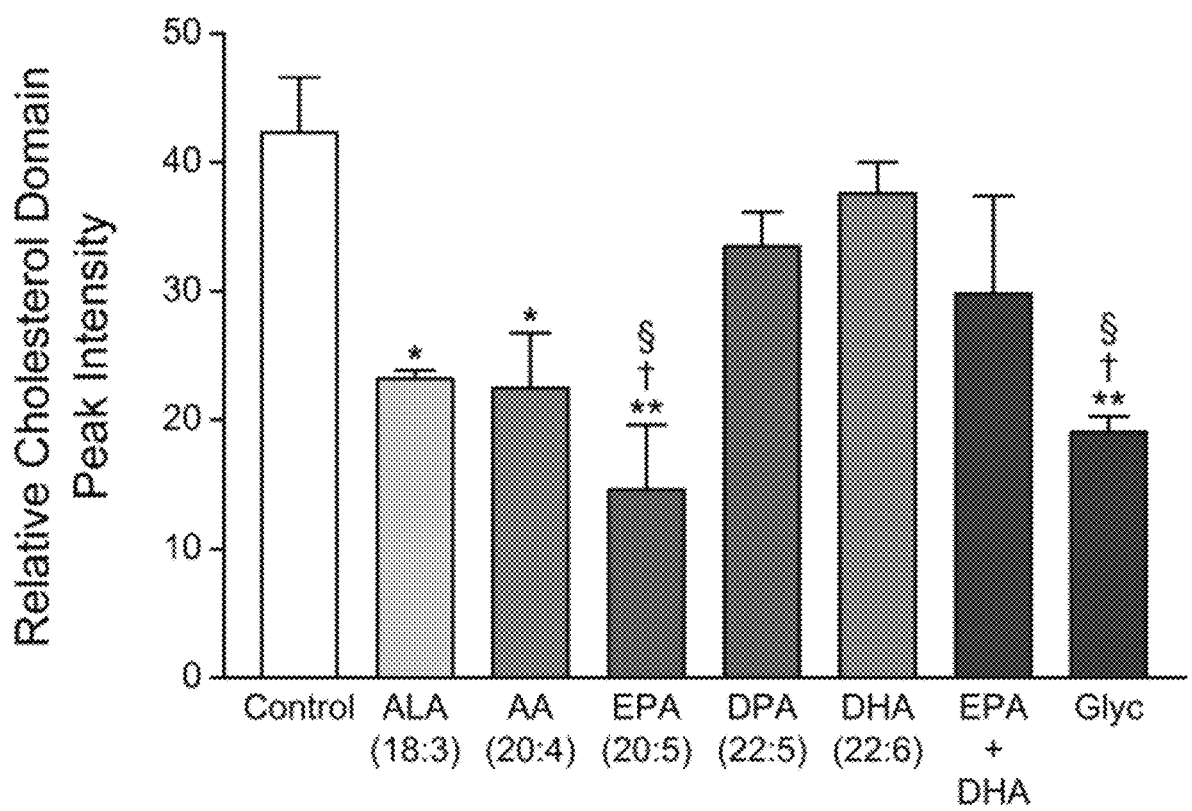

FIG. 36 shows the comparative effects of α-linolenic acid (ALA), arachidonic acid (AA), eicosapentaenoic acid (EPA), docosapentaenoic acid (DPA), docosahexaenoic acid (DHA), EPA-DHA combination treatment, and glycyrrhizin (Glyc) on membrane cholesterol domain structural integrity. Each agent was tested at D/P mole ratio of 1:30. Values are mean±SEM (N=3-6). *p<0.05 and **p<0.01 versus control; †p<0.01 vs. DHA; § p<0.05 versus DPA (Student-Newman-Keuls multiple comparisons analysis; overall ANOVA: p=0.0004, F=6.855).

Figure 37:
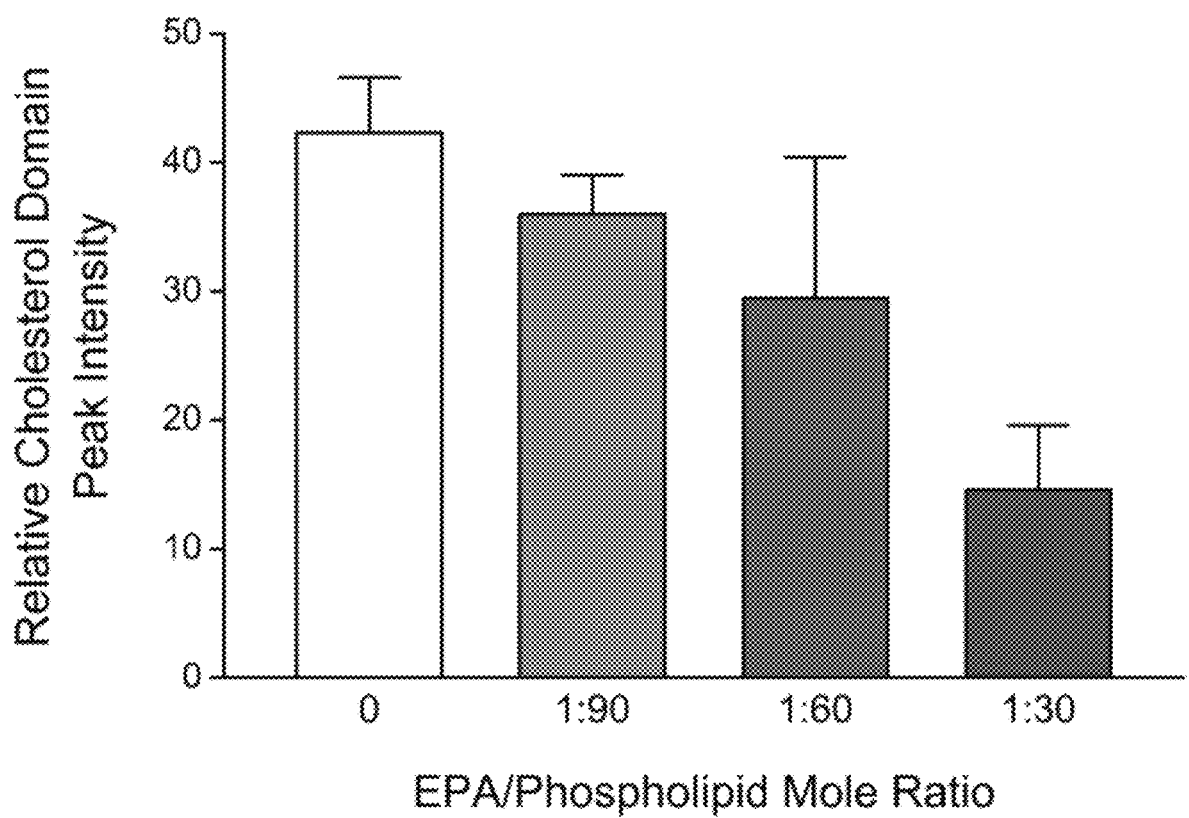

FIG. 37 shows the dose-dependent disruptive effects of EPA on the structural integrity of pre-existing membrane cholesterol domains.

Figure 38:
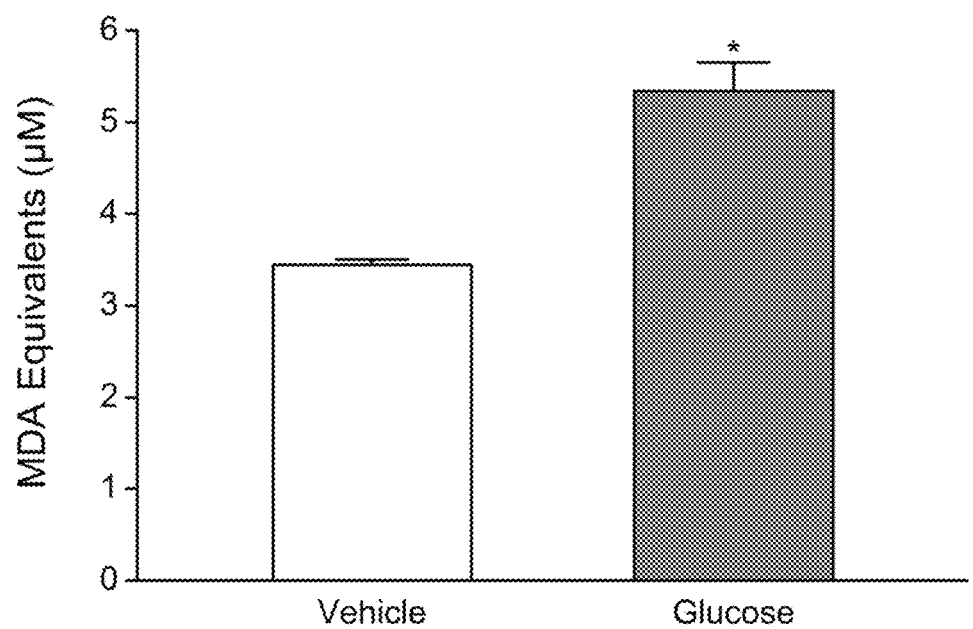

FIG. 38 shows sdLDL oxidation in the presence or absence of hyperglycemic conditions.

Figure 39:
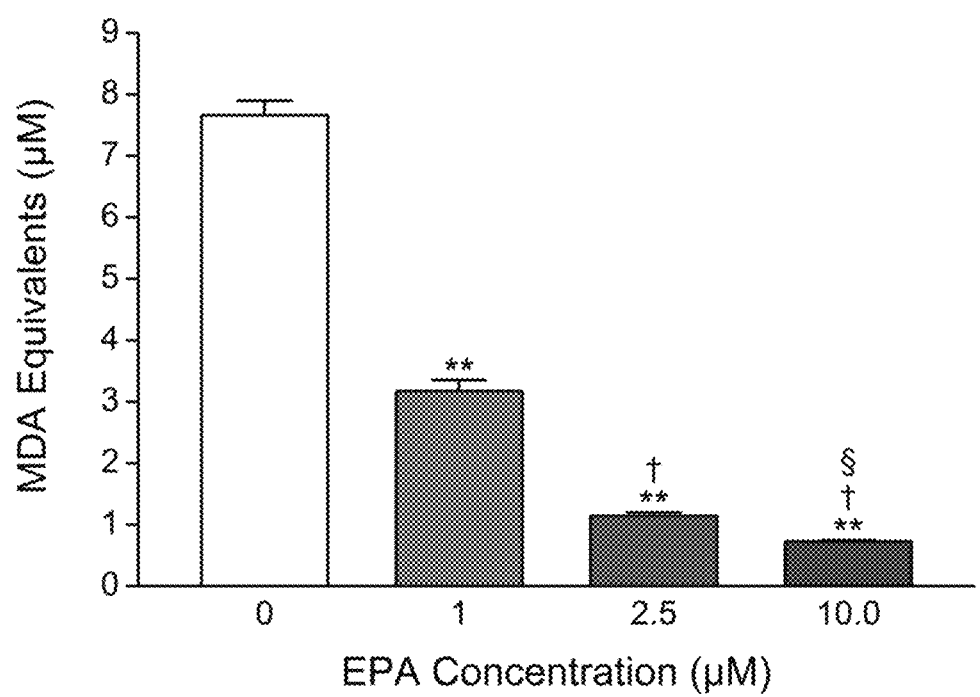

FIG. 39 depicts the reduction of glucose-induced sdLDL oxidation by EPA in a dose-dependent manner.

Figure 40:
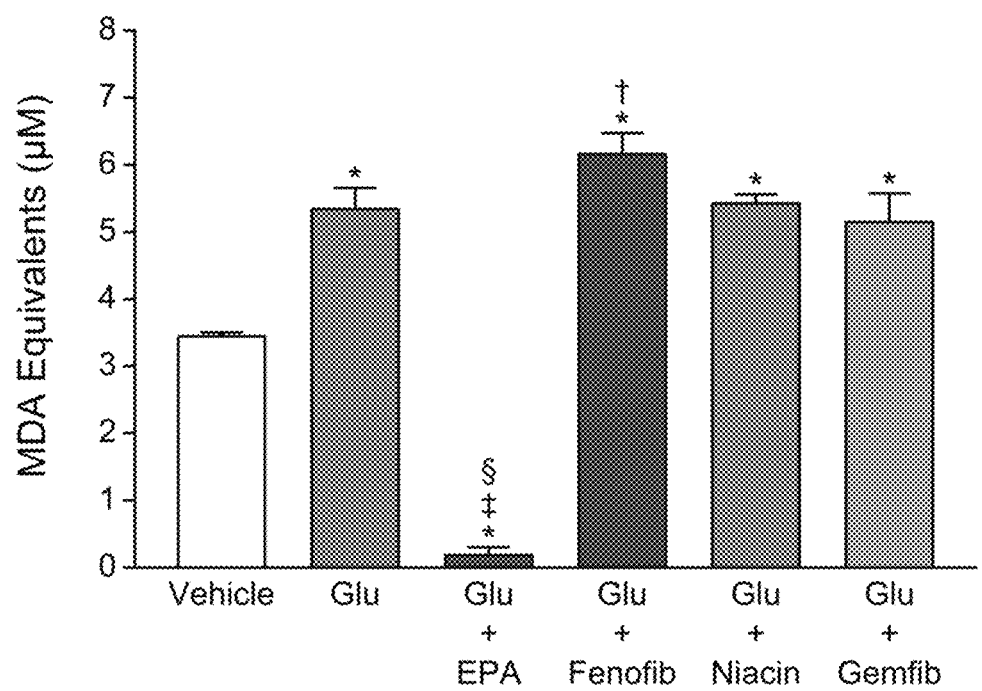

FIG. 40 shows comparative reductions in glucose-induced sdLDL oxidation by various agents. Each agent was tested at 10 μM. Data were collected following exposure to oxidation conditions for 1 hr. Values are mean±S.D. (N=3). *p<0.001 versus vehicle-treated control; †p<0.01 and ‡p<0.001 versus glucose (Glu; 200 mg/dL) alone; § p<0.001 versus Fenofib, Niacin, or Gemfib (with glucose) treatments (Student-Newman-Keuls multiple comparisons test; overall ANOVA: p<0.0001, F=211.23).

Figure 41:
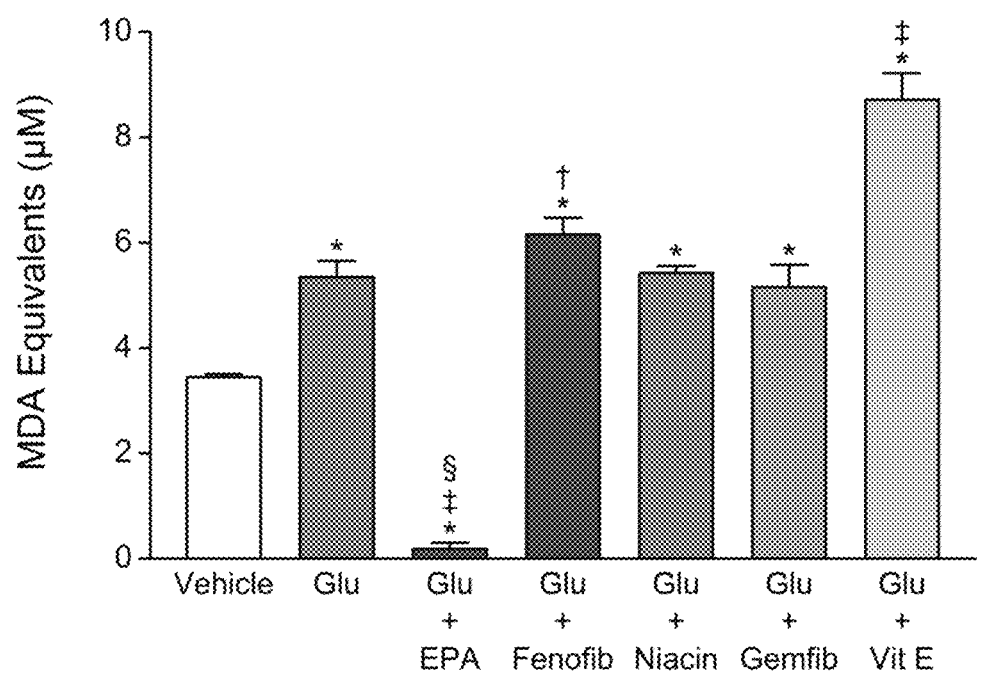

FIG. 41 shows the increase in glucose-induced sdLDL oxidation with Vitamin E. Each agent was tested at 10 μM. Data were collected following exposure to oxidation conditions for 1 hr. Values are mean±S.D. (N=3). *p<0.001 versus vehicle-treated control; †p<0.05 and ‡p<0.001 versus glucose (Glu; 200 mg/dL) alone; § p<0.001 versus Fenofib, Niacin, or Gemfib (with glucose) treatments (Student-Newman-Keuls multiple comparisons test; overall ANOVA: p<0.0001, F=216.14).

Figure 42:
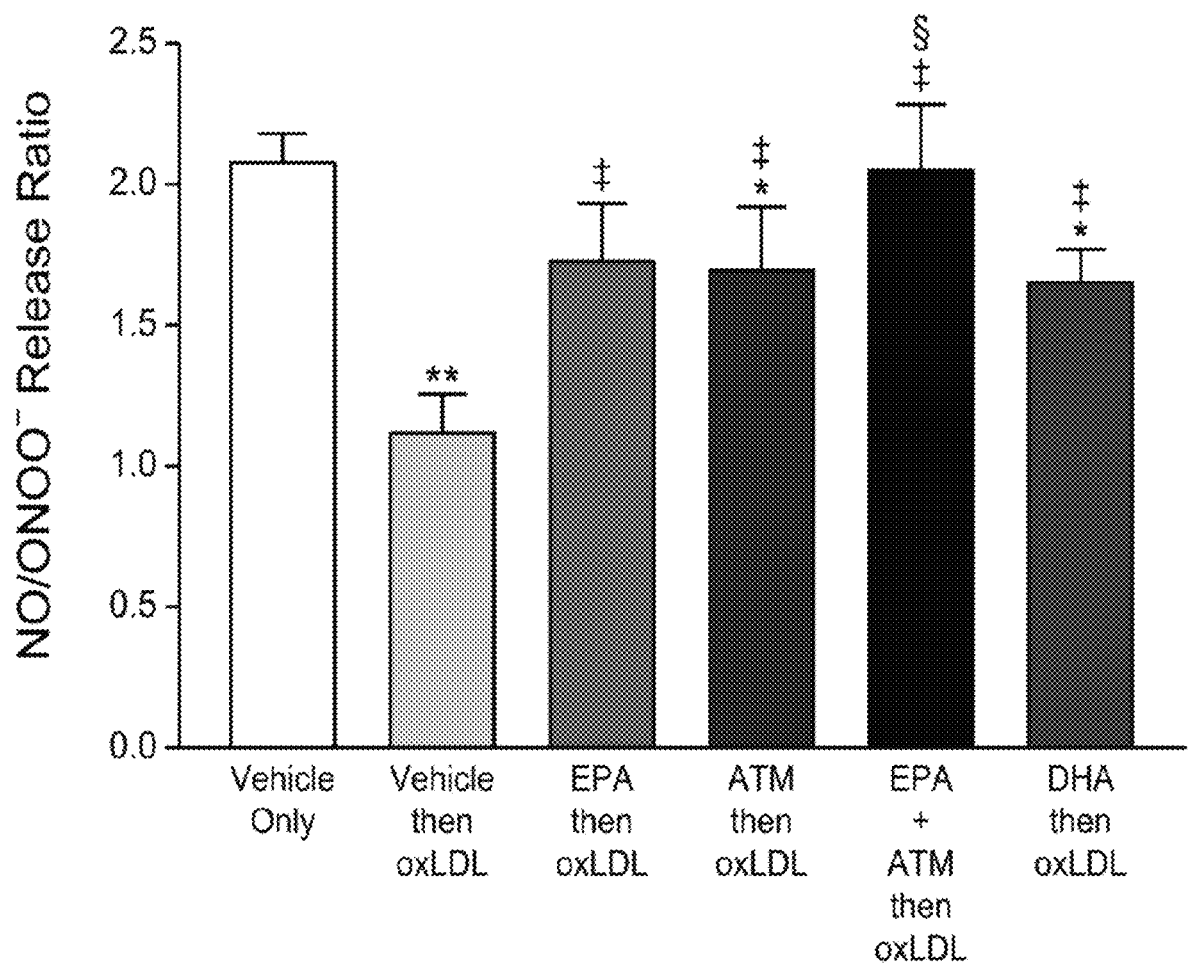

FIG. 42 shows the effects of oxidized low-density lipoprotein (oxLDL) on nitric oxide (NO) and peroxynitrite (ONOO⁻) release from human umbilical vein endothelial cells (HUVECs) pre-treated with eicosapentaenoic acid (EPA), atorvastatin o-hydroxy (active) metabolite (ATM), EPA/ATM combination, docosahexaenoic acid (DHA), fenofibrate (Fenofib), gemfibrozil (Gemfib), or nicotinic acid (Niacin).

Figure 43:
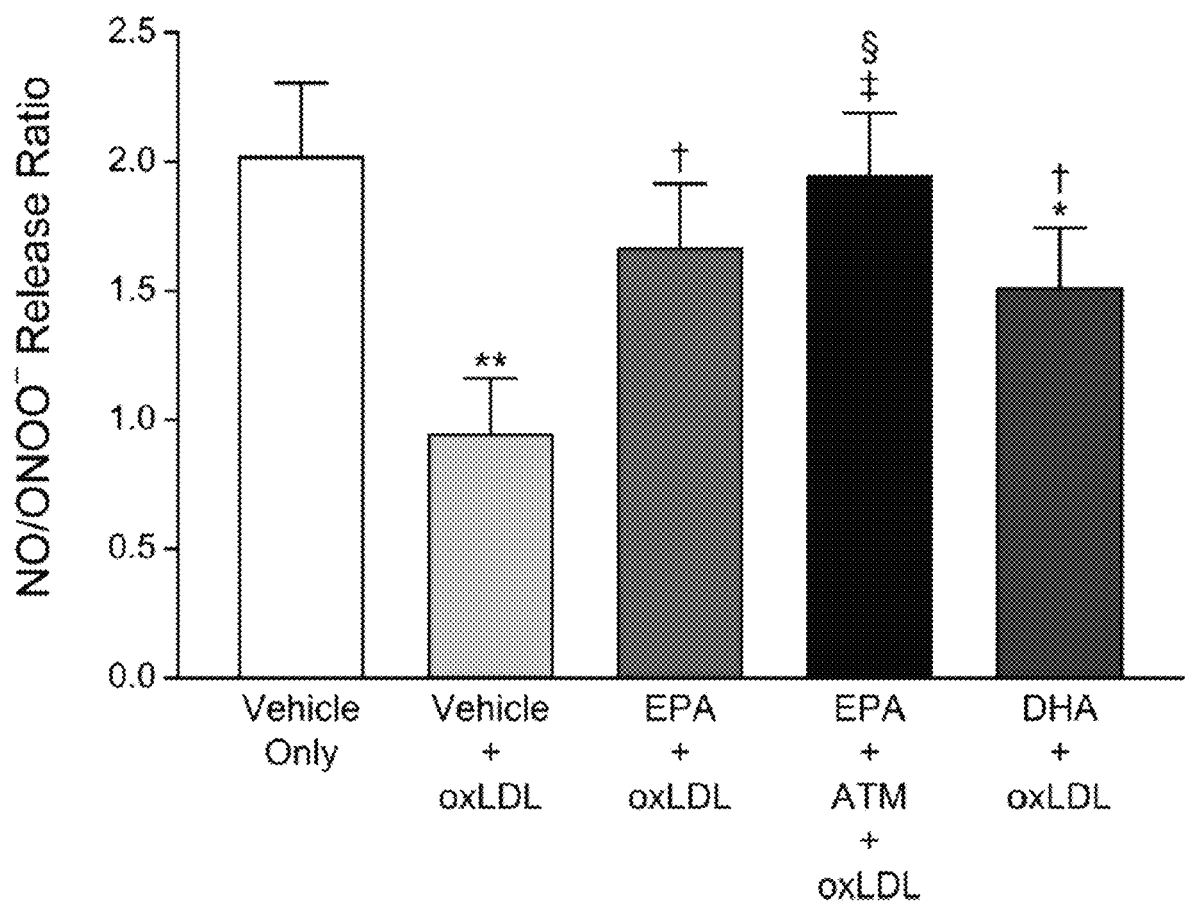

FIG. 43 compares the effects of EPA, DHA, and EPA/ATM combination treatment NO and ONOO⁻ release from HUVECs treated concomitantly with oxLDL.

Figure 44:
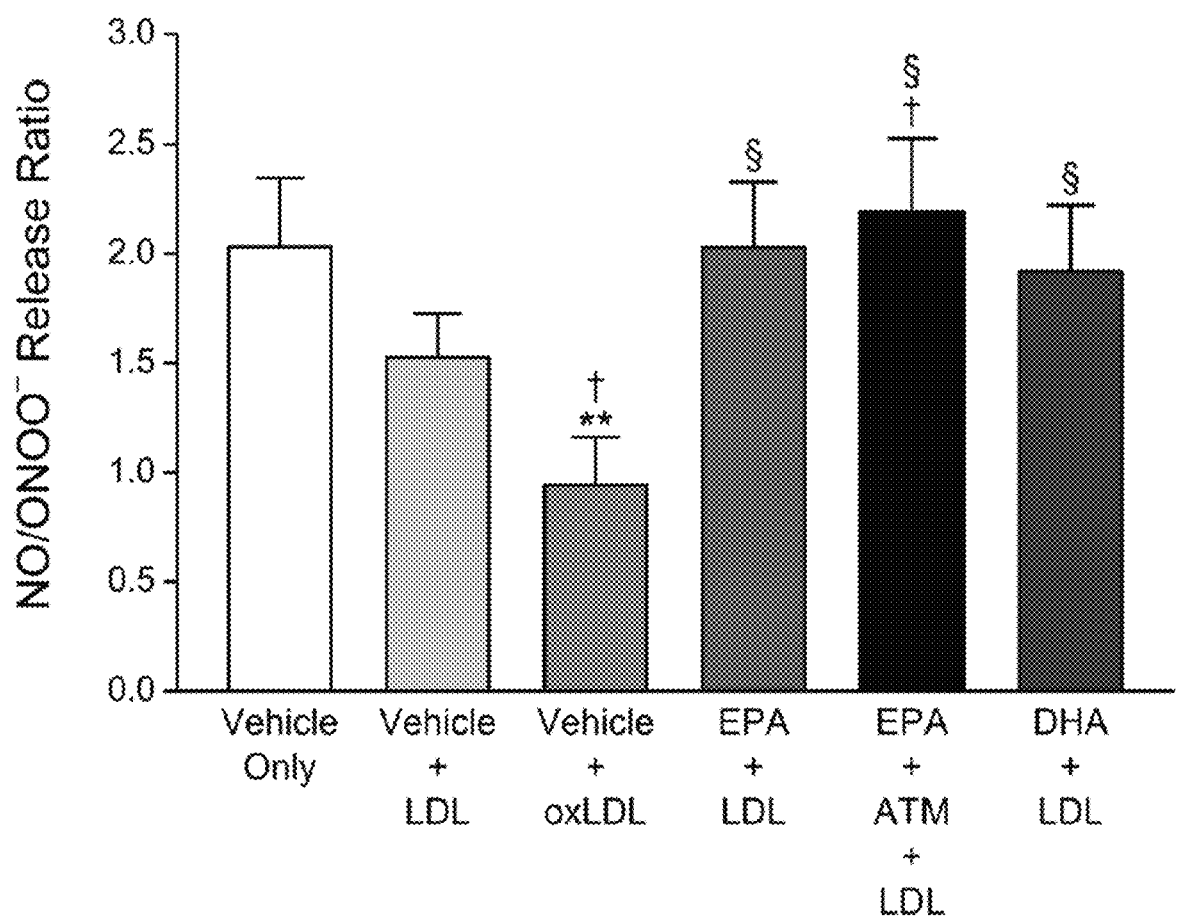

FIG. 44 compares the effects of EPA, DHA, and EPA/ATM combination treatment on NO and ONOO⁻ release from HUVECs treated concomitantly with native LDL (and then exposed to oxidative conditions) versus cells treated with oxLDL directly.

Figure 45:
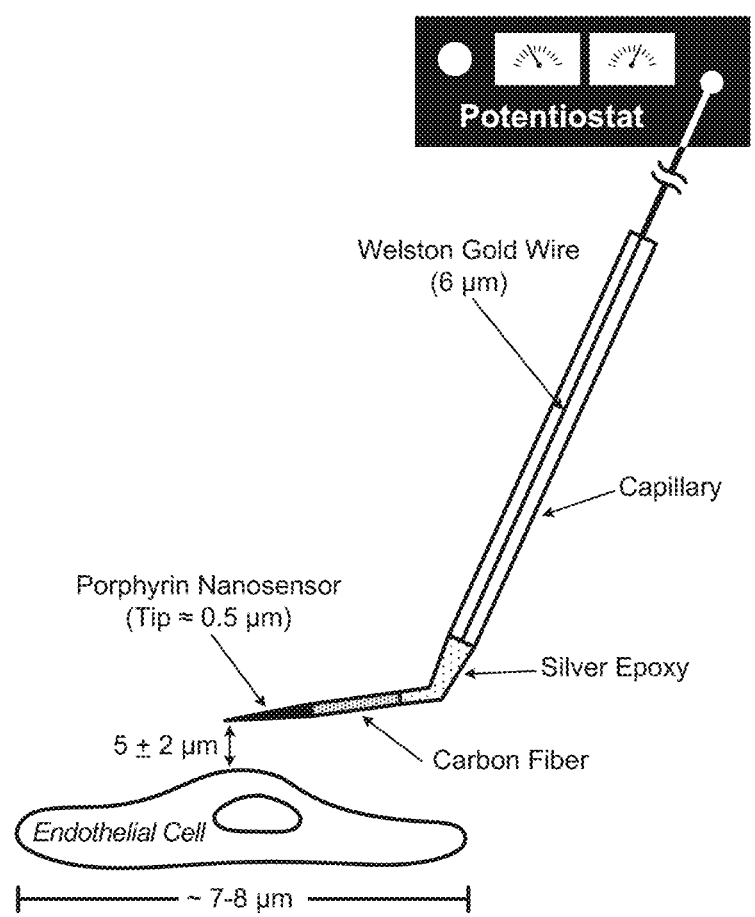

FIG. 45 shows a schematic diagram of a NO/ONOO⁻ nanosensor positioned to measure NO and/or ONOO⁻ emitted by an endothelial cell. The sensor is made by depositing a sensing material on the tip of carbon fiber with a diameter of 0.5 μm. The fiber is sealed with nonconductive epoxy and electrically connected to wires (gold, copper) with conductive silver epoxy. Conductive films of polymeric Ni(II) tetrakis (3-methoxy-4-hydroxyphenyl) porphyrin and Mn(III) [2.2] paracyclophanylporphyrin were used for the NO and ONOO⁻ sensors, respectively.

Figure 46:
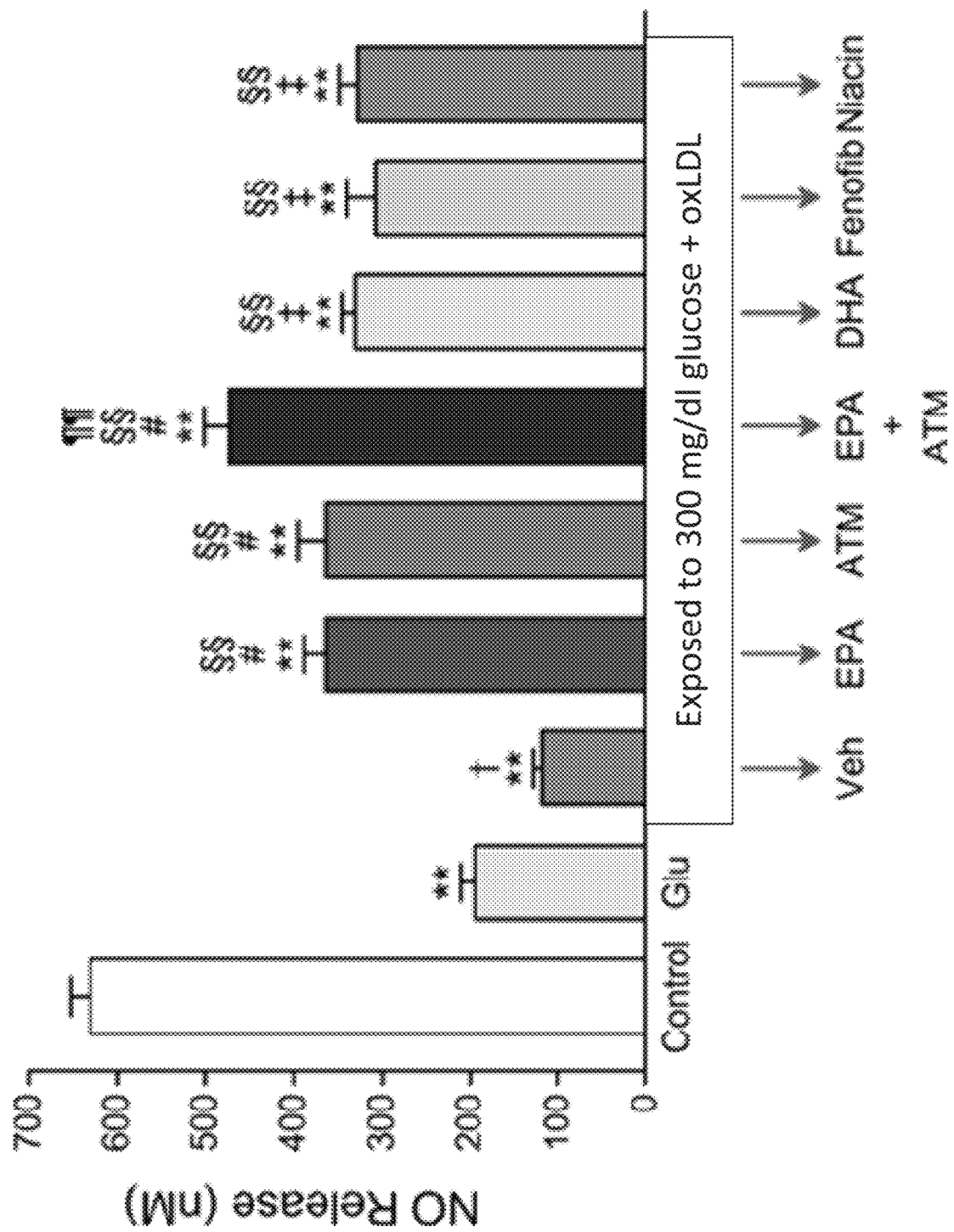

FIG. 46 shows the comparative effects of EPA, ATM, EPA+ATM combination treatment, DHA, fenofibrate (Fenofib), and Niacin on nitric oxide (NO) release from glomerular endothelial cells exposed ex vivo to hyperglycemic conditions (300 mg/dL glucose) and oxidized LDL (oxLDL). Values are mean SEM (N=4-8). **p<0.001 vs. control; †p<0.05, ‡p<0.01, and #p<0.001 vs. glucose (Glu); §§ p<0.001 vs. vehicle (Veh); ¶¶p<0.01 vs. separate EPA, ATM, DHA, Fenofib, or Niacin treatments (Student-Newman-Keuls multiple comparisons test; overall ANOVA: p<0.0001, F=44.005).

Figure 47:
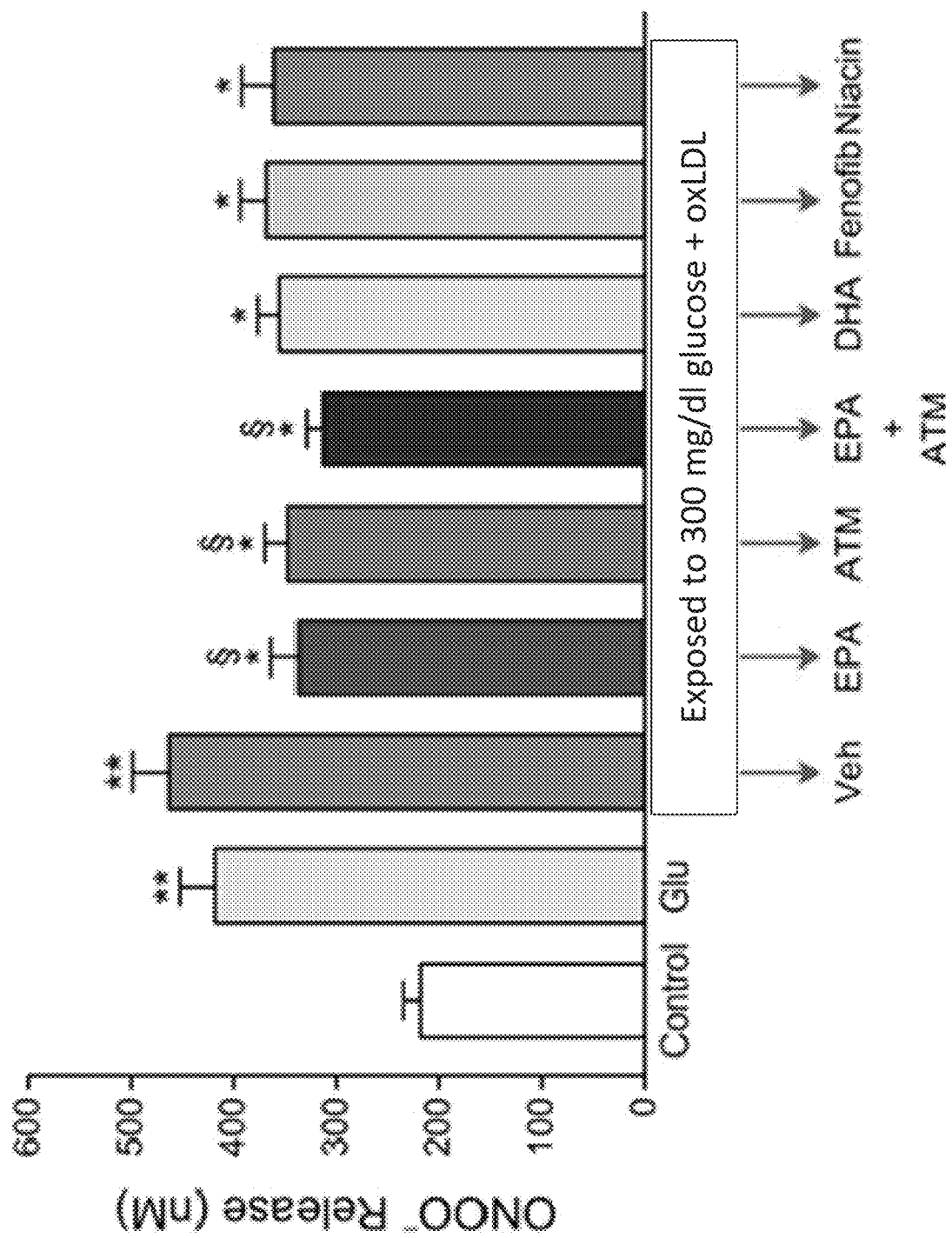

FIG. 47 shows the comparative effects of EPA, ATM, EPA+ATM combination treatment, DHA, Niacin, and Fenofibrate (Fenofib), on peroxynitrite (ONOO⁻) release from glomerular endothelial cells exposed to hyperglycemic conditions (300 mg/dL glucose) and oxidized LDL (oxLDL) ex vivo. Values are mean SEM (N=4-7). *p<0.05 and **p<0.001 vs. control; § p<0.05 vs. vehicle (Veh) (Student-Newman-Keuls multiple comparisons test; overall ANOVA: p<0.0001, F=6.6064).

Figure 48:
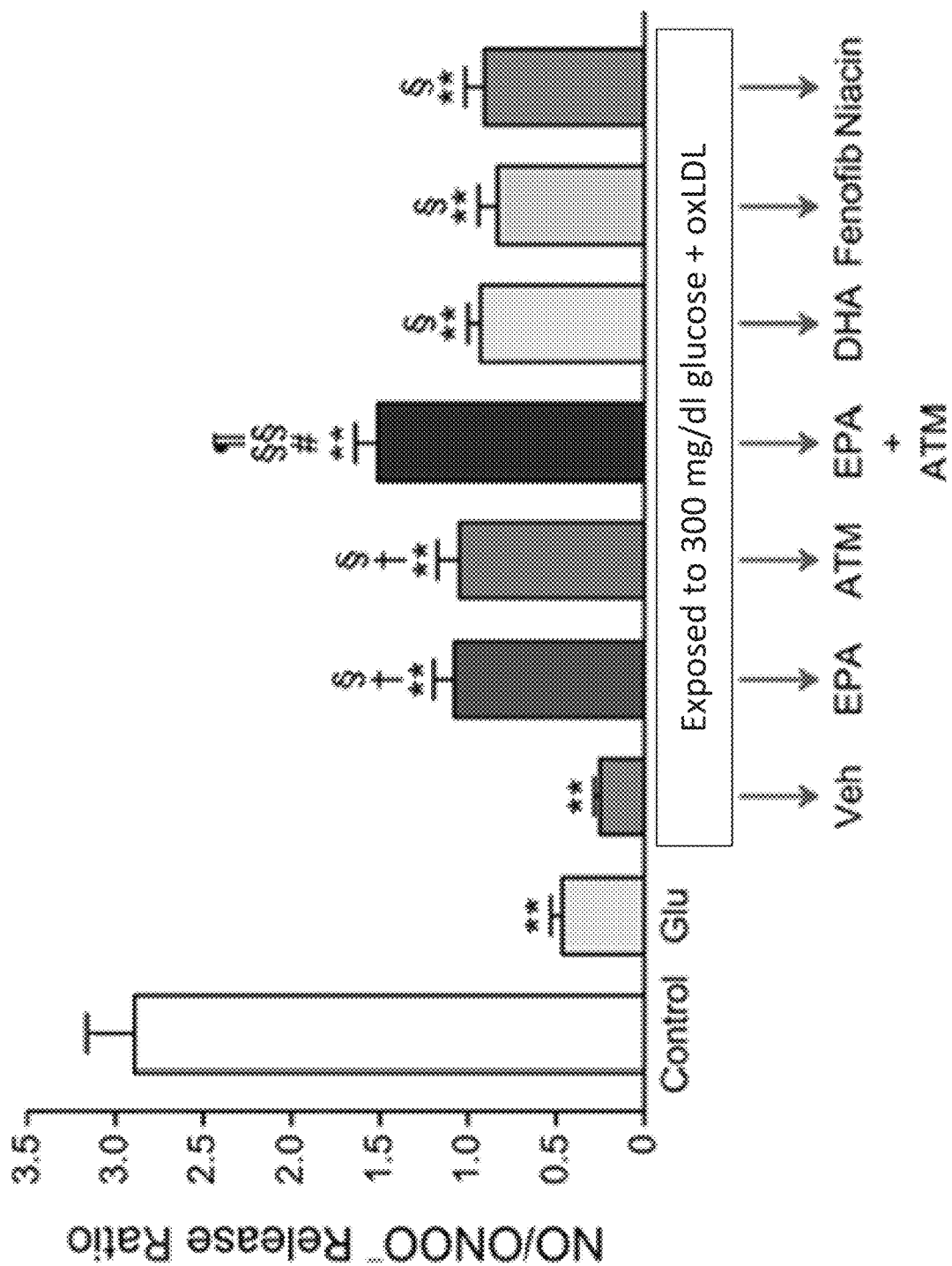

FIG. 48 shows the comparative effects of EPA, ATM, EPA+ATM combination treatment, Niacin, and Fenofibrate (Fenofib), on the ratio of NO to ONOO⁻ release from glomerular endothelial cells exposed to hyperglycemic conditions (300 mg/dL glucose) and oxidized LDL (oxLDL) ex vivo. Values are mean SEM (N=4-5). **p<0.001 vs. control; †p<0.05 and #p<0.001 vs. glucose (Glu); § p<0.05 and §§ p<0.001 vs. vehicle (Veh); ¶p<0.05 vs. separate EPA, ATM, DHA, Fenofib, or Niacin treatments (Student-Newman-Keuls multiple comparisons test; overall ANOVA: p<0.0001, F=34.416).

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

In one embodiment, the invention provides a method for treatment and/or prevention of a cardiovascular-related disease. The term "cardiovascular-related disease" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present invention provides a method of reducing or preventing membrane cholesterol domain formation in a subject in need thereof, the method comprising administering to the subject a pharmaceutical composition comprising eicosapentaenoic acid or a derivative thereof. In one embodiment, the method comprises measuring membrane cholesterol domain formation in the subject prior to and/or after administering to the subject a pharmaceutical composition comprising eicosapentaenoic acid or a derivative thereof. In one embodiment, the method comprises a step of determining a reduction in or absence of an increase in cholesterol domain formation in the subject.

In another embodiment, the present invention provides a method of reducing or preventing oxidative modification of membrane polyunsaturated fatty acids in a subject in need thereof, the method comprising administering to the subject a pharmaceutical composition comprising eicosapentaenoic acid or a derivative thereof. In one embodiment, the method comprises comprising a step of measuring oxidative modification of membrane polyunsaturated fatty acids in the subject before and/or after administering to the subject the pharmaceutical composition comprising eicosapentaenoic acid or a derivative thereof. In one embodiment, the method comprises a step of determining a reduction in or absence of an increase in oxidative modification of membrane polyunsaturated fatty acids in the subject.

In one embodiment, the subject or subject group in need thereof has one or more of: hypercholesterolemia, familial hypercholesterolemia, high LDL-C serum levels, high total cholesterol levels, and/or low HDL-C serum levels.

In another embodiment, the subject or subject group being treated has a baseline triglyceride level (or median baseline triglyceride level in the case of a subject group), fed or fasting, of at least about 300 mg/dl, at least about 400 mg/dl, at least about 500 mg/dl, at least about 600 mg/dl, at least about 700 mg/dl, at least about 800 mg/dl, at least about 900 mg/dl, at least about 1000 mg/dl, at least about 1100 mg/dl, at least about 1200 mg/dl, at least about 1300 mg/dl, at least about 1400 mg/dl, or at least about 1500 mg/dl, for example about 400 mg/dl to about 2500 mg/dl, about 450 mg/dl to about 2000 mg/dl or about 500 mg/dl to about 1500 mg/dl.

In one embodiment, the subject or subject group treated in accordance with methods of the invention has previously been treated with Lovaza® and has experienced an increase in, or no decrease in, LDL-C levels and/or non-HDL-C levels. In one such embodiment, Lovaza® therapy is discontinued and replaced by a method of the present invention.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of total fatty acid (or mean thereof) not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline plasma, serum or red blood cell membrane EPA level not greater than about 70 µg/ml, not greater than about 60 µg/ml, not greater than about 50 µg/ml, not greater than about 40 µg/ml, not greater than about 30 µg/ml, or not greater than about 25 µg/ml.

In another embodiment, methods of the present invention comprise a step of measuring the subject's (or subject group's mean) baseline lipid profile prior to initiating therapy. In another embodiment, methods of the invention comprise the step of identifying a subject or subject group having one or more of the following: baseline non-HDL-C value of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl; baseline vLDL-C value of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl.

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits one or more of the following outcomes:

(a) reduced triglyceride levels compared to baseline or control;

(b) reduced Apo B levels compared to baseline or control;

(c) increased HDL-C levels compared to baseline or control;

(d) no increase in LDL-C levels compared to baseline or control;

(e) a reduction in LDL-C levels compared to baseline or control;

(f) a reduction in non-HDL-C levels compared to baseline or control;

(g) a reduction in VLDL levels compared to baseline or control;

(h) an increase in apo A-I levels compared to baseline or control;

(i) an increase in apo A-I/apo B ratio compared to baseline or control;

(j) a reduction in lipoprotein A levels compared to baseline or control;

(k) a reduction in LDL particle number compared to baseline or control;

(l) an increase in LDL size compared to baseline or control;

(m) a reduction in remnant-like particle cholesterol compared to baseline or control;

(n) a reduction in oxidized LDL compared to baseline or control;

(o) no change or a reduction in fasting plasma glucose (FPG) compared to baseline or control;

(p) a reduction in hemoglobin $A_{1c}$ ($HbA_{1c}$) compared to baseline or control;

(q) a reduction in homeostasis model insulin resistance compared to baseline or control;

(r) a reduction in lipoprotein associated phospholipase A2 compared to baseline or control;

(s) a reduction in intracellular adhesion molecule-1 compared to baseline or control;

(t) a reduction in interleukin-6 compared to baseline or control;

(u) a reduction in plasminogen activator inhibitor-1 compared to baseline or control;

(v) a reduction in high sensitivity C-reactive protein (hsCRP) compared to baseline or control;

(w) an increase in serum or plasma EPA compared to baseline or control;

(x) an increase in red blood cell (RBC) membrane EPA compared to baseline or control;

(y) a reduction or increase in one or more of serum phospholipid and/or red blood cell content of docosahexaenoic acid (DHA), docosapentaenoic acid (DPA), arachidonic acid (AA), palmitic acid (PA), stearidonic acid (SA) or oleic acid (OA) compared to baseline or control;

(z) a reduction in or prevention of membrane cholesterol domain formation compared to baseline or control; and/or (aa) a reduction in or prevention of oxidative modification of membrane polyunsaturated fatty acids compared to baseline or control; and or (bb) no increase, no substantial increase, or a reduction in oxidized sdLDL compared to baseline or control.

In one embodiment, upon administering a composition of the invention to a subject, the subject exhibits a decrease in triglyceride levels, an increase in the concentrations of EPA and DPA (n-3) in red blood cells, and an increase of the ratio of EPA:arachidonic acid in red blood cells. In a related embodiment the subject exhibits substantially no or no increase in RBC DHA.

In one embodiment, methods of the present invention comprise measuring baseline levels of one or more markers set forth in (a)-(bb) above prior to dosing the subject or subject group. In another embodiment, the methods comprise administering a composition as disclosed herein to the subject after baseline levels of one or more markers set forth in (a)-(bb) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, any 25 or more of, any 26 or more of, any 27 or more of, or all 28 of outcomes (a)-(bb) described immediately above.

In another embodiment, upon treatment with a composition of the present invention, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(c) substantially no change in HDL-C levels, no change in HDL-C levels, or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(d) a less than 60% increase, a less than 50% increase, a less than 40% increase, a less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(i) a reduction in lipoprotein (a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(n) substantially no change, no significant change, or a reduction (e.g. in the case of a diabetic subject) in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(o) substantially no change, no significant change or a reduction in hemoglobin $A_{1c}$ (Hb$A_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, at least about 50%, at least about 100%, at least about 200%, or at least about 400% (actual % change or median % change) compared to baseline;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline;

(y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline;

(z) a reduction in membrane cholesterol domain formation of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or about 100% (actual % change or median % change) compared to baseline or control;

(aa) a reduction in oxidative modification of membrane polyunsaturated fatty acids of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or about 100% (actual % change or median % change) compared to baseline or control; and/or (bb) no increase, no substantial increase, or a reduction in oxidized sdLDL of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or greater than 95% (actual % change or median % change) compared to baseline or control.

In one embodiment, methods of the present invention comprise measuring baseline levels of one or more markers set forth in (a)-(bb) prior to dosing the subject or subject group. In another embodiment, the methods comprise administering a composition as disclosed herein to the subject after baseline levels of one or more markers set forth in (a)-(bb) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, any 25 or more of, any 26 or more of, any 27 or more of, or all 28 of outcomes (a)-(bb) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnant lipoproteins and LDL-phospholipase A2 can be determined from EDTA plasma or serum and serum, respectively, using enzymatic immunoseparation techniques. Oxidized LDL, intercellular adhesion molecule-1 and interleukin-6 levels can be determined from serum using standard enzyme immunoassay techniques. These techniques are described in detail in standard textbooks, for example Tietz Fundamentals of Clinical Chemistry, $6^{th}$ Ed. (Burtis, Ashwood and Borter Eds.), WB Saunders Company. Parameters (z) to (bb) can be measured in accordance with any clinically acceptable methodology or can be estimated by any suitable in vitro experiment, for example, one similar to that described in Examples 3-7.

In one embodiment, subjects fast for up to 12 hours prior to blood sample collection, for example about 10 hours.

In another embodiment, the present invention provides a method of treating or preventing primary hypercholesterolemia and/or mixed dyslipidemia (Fredrickson Types IIa and IIb) in a patient in need thereof, comprising administering to the patient one or more compositions as disclosed herein. In a related embodiment, the present invention provides a method of reducing triglyceride levels in a subject or subjects when treatment with a statin or niacin extended-release monotherapy is considered inadequate (Frederickson type IV hyperlipidemia).

In another embodiment, the present invention provides a method of treating or preventing risk of recurrent nonfatal myocardial infarction in a patient with a history of myocardial infarction, comprising administering to the patient one or more compositions as disclosed herein.

In another embodiment, the present invention provides a method of slowing progression of or promoting regression of atherosclerotic disease in a patient in need thereof, comprising administering to a subject in need thereof one or more compositions as disclosed herein.

In another embodiment, the present invention provides a method of treating or preventing very high serum triglyceride levels (e.g. Types IV and V hyperlipidemia) in a patient in need thereof, comprising administering to the patient one or more compositions as disclosed herein.

In another embodiment, the present invention provides a method of treating subjects having very high serum triglyceride levels (e.g. greater than 1000 mg/dl or greater than 2000 mg/dl) and that are at risk of developing pancreatitis, comprising administering to the patient one or more compositions as disclosed herein.

In one embodiment, a composition of the invention is administered to a subject in an amount sufficient to provide a daily dose of eicosapentaenoic acid of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In another embodiment, any of the methods disclosed herein are used in treatment or prevention of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In one embodiment, a composition for use in methods of the invention comprises eicosapentaenoic acid, or a pharmaceutically acceptable ester, derivative, conjugate or salt thereof, or mixtures of any of the foregoing, collectively referred to herein as "EPA." The term "pharmaceutically acceptable" in the present context means that the substance in question does not produce unacceptable toxicity to the subject or interaction with other components of the composition.

In one embodiment, the EPA comprises all-cis eicosa-5, 8,11,14,17-pentaenoic acid. In another embodiment, the EPA comprises an eicosapentaenoic acid ester. In another embodiment, the EPA comprises a $C_1$-$C_5$ alkyl ester of eicosapentaenoic acid. In another embodiment, the EPA comprises eicosapentaenoic acid ethyl ester, eicosapentaenoic acid methyl ester, eicosapentaenoic acid propyl ester, or eicosapentaenoic acid butyl ester. In another embodiment, the EPA comprises In one embodiment, the EPA comprises all-cis eicosa-5,8,11,14,17-pentaenoic acid ethyl ester.

In another embodiment, the EPA is in the form of ethyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

In another embodiment, EPA is present in a composition useful in accordance with methods of the invention in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, or about 5000 mg In another embodiment, a composition useful in accordance with the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of all fatty acids (and/or derivatives thereof) present, docosahexaenoic acid (DHA), if any. In another embodiment, a composition of the invention contains substantially no docosahexaenoic acid. In still another embodiment, a composition useful in the present invention contains no docosahexaenoic acid and/or derivative thereof.

In another embodiment, EPA comprises at least 70%, at least 80%, at least 90%, at least 95%, at least 96%, at least 97%, at least 98%, at least 99%, or 100%, by weight of all fatty acids (and/or derivatives thereof) present, in a composition that is useful in methods of the present invention.

In one embodiment, a composition of the invention comprises ultra-pure EPA. The term "ultra-pure" as used herein with respect to EPA refers to a composition comprising at least 95%, by weight of all fatty acids (and/or derivatives thereof) present, EPA (as the term "EPA" is defined and exemplified herein). Ultra-pure EPA comprises at least 96%, by weight of all fatty acids (and/or derivatives thereof) present, EPA, at least 97%, by weight of all fatty acids (and/or derivatives thereof) present, EPA, or at least 98%, by weight of all fatty acids (and/or derivatives thereof) present, EPA, wherein the EPA is any form of EPA as set forth herein.

In another embodiment, a composition useful in accordance with methods of the invention contains less than 10%, less than 9%, less than 8%, less than 7%, less than 6%, less than 5%, less than 4%, less than 3%, less than 2%, less than 1%, less than 0.5% or less than 0.25%, by weight of all fatty acids (and/or derivatives thereof) present, of any fatty acid other than EPA. Illustrative examples of a "fatty acid other than EPA" include linolenic acid (LA), arachidonic acid (AA), docosahexaenoic acid (DHA), alpha-linolenic acid (ALA), stearidonic acid (STA), eicosatrienoic acid (ETA) and/or docosapentaenoic acid (DPA). In another embodiment, a composition useful in accordance with methods of the invention contains about 0.1% to about 4%, about 0.5% to about 3%, or about 1% to about 2%, by weight of all fatty acids (and/or derivatives thereof) present, other than EPA and/or DHA.

In another embodiment, a composition useful in accordance with the invention has one or more of the following features: (a) eicosapentaenoic acid ethyl ester represents at least about 96%, at least about 97%, or at least about 98%, by weight of all fatty acids (and/or derivatives thereof) present, in the composition; (b) the composition contains not more than about 4%, not more than about 3%, or not more than about 2%, by weight of all fatty acids (and/or derivatives thereof) present, other than eicosapentaenoic acid ethyl ester; (c) the composition contains not more than about 0.6%, not more than about 0.5%, or not more than about 0.4%, by weight of all fatty acids (and/or derivatives thereof) present, of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (e) the composition contains not more than about 20 ppm, not more than about 15 ppm or not more than about 10 ppm heavy metals, (f) the composition contains not more than about 5 ppm, not more than about 4 ppm, not more than about 3 ppm, or not more than about 2 ppm arsenic, and/or (g) the composition has a peroxide value of not more than about 5 meq/kg, not more than about 4 meq/kg, not more than about 3 meq/kg, or not more than about 2 meq/kg.

In another embodiment, a composition useful in accordance with the invention comprises, consists of or consists essentially of at least 95%, by weight of all fatty acids (and/or derivatives thereof) present, ethyl eicosapentaenoate (EPA-E), about 0.2% to about 0.5%, by weight of all fatty acids (and/or derivatives thereof) present, ethyl octadecatetraenoate (ODTA-E), about 0.05% to about 0.25%, by weight of all fatty acids (and/or derivatives thereof) present, ethyl nonadecapentaenoate (NDPA-E), about 0.2% to about 0.45%, by weight of all fatty acids (and/or derivatives thereof) present, ethyl arachidonate (AA-E), about 0.3% to about 0.5%, by weight of all fatty acids (and/or derivatives thereof) present, ethyl eicosatetraenoate (ETA-E), and about 0.05% to about 0.32%, by weight of all fatty acids (and/or derivatives thereof) present, ethyl heneicosapentaenoate (HPA-E). In another embodiment, the composition is present in a capsule shell.

In another embodiment, compositions useful in accordance with the invention comprise, consist essential of, or consist of at least 95%, 96% or 97%, by weight of all fatty acids (and/or derivatives thereof) present, ethyl eicosapentaenoate, about 0.2% to about 0.5% by weight ethyl octadecatetraenoate, about 0.05% to about 0.25%, by weight of all fatty acids (and/or derivatives thereof) present, ethyl nonadecapentaenoate, about 0.2% to about 0.45%, by weight of all fatty acids (and/or derivatives thereof) present, ethyl arachidonate, about 0.3% to about 0.5%, by weight of all fatty acids (and/or derivatives thereof) present, ethyl eicosatetraenoate, and about 0.05% to about 0.32%, by weight of all fatty acids (and/or derivatives thereof) present, ethyl heneicosapentaenoate. Optionally, the composition contains not more than about 0.06%, about 0.05%, or about 0.04%, by weight of all fatty acids (and/or derivatives thereof) present, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell.

In another embodiment, compositions useful in accordance with the invention comprise, consist essential of, or consist of at least 96%, by weight of all fatty acids (and/or derivatives thereof) present, ethyl eicosapentaenoate, about 0.22% to about 0.4%, by weight of all fatty acids (and/or derivatives thereof) present, ethyl octadecatetraenoate, about 0.075% to about 0.20%, by weight of all fatty acids (and/or derivatives thereof) present, ethyl nonadecapentaenoate, about 0.25% to about 0.40%, by weight of all fatty acids (and/or derivatives thereof) present, ethyl arachidonate, about 0.3% to about 0.4%, by weight of all fatty acids (and/or derivatives thereof) present, ethyl eicosatetraenoate and about 0.075% to about 0.25%, by weight of all fatty acids (and/or derivatives thereof) present, ethyl heneicosapentaenoate. Optionally, the composition contains not more than about 0.06%, about 0.05%, or about 0.04%, by weight of all fatty acids (and/or derivatives thereof) present, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel or liquid capsule and is packaged in blister packages of about 1 to about 20 capsules per sheet.

In another embodiment, compositions useful in accordance with the invention comprise, consist essential of, or consist of at least 96%, 97% or 98%, by weight of all fatty acids (and/or derivatives thereof) present, ethyl eicosapentaenoate, about 0.25% to about 0.38%, by weight of all fatty acids (and/or derivatives thereof) present, ethyl octadecatetraenoate, about 0.10% to about 0.15%, by weight of all fatty acids (and/or derivatives thereof) present, ethyl nonadecapentaenoate, about 0.25% to about 0.35%, by weight of all fatty acids (and/or derivatives thereof) present, ethyl arachidonate, about 0.31% to about 0.38%, by weight of all fatty acids (and/or derivatives thereof) present, ethyl eicosatetraenoate, and about 0.08% to about 0.20%, by weight of all fatty acids (and/or derivatives thereof) present, ethyl heneicosapentaenoate. Optionally, the composition contains not more than about 0.06%, about 0.05%, or about 0.04%, by weight of all fatty acids (and/or derivatives thereof) present, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

In one embodiment, a subject being treated in accordance with methods of the invention is not otherwise on lipid-altering therapy, for example statin, fibrate, niacin and/or ezetimibe therapy.

In another embodiment, compositions useful in accordance with methods of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the invention can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In another embodiment, the invention provides use of any composition described herein for treating moderate to severe hypertriglyceridemia in a subject in need thereof, comprising: providing a subject having a fasting baseline triglyceride level of 500 mg/dl to about 1500 mg/dl and administering to the subject a pharmaceutical composition as described herein. In one embodiment, the composition comprises about 1 g to about 4 g of eicosapentaenoic acid ethyl ester, wherein the composition contains substantially no docosahexaenoic acid or derivative thereof. In some embodiments, cholesterol domain formation in membranes of the subject is reduced or prevented. In some embodiments, the subject experiences no substantial increase, or no increase, or a reduction, in LDL-C levels.

In another embodiment, the invention provides use of any composition described herein for treating moderate to severe hypertriglyceridemia in a subject in need thereof, comprising: providing a subject on statin therapy and having a fasting baseline triglyceride level of about 200 mg/dl to 499 mg/dl and administering to the subject a pharmaceutical composition as described herein. In one embodiment, the composition comprises about 1 g to about 4 g of eicosapentaenoic acid ethyl ester, wherein the composition contains substantially no docosahexaenoic acid. In some embodiments, cholesterol domain formation in membranes of the subject is reduced or prevented. In some embodiments, the subject experiences no substantial increase, or no increase, or a reduction, in LDL-C levels.

In one embodiment, compositions of the invention, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

In one embodiment, the present disclosure provides a method of treating or preventing atherosclerosis in a subject having a high baseline serum glucose level, the method comprising administering to the subject a pharmaceutical composition comprising eicosapentaenoic acid or a derivative thereof. In some embodiments, the pharmaceutical composition comprises at least 80%, at least 90%, at least 95%, or at least 96%, by weight of all fatty acids (and/or derivatives thereof) present, eicosapentaenoic acid or a derivative thereof. In some embodiments, the pharmaceutical composition comprises no docosahexaenoic acid or esters thereof. In some embodiments, the reduction or prevention occurs by a free radical chain-breaking mechanism. In some embodiments, the method further comprises determining a baseline oxidized sdLDL level in the subject prior to administering to the subject the pharmaceutical composition. In some embodiments, the method further comprises determining a second oxidized sdLDL level in the subject after administering to the subject a pharmaceutical composition comprising eicosapentaenoic acid or a derivative thereof, wherein the second oxidized sdLDL level is not greater than, not significantly greater than, or lower than the baseline oxidized sdLDL level and/or wherein the second oxidized sdLDL level is not greater than, not significantly greater than, or lower than the baseline oxidized sdLDL level in comparison to a second subject who has not received the pharmaceutical composition. In some embodiments, the method further comprises administering atorvastatin and/or o-hydroxyatorvastatin to the subject. In some embodiments, the second oxidized sdLDL level is not greater than, not significantly greater than, or lower than the baseline oxidized sdLDL level in comparison to a second subject who has received the atorvastatin and/or the o-hydroxyatorvastatin but not the pharmaceutical composition. In some embodiments, the second oxidized sdLDL level is not greater than, not significantly greater than, or lower than the baseline oxidized sdLDL level in comparison to a second subject who has received the pharmaceutical composition but not the o-hydroxyatorvastatin. In some embodiments, the subject has a baseline triglyceride level of at least 500 mg/dL. In some embodiments, the subject has a baseline triglyceride level of about 200 mg/dL to 499 mg/dL. In some embodiments, the subject is on statin therapy, optionally stable statin therapy. In some embodiments, the subject is diabetic. In some embodiments, the high baseline serum glucose level is a fasting serum glucose level of at least 126 mg/dL. In some embodiments, the high baseline serum glucose level is a fasting serum glucose level of at least 160 mg/dL. In some embodiments, the high baseline serum glucose level is a non-fasting serum glucose level of at least 200 mg/dL.

In one embodiment, the invention provides use of a composition as described herein in manufacture of a medicament for treatment of any of a cardiovascular-related disease. In another embodiment, the subject is diabetic.

In one embodiment, a composition as set forth herein is packaged together with instructions for using the composition to treat a cardiovascular disorder.

EXAMPLES

Example 1

A multi-center, placebo-controlled randomized, double-blind, 12-week study with an open-label extension was performed to evaluate the efficacy and safety of AMR101 in patients with fasting triglyceride levels ≥500 mg/dL. The primary objective of the study was to determine the efficacy of AMR101 2 g daily and 4 g daily, compared to placebo, in lowering fasting TG levels in patients with fasting TG levels ≥500 mg/dL and ≤1500 mg/dL (≥5.65 mmol/L and ≤16.94 mmol/L).

The secondary objectives of this study were the following:
1. To determine the safety and tolerability of AMR101 2 g daily and 4 g daily;
2. To determine the effect of AMR101 on lipid and apolipoprotein profiles;
3. To determine the effect of AMR101 on low-density lipoprotein (LDL) particle number and size;
4. To determine the effect of AMR101 on oxidized LDL;
5. To determine the effect of AMR101 on fasting plasma glucose (FPG) and hemoglobin $A_{1c}$ ($HbA_{1c}$);
6. To determine the effect of AMR101 on insulin resistance;
7. To determine the effect of AMR101 on high-sensitivity C-reactive protein (hsCRP);
8. To determine the effects of AMR101 2 g daily and 4 g daily on the incorporation of fatty acids into red blood cell membranes and into plasma phospholipids;
9. To explore the relationship between baseline fasting TG levels and the reduction in fasting TG levels; and
10. To explore the relationship between an increase in red blood cell membrane eicosapentaenoic acid (EPA) concentrations and the reduction in fasting TG levels.

The population for this study was men and women (women of childbearing potential needed to be on contraception or practice abstinence)>18 years of age with a body mass index≤45 kg/m² who were not on lipid-altering therapy or were not currently on lipid-altering therapy. Patients currently on statin therapy (with or without ezetimibe) were evaluated by the investigator as to whether this therapy could be safely discontinued at screening, or if it should have been continued. If statin therapy (with or without ezetimibe) was to be continued, dose(s) must have been stable for ≥4 weeks prior to randomization. Patients taking non-statin, lipid-altering medications (niacin>200 mg/day, fibrates, fish oil, other products containing omega-3 fatty acids, or other herbal products or dietary supplements with potential lipid-altering effects), either alone or in combination with statin therapy (with or without ezetimibe), must have been able to safely discontinue non-statin, lipid-altering therapy at screening.

Approximately 240 patients were randomized at approximately 50 centers in North America, South America, Central America, Europe, India, and South Africa. The study was a 58- to 60-week, Phase 3, multi-center study consisting of 3 study periods: (1) a 6- to 8-week screening period that included a diet and lifestyle stabilization and washout period and a TG qualifying period; (2) a 12-week, double-blind, randomized, placebo-controlled treatment period; and (3) a 40-week, open-label, extension period.

During the screening period and double-blind treatment period, all visits were within ±3 days of the scheduled time. During the open-label extension period, all visits were within ±7 days of the scheduled time. The screening period included a 4- or 6-week diet and lifestyle stabilization period and washout period followed by a 2-week TG qualifying period.

The screening visit (Visit 1) occurred for all patients at either 6 weeks (for patients not on lipid-altering therapy at screening or for patients who did not need to discontinue their current lipid-altering therapy) or 8 weeks (for patients who required washout of their current lipid-altering therapy at screening) before randomization, as follows:

Patients who did not require a washout: The screening visit will occur at Visit 1 (Week—6). Eligible patients entered a 4-week diet and lifestyle stabilization period. At the screening visit, all patients received counseling regarding the importance of the National Cholesterol Education Program (NCEP) Therapeutic Lifestyle Changes (TLC) diet and received instructions on how to follow this diet. Patients who required a washout: The screening visit occurred at Visit 1 (Week—8). Eligible patients began a 6-week washout period at the screening visit. Patients received counseling regarding the NCEP TLC diet and received instructions on how to follow this diet. Site personnel contacted patients who did not qualify for participation based on screening laboratory test results to instruct them to resume their prior lipid-altering medications.

At the end of the 4-week diet and lifestyle stabilization period or the 6-week diet and stabilization and washout period, eligible patients entered the 2-week TG qualifying period and had their fasting TG level measured at Visit 2 (Week—2) and Visit 3 (Week—1). Eligible patients must have had an average fasting TG level≥500 mg/dL and ≤1500 mg/dL (≥5.65 mmol/L and ≤16.94 mmol/L) to enter the 12-week double-blind treatment period. The TG level for qualification was based on the average (arithmetic mean) of the Visit 2 (Week—2) and Visit 3 (Week—1) values. If a patient's average TG level from Visit 2 and Visit 3 fell outside the required range for entry into the study, an additional sample for fasting TG measurement was collected 1 week later at Visit 3.1. If a third sample was collected at Visit 3.1, entry into the study was based on the average (arithmetic mean) of the values from Visit 3 and Visit 3.1.

After confirmation of qualifying fasting TG values, eligible patients entered a 12-week, randomized, double-blind treatment period. At Visit 4 (Week 0), patients were randomly assigned to one of the following treatment groups:
AMR101 2 g daily,
AMR101 4 g daily, or
Placebo.

During the double-blind treatment period, patients returned to the site at Visit 5 (Week 4), Visit 6 (Week 11), and Visit 7 (Week 12) for efficacy and safety evaluations.

Patients who completed the 12-week double-blind treatment period were eligible to enter a 40-week, open-label, extension period at Visit 7 (Week 12). All patients received open-label AMR101 4 g daily. From Visit 8 (Week 16) until the end of the study, changes to the lipid-altering regimen were permitted (e.g., initiating or raising the dose of statin or adding non-statin, lipid-altering medications to the regimen), as guided by standard practice and prescribing information. After Visit 8 (Week 16), patients returned to the site every 12 weeks until the last visit at Visit 11 (Week 52).

Eligible patients were randomly assigned at Visit 4 (Week 0) to orally receive AMR101 2 g daily, AMR101 4 g daily, or placebo for the 12-week double-blind treatment period. AMR101 was provided in 1 g liquid-filled, oblong, gelatin capsules. The matching placebo capsule was filled with light liquid paraffin and contained 0 g of AMR101. During the double-blind treatment period, patients took 2 capsules (AMR101 or matching placebo) in the morning and 2 in the evening for a total of 4 capsules per day. Patients in the AMR101 2 g/day treatment group received 1 AMR101 1 g capsule and 1 matching placebo capsule in the morning and in the evening. Patients in the AMR100 4 g/day treatment group received 2 AMR101 1 g capsules in the morning and evening.

Patients in the placebo group received 2 matching placebo capsules in the morning and evening. During the extension period, patients received open-label AMR101 4 g daily. Patients took 2 AMR101 1 g capsules in the morning and 2 in the evening.

The primary efficacy variable for the double-blind treatment period was percent change in TG from baseline to Week 12 endpoint. The secondary efficacy variables for the double-blind treatment period included the following:

Percent changes in total cholesterol (TC), high-density lipoprotein cholesterol (HDL-C), calculated low-density lipoprotein cholesterol (LDL-C), calculated non-high-density lipoprotein cholesterol (non-HDL-C), and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein(a) from baseline to Week 12 (selected sites only);

Percent changes in LDL particle number and size, measured by nuclear magnetic resonance, from baseline to Week 12 (selected sites only);

Percent change in remnant-like particle cholesterol from baseline to Week 12 (selected sites only);

Percent change in oxidized LDL from baseline to Week 12 (selected sites only);

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase A2 from baseline to Week 12 (selected sites only);

Change in intracellular adhesion molecule-1 from baseline to Week 12 (selected sites only);

Change in interleukin-6 from baseline to Week 12 (selected sites only);

Change in plasminogen activator inhibitor-1 from baseline to Week 12 (selected sites only);

Change in hsCRP from baseline to Week 12 (selected sites only);

Change in serum phospholipid EPA content from baseline to Week 12;

Change in red blood cell membrane EPA content from baseline to Week 12; and

Change in serum phospholipid and red blood cell membrane content in the following fatty acids from baseline to Week 12: docosapentaenoic acid, docosahexaenoic acid, arachidonic acid, palmitic acid, stearic acid, and oleic acid.

The efficacy variable for the open-label extension period was percent change in fasting TG from extension baseline to end of treatment. Safety assessments included adverse events, clinical laboratory measurements (chemistry, hematology, and urinalysis), 12-lead electrocardiograms (ECGs), vital signs, and physical examinations For TG, TC, HDL-C, calculated LDL-C, calculated non-HDL-C, and VLDL-C, baseline was defined as the average of Visit 4 (Week 0) and the preceding lipid qualifying visit (either Visit 3 [Week—1] or if it occurs, Visit 3.1) measurements. Baseline for all other efficacy parameters was the Visit 4 (Week 0) measurement.

For TC, HDL-C, calculated LDL-C, calculated non-HDL-C, and VLDL-C, Week 12 endpoint was defined as the average of Visit 6 (Week 11) and Visit 7 (Week 12) measurements. Week 12 endpoint for all other efficacy parameters was the Visit 7 (Week 12) measurement.

The primary efficacy analysis was performed using a 2-way analysis of covariance (ANCOVA) model with treatment as a factor and baseline TG value as a covariate. The least-squares mean, standard error, and 2-tailed 95% confidence interval for each treatment group and for each comparison was estimated. The same 2-way ANCOVA model was used for the analysis of secondary efficacy variables.

The primary analysis was repeated for the per-protocol population to confirm the robustness of the results for the intent-to-treat population.

The primary efficacy variable was the percent change in fasting TG levels from baseline to Week 12. A sample size of 69 completed patients per treatment group was expected to provide ≥90% power to detect a difference of 30% between AMR101 and placebo in percent change from baseline in fasting TG levels, assuming a standard deviation of 45% in TG measurements and a significance level of $p<0.01$. To accommodate a 15% drop-out rate from randomization to completion of the double-blind treatment period, a total of 240 randomized patients was planned (80 patients per treatment group).

Example 2

A multi-center, placebo-controlled, randomized, double-blind, 12-week study was performed to evaluate the efficacy and safety of >96% E-EPA in patients with fasting triglyceride levels≥200 mg/dl and <500 mg/dl despite statin therapy (the mean of two qualifying entry values needed to be >185 mg/dl and at least one of the values needed to be >200 mg/dl). The primary objective of the study was to determine the efficacy of >96% E-EPA 2 g daily and 4 g daily, compared to placebo, in lowering fasting TG levels in patients with high risk for cardiovascular disease and with fasting TG levels 200 mg/dl and <500 mg/dl, despite treatment to LDL-C goal on statin therapy.

The secondary objectives of this study were the following:

1. To determine the safety and tolerability of >96% E-EPA 2 g daily and 4 g daily;
2. To determine the effect of >96% E-EPA on lipid and apolipoprotein profiles including total cholesterol (TC), non-high-density lipoprotein cholesterol (non-HDL-C), low density lipoprotein cholesterol (LDL-C), high density lipoprotein cholesterol (HDL-C), and very high density lipoprotein cholesterol (VHDL-C);
3. To determine the effect of >96% E-EPA on lipoprotein associated phospholipase $A_2$ (Lp-$PLA_2$) from baseline to week 12;
4. To determine the effect of >96% E-EPA on low-density lipoprotein (LDL) particle number and size;
5. To determine the effect of >96% E-EPA on oxidized LDL;
6. To determine the effect of >96% E-EPA on fasting plasma glucose (FPG) and hemoglobin $A_{1c}$ ($HbA_{1c}$);
7. To determine the effect of >96% E-EPA on insulin resistance;
8. To determine the effect of >96% E-EPA on high-sensitivity C-reactive protein (hsCRP);
9. To determine the effects of >96% E-EPA 2 g daily and 4 g daily on the incorporation of fatty acids into red blood cell membranes and into plasma phospholipids;
10. To explore the relationship between baseline fasting TG levels and the reduction in fasting TG levels; and 11. To explore the relationship between changes of fatty acid concentrations in plasma and red blood cell membranes, and the reduction in fasting TG levels.

The population for this study was men and women >18 years of age with a body mass index; 45 kg/m² with fasting TG levels greater than or equal to 200 mg/dl and less than 500 mg/dl and on a stable does of statin therapy (with or without ezetimibe). The statin was atorvostatin, rosuvastatin or simvastatin. The dose of statin must have been stable for >4 weeks prior to the LDL-C/TG baseline qualifying measurement for randomization. The statin dose was optimized such that the patients are at their LDL-C goal at the LDL-C/TG baseline qualifying measurements. The same statin at the same dose was continued until the study ended.

Patients taking any additional non-statin, lipid-altering medications (niacin>200 mg/day, fibrates, fish oil, other products containing omega-3 fatty acids, or other herbal products or dietary supplements with potential lipid-altering effects), either alone or in combination with statin therapy (with or without ezetimibe), must have been able to safely discontinue non-statin, lipid-altering therapy at screening.

Patients at high risk for CVD, i.e., patients with clinical coronary heart disease (CHD) or clinical CHD risk equivalents (10-year risk >20%) as defined in the National Cholesterol Education Program (NCEP) Adult Treatment Panel III (ATP III) Guidelines were eligible to participate in this study. Those included patients with any of the following criteria: (1) Known CVD, either clinical coronary heart disease (CHD), symptomatic carotid artery disease (CAD), peripheral artery disease (PAD) or abdominal aortic aneurism; or (2) Diabetes Mellitus (Type 1 or 2).

Approximately 702 patients were randomized at approximately 80 centers in the U.S. The study was a 18- to 20-week, Phase 3, multi-center study consisting of 2 study periods: (1) A 6- to 8-week screening period that included a diet and lifestyle stabilization, a non-statin lipid-altering treatment washout, and an LDL-C and TG qualifying period and (2) A 12-week, double-blind, randomized, placebo-controlled treatment period.

During the screening period and double-blind treatment period, all visits were within ±3 days of the scheduled time. All patients continued to take the statin product (with or without ezetimibe) at the same dose they were taking at screening throughout their participation in the study.

The 6- to 8-week screening period included a diet and lifestyle stabilization, a non-statin lipid-altering treatment washout, and an LDL-C and TG qualifying period. The screening visit (Visit 1) occurred for all patients at either 6 weeks (for patients on stable statin therapy [with or without ezetimibe] at screening) or 8 weeks (for patients who will require washout of their current non-statin lipid-altering therapy at screening) before randomization, as follows:

Patients who did not require a washout: The screening visit occurred at Visit 1 (Week—6). Eligible patients entered a 4-week diet and lifestyle stabilization period. At the screening visit, all patients received counseling regarding the importance of the National Cholesterol Education Program (NCEP) Therapeutic Lifestyle Changes (TLC) diet and received basic instructions on how to follow this diet.

Patients who required a washout: The screening visit occurred at Visit 1 (Week—8). Eligible patients began a 6-week washout period at the screening visit (i.e. 6 weeks washout before the first LDL-C/TG qualifying visit). Patients received counseling regarding the NCEP TLC diet and received basic instructions on how to follow this diet. Site personnel contacted patients who did not qualify for participation based on screening laboratory test results to instruct them to resume their prior lipid-altering medications.

At the end of the 4-week diet and lifestyle stabilization period or the 6-week diet and stabilization and washout period, eligible patients entered the 2-week LDL-C and TG qualifying period and had their fasting LDL-C and TG levels measured at Visit 2 (Week—2) and Visit 3 (Week—1). Eligible patients must have had an average fasting LDL-C level≥40 mg/dL and <100 mg/dL and an average fasting TG level≥200 mg/dL and <500 mg/dL to enter the 12-week double-blind treatment period. The LDL-C and TG levels for qualification were based on the average (arithmetic mean) of the Visit 2 (Week—2) and Visit 3 (Week—1) values. If a patient's average LDL-C and/or TG levels from Visit 2 and Visit 3 fell outside the required range for entry into the study, an additional fasting lipid profile was collected 1 week later at Visit 3.1. If a third sample was collected at Visit 3.1, entry into the study was based on the average (arithmetic mean) of the values from Visit 3 and Visit 3.1.

After confirmation of qualifying fasting LDL-C and TG values, eligible patients entered a 12-week, randomized, double-blind treatment period. At Visit 4 (Week 0), patients were randomly assigned to 1 of the following treatment groups:
>96% E-EPA 2 g daily,
>96% E-EPA 4 g daily, or
Placebo.

226 to 234 patients per treatment group were randomized in this study. Stratification was by type of statin (atorvastatin, rosuvastatin or simvastatin), the presence of diabetes, and gender.

During the double-blind treatment period, patients returned to the site at Visit 5 (Week 4), Visit 6 (Week 11), and Visit 7 (Week 12) for efficacy and safety evaluations.

Eligible patients were randomly assigned at Visit 4 (Week 0) to receive orally >96% E-EPA 2 g daily, >96% E-EPA 4 g daily, or placebo.

>96% E-EPA was provided in 1 g liquid-filled, oblong, gelatin capsules. The matching placebo capsule was filled with light liquid paraffin and contained 0 g of >96% E-EPA. >96% E-EPA capsules were to be taken with food (i.e. with or at the end of a meal).

During the double-blind treatment period, patients were to take 2 capsules (>96% E-EPA or matching placebo) in the morning and 2 capsules in the evening for a total of 4 capsules per day.

Patients in the >96% E-EPA 2 g/day treatment group received 1 >96% E-EPA 1 g capsule and 1 matching placebo capsule in the morning and in the evening.

Patients in the >96% E-EPA 4 g/day treatment group received 2 >96% E-EPA 1 g capsules in the morning and evening.

Patients in the placebo group received 2 matching placebo capsules in the morning and evening.

The primary efficacy variable for the double-blind treatment period was percent change in TG from baseline to Week 12 endpoint. The secondary efficacy variables for the double-blind treatment period included the following:

Percent changes in total cholesterol (TC), high-density lipoprotein cholesterol (HDL-C), LDL-C, calculated non-HDL-C, and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein(a) from baseline to Week 12;

Percent changes in LDL particle number and size, measured by nuclear magnetic resonance, from baseline to Week 12;

Percent change in remnant-like particle cholesterol from baseline to Week 12;

Percent change in oxidized LDL from baseline to Week 12;

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase $A_2$ (Lp-$PLA_2$) from baseline to Week 12;

Change in intracellular adhesion molecule-1 from baseline to Week 12;

Change in interleukin-2 from baseline to Week 12;

Change in plasminogen activator inhibitor-1 from baseline to Week 12. Note: this parameter will only be collected at sites with proper storage conditions;

Change in hsCRP from baseline to Week 12; and

Change in plasma concentration and red blood cell membrane content of fatty acid from baseline to Week 12 including EPA, docosapentaenoic acid (DPA), docosahexaenoic acid (DHA), arachidonic acid (AA), dihomo-γ-linolenic acid (DGLA), the ratio of EPA/AA, ratio of oleic acid/stearic acid (OA/SA), and the ratio of total omega-3 acids over total omega-6 acids.

Safety assessments included adverse events, clinical laboratory measurements (chemistry, hematology, and urinalysis), 12-lead electrocardiograms (ECGs), vital signs, and physical examinations.

For TG, TC, HDL-C, LDL-C, calculated non-HDL-C, and VLDL-C, baseline was defined as the average of Visit 4 (Week 0) and the preceding lipid qualifying visit (either Visit 3 [Week—1] or if it occurs, Visit 3.1) measurements. Baseline for all other efficacy parameters was the Visit 4 (Week 0) measurement.

For TG, TC, HDL-C, LDL-C, calculated non-HDL-C, and VLDL-C, Week 12 endpoint was defined as the average of Visit 6 (Week 11) and Visit 7 (Week 12) measurements.

Week 12 endpoint for all other efficacy parameters were the Visit 7 (Week 12) measurement.

The primary efficacy analysis was performed using a 2-way analysis of covariance (ANCOVA) model with treatment as a factor and baseline TG value as a covariate. The least-squares mean, standard error, and 2-tailed 95% confidence interval for each treatment group and for each comparison were estimated. The same 2-way ANCOVA model was used for the analysis of secondary efficacy variables.

The primary analysis was repeated for the per-protocol population to confirm the robustness of the results for the intent-to-treat population.

Non-inferiority tests for percent change from baseline in LDL-C were performed between >96% E-EPA doses and placebo using a non-inferiority margin of 6% and a significant level at 0.05.

For the following key secondary efficacy parameters, treatment groups were compared using Dunnett's test to control the Type 1 error rate: TC, LDL-C, HDL-C, non-HDL-C, VLDL-C, Lp-$PLA_2$, and apo B. For the remaining secondary efficacy parameters, Dunnett's test was be used and the ANCOVA output were considered descriptive.

The evaluation of safety was based primarily on the frequency of adverse events, clinical laboratory assessments, vital signs, and 12-lead ECGs. The primary efficacy variable is the percent change in fasting TG levels from baseline to Week 12. A sample size of 194 completed patients per treatment group provided 90.6% power to detect a difference of 15% between >96% E-EPA and placebo in percent change from baseline in fasting TG levels, assuming a standard deviation of 45% in TG measurements and a significance level of $p<0.05$.

Previous data on fasting LDL-C show a difference in percent change from baseline of 2.2%, with a standard deviation of 15%, between study drug and placebo. A sample size of 194 completed patients per treatment group provided 80% power to demonstrate non-inferiority ($p<0.05$, one-sided) of the LDL-C response between >96% E-EPA 4 g daily and placebo, within a 6% margin. To accommodate a 10% drop-out rate from randomization to completion of the double-blind treatment period, a total of 648 randomized patients was planned (216 patients per treatment group); 702 subjects were randomized, as further described below.

Results

Of the 702 randomized subjects, 687 were in the intent-to-treat ("ITT") population as follows:

Ultra-pure EPA, 4 g/day: 226 subjects
Ultra-pure EPA, 2 g/day: 234 subjects
Placebo: 227 subjects Lipids were extracted from plasma and red blood cell ("RBC") suspensions and converted into fatty acid methyl esters for analysis using a standard validated gas chromatography/flame ionization detection method. Fatty acid parameters were compared between EPA treatment groups and placebo using an ANCOVA model with treatment, gender, type of statin therapy, and presence of diabetes as factors, and the baseline parameter value as a covariate. LSMs, SEs, and 2-tailed 95% confidence intervals for each treatment group and for each comparison were determined.

Baseline characteristics of the three ITT groups were comparable, with 61.4% of the ITT subjects being male, 96.3% being white, having a mean age of 61.4 years, a weight of 95.7 kg and a BMI of 32.9 kg/m$^2$. ITT subjects with incomplete fatty acid data at baseline and/or at 12 weeks were excluded from the analyses described below.

Example 3

An experiment was conducted to test EPA in model membranes enriched with PUFAs and cholesterol at levels that reproduce disease or high CV-risk conditions (i.e., hypercholesterolemia).

The effects of EPA on lipid peroxide (LOOH) formation were examined at a cholesterol-to-phospholipid (C/P) mole ratio of 0.6:1. Levels of lipid hydroperoxides were also measured in cholesterol-enriched membrane prepared in the absence of EPA as a control.

1,2-Dilinoleoyl-3-sn-phosphatidylcholine (DLPC) was obtained from Avanti Polar Lipids (Alabaster, Ala.) and stored in chloroform (25 mg/ml) at −80° C. until use. Cholesterol obtained and stored in chloroform (10 mg/ml) at −20° C. CHOD-iodide color reagent (stock) was prepared according to a procedure modified from El-Saadani et al. (El-Saadani M, Esterbauer H, El-Sayed M, Goher M, Nassar A Y, Jurgens G. A spectrophotometric assay for lipid peroxides in serum lipoproteins using commercially available reagent. *J. Lipid. Res.* 1989; 30:627-30) consisted of 0.2 M $K_2HPO_4$, 0.12 M KI, 0.15 mM $NaN_3$, 10 μM ammonium molybdate, and 0.1 g/L benzalkonium chloride. Prior to experimental use, the CHOD reagent was activated by adding 24 µM ethylenediaminetetraacetic acid (EDTA), 20 M butylated hydroxytoluene (BHT), and 0.2% Triton X-100. The EPA and lipids were added in a ratio of 1:30 during membrane sample preparation to ensure full incorporation into the lipid bilayers.

Membrane samples consisting of DLPC±cholesterol were prepared as follows. Component lipids (in chloroform) were transferred to 13×100 mm test tubes and shell-dried under a steady stream of nitrogen gas while vortex mixing. The lipid was co-dried with EPA.

Residual solvent was removed by drying for a minimum of 3 h under vacuum. After desiccation, each membrane sample was resuspended in diffraction buffer (0.5 mM HEPES, 154 mM NaCl, pH 7.3) to yield a final phospholipid concentration of 1.0 mg/mL. Multilamellar vesicles (MLV) were formed by vortex mixing for 3 minutes at ambient temperature. Bangham A D, Standish M M, Watkins J C. Diffusion of univalent ions across the lamellae of swollen phospholipids. *J. Mol. Biol.* 1965; 13:238-52. Immediately after initial MLV preparation, aliquots of each membrane sample will be taken for baseline (0 h) peroxidation analyses.

All lipid membrane samples were subjected to time-dependent autoxidation by incubating at 37° C. in an uncovered, shaking water bath for 72 hours. Small aliquots of each sample were removed at 24 h intervals and combined with 1.0 mL of active CHOD-iodide color reagent. To ensure spectrophotometric readings within the optimum absorbance range, sample volumes taken for measurement of lipid peroxide formation were adjusted for length of peroxidation and range between 100 and 10 µL. Test samples were immediately covered with foil and incubated at room temperature for >4 h in the absence of light. Absorbances were measured against a CHOD blank at 365 nm using a Beckman DU-640 spectrophotometer.

The CHOD colorimetric assay is based on the oxidation of iodide (I⁻) by lipid hydroperoxides (LOOH) and proceeds according to the following reaction scheme:

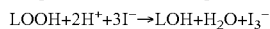

$$LOOH + 2H^+ + 3I^- \rightarrow LOH + H_2O + I_3^-$$

The quantity of triiodide anion ($I_3^-$) liberated in this reaction is directly proportional to the amount of lipid hydroperoxides present in the membrane sample. The molar absorptivity value (E) of $I_3^-$ is $2.46 \times 10^4$ $M^{-1}$ $cm^{-1}$ at 365 nm.

Cholesterol domain peak intensity was calculated from multiple small angle x-ray diffraction measurements, which are directly proportional to domain levels. After exposure to autoxidation as described above, vehicle-treated controls displayed a cholesterol domain peak intensity of 77.6±58.5, corresponding to an increase in LOOH formation from 89±1 µM to 6616±250 µM (p<0.001). EPA-treated membranes reduced LOOH levels by greater than 90% (728±30 µM) compared to untreated controls (p<0.001).

This example demonstrates that EPA inhibits cholesterol crystalline domain formation in a manner related to its potent antioxidant effects in PUFA-enriched model membranes. These data suggest that EPA blocks membrane lipid oxidation and structural reorganization through free radical chain-breaking mechanisms.

Example 4

An experiment was conducted to test the ability of EPA to interfere with the effects of high glucose on membrane lipid peroxidation and organization in vesicles enriched with PUFAs.

At elevated levels, the aldose sugar glucose produces non-enzymatic chemical modifications to membrane proteins and phospholipids, leading to advanced glycation endproducts (AGEs) and cell injury. Oxidative stress and AGEs have been implicated in both the microvascular and macrovascular complications of diabetes and other metabolic disorders. In membranes enriched with polyunsaturated fatty acids (PUFA), hyperglycemia promotes the formation of free radicals and cholesterol crystalline domains associated with atherosclerosis. The non-enzymatic effects of glucose on cholesterol crystalline domain formation were shown to be enhanced under conditions of high cholesterol and could not be reproduced by mannitol. Oxidative damage to PUFAs with glucose is of particular interest given its role in the propagation of free radicals during vascular injury and insulin resistance. In addition to cellular membranes, oxidation of PUFAs in low-density lipoproteins (LDL) contributes to endothelial dysfunction, inflammation, and atherosclerotic foam cell formation.

1,2-Dilinoleoyl-sn-glycero-3-phosphocholine (DLPC) and monomeric cholesterol (isolated from ovine wool) were purchased from Avanti Polar Lipids (Alabaster, Ala.) and solubilized at 25 and 10 mg/mL, respectively. EPA, α-linolenic acid (ALA; 18:3, n-3) was purchased from Sigma-Aldrich (Saint Louis, Mo.) and solubilized in ethanol to 1 mM under nitrogen atmosphere. Vitamin E (α-tocopherol) was also purchased from Sigma-Aldrich and prepared in ethanol at 1.0 mM ($\varepsilon = 3.06 \times 10^4$ $M^{-1}$ $cm^{-1}$ at 294 nm) just prior to experimental use. Atorvastatin ortho- (o-) hydroxy (active) metabolite was purchased from Toronto Research Chemicals (North York, Ontario, Canada) and solubilized in methanol to 1.0 mM. All test compounds were further diluted in ethanol or aqueous buffer as needed. Glucose was prepared in saline buffer (0.5 mM HEPES, 154 mM NaCl, pH 7.3) at 11.0 mM (200 mg/dL).

CHOD-iodide color reagent (stock) was prepared, with slight modification, as described by from El-Saadani et al. (*J. Lipid Res.*, vol. 30, pages 627-630 (1989)) and consisted of 0.2 M $K_2HPO_4$, 0.12 M KI, 0.15 mM $NaN_3$, 10 µM ammonium molybdate, and 0.1 g/L benzalkonium chloride. Prior to experimental use, the CHOD reagent was activated by adding 24 µM ethylenediaminetetraacetic acid (EDTA), 20 µM butylated hydroxytoluene (BHT), and 0.2% Triton X-100.

Multilamellar vesicles (MLVs) were prepared as binary mixtures of DLPC (1.0 or 2.5 mg total phospholipid per sample) and cholesterol at a fixed cholesterol-to-phospholipid (C/P) mole ratio of 0.6:1. Component lipids (in chloroform) were transferred to 13×100 mm borosilicate culture tubes and combined with vehicle (ethanol) or an equal volume of fatty acid, vitamin E, or ATM stock solutions, each adjusted to achieve desired treatment concentrations. Samples were shell-dried under nitrogen gas and placed under vacuum for 1 h to remove residual solvent. After desiccation, each sample was resuspended in 1.0 mL glucose-containing saline to yield final phospholipid concentrations of 1.0 or 2.5 mg/mL (for lipid peroxidation or x-ray diffraction analysis, respectively). Lipid suspensions were then vortexed for 3 min at ambient temperature to form MLVs.

All MLV samples were subjected to time-dependent autoxidation by incubating at 37° C. in an uncovered, shaking water bath. This method allows lipid peroxidation to occur gradually without requiring the use of exogenous initiators. Small aliquots (5-100 µL) of each sample were removed, immediately following MLV preparation (0 hour) and after exposing samples to oxidative conditions for 72 or 96 hour, and combined with 1.0 mL of activated CHOD-iodide color reagent. Aliquot volume was reduced with each successive time point to ensure that spectrophotometric readings were within the optimal adsorption range. Test samples were covered and incubated in darkness at room temperature for at least 4 hr. Sample absorbances were then measured against a CHOD blank at 365 nm using a Beckman DU-640 spectrophotometer. The CHOD colorimetric assay is based on the oxidation of iodide ($I^-$) by lipid hydroperoxide (LOOH) to form triiodide ($I_3^-$), the quantity of which is directly proportional to the amount of LOOH present in the lipid sample. The molar absorptivity ($I_3^-$) of $I_3^-$ is $2.46 \times 10^4$ $M^{-1}$ $cm^{-1}$ at 365 nm.

The membrane structural effects of glucose and the various compounds examined in this study were measured at 0, 72, and 96 hour intervals. Membrane lipid vesicles were oriented for x-ray diffraction analysis as described by others (e.g., Herbette et al., *Biophys. J.*, vol. 20(2), pages 245-272 (1977)). Briefly, a 100 µL aliquot (containing 250 g MLV) was aspirated from each sample and transferred to a Lucite® sedimentation cell fitted with an aluminum foil substrate upon which a given sample could be collected by centrifugation. Samples were then loaded into a Sorvall AH-629 swinging bucket rotor (DuPont Corp., Wilmington, Del.) and centrifuged at 35,000 g, 5° C., for 90 min.

After centrifugal orientation, sample supernatants were aspirated and aluminum foil substrates, each supporting a single membrane pellet, were removed from the sedimentation cells. Sample pellets were dried for 5-10 min at ambient conditions, mounted onto curved glass supports, and placed in hermetically-sealed, brass or glass containers (for immediate analysis or temporary storage, respectively). All x-ray diffraction experiments were conducted at 20° C., 74% relative humidity. The latter was established by exposing membrane samples to saturated solutions of L-(+) tartaric acid ($K_2C_4H_4O_6 \cdot \frac{1}{2}H_2O$). Samples were incubated at these conditions for at least 1 hour prior to experimental analysis.

Oriented membrane samples were aligned at grazing incidence with respect to a collimated, mono-chromatic $CuK_\alpha$ x-ray beam ($K_{\alpha 1}$ and $K_{\alpha 2}$ unresolved; $\lambda = 1.54$ Å) produced by a Rigaku Rotaflex RU-200, high-brilliance microfocus generator (Rigaku-MSC, The Woodlands, Tex.) as previously described (Mason et al., *Biophys. J.*, vol. 55(4), pages 769-778 (1989)). Diffraction data were collected on a one-dimensional, position-sensitive electron detector (Hecus X-ray Systems, Graz, Austria) at a sample-to-detector distance of 150 mm. Detector calibration was performed by the manufacturer and verified using crystalline cholesterol monohydrate.

The d-space for any given membrane multibilayer is a measurement of the unit cell periodicity of the membrane lipid bilayer (e.g., the distance from the center of one lipid bilayer to the next including surface hydration), and is calculated from Bragg's Law, $h\lambda = 2d\sin\theta$, where h is the diffraction order, $\lambda$ is the wavelength of the x-ray radiation (1.54 Å), d is the membrane lipid bilayer unit cell periodicity, and $\theta$ is the Bragg angle equal to one-half the angle between the incident beam and scattered beam.

The presence of cholesterol domains in a given membrane sample results in the production of distinct Bragg (diffraction) peaks having singular periodicity values of 34 and 17 Å (typically referred to as first- and second-order cholesterol domain peaks). Under the specific temperature and relative humidity conditions established for these experiments, the second-order, 17 Å cholesterol domain peak was well-delineated from other, neighboring cholesterol and phospholipid diffraction peaks and was thus used to quantitate relative cholesterol domain peak intensity. Routines written in Origin 8.6 (OriginLab Corporation, Northampton, Mass.) were used to determine total peak area (associated with all diffraction peaks in a given pattern) against which the second-order cholesterol domain peak was normalized.

Effects of EPA and Vitamin E on Glucose-Induced Lipid Peroxidation

Figure 1:
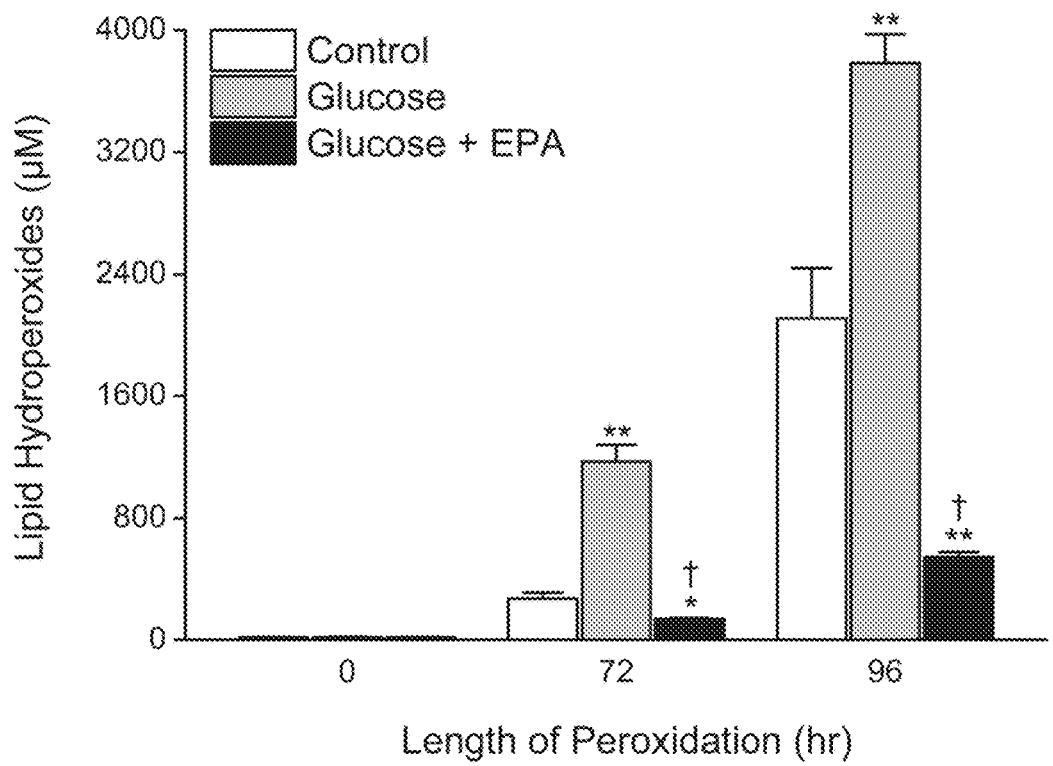
FIG. 1 depicts the effects of ethyl eicosapentaenoate ("EPA") on glucose-induces membrane lipid peroxidation from 0-96 hours compared to glucose or vehicle control.

The effects of hyperglycemia (200 mg/dL) on LOOH formation in lipid vesicles enriched with PUFAs and cholesterol and prepared in the absence (vehicle only) or presence of EPA or vitamin E (each at a 1:30 drug-to-phospholipid mole ratio) were measured. The concentration of glucose selected was consistent with previous experimental studies of hyperglycemia under controlled laboratory conditions or observed in well-defined animal models of Type II diabetes following a glucose challenge. As shown in FIG. 1, glucose significantly increased LOOH formation in a time-dependent manner as compared to vehicle treatment alone. Values in FIG. 1 are mean±S.D. (N=6). EPA inhibited the peroxidative effects of glucose by 88% and 86% at 72 and 96 hours, respectively, which was highly significant ($p<0.001$) as compared to glucose treatment alone. LOOH levels measured in samples treated with EPA were also significantly lower (at the 72- and 96-hour time points) as compared to non-glucose-treated controls. Overall ANOVA-0 hour data: $p=0.6655$, $F=0.4185$; 72 hour data: $p<0.0001$, $F=428.72$; 96 hour data: $p<0.0001$, $F=322.01$.

Figure 2:
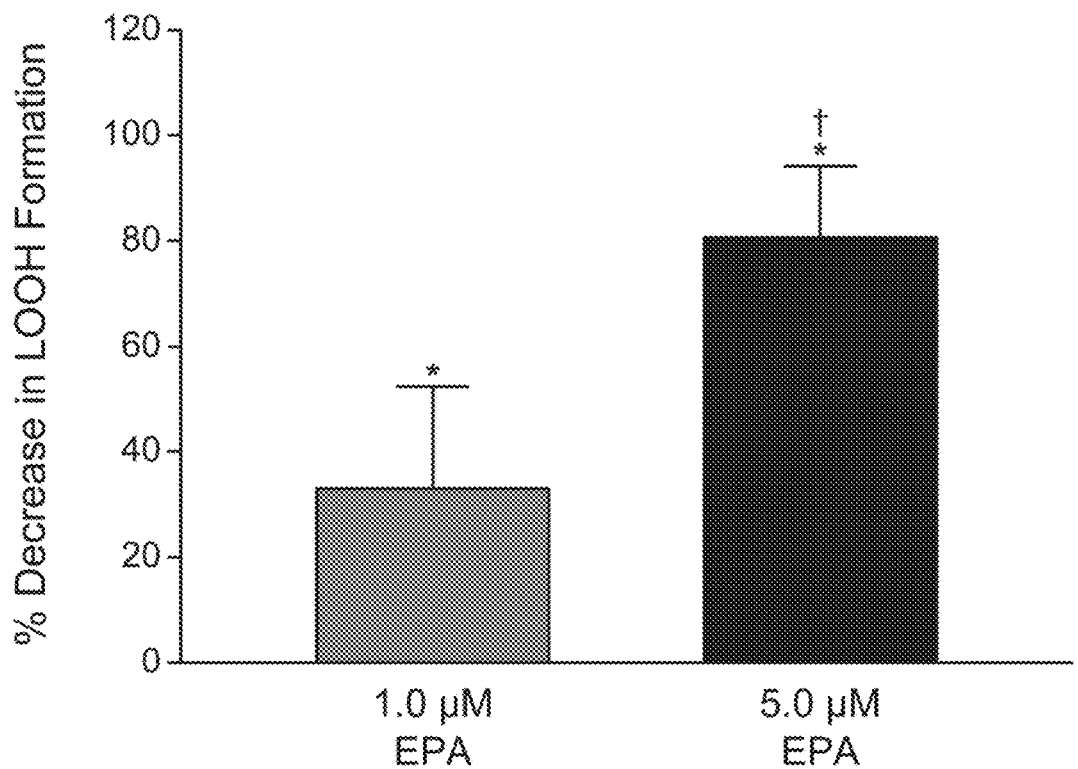
FIG. 2 depicts dose-dependent effects of EPA on glucose-induced membrane lipid peroxidation in model membranes.

EPA was also tested at 1.0 and 5.0 µM and found to inhibit membrane LOOH formation in a dose-dependent manner, as shown in FIG. 2. Values in FIG. 2 are mean±S.D. (N=6-8) and represent % difference between treatment and glucose-treated controls. These concentrations are similar to those measured in the plasma of patients with prescribed levels of EPA. Overall ANOVA: $p<0.0001$, $F=99.900$.

Figure 3:
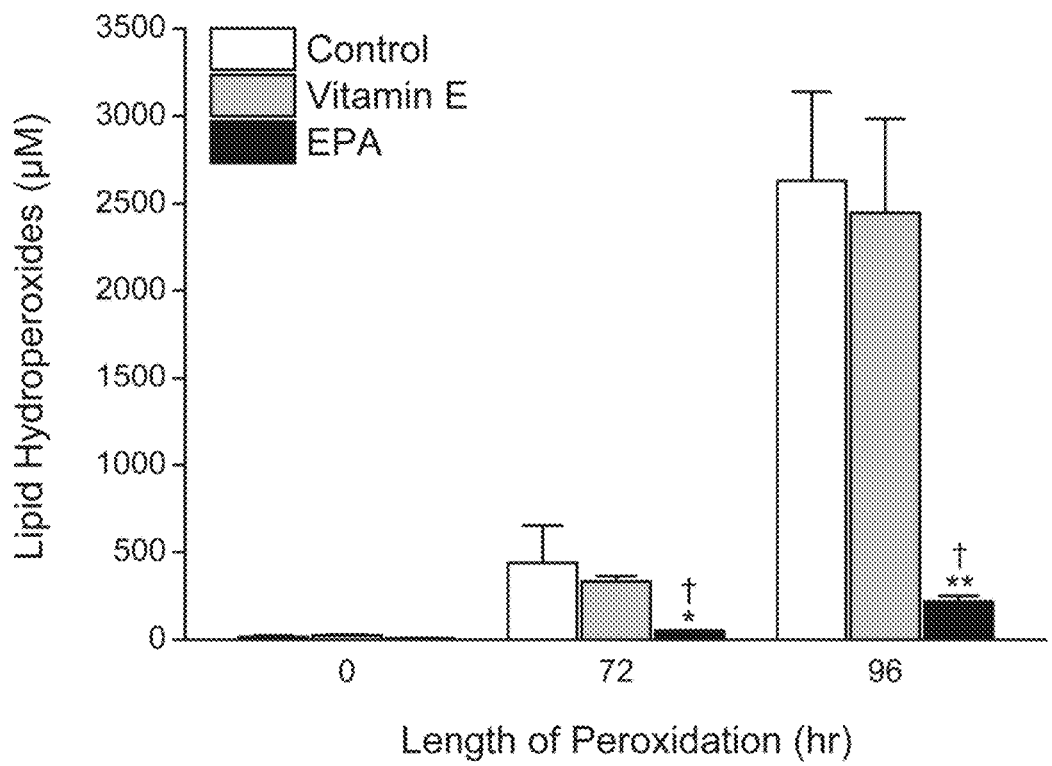
FIG. 3 shows a comparison of the effects of vitamin E and EPA on glucose-induced membrane lipid peroxidation in model membranes.

Vitamin E was also examined in this assay at the same drug-to-phospholipid mole ratio used for testing the basic antioxidant effects of EPA. As shown in FIG. 3, EPA significantly inhibited LOOH formation at the 72- and 96-hour time points. Values in FIG. 3 are mean+S.D. (N=3). By contrast, vitamin E had no significant effect on lipid peroxidation under identical conditions. Overall ANOVA-0 hour data: $p=0.0073$, $F=12.474$; 72 hour data: $p=0.0204$, $F=7.986$; 96 hour data: $p=0.0008$, $F=29.764$.

Figure 4:
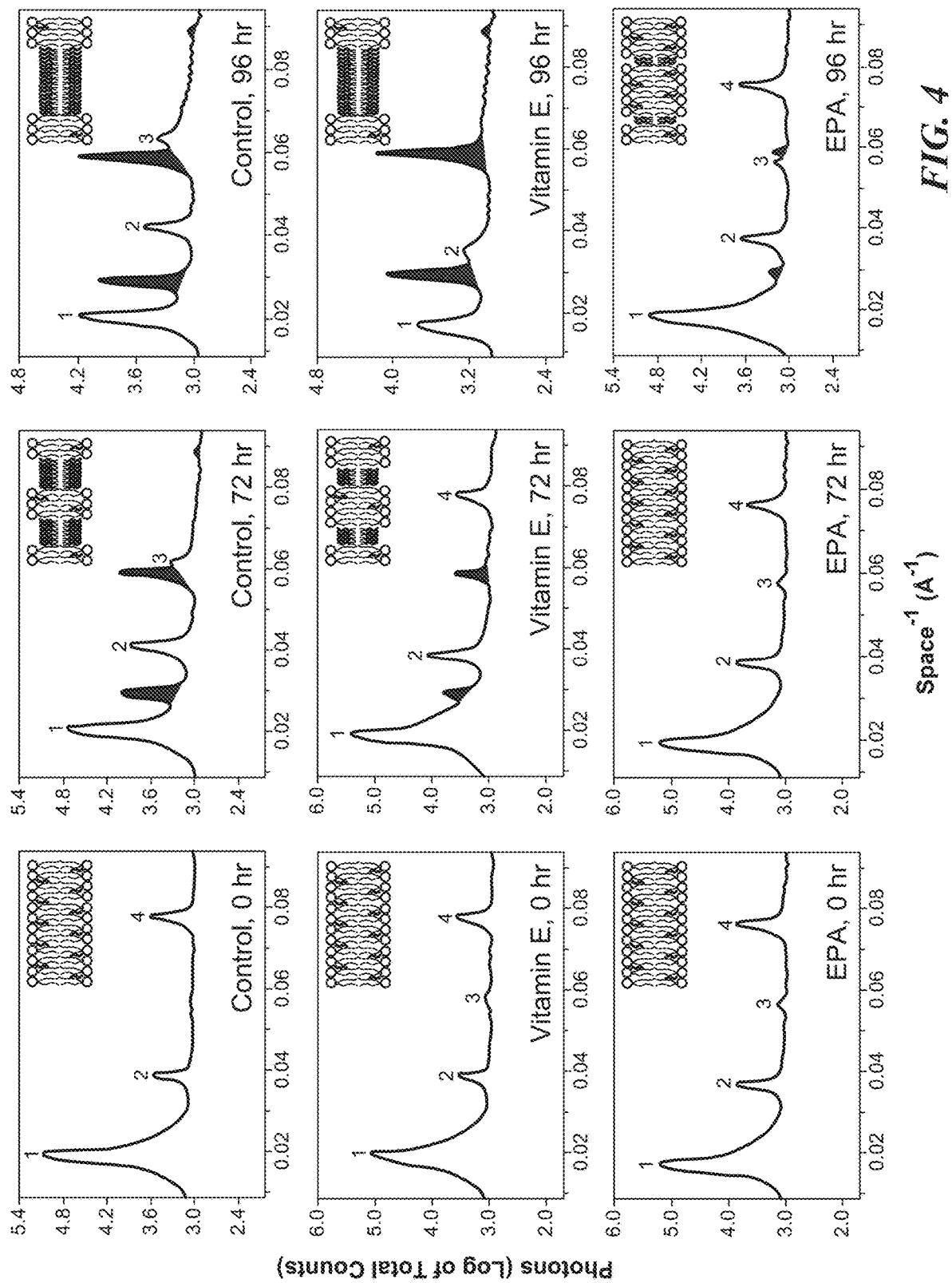
FIG. 4 shows representative X-ray diffraction patterns for model membranes prepared in the presence of glucose and treated with vehicle control (top row), vitamin E (middle row), or EPA (bottom row) at 0 hours (left column), 72 hours (middle column) and 96 hours (right column).

Effects of EPA and Vitamin E on Glucose- and Peroxidation-Induced Changes in Membrane Lipid Structural Organization Lipid peroxidation is highly disruptive to the structural organization of biological membranes and has been shown, in previous studies by Jacob et al. (*J. Biol. Chem.*, vol. 280, pages 39380-39387 (2005)) and Mason et al. (*J. Biol. Chem.*, vol. 281(1), pages 9337-9345 (2006)), to contribute directly to the formation of cholesterol crystalline domains. Glucose has also been reported to promote similar changes in membrane structural organization by increasing lipid peroxidation (Self-Medlin et al., *Biochim. Biophys. Acta*, vol. 1788(6), pages 1398-1403 (2009)). In this study, we used small angle x-ray diffraction to characterize the structural properties of model membranes treated with glucose (200 mg/dL) and prepared in the absence or presence of vitamin E or EPA (each at 1:30 drug-to-phospholipid mole ratio), before and after exposure to oxidative conditions (FIG. 4). At the start of this experiment, vitamin E and EPA were observed to have no appreciable effect on membrane structure as compared to control samples (FIG. 4, left column). Scattering data collected from each membrane preparation yielded up to four diffraction orders having an average unit cell periodicity (d-space) of 51.5 Å, and consistent with a homogenously-distributed, lipid bilayer phase. Following exposure to oxidative conditions for 72 hours, additional peaks, with an average d-space value of 34 Å and consistent with a cholesterol crystalline domain phase, were observed in control and vitamin E-treated membrane samples (FIG. 4, middle column, highlighted peaks). At 96 hours, cholesterol domains peaks were observed in all experimental samples; however, these peaks were disproportionately greater in control and vitamin E-treated samples (FIG. 4, right column, highlighted peaks).

Figure 5:
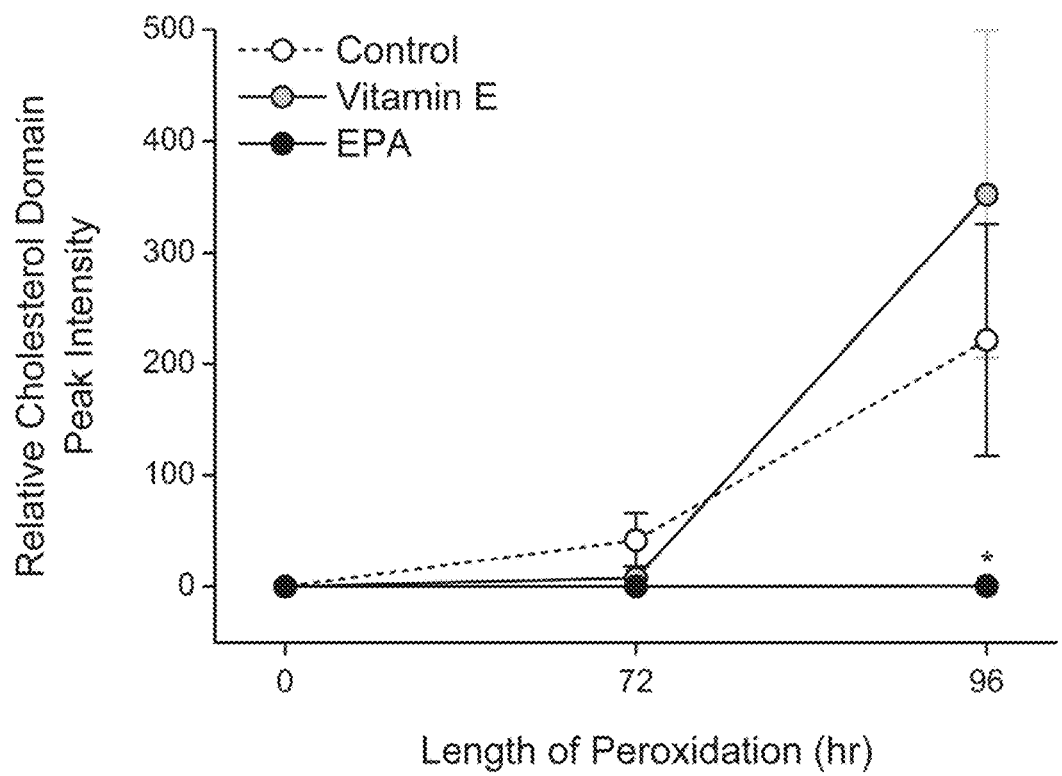
FIG. 5 depicts the quantitative assessment of the comparative effects of vitamin E and EPA on glucose- and peroxidation-induced cholesterol domain formation.

Quantitative assessment of cholesterol domain peak intensity (expressed as the quotient of cholesterol- to total lipid-peak area) indicated that vitamin E had no significant effect on cholesterol domain formation as compared to control at any experimental time point (FIG. 5). Values in FIG. 5 are mean±S.D. (N=3). In contrast, EPA inhibited relative cholesterol domain peak intensity by more than 99% at the 96-hour time point, as compared to either vehicle or vitamin E treatments. Overall ANOVA: $p=0.0075$, $F=8.849$.

Figure 6:
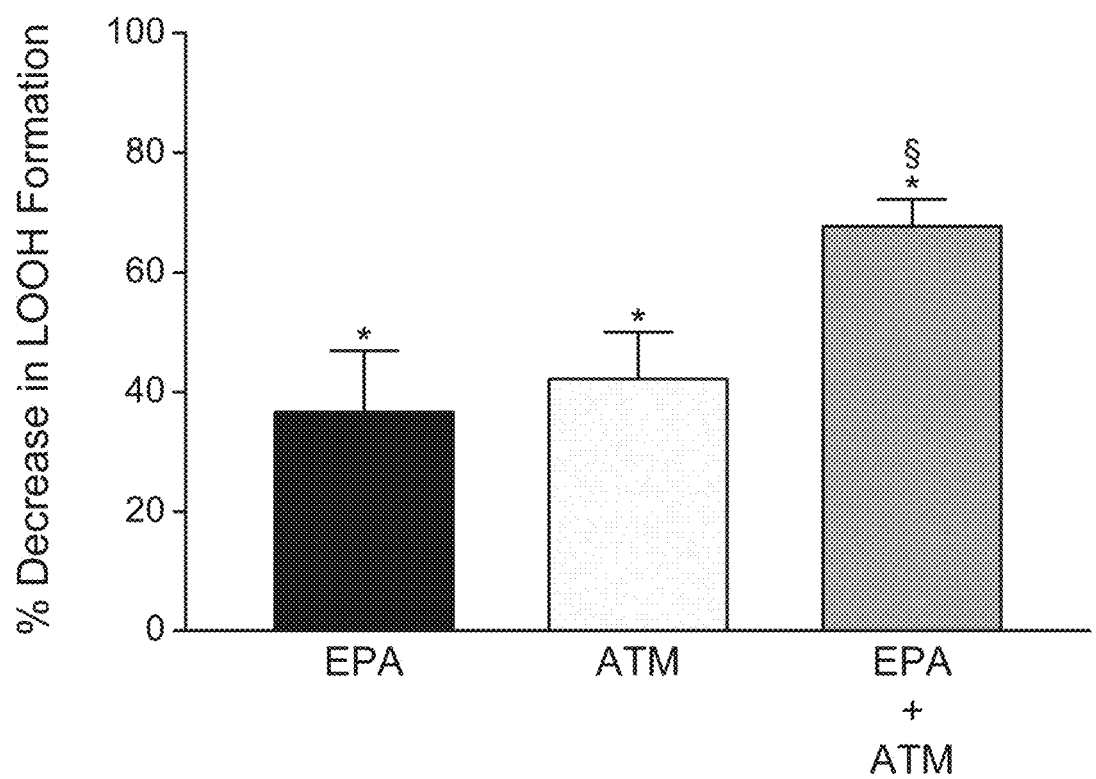
FIG. 6 shows a comparison of the combined effects of EPA and atorvastatin o-hydroxy (active) metabolite ("ATM") to EPA alone and ATM alone on glucose-induced membrane lipid peroxidation.

Separate and Combined Effects of EPA and ATM on Glucose-Induced Membrane Lipid Peroxidation ATM has been shown in previous studies by Teissier et al. (*Circ. Res.*, vol. 95(12), pages 1174-1182 (2004)) and Mason et al. (*Am. J. Cardiol.*, vol. 96(5A), pages 11F-23F (2005)) to have potent antioxidant properties, as observed in human low density lipoprotein as well as model liposomes. The antioxidant effects of ATM were re-examined, separately and in combination with EPA (each at 1.0 µM), in membrane lipid vesicles treated with glucose at 200 mg/dL and exposed to oxidative conditions for 96 hours. Both EPA and ATM were observed to have separate and potent antioxidant effects under these conditions; however, their combination was even more effective, decreasing LOOH formation by >60% ($p<0.001$) as compared to either treatment alone (FIG. 6). Values in FIG. 6 are mean±S.D. (N=6) and represent % difference between treatment and glucose-treated controls. *$p<0.001$ versus glucose-treated control (Student-Newman-Keuls multiple comparisons test; overall ANOVA: $p<0.0001$, $F=111.69$. § $p<0.001$ versus separate EPA or ATM treatments (Student-Newman-Keuls multiple comparisons test; overall ANOVA: $p<0.0001$, $F=26.635$).

Figure 7:
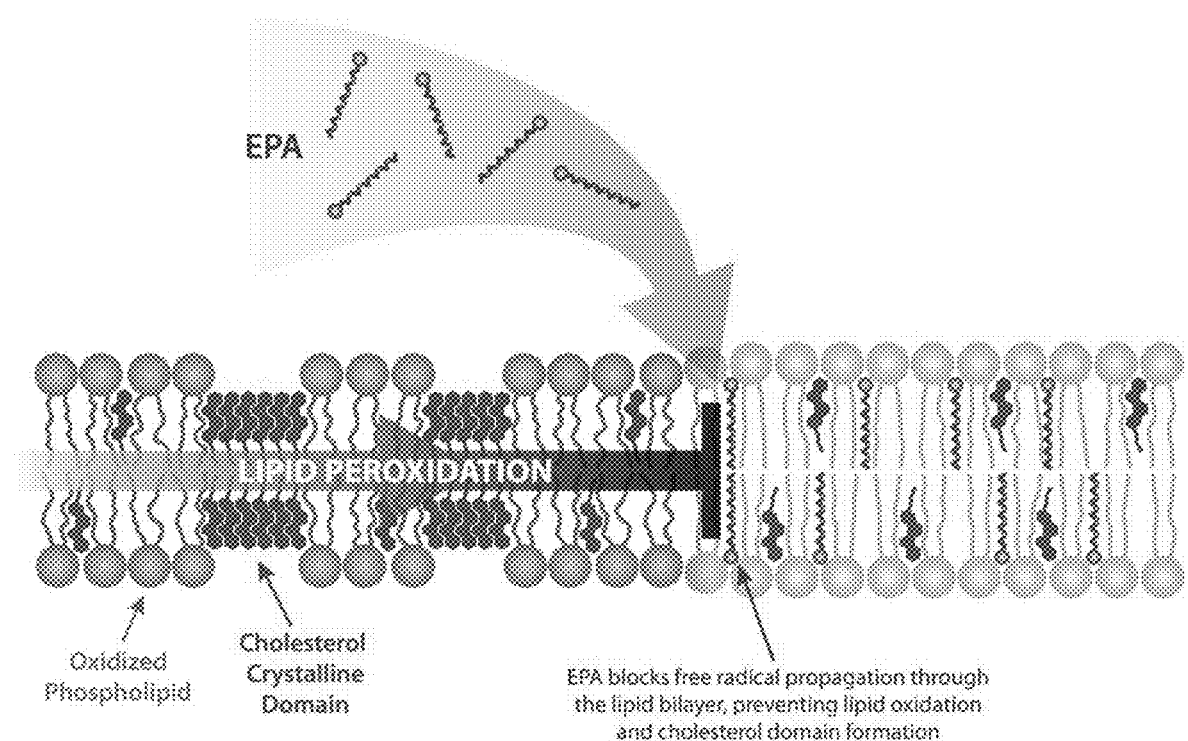
FIG. 7 depicts a schematic representation of one possible mechanism to explain antioxidant and membrane structural effects of EPA.

These data demonstrate that EPA significantly inhibits glucose-induced lipid peroxidation and cholesterol crystalline domain formation in model membrane lipid vesicles. Without wishing to be bound by theory, it is possible that these antioxidant effects are due at least in part to the ability of EPA to quench reactive oxygen species (ROS) associated with the membrane lipid bilayer, thereby preserving normal membrane structure and organization. Following intercalation into the membrane lipid bilayer, the conjugated double bonds associated with EPA may facilitate electron stabilization mechanisms that interfere with free radical propagation (for example, as depicted in FIG. 7). The effects of EPA could not be reproduced with vitamin E, a natural scavenging antioxidant. These findings indicate a potentially preferred intercalation of the EPA molecule into the membrane where it can trap free radicals. The absence of activity for vitamin E under these conditions may be due to its limited lipophilicity and scavenging potential, as previously observed by Mason et al. (*J. Biol. Chem.*, vol. 281(14), pages 9337-9345 (2006)) in membranes enriched with cholesterol. Vitamin E was also unable to interfere with cholesterol crystalline domain development with hyperglycemia. Finally, the antioxidant effects of EPA were enhanced in the presence of ATM which, unlike vitamin E, has been shown by Self-Medlin et al. (*Biochim. Biophys. Acta*, vol. 1788(6), pages 1398-1403 (2009)) and Mason et al. (*J. Biol. Chem.*, vol. 281(14), pages 9337-9345 (2006)) to have potent free radical scavenging properties and high lipophilicity that reduces the formation of cholesterol crystalline domains following oxidative stress or exposure to hyperglycemic conditions. Mason et al. (*J. Biol. Chem.*, vol. 281(14), pages 9337-9345 (2006)) and Aviram et al. (*Atherosclerosis*, vol. 138(2), pages 271-280 (1998)) have attributed the chain-breaking antioxidant mechanism of ATM to its phenoxy moiety. Clinical support for an antioxidant benefit with atorvastatin has also been reported from prospective trials by Tsimikas et al. (*Circulation*, vol. 110(11), pages 1406-1412 (2004)) and Shishehbor et al. (*Circulation*, vol. 108(4), pages 426-431 (2003)).

At high levels, glucose promoted the formation of LOOH, prominent intermediates of peroxidative reactions that have been shown by Girotti et al. (*J. Lipid Res.*, vol. 39(8), pages 1529-1542 (1998)) to lead to changes in the organization of membrane lipid components. Lipid peroxidation is well-known to induce changes in membrane fluidity, increased membrane permeability, and changes in membrane protein activity. Oxidative modification of PUFAs is also known to cause a marked reduction in membrane d-space associated with interdigitation of the phospholipid acyl chain terminal methyl segments. These alterations in the intermolecular packing characteristics of membrane phospholipids promote the displacement of cholesterol into discrete domains (d-space of 34 Å) within the phospholipid bilayer environment. Cholesterol crystalline domains have been shown by Ruocco et al. (*Biophys. J.*, vol. 46, pages 695-707 (1984)) to be induced in model membranes by increasing membrane cholesterol to very high levels (>50 mol %). Similar changes in cholesterol domain formation have been observed in models of atherosclerosis, including in model macrophage foam cells (Kellner-Weibel et al., *Arterioscler. Thromb. Vasc. Biol.*, vol. 19(8), pages 1891-1898 (1999)), in rabbit or rat thoracic mesenteric or pericardium membranes (Abela et al., *Clin. Cardiol.*, vol. 28(9), pages 413-420 (2005)), and rabbit smooth muscle cell plasma membranes (Tulenko et al., *J. Lipid Res.*, vol. 39, pages 947-956 (1998)). The formation of these domains in membranes prepared at constant cholesterol levels but exposed to glucose and glucose-induced lipid peroxidation has also been observed by Self-Medlin et al. (*Biochim. Biophys. Acta*, vol. 1788(6), pages 1398-1403 (2009)). Thus, agents that slow or block the formation of cholesterol into discrete domains and crystals may interfere with mechanisms of atherogenesis associated with hyperglycemia without reductions in cholesterol levels.

As a reducing monosaccharide, glucose is known to be susceptible to reaction at its anomeric carbon with singlet oxygen or other radical initiators. This redox reaction can generate glucose radicals or other reactive oxygen species that have a pro-oxidant effect in biological membranes. Several reaction mechanisms are believed to be responsible for the formation of glycoxidation and lipoxidation products resulting from the reaction of glucose radicals with proteins or lipids to form sugar-amine adducts. The presence of cholesterol in the membrane also contributes to rates of LOOH formation, allowing more efficient radical penetration and propagation through the bilayer. The steroid nucleus of cholesterol has been explained to induce an ordering effect on adjacent phospholipid molecules, thus reducing the intermolecular distance between adjacent PUFA chains of the lipids and facilitating the exchange of free radicals within the hydrocarbon core. Previous studies by Self-Medlin et al. (*Biochim. Biophys. Acta*, vol. 1788(6), pages 1398-1403 (2009)) have demonstrated a cholesterol-dependent increase in LOOH formation, which was enhanced by glucose treatment, in similar model membrane preparations. Others including Bertelsen et al. (*Diabetologia*, vol 44(5), pages 605-613 (2001)) and Cohen et al. (*Am. J. Physiol. Endocrin. Metabol.*, vol. 285(6), pages E1151-1160 (2003)) have suggested that even minor physico-chemical modifications to the cell membrane may lead to the disruption of cholesterol-enriched membrane domains that are critical to many cellular processes (e.g., caveolae) leading to loss in insulin receptor activity and endothelial nitric oxide synthase (eNOS) function.

Glucose-mediated oxidative stress is known to contribute to inflammatory pathways associated with diabetes and atherosclerosis pathophysiology. Glucose, obesity, and oxidative stress reduce intracellular antioxidant defense mechanisms while activating inflammatory responses from transcription factors and kinases, such as c-Jun N-terminal kinase (JNK), protein kinase C (PKC), and inhibitor of kappa B kinase-β (IKKβ). Some inflammatory pathways, such as activation of IKKβ, have a causative role in the deleterious effects of hyperglycemia on endothelial cell function. Hyperglycemia also stimulates NF-kB, which in turn promotes the overexpression of NADPH, a primary source of cellular superoxide. Overproduction of superoxide, accompanied by increased nitric oxide generation, leads to formation of the highly reactive peroxynitrite molecule. Agents with antioxidant activity at the cellular level including, for example, statins, glitazones, and angiotensin converting enzyme (ACE) inhibitors, have been shown to be beneficial in improving insulin resistance.

The present Example demonstrates surprisingly that EPA ameliorates the effects of hyperglycemia, likely due to its potent antioxidant properties. In clinical studies performed by others, compositions including EPA reduced CAD-related events in hypercholesterolemic patients receiving statin treatment. In addition to reductions in triglycerides, treatment with highly purified EPA was associated with significant reductions in levels of oxidized LDL, Lp-PLA$_2$, and hsCRP as compared to placebo. These antioxidant effects are consistent with the presently disclosed findings, which demonstrate EPA to be a potent and direct scavenger of free radicals. ROS and related oxidative damage have been implicated in the pathogenesis of various human chronic diseases. Due to its multiple conjugated double bonds, EPA has higher singlet oxygen quenching ability compared to vitamin E. EPA is expected to fully incorporate into the membrane bilayer, where it can exercise maximum free radical scavenging effects as shown in this study.

The antioxidant effects of EPA were enhanced in combination with the active metabolite of atorvastatin. According to primary pharmacokinetic studies, atorvastatin (parent) is extensively metabolized by hepatic cytochrome P450 to yield a number of active metabolites, which together reportedly account for approximately 70% of circulating HMG-CoA reductase inhibitory activity. This is in contrast to other statins like pravastatin and rosuvastatin that are not metabolized into active metabolites. Beyond their enzymatic effects on serum LDL-C levels, the active metabolites of atorvastatin may provide benefit by interfering with oxidative stress pathways. In a small study by Shishehbor et al. (*Circulation*, vol. 108(4), pages 426-431 (2003)) designed to evaluate the effects of atorvastatin therapy on markers of protein oxidation and inflammation, atorvastatin was found to significantly reduce circulating levels of chlorotyrosine, nitrotyrosine, and dityrosine, all of which act as surrogate markers for specific oxidative pathways upregulated in the atheroma. Interestingly, these effects were observed at a relatively low treatment dose (10 mg, administered for just 12 weeks) and were more significant than reductions in other inflammatory markers, including C-reactive protein. In a larger study by Tsimikas et al. (*Circulation*, vol. 110(11), pages 1406-1412 (2004)) involving 2,341 patients, treatment with a high dose of atorvastatin (80 mg) for 16 weeks caused a significant reduction in levels of oxidized lipids associated with all apoB100-containing lipid particles.

The ability of EPA to interfere with oxidative stress under conditions of hyperglycemia has important clinical implications. Levels of oxidized lipid, measured using monoclonal antibodies against oxLDL, have been shown by Ehara et al. (*Circulation*, vol. 103(15), pages 1955-1960 (2001)) to correlate with the severity of acute coronary syndromes and plaque instability. A more recent longitudinal investigation of 634 patients found that patients with baseline levels of thiobarbituric acid reactive substances ("TBARS") in the highest quartile had significantly increased relative risk for major vascular events and procedures (Walter et al., *J. Am. Coll. Cardiol.*, vol. 44(10), pages 1996-2002 (2004)). The predictive effect of TBARS was observed in a multivariate model adjusted for inflammatory markers (C-reactive protein, sICAM-1, IL-6) and other risk factors (age, LDL-C, high density lipoprotein cholesterol (HDL-C), total cholesterol, triglycerides, BMI, and blood pressure). These analyses indicated that TBARS had an independent effect on major vascular events and procedures. Similar predictive value was observed for LOOH in these same subjects in a follow-up study (Walter et al., *J. Am. Coll. Cardiol.*, vol. 51(12), pages 1196-1202 (2008)). More recently, EPA treatment was associated with significant reductions in triglycerides along with reduced levels of markers of inflammation including hsCRP, Lp-PLA$_2$ and oxidized LDL, as compared to placebo, by Ballantyne et al. (*Am. J. Cardiol.*, vol. 110(7), pages 984-992 (2012)) and Bays et al. (*Am. J. Cardiovasc. Drugs*, vol. 13(1), pages 37-46 (2013); *Am. J. Cardiol.*, vol. 108(5), pages 682-690 (2011)).

In sum, pronounced changes in membrane lipid organization were observed with hyperglycemia, including the formation of cholesterol crystalline domains that correlate with an increase in lipid hydroperoxide (LOOH) formation (an intermediate product of oxidative lipid damage). Treatment of membranes with EPA, but not vitamin E, inhibited changes in membrane structure possibly due to potent chain-breaking antioxidant actions of the EPA molecules.

Example 5

An experiment was conducted to compare the ability of EPA to prevent lipid hydroperoxide formation in model membranes treated with glucose to two other 20-carbon fatty acids: eicosanoic acid ("EA," also referred to as arachidic acid, C20:0) and eicosatrienoic acid ("ETE," C20:3, n-3). All MLV samples were subjected to time-dependent autoxidation by incubating at 37° C. in an uncovered, shaking water bath. This method allows lipid peroxidation to occur gradually without requiring the use of exogenous initiators. Small aliquots (5-100 µL) of each sample were removed, immediately following MLV preparation (0 hr) and after exposing samples to oxidative conditions for 72 or 96 hr, and combined with 1.0 mL of activated CHOD-iodide color reagent. Aliquot volume was reduced with each successive time point to ensure that spectrophotometric readings were within the optimal adsorption range. Test samples were covered and incubated in darkness at room temperature for at least 4 hr. Sample absorbances were then measured against a CHOD blank at 365 nm using a Beckman DU-640 spectrophotometer. The CHOD colorimetric assay is based on the oxidation of iodide (I⁻) by lipid hydroperoxide (LOOH) to form triiodide ($I_3^-$), the quantity of which is directly proportional to the amount of LOOH present in the lipid sample. The molar absorptivity (s) of $I_3^-$ is $2.46 \times 10^4$ $M^{-1}$ $cm^{-1}$ at 365 nm.

Figure 8:
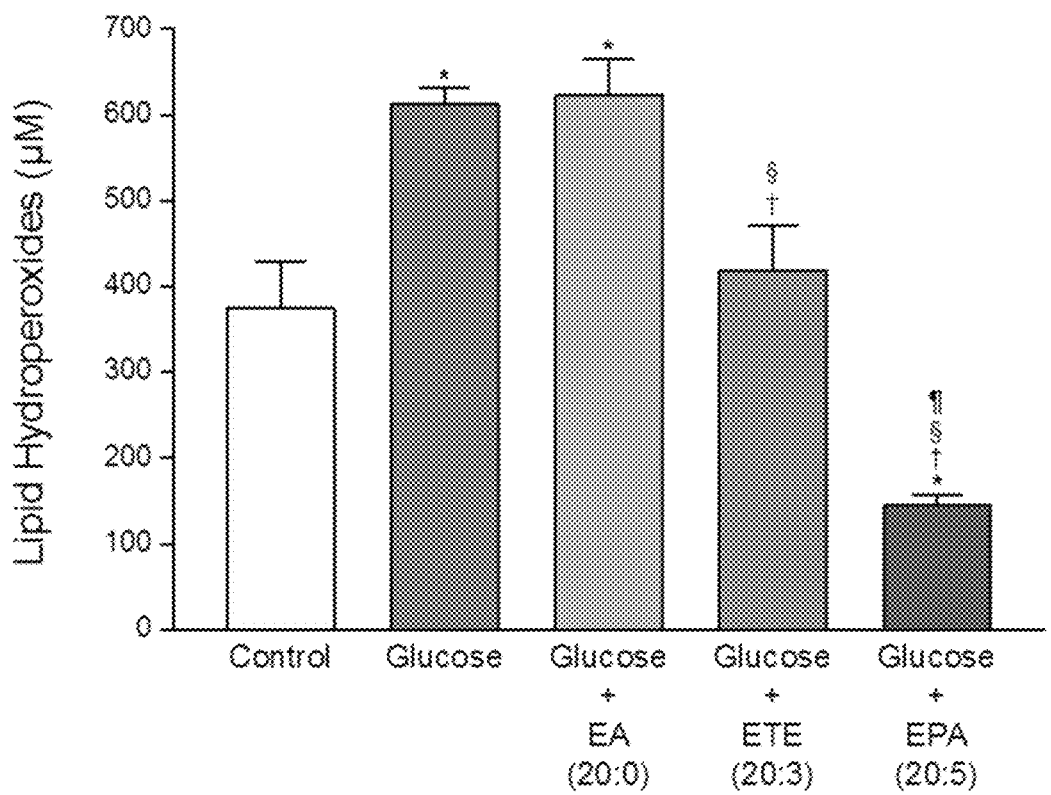
FIG. 8 depicts the effects of glucose with or without any one of EA, ETE or EPA on lipid hydroperoxide formation compared to control.
Figure 9:
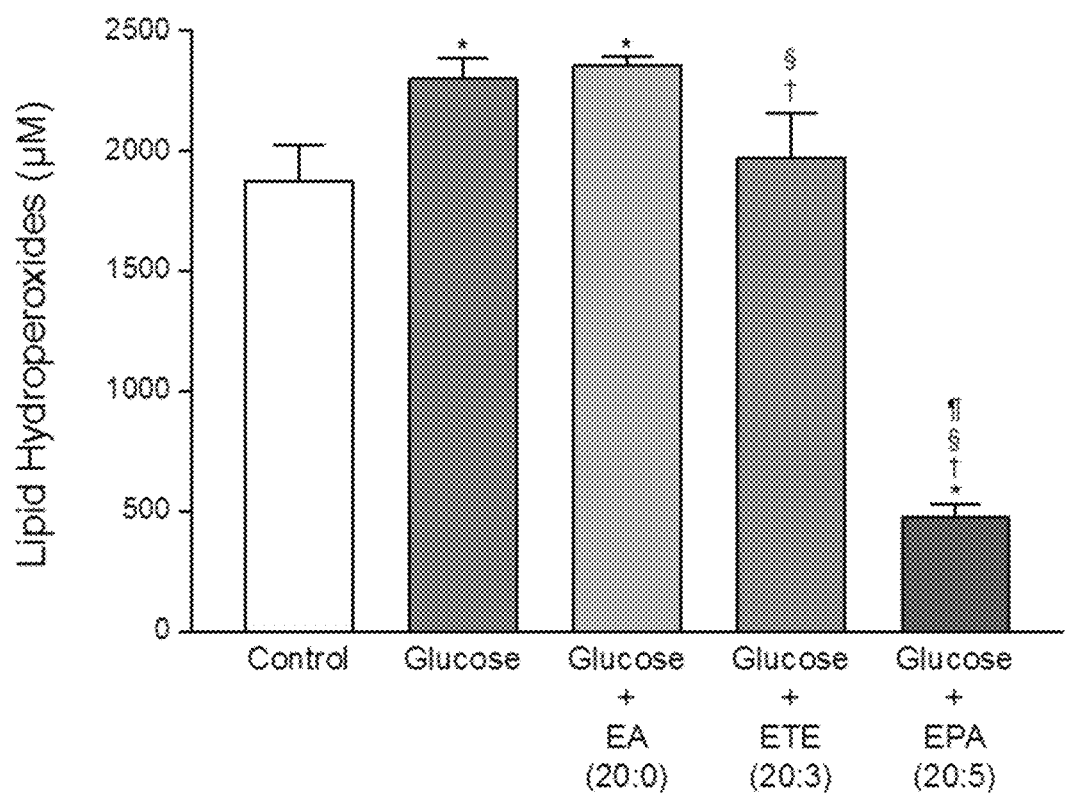
FIG. 9 depicts the effects of glucose with or without any one of EA, ETE or EPA on lipid hydroperoxide formation compared to control after 96 hours.

As shown in FIG. 8, model membranes treated with EPA had significantly less LOOH formation compared to model membranes treated with vehicle only (control), with glucose only, with glucose and EA, or with glucose and ETE. Values in FIG. 8 are mean±S.D. (N=6). After 96 hours (FIG. 9), the differences between EPA-treated model membranes and model membranes treated with vehicle only (control), with glucose only, with glucose and EA, or with glucose and ETE were even more pronounced. Values in FIG. 8 are mean±S.D. (N=6). *$p<0.001$ versus vehicle-treated control; †$p<0.001$ versus glucose-treated control; § $p<0.001$ versus EA; ¶$p<0.001$ versus ETE (Student-Newman-Keuls multiple comparisons test; overall ANOVA: $p<0.0001$, $F=148.57$). *$p<0.001$ versus vehicle-treated control; †$p<0.001$ versus glucose-treated control; § $p<0.001$ versus EA; ¶$p<0.001$ versus ETE (Student-Newman-Keuls multiple comparisons test; overall ANOVA: $p<0.0001$, $F=248.73$).

Example 6

An experiment to study the antioxidant effect of EPA in small dense LDL ("sdLDL") was performed. EPA was purchased from Sigma-Aldrich (Saint Louis, Mo.) and solubilized in ethanol to 1 mM under nitrogen atmosphere. Vitamin E (α-tocopherol) was purchased from Sigma-Aldrich and prepared in ethanol at 1.0 mM ($\varepsilon=3.06\times10^4$ $M^{-1}$ $cm^{-1}$ at 294 nm) just prior to experimental use. All test compounds were further diluted in ethanol or aqueous buffer as needed.

Venous blood was collected from healthy volunteers into vacutainer tubes containing sodium EDTA. Plasma was separated by centrifugation at 3000 g for 25 min at 4° C. and adjusted to a density of 1.020 g/mL with KBr. Triglyceride-rich lipoproteins (TGRL) and LDL fractions were then isolated bysequential centrifugation at 70,000 rpm at 4° C. in a Beckman LE-80 ultracentrifuge using a Beckman 50.4Ti rotor (Beckman Coulter, Inc., Fullerton, Calif.). The TGRL fraction (with a relative density of <1.020) was aspirated from the top of the centrifugate and discarded, leaving an LDL-enriched infranate (with a relative density of 1.020 to 1.063). The plasma LDL fraction was further fractionated into LDL1, LDL2, LDL3, and LDL4 (sdLDL) subfractions with relative densities of 1.020 to 1.035, 1.035 to 1.050, 1.050 to 1.063, and 1.063 to 1.075, respectively. The sdLDL subfraction was retained for additional experimentation. Plasma and lipoprotein fractions were maintained at 4° C. and protected from excessive exposure to light. Prior to oxidation experiments, EDTA was removed from the lipoprotein fraction using PD-10 desalting columns (GE Healthcare, Piscataway N.J.). After equilibration of the column with phosphate buffered saline (PBS), 2.5 mL of the lipoprotein fraction was loaded on the column and the flow-through discarded. The lipoprotein was then eluted with 3 mL of PBS. The LDL fractions were further diluted with PBS to obtain a 100 μg/mL apoB100 concentration.

LDL and sdLDL subfractions (0.6 mL each) were incubated with either 10 μL vehicle (ethanol) or 10 μL drug stock solution for 30 min to 1 hr at 37° C. Oxidation was initiated by the addition of 10 μM CuSO₄. After 2 hr, 100 μL aliquots were removed from each subfraction and combined with 1.0 mL thiobarbituric acid (0.5%), 10 μL trichloroacetic acid (5%), 10 μL BHT (5 mg/mL in methanol), and 10 μL EDTA (5 mM). Sample aliquots were incubated at 100° C. for 20 min and then assayed for the formation of thiobarbituric acid-reactive substances (TBARS), which have a molar absorptivity (ε) value of $1.56\times10^5$ $M^{-1}$ $cm^{-1}$ at 532 nm and are derived principally from the reaction of thiobarbituric acid with malondialdehyde (MDA), a reactive aldehyde produced by LDL oxidation. Sample TBARS concentrations were determined spectrophotometrically by measuring sample absorbances against a standard curve derived from the hydrolysis of 1,1,3,3-tetramethoxypropane.

Data are presented as mean±S.D. for (N) separate samples or treatment groups. Differences between groups were analyzed using the two-tailed, Student's t-test (for comparisons between only two groups) or ANOVA followed by Dunnett or Student-Newman-Keuls multiple comparisons post-hoc analysis (for comparisons between three or more groups). Only differences with probability values less than 0.05 were considered significant.

Figure 10:
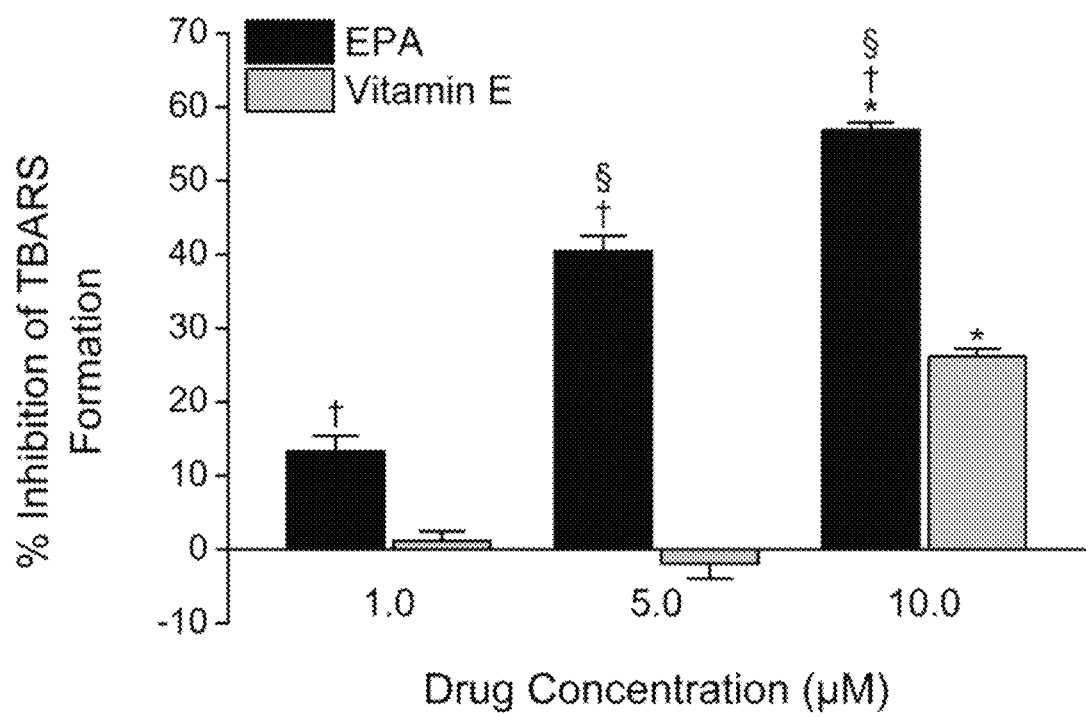
FIG. 10 depicts the dose-dependent effects of EPA and vitamin E on sdLDL oxidation after 2 hours.

EPA has been shown in previous studies to inhibit lipid oxidation in phospholipid vesicles following exposure to high glucose levels and autoxidation (unpublished results). In this study these analyses were extended to human LDL and sdLDL fractions. As shown in FIG. 10, EPA inhibited sdLDL oxidation over a broad range of concentrations (1.0 μM to 10.0 μM). These concentrations are similar to the level of unesterified EPA measured in the plasma of humans ($C_{max}$:1.4 μg/mL, or ~5 μM) with normally prescribed levels (e.g., 4 g/day) of EPA. At the lowest dose tested (1.0 μM), EPA reduced TBARS levels by 13% ($p<0.001$) compared to vehicle-treated controls; this inhibitory effect was dose-dependent and increased to 57% ($p<0.001$) at 10.0 μM. The comparative effects of vitamin E on sdLDL oxidation were also tested under identical conditions (FIG. 10). In contrast to EPA, vitamin E did not inhibit sdLDL oxidation except at the highest concentration (10.0 μM) where it reduced TBARS levels by 26% ($p<0.05$). These data indicate different interactions of these lipophilic, chain-breaking antioxidants with respect to sdLDL oxidation. Values in FIG. 10 are mean±S.D. (N=4). *$p<0.05$ versus control (Dunnett multiple comparisons test; overall ANOVA: $p=0.0039$, $F=4.616$); †$p<0.0001$ versus vitamin E treatment(s); § $p<0.001$ versus other EPA treatments (Student-Newman-Keuls multiple comparisons test; overall ANOVA: $p<0.0001$, $F=764.91$).

Figure 11:
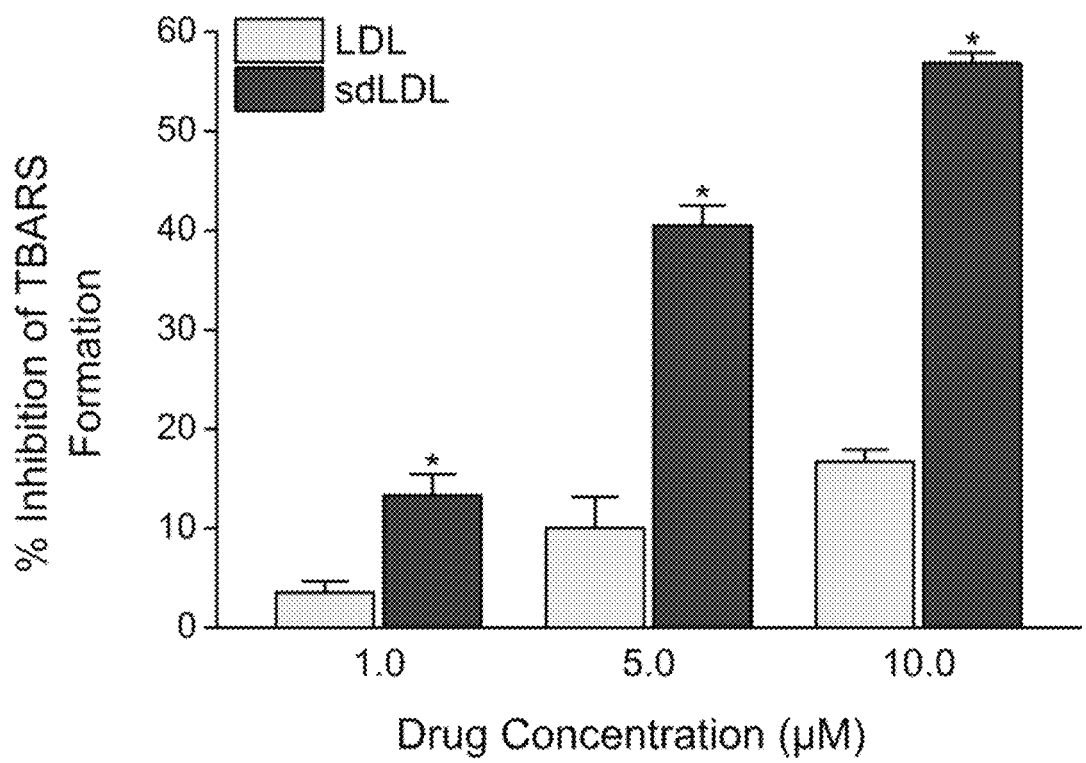
FIG. 11 depicts the dose-dependent antioxidant effects of EPA in human sdLDL compared to non-fractionated LDL.

The antioxidant effects of EPA were further examined in unfractionated LDL particles (FIG. 11). LDL was isolated from human plasma, treated with vehicle, vitamin E, or EPA over a broad range of concentrations (1.0 μM to 10.0 μM) and examined for changes in lipid oxidation rates. EPA was found to generally inhibit LDL oxidation; however, the effects were less evident as compared to those observed for a similar number of sdLDL particles. At each concentration tested, the reduction in TBARS levels was several fold lower in the unfractionated LDL versus sdLDL ($p<0.001$). At the highest concentration tested (10.0 μM), EPA reduced TBARS levels by 17% and was similar to what was observed at the lowest dose tested (1.0 μM) in sdLDL. By contrast, vitamin E did not inhibit LDL oxidation at any concentration (data not shown). These data suggest that EPA has a disproportionately greater benefit in sdLDL as compared to the larger LDL species. Values in FIG. 11 are mean±S.D. (N=3-4).

Example 7

An experiment to study the antioxidant effect of EPA in LDL and small dense LDL ("sdLDL") was performed. LDL and sdLDL were isolated from the plasma of healthy volunteers by iodixanol density gradient ultracentrifugation, and adjusted to a final apolipoprotein concentration of 2 mg/mL. Sample aliquots (100 μg apolipoprotein each) were incubated with EPA, fenofibrate, gemfibrozil, or niacin (each at 1.0, 5.0, or 10.0 μM) for 30 min at 37° C. Fenofibrate, gemfibrozil, and niacin were purchased from Sigma-Aldrich. Lipid oxidation was initiated with 10 μM $CuSO_4$ and monitored by the colorimetric detection of thiobarbituric acid reactive substances (TBARS) for 1 hr. Vitamin E was also incubated with sample aliquots as a positive control. For comparison, the active o-hydroxy metabolite of atorvastatin (ATM, Toronto Research Chemicals, North York, Ontario, Canada), alone or in combination with EPA or DHA, was also incubated with sample aliquots.

Results: sdLDL

Figure 12:
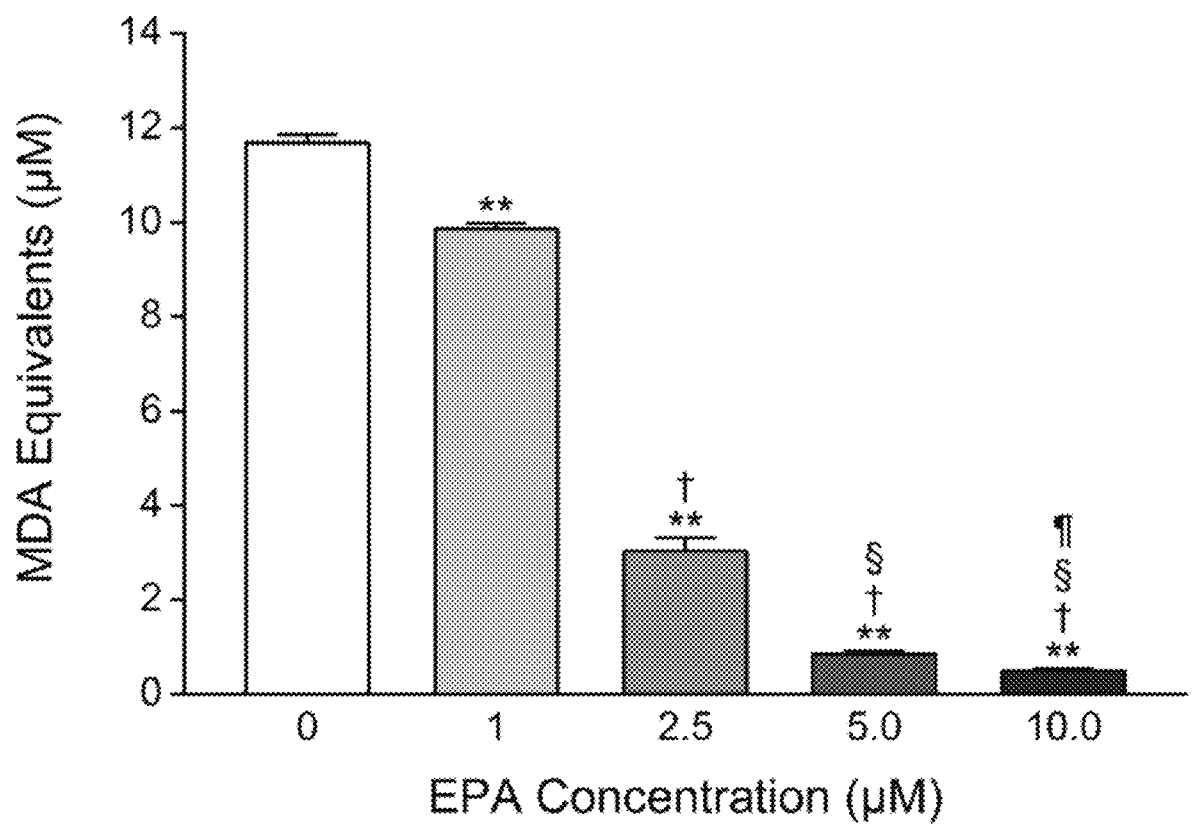
FIG. 12 shows the dose-dependent effects of EPA on human sdLDL oxidation as measured by colorimetric assay of TBARS formation and expressed as molar equivalents of malondialdehyde ("MDA"). Values are mean+/−S.D. (N=3). **$p<0.001$ versus vehicle-treated control; †$p<0.001$ versus 1.0 µM EPA; § $p<0.001$ versus 2.5 µM EPA; ¶$p<0.05$ versus 5.0 µM EPA (Student-Newman-Keuls multiple comparisons test; overall ANOVA: $p<0.0001$, F=2960.1).
Figure 13:
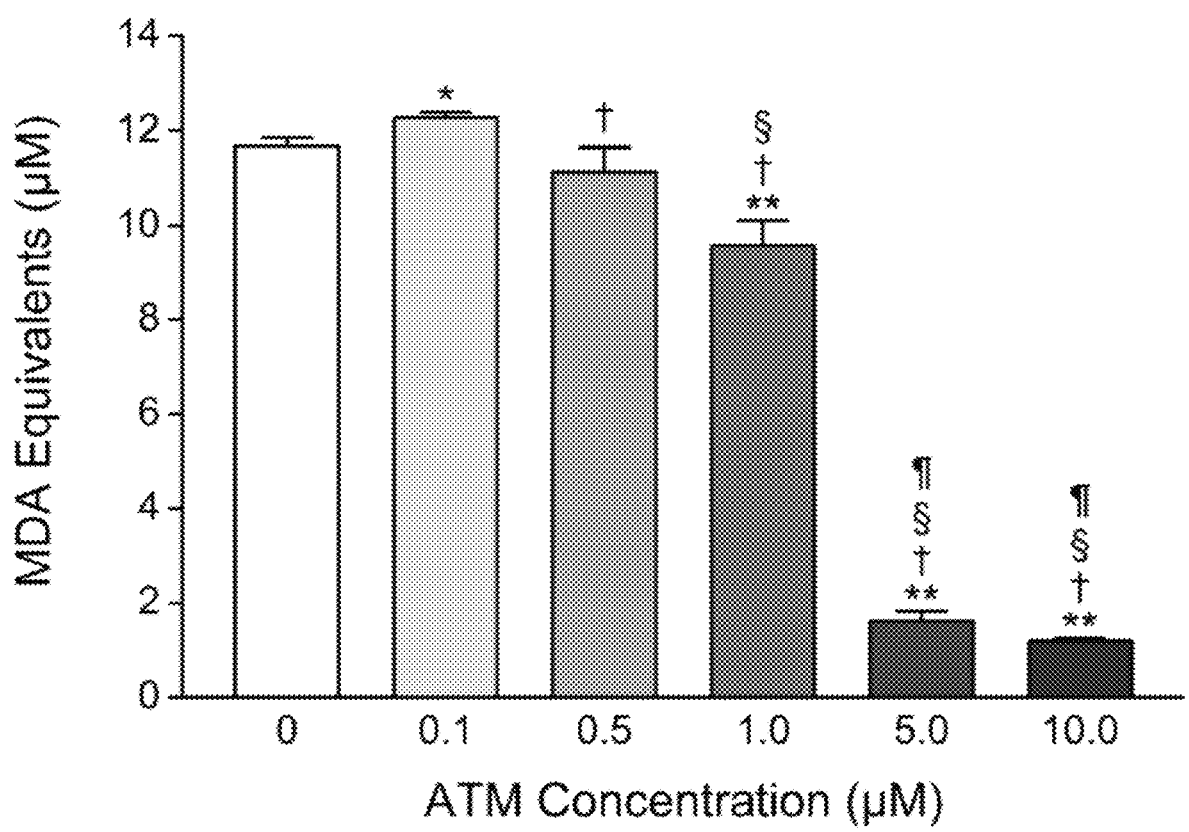
FIG. 13 shows the dose-dependent effects of atorvastatin o-hydroxy (active) metabolite ("ATM") on human sdLDL oxidation as measured by colorimetric assay of TBARS formation and expressed as molar equivalents of MDA. Values are mean+/−S.D. (N=3). *$p<0.05$ and **$p<0.001$ versus vehicle-treated control; †$p<0.01$ versus 0.10 µM ATM; § $p<0.001$ versus 0.5 µM ATM; ¶$p<0.001$ versus 1.0 µM ATM (Student-Newman-Keuls multiple comparisons test; overall ANOVA: $p<0.0001$, F=745.92).

As shown in FIG. 12, EPA significantly and reproducibly inhibited sdLDL oxidation in a dose-dependent manner with an $IC_{50}$ of ~2.0 μM. At the highest treatment concentration (10 μM), EPA inhibited TBARS formation by 93±2% (p<0.001). Inhibition was significant and reproducible with EPA by 19±8% (p<0.001) even at the lowest dose of 1.0 μM. The $IC_{50}$ for EPA was calculated to be approximately 2 μM. ATM also showed a dose-dependent inhibition of sdLDL oxidation with a significant effect of 18±5% (p<0.001) beginning at 1.0 μM as shown in FIG. 13. At the highest dose, the inhibition with ATM was 90±2% (p<0.001).

Figure 14:
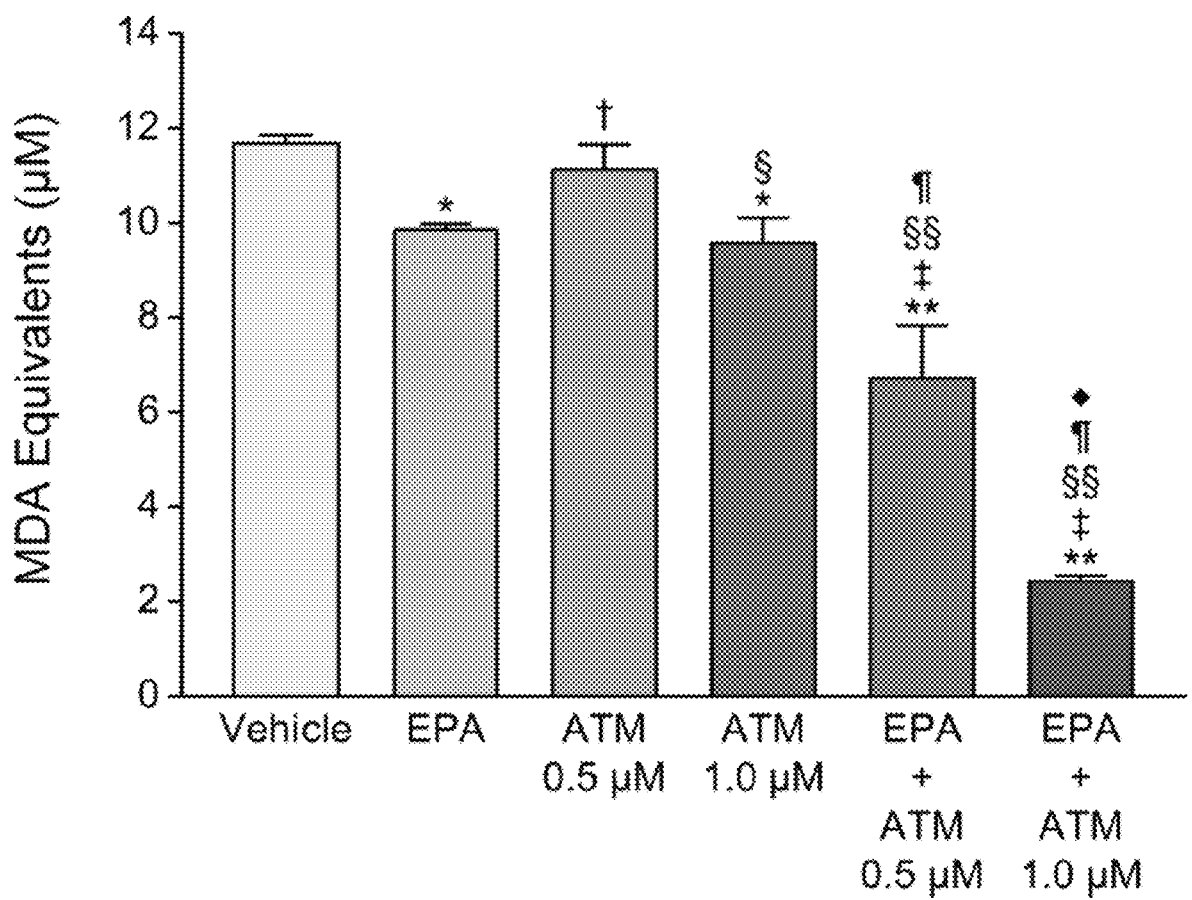
FIG. 14 shows the separate and combined effects of EPA and ATM on human sdLDL oxidation as measured by colorimetric assay of TBARS formation and expressed as molar equivalents of MDA. Values are mean+/−S.D. (N=3). *$p<0.01$ and **$p<0.001$ versus vehicle-treated control; †$p<0.05$ and ‡$p<0.001$ versus EPA; § $p<0.05$ and §§ $p<0.001$ versus 0.5 µM ATM; ¶$p<0.001$ versus 1.0 µM ATM; "$p<0.001$ versus EPA+0.5 µM ATM (Student-Newman-Keuls multiple comparisons test; overall ANOVA: $p<0.0001$, F=118.22).
Figure 15:
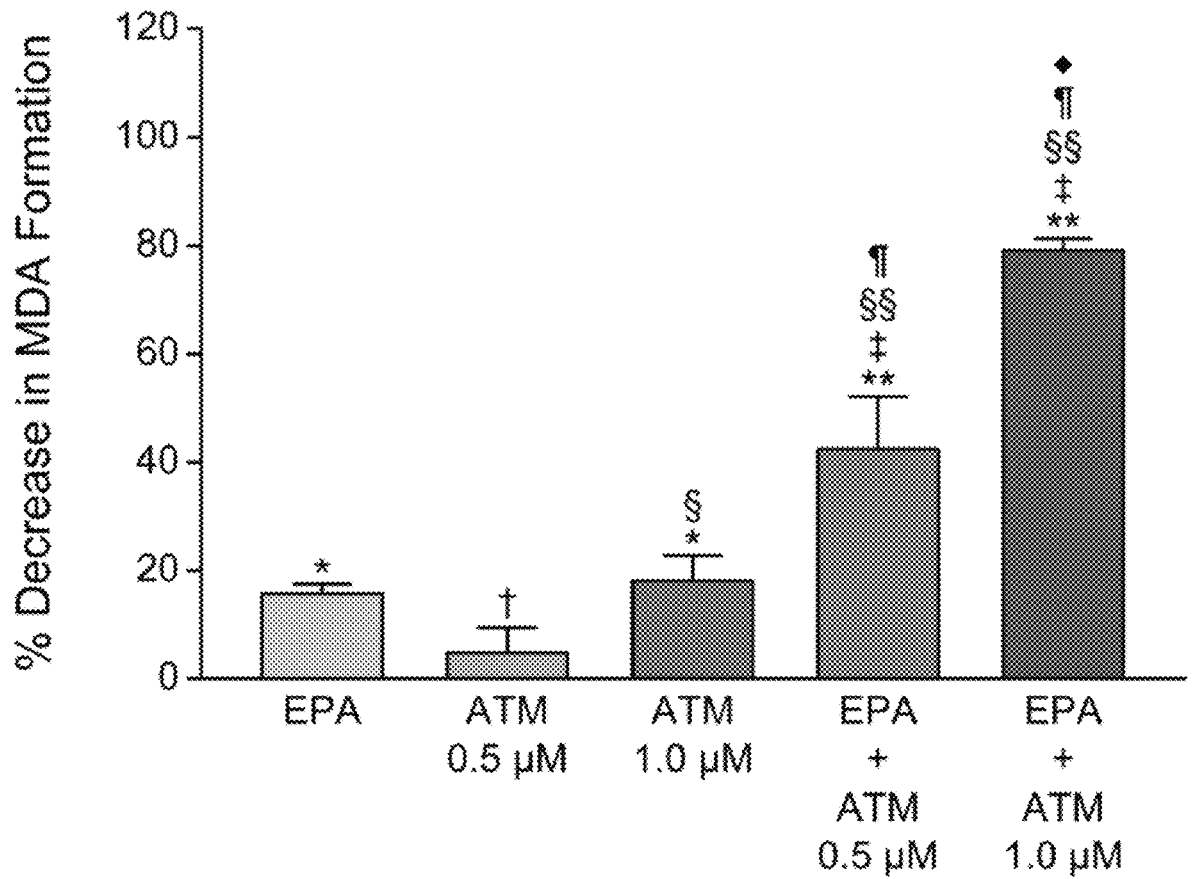
FIG. 15 shows the separate and combined effects of EPA (1.0 µM) and ATM on human sdLDL oxidation expressed as percent decrease in MDA formation relative to vehicle-treated control. Data was collected after 1 hour of exposure to oxidative conditions. Values are mean+/−S.D. (N=3). *$p<0.01$ and **$p<0.001$ versus vehicle-treated control (Student-Newman-Keuls multiple comparisons test; overall ANOVA: $p<0.0001$, F=118.22). †$p<0.05$ and ‡$p<0.001$ versus EPA; § $p<0.05$ and §§ $p<0.001$ versus 0.5 µM ATM; ¶$p<0.001$ versus 1.0 µM ATM; ♦$p<0.001$ versus EPA+0.5 µM ATM (Student-Newman-Keuls multiple comparisons test; overall ANOVA: $p<0.0001$, F=92.011).
Figure 16:
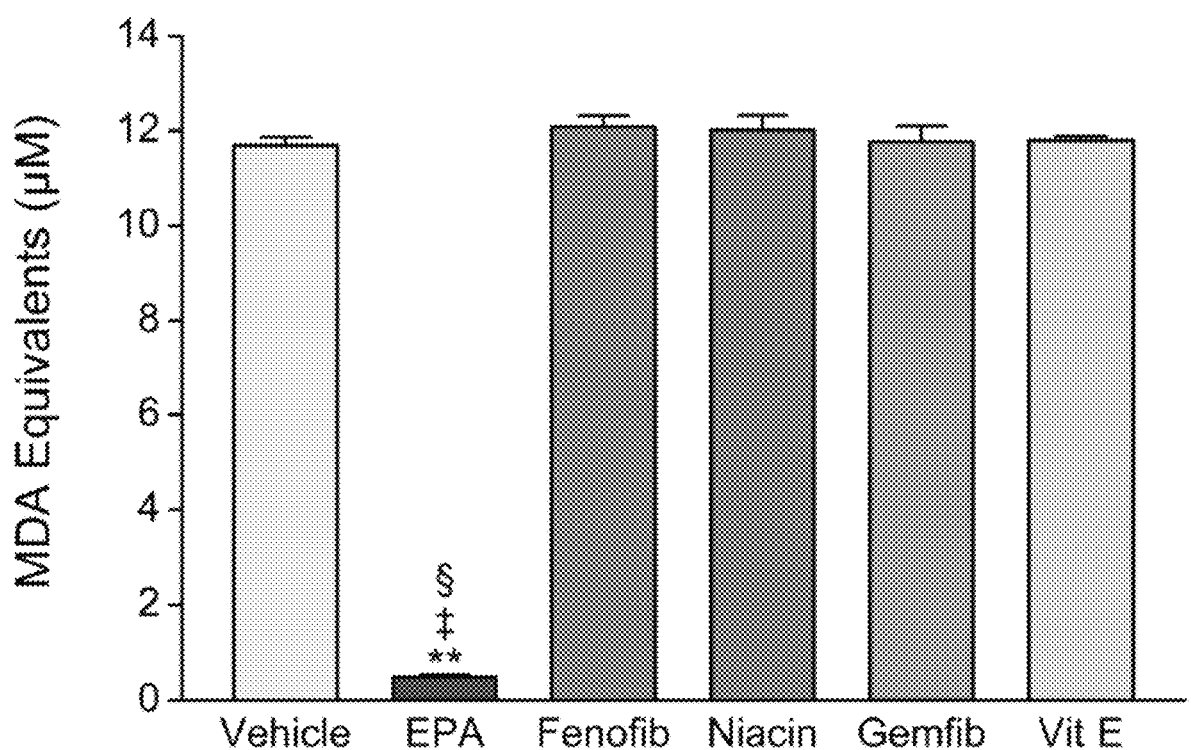
FIG. 16 shows the comparative effects of EPA, fenofibrate ("Fenofib"), nicotinic acid (niacin), gemfibrozil ("Gemfib") and vitamin E (all at 10 μM) on human sdLDL oxidation. Data were collected after 1 hour of exposure to oxidative conditions. Values are mean+/−S.D. (N=3). **$p<0.001$ versus vehicle-treated control; †$p<0.001$ versus fenofibrate, niacin, or gemfibrozil; § $p<0.001$ versus Vit E (Student-Newman-Keuls multiple comparisons test; overall ANOVA: $p<0.0001$, F=1268.1).

Pretreatment with a combination of EPA and ATM followed by oxidative stress reduced sdLDL oxidation to an extent that was not observed with their individual treatments at equimolar concentrations. (FIGS. 14-15). Individual EPA and ATM treatments inhibited sdLDL oxidation at 1.0 μM by 19±8% and 18±5%, respectively, while the combination inhibited sdLDL oxidation by 75±8% as compared to vehicle (p<0.001). The effects of the combination at a lower dose of ATM (0.5 μM) resulted in inhibition of only 5±5% (ATM alone) but 57±9% (p<0.001) in combination with EPA (1.0 μM). The inhibition with the ATM/EPA combination was much greater than the sum of their separate effects at the concentrations we tested in this study. As shown in FIG. 16, fenofibrate, gemfibrozil, niacin, and vitamin E had no significant effect on sdLDL oxidation as compared to vehicle-treated controls.

Figure 17:
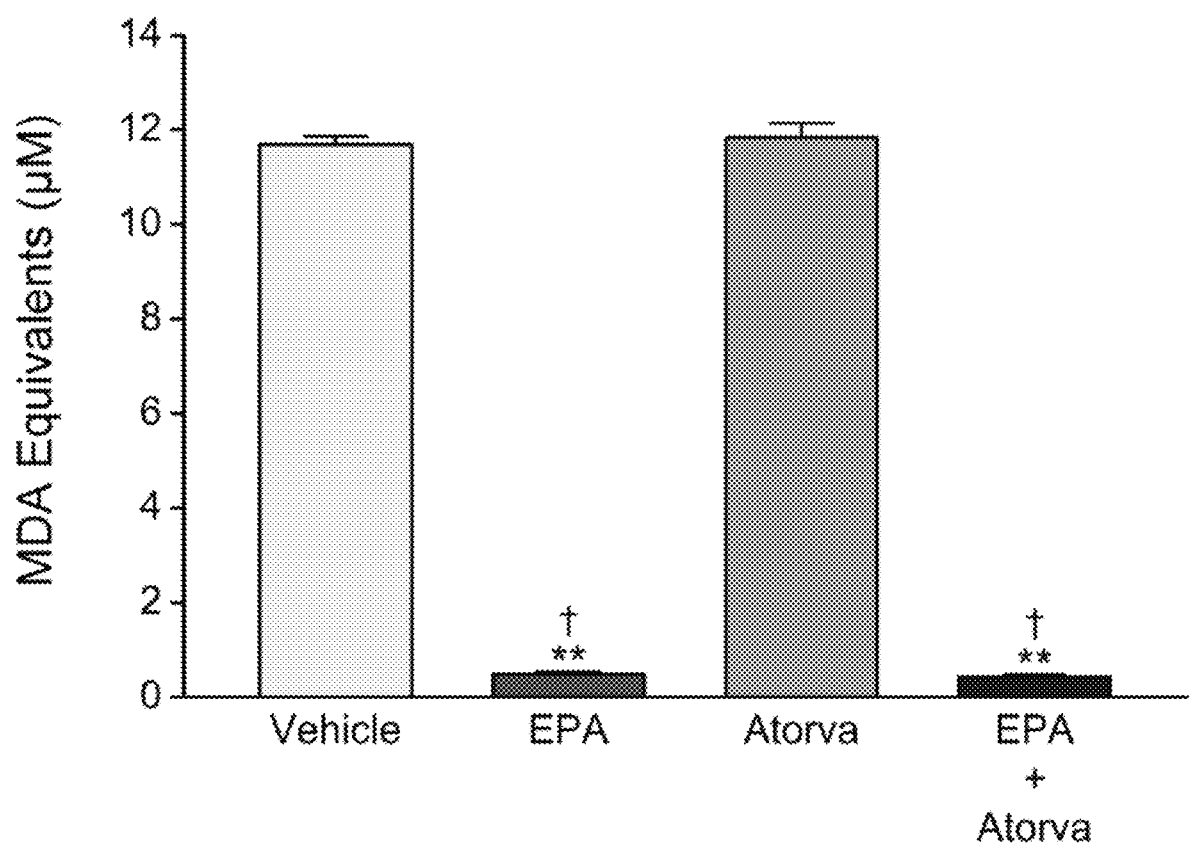
FIG. 17 shows the separate and combined effects of EPA and atorvastatin ("Atorva") on human sdLDL oxidation. Each agent was tested at 10 μM. Data were collected after 1 hour of exposure to oxidative conditions. Values are mean+/−S.D. (N=3). **$p<0.001$ versus vehicle-treated control; †$p<0.001$ versus atorvastatin alone (Student-Newman-Keuls multiple comparisons test; overall ANOVA: $p<0.0001$, F=3962.4).
Figure 18:
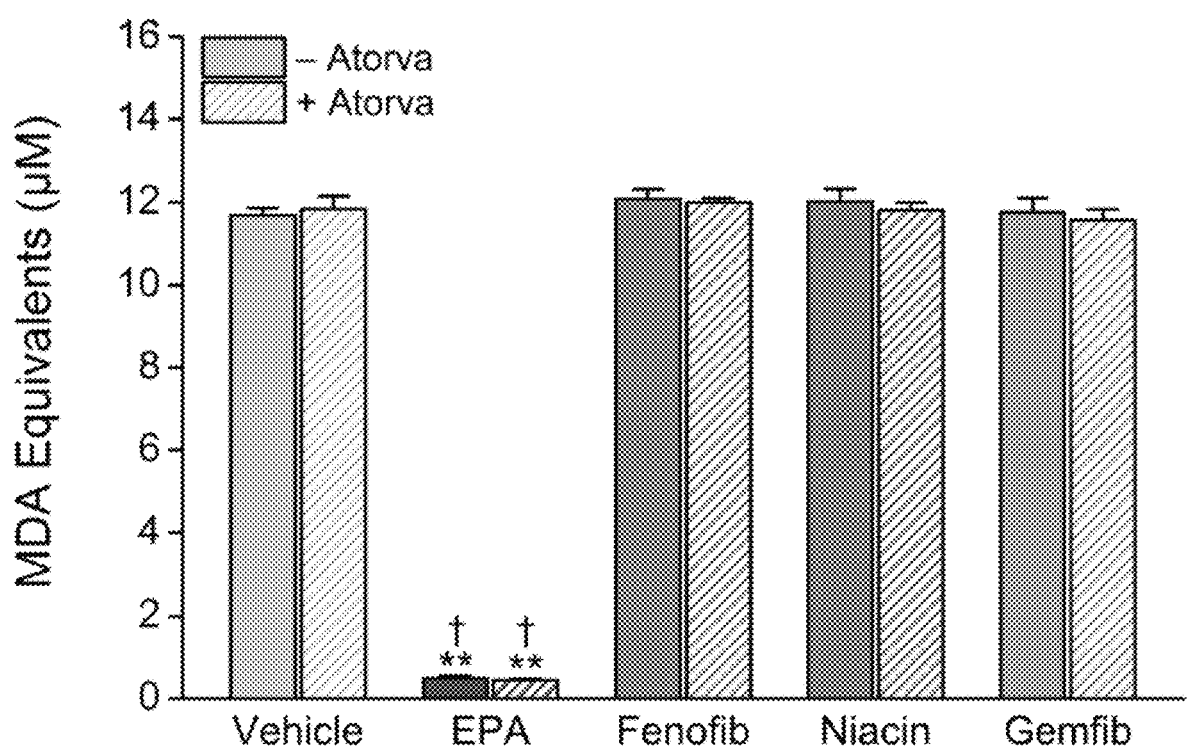
FIG. 18 shows the comparative effects of EPA, fenofibrate, nicotinic acid and gemfibrozil, alone or in combination with atorvastatin, on human sdLDL oxidation. Each agent was tested at 10 μM. Data were collected after 1 hours of exposure to oxidative conditions. Values are mean±S.D. (N=3). **$p<0.001$ versus vehicle-treated control; ‡$p<0.001$ versus all other TG-lowering agents, alone or in combination with Atorva (Student-Newman-Keuls multiple comparisons test; overall ANOVA: $p<0.0001$, F=1365.7).

The individual and combined effects of EPA and atorvastatin (parent) pretreatment of sdLDL at 10.0 μM followed by stimulation of oxidative stress were tested. As shown in FIG. 17, the combination of EPA and atorvastatin reduced sdLDL oxidation to the same extent that was observed with EPA alone. Separately, atorvastatin did not have any significant antioxidant activity. The individual EPA and atorvastatin treatments inhibited sdLDL oxidation at 10.0 μM by 92±8% and 0.1±7%, respectively, while the combination inhibited sdLDL oxidation by 91±8% as compared to vehicle (p<0.001). The inhibition of sdLDL oxidation with EPA/atorvastatin combination was thus similar to that observed separately for EPA alone and not observed in combination with other TG-lowering agents (FIG. 18).

Figure 19:
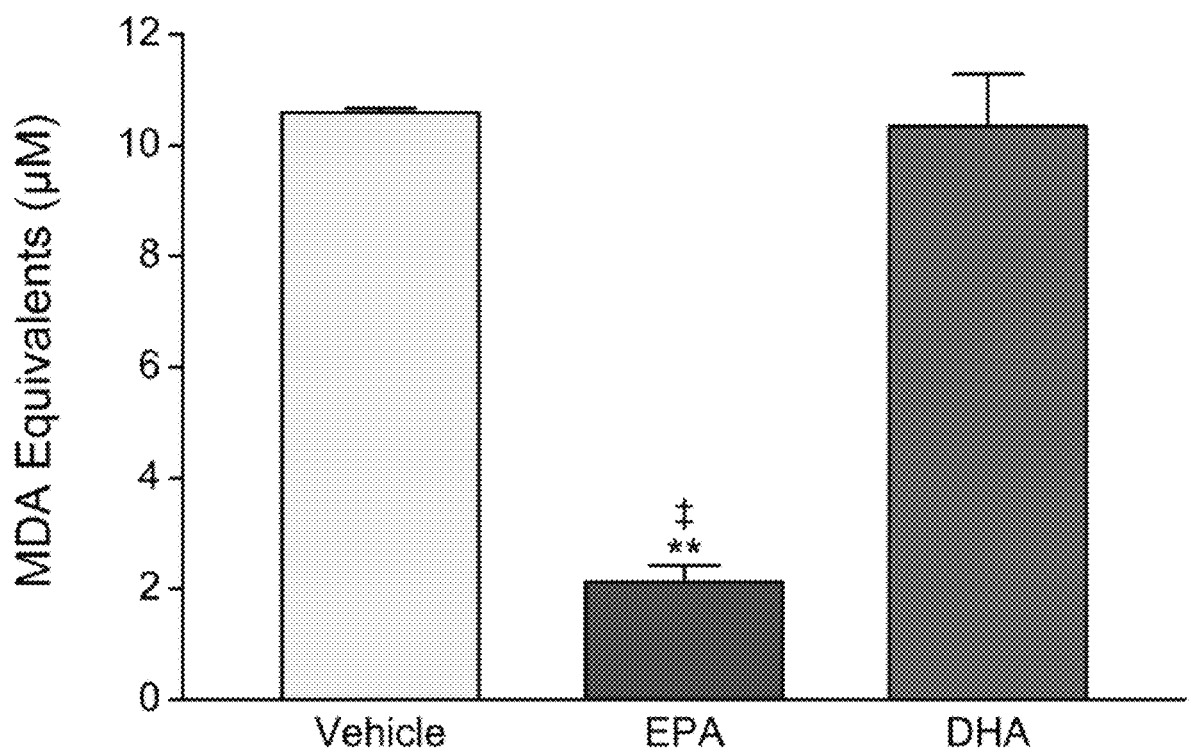
FIG. 19 shows the comparative effects of EPA and DHA on human sdLDL oxidation. Both agents were tested at 10 μM. Data were collected after 4 hours of exposure to oxidative conditions. Values are mean+/−S.D. (N=3). **$p<0.001$ versus vehicle-treated control; ‡$p<0.001$ versus DHA (Student-Newman-Keuls multiple comparisons test; overall ANOVA: $p<0.0001$, F=211.20).
Figure 20:
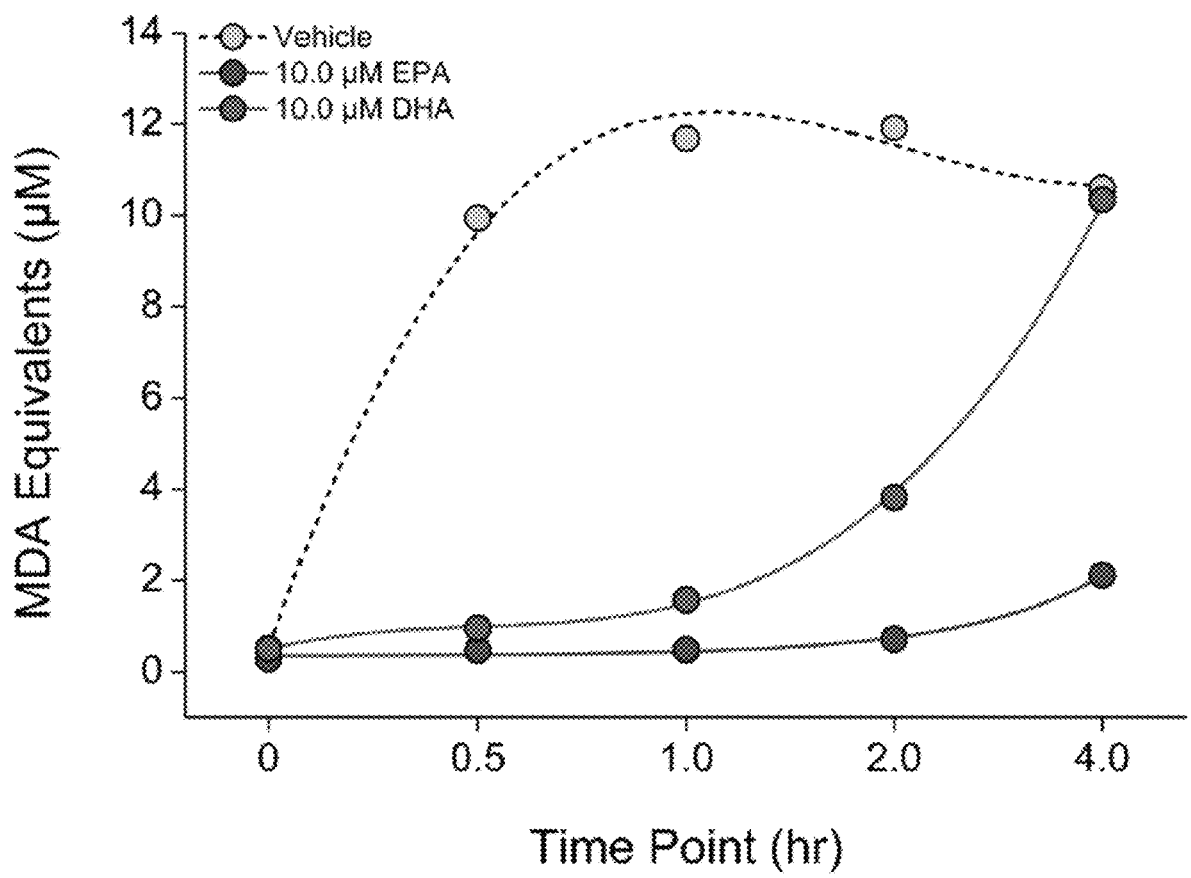
FIG. 20 shows the comparative effects of EPA and DHA on the rate of lipid oxidation in human sdLDL. Samples were prepared at 100 μg/mL sdLDL and incubated with EPA or DHA (10.0 μM each) for 30 minutes prior to initiating lipid oxidation using 10 μM $CuSO_4$. Samples were maintained at 37° C. in a shaking water bath for 1 hour. Lipid oxidation was measured by colorimetric assay of TBARS formation and expressed as molar equivalents of MDA. Values shown are the averages calculated from three separate measurements.

The antioxidant activity of EPA to DHA was tested by pretreatment at an equimolar concentration (10.0 μM) followed by stimulation of oxidative stress. As shown in FIG. 19, only EPA significantly inhibited sdLDL oxidation after 4 hours as compared to vehicle or DHA (p<0.001). The differences in activity between EPA and DHA became more apparent during the time course of the experiment with significant differences as early as 1 hour (FIG. 20).

Results: Unfractionated LDL

Figure 21:
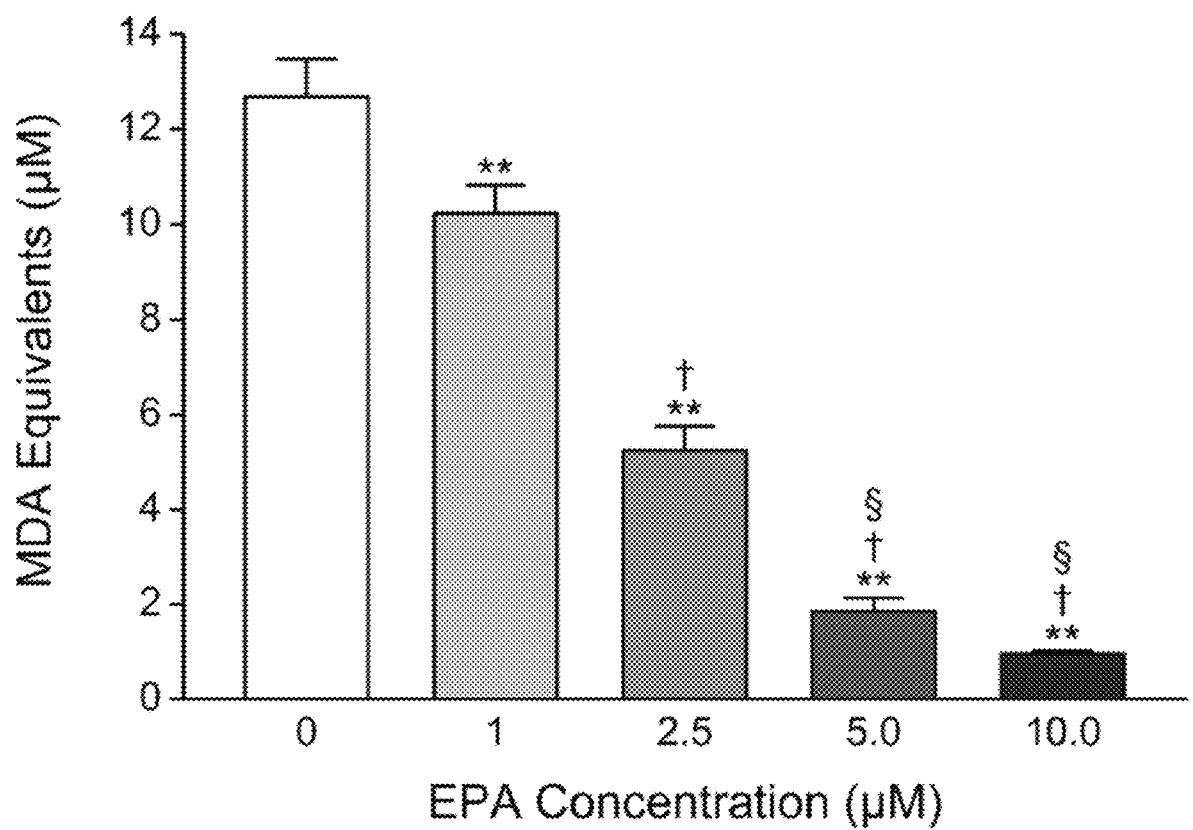
FIG. 21 shows the dose-dependent effects of eicosapentaenoic acid (EPA) on human LDL oxidation. Samples were prepared at 100 μg/mL LDL and incubated with test agents (at doses indicated) for 30 minutes prior to initiating lipid oxidation using 10 μM $CuSO_4$. Samples were maintained at 37° C. in a shaking water bath for 1 hour. Lipid oxidation was measured by colorimetric assay of TBARS formation and expressed as molar equivalents of MDA. Values are mean+/−S.D. (N=3). **$p<0.001$ versus vehicle-treated control; †$p<0.001$ versus 1.0 M EPA; § $p<0.001$ versus 2.5 μM EPA (Student-Newman-Keuls multiple comparisons test; overall ANOVA: $p<0.0001$, F=298.14).
Figure 22:
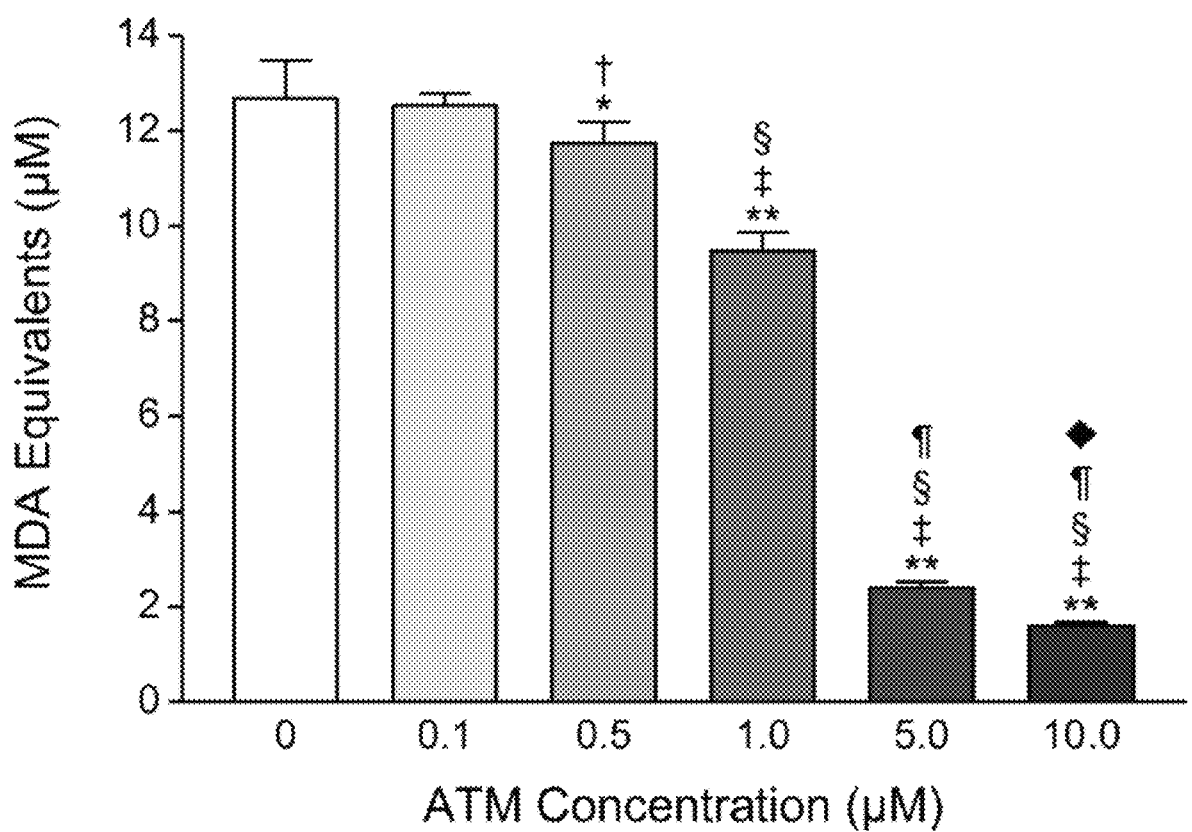
FIG. 22 shows the dose-dependent effects of atorvastatin o-hydroxy (active) metabolite (ATM) on human LDL oxidation. Samples were prepared at 100 μg/mL LDL and incubated with test agents (at doses indicated) for 30 minutes prior to initiating lipid oxidation using 10 μM $CuSO_4$. Samples were maintained at 37° C. in a shaking water bath for 1 hour. Lipid oxidation was measured by colorimetric assay of TBARS formation and expressed as molar equivalents of MDA. Values are mean+/−S.D. (N=3). *$p<0.05$ and **$p<0.001$ versus vehicle-treated control; †$p<0.05$ and ‡$p<0.001$ versus 0.10 μM ATM; § $p<0.001$ versus 0.5 μM ATM; ¶$p<0.001$ versus 1.0 μM ATM; ♦$p<0.05$ versus 5.0 μM ATM (Student-Newman-Keuls multiple comparisons test; overall ANOVA: $p<0.0001$, F=438.91). Values are mean±S.D. (N=3).

As shown in FIG. 21, EPA also significantly and reproducibly inhibited unfractionated LDL oxidation in a dose-dependent manner. At the highest treatment concentration (10 μM), EPA inhibited TBARS formation by >90% (p<0.001) compared to vehicle-treated control. Inhibition was significant with EPA even at the lowest dose (1 μM). As shown in FIG. 22, ATM also showed a significant and dose-dependent inhibition of unfractionated LDL oxidation beginning at 1.0 μM.

Figure 23:
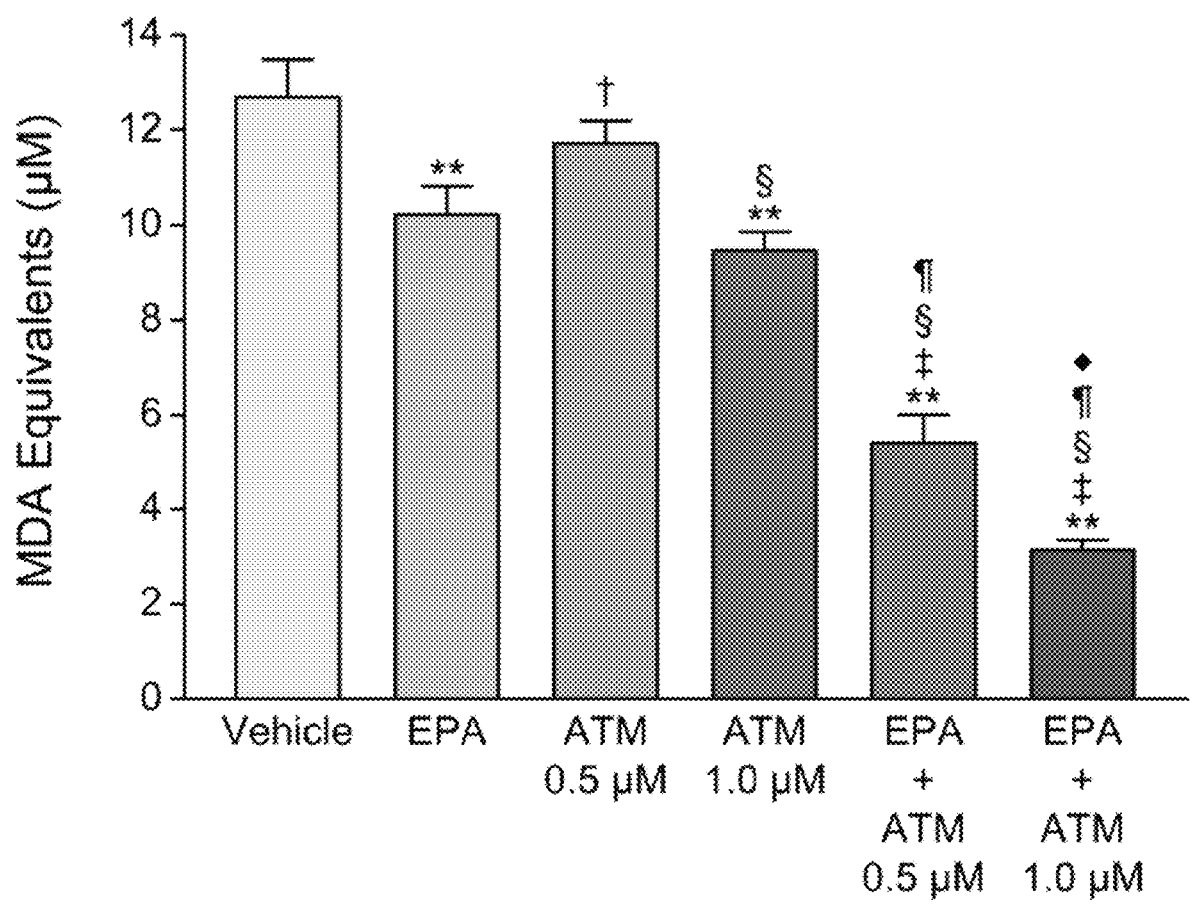
FIG. 23 shows the separate and combined effects of EPA and ATM on human LDL oxidation (expressed as molar MDA equivalents). EPA was tested at 1.0 μM. Data were collected after 1 hour of exposure to oxidative conditions. Values are mean+/−S.D. (N=3). **$p<0.001$ versus vehicle-treated control; †$p<0.05$ and ‡$p<0.001$ versus EPA; § $p<0.001$ versus 0.5 μM ATM; ¶$p<0.001$ versus 1.0 μM ATM; ♦$p<0.001$ versus EPA+0.5 μM ATM (Student-Newman-Keuls multiple comparisons test; overall ANOVA: $p<0.0001$, F=142.74).
Figure 24:
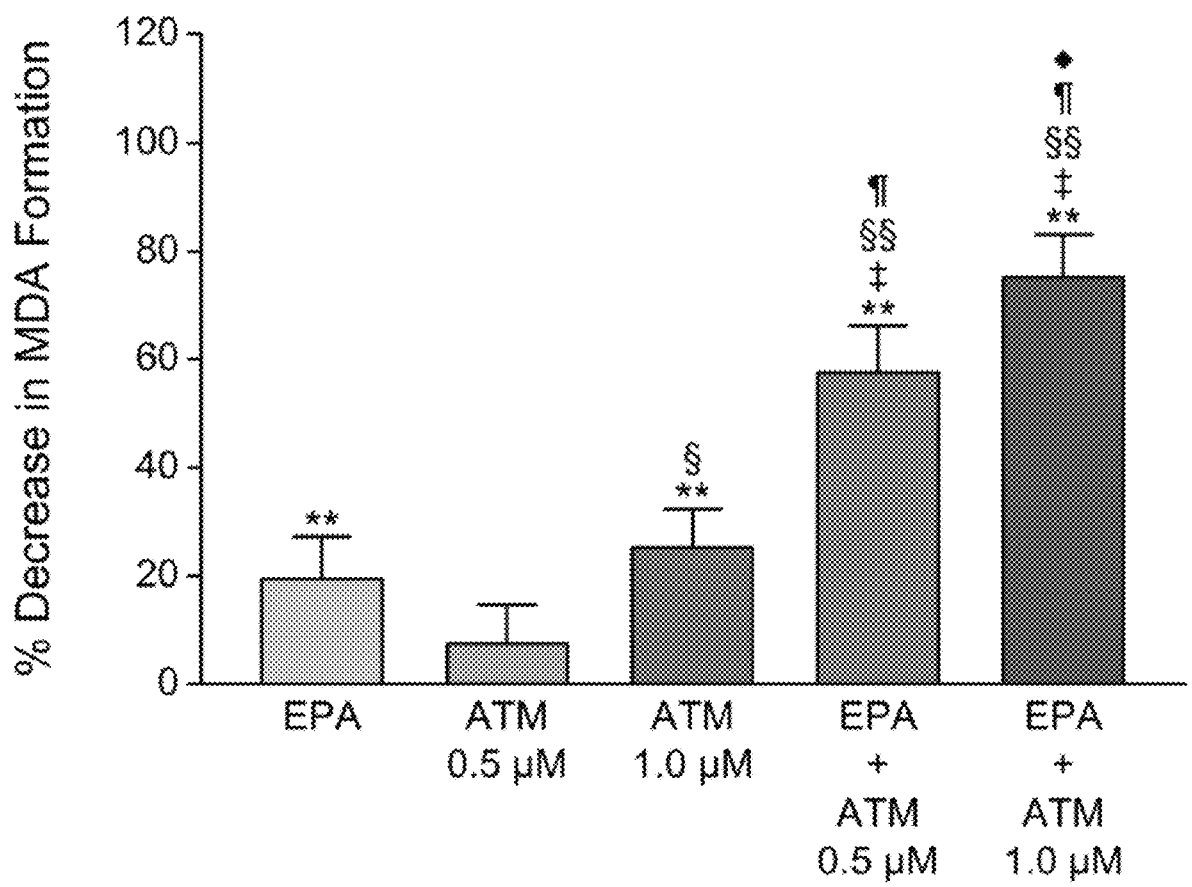
FIG. 24 shows the separate and combined effects of EPA and ATM on human LDL oxidation (expressed as % decrease in MDA formation relative to vehicle-treated control). EPA was tested at 1.0 μM. Data were collected after 1 hour of exposure to oxidative conditions. Values are mean+/−S.D. (N=3). **$p<0.001$ versus vehicle-treated control (Student-Newman-Keuls multiple comparisons test; overall ANOVA: $p<0.0001$, F=142.74). ‡$p<0.001$ versus EPA; § $p<0.05$ and §§ $p<0.001$ versus 0.5 μM ATM; ¶$p<0.001$ versus 1.0 μM ATM; ♦$p<0.05$ versus EPA+0.5 μM ATM (Student-Newman-Keuls multiple comparisons test; overall ANOVA: $p<0.0001$, F=39.502).
Figure 25:
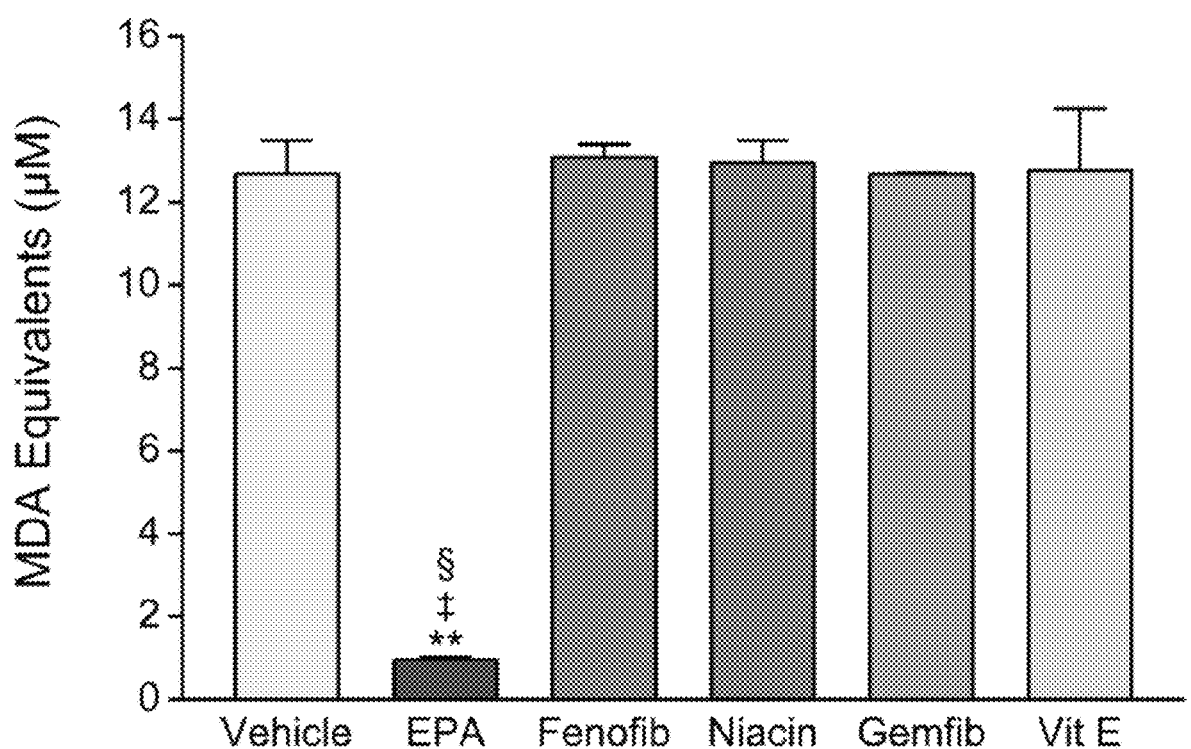
FIG. 25 shows the comparative effects of EPA, fenofibrate, nicotinic acid, gemfibrozil, and vitamin E on human LDL oxidation. All agents were tested at 10 M. Data were collected after 1 hour of exposure to oxidative conditions. Values are mean+/−S.D. (N=3). **$p<0.001$ versus vehicle-treated control; †$p<0.01$ versus fenofibrate, nicotinic acid, or gemfibrozil; § $p<0.001$ versus vitamin E (Student-Newman-Keuls multiple comparisons test; overall ANOVA: $p<0.0001$, F=132.37).

Pretreatment with a combination of EPA and ATM followed by oxidative stress reduced unfractionated LDL oxidation to an extent that was not observed with their individual treatments at equimolar concentrations. (FIGS. 23-24). The inhibition with the ATM/EPA combination was much greater than the sum of their separate effects at the concentrations we tested in this study. As shown in FIG. 25, fenofibrate, gemfibrozil, niacin, and vitamin E had no significant effect on unfractionated LDL oxidation as compared to vehicle-treated controls.

Figure 26:
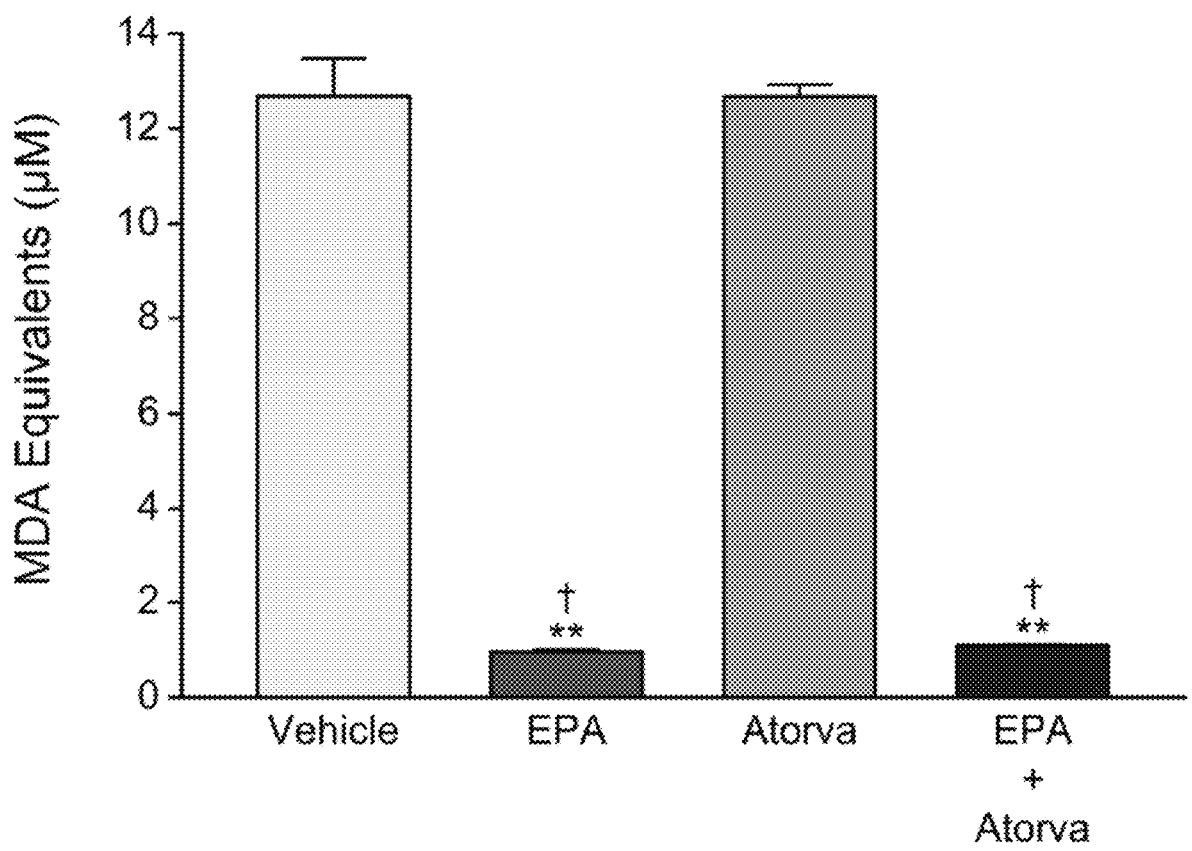
FIG. 26 shows the separate and combined effects of EPA and atorvastatin on human LDL oxidation. Each agent was tested at 10 M. Data were collected after 1 hour of exposure to oxidative conditions. Values are mean+/−S.D. (N=3). *$p<0.001$ versus vehicle-treated control; †$p<0.001$ versus atorvastatin alone (Student-Newman-Keuls multiple comparisons test; overall ANOVA: $p<0.0001$, F=790.78).

The individual and combined effects of EPA and atorvastatin (parent) pretreatment of unfractionated LDL at 10.0 μM followed by stimulation of oxidative stress were tested. As shown in FIG. 26, the combination of EPA and atorvastatin reduced unfractionated LDL oxidation to the same significant extent (p<0.001 vs. vehicle or atorvastatin alone) that was observed with EPA alone. Separately, atorvastatin did not have any significant antioxidant activity.

These data show that EPA effectively blocks sdLDL and LDL oxidation at pharmacologic concentrations in vitro and in a manner that could not be reproduced with vitamin E or other TG-lowering agents. ATM had similar activity that was enhanced in combination with EPA.

Example 8

Materials

Human umbilical vein endothelial cells (HUVECs) were isolated into primary cultures from female donors by Clonetics (San Diego, Calif.) and purchased as proliferating cells. All cell culture donors were healthy, with no pregnancy or prenatal complications. The cultured cells were incubated in 95% air/5% $CO_2$ at 37° C. and passaged by an enzymatic (trypsin) procedure. The confluent cells (4 to $5 \times 10^5$ cells/35 mm dish) were placed with minimum essential medium containing 3 mM L-arginine and 0.1 mM BH4 [(6R)-5,6,7,8-tetrahydrobiopterin]. Before experimental use, the cells (from second or third passage) were rinsed twice with Tyrode-HEPES buffer with 1.8 mM $CaCl_2$.

The omega-3 fatty acids (O3FAs) cis-5,8,11,14,17-eicosapentaenoic acid (EPA) and docosahexaenoic acid (DHA) were purchased from Sigma-Aldrich (St. Louis, Mo.) and prepared initially at 11 mM in redistilled ethanol. Primary and secondary O3FA stock solutions were prepared and stored under argon at −20° C. Ortho (o)-hydroxy atorvastatin metabolite (ATM) was synthesized and purchased from Toronto Research Chemicals (North York, Ontario, Canada) and solubilized in ethanol at 1 mM; subsequent dilutions were prepared in ethanol or aqueous buffer as needed.

LDL Isolation

We tested the effects of EPA treatment in the absence and presence of ATM in HUVECs following exposure to oxidized LDL (oxLDL). The oxLDL causes eNOS uncoupling and endothelial dysfunction to reproduce disease-like conditions. 25 Venous blood from healthy normolipidemic volunteers was collected into Na-EDTA (1 mg/mL blood) vacuum tubes after a 12-hour fast. Plasma was immediately separated by centrifugation at 3,000 g for 10 minutes at 4°

C. LDL (δ=1.020 to 1.063 g/mL) was separated from freshly drawn plasma by preparative ultracentrifugation with a Beckman ultracentrifuge equipped with an SW-41 rotor. The density of plasma was adjusted to 1.020 g/mL with sodium chloride solution, the plasma was centrifuged at 150,000 g for 24 hours, and the chylomicron-rich layers were discarded. The remaining fraction, after adjustment of density at 1.063 g/mL with potassium bromide, was centrifuged at 150,000 g for 24 hours to isolate LDL from the HDL fraction. The purified LDL was dialyzed for 96 hours against PBS containing 0.3 mM EDTA at 4° C., then stored at 4° C.
LDL Oxidation A sample of LDL was dialyzed against Tris/NaCl Buffer (50 mM Tris in 0.15 M NaCl, pH 8.0) to remove the EDTA. Tris-NaCl buffer was added to the dialyzed LDL to adjust the protein concentration to 30 mg/mL. A 1-mL aliquot of 20 µM $CuSO_4$ was added to 1 mL of dialyzed normal LDL. Oxidation at 37° C. was followed spectrophotometrically (234 nm) over a period of 24 hours until oxidation was complete. The oxLDL was then dialyzed at 4° C. with 4 L Tris buffer, filtered with a 0.22 µm filter, and stored under nitrogen at 4° C.

Oxidation was monitored by the use of measurements of TBARS. Briefly, LDL was incubated with thiobarbituric acid (0.5 wt/vol, in $H_2SO_4$, 50 mM) for 30 minutes at 100° C. The solution then was centrifuged for 5 minutes, and the difference in absorbency at 532 and 580 nm was calculated. TBARS concentration was determined as malondialdehyde (MDA) equivalents with the use of an MDA standard curve.
NO and ONOO⁻ Nanosensors Concurrent measurements of NO and ONOO⁻ were performed with tandem electrochemical nanosensors combined into one working unit with a total diameter of 200-400 nm. Their design was based on previously developed and chemically modified carbon-fiber technology. Each of the nanosensors was made by depositing a sensing material on the tip of a carbon fiber (length 4 to 5 µm, diameter 100-200 nm). The fibers were sealed with nonconductive epoxy and electrically connected to copper wires with conductive silver epoxy. Conductive films of polymeric Ni(II) tetrakis (3-methoxy-4-hydroxyphenyl) porphyrin and Mn(III) [2.2] paracyclophanylporphyrin were used for the NO and ONOO⁻ sensors, respectively.

The amperometric method (with a response time of 0.1 ms) provides a quantitative signal (current) that is directly proportional to changes (from basal levels) in NO or ONOO⁻ concentration. Amperometric measurements were performed with a Gamry III double-channel potentiostat. Basal NO or ONOO⁻ levels were measured by differential pulse voltammetry in separate experiments.

All measurements of NO and ONOO⁻ were performed on intact endothelial cells. The NO/ONOO⁻ nanosensor module was positioned 5±2 µm from the surface of each individual endothelial cell using a computer-controlled M3301 micromanipulator (x-y-z resolution of 0.2 µm) and microscope (both from World Precision Instruments, Berlin, Germany) fitted with a CD camera. After establishing a background current, EPA, in the absence and presence of ATM, was added to the cells. Rapid changes in current (proportional to the molar concentrations of NO or ONOO⁻ released) were observed after the addition of Ca and were monitored continuously.
Treatment with oxLDL, EPA and Statins Primary human umbilical vein endothelial cells (HUVECs) were incubated with vehicle or oxidized human low density lipoprotein (oxLDL) for 20 min prior to treatment with EPA and/or ATM. After this incubation period, the cells were treated with vehicle or with 10 µM EPA in the absence or presence of 1.0 µM ATM for 1 hour. Endothelial basal media was used for all the treatments. Controls were supplied with an equivalent volume of endothelial basal media.
Statistical Analyses Data are presented as mean±S.D. for (N) separate samples or experiments. Differences between groups were analyzed using the two-tailed, Student t-test (for comparisons between only two groups) or ANOVA followed by Student-Newman-Keuls multiple comparisons post-hoc analysis (for comparisons between three or more groups). Only differences with probability values less than 0.05 were considered significant.
Results A summary of all measurements of NO and ONOO⁻ release in HUVECs, along with the NO/ONOO⁻ ratios, is included in Table 1.

TABLE 1

NO and ONOO⁻ Release from HUVECs.

| Treatment | NO | ONOO⁻ | NO/ONOO⁻ Ratio |
|---|---|---|---|
| Vehicle | 376 ± 85 | 239 ± 41 | 1.57 ± 0.45 |
| oxLDL + Vehicle | 292 ± 53 | 246 ± 26 | 1.19 ± 0.25 |
| oxLDL + EPA | 423 ± 163 | 189 ± 25 | 2.24 ± 0.91 |
| oxLDL + ATM | 480 ± 75 | 196 ± 34 | 2.45 ± 0.57 |
| oxLDL + EPA + ATM | 590 ± 190 | 172 ± 12 | 3.43 ± 1.13 |
| oxLDL + DHA | 567 ± 103 | 167 ± 18 | 3.39 ± 0.72 |
| oxLDL + DHA + ATM | 462 ± 117 | 133 ± 28 | 3.48 ± 1.14 |
| oxLDL + Fenofibrate | 327 ± 187 | 299 ± 24 | 1.09 ± 0.63 |
| oxLDL + Fenofibrate + ATM | 471 ± 106 | 243 ± 30 | 1.94 ± 0.50 |
| oxLDL + Niacin | 431 ± 100 | 215 ± 25 | 2.00 ± 0.52 |
| oxLDL + Niacin + ATM | 436 ± 118 | 198 ± 28 | 2.20 ± 0.67 |
| oxLDL + Gemfibrozil | 192 ± 34 | 266 ± 34 | 0.72 ± 0.16 |
| oxLDL + Gemfibrozil + ATM | 418 ± 85 | 214 ± 31 | 1.95 ± 0.49 |
| EPA + oxLDL | 663 ± 50 | 247 ± 17 | 2.68 ± 0.28 |

Values in Table 1 are reported as mean +/− S.D. (N = 3-16).

In comparison to vehicle, EPA, DHA, and niacin separately have beneficial effects on the release of NO, ONOO⁻ and their ratio. By contrast, fenofibrate treatment produced an increase in NO release but caused a disproportionate and detrimental increase in ONOO⁻ release, thereby reducing the ratio of NO to ONOO⁻. Gemfibrozil treatment reduced both NO release and the NO to ONOO⁻ ratio.

We also tested the effects of EPA and other TG-lowering agents, along with DHA, to ATM alone and in combination as reviewed in Table 1. We observed that EPA+ATM treatment was associated with a similar benefit in the relative release of NO and ONOO⁻. As a result, treatment with EPA+ATM continued to demonstrate an overall benefit in the NO to ONOO⁻ ratio. Treatment with DHA+ATM also produced an overall benefit in the NO to ONOO⁻ ratio, but this was primarily attributed to a decrease in ONOO⁻ release but no improvement in NO production. This is in contrast to the effects with EPA and even DHA monotherapy. The combination of ATM+niacin resulted in its relative loss in benefit as compared to monotherapy. As compared to ATM alone, fenofibrate+ATM treatment caused a loss in any minimal benefit in NO and even preserved the detrimental effects on ONOO⁻ release. This resulted in an adverse effect on the NO to ONOO⁻ ratio. Finally, gemfibrozil+ATM treatment had a minimal effect on ONOO⁻ release and a detrimental effect on NO release, along with the NO to ONOO⁻ ratio.

Figure 27:
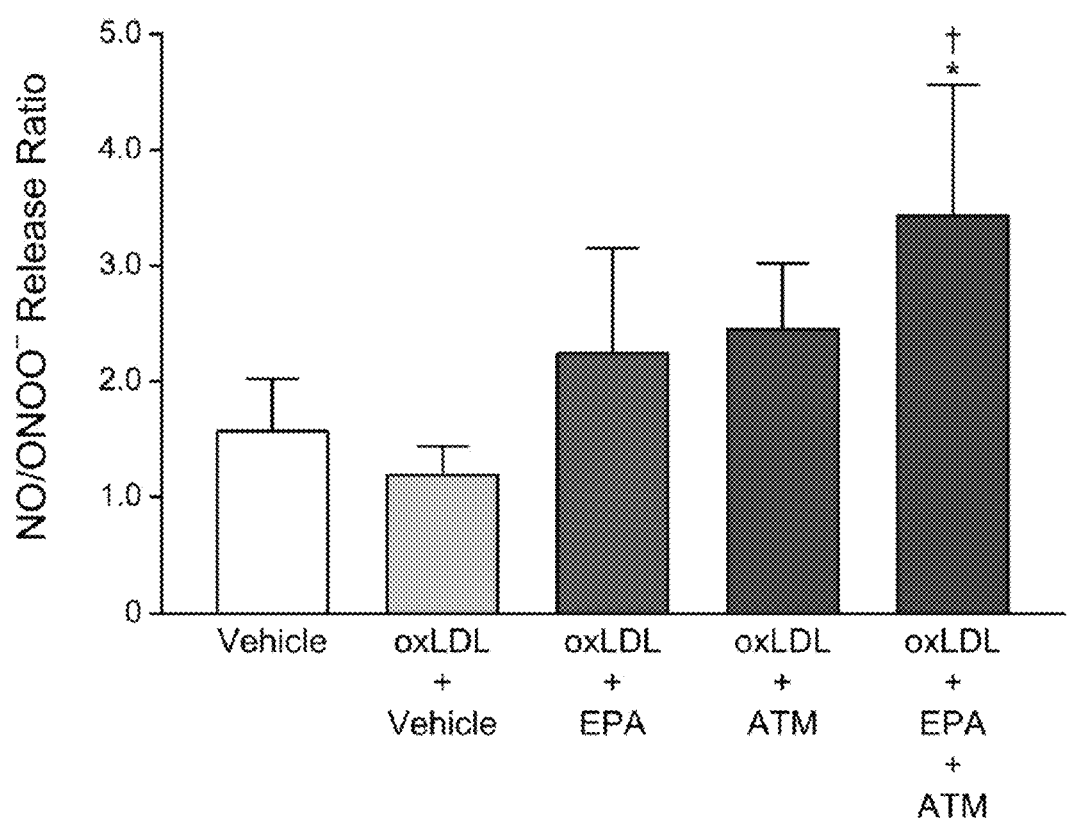
FIG. 27 shows the separate and combined effects of EPA and atorvastatin o-hydroxy (active) metabolite (ATM) on the ratio of NO to $ONOO^-$ released from HUVECs exposed to oxidized low-density lipoprotein (oxLDL). Values are mean+/−S.D. (N=3-7). *$p<0.05$ versus vehicle alone (no oxLDL); †$p<0.05$ versus oxLDL+vehicle (Student-Newman-Keuls multiple comparisons test; overall ANOVA: $p<0.0307$, F=4.162).
Figure 28:
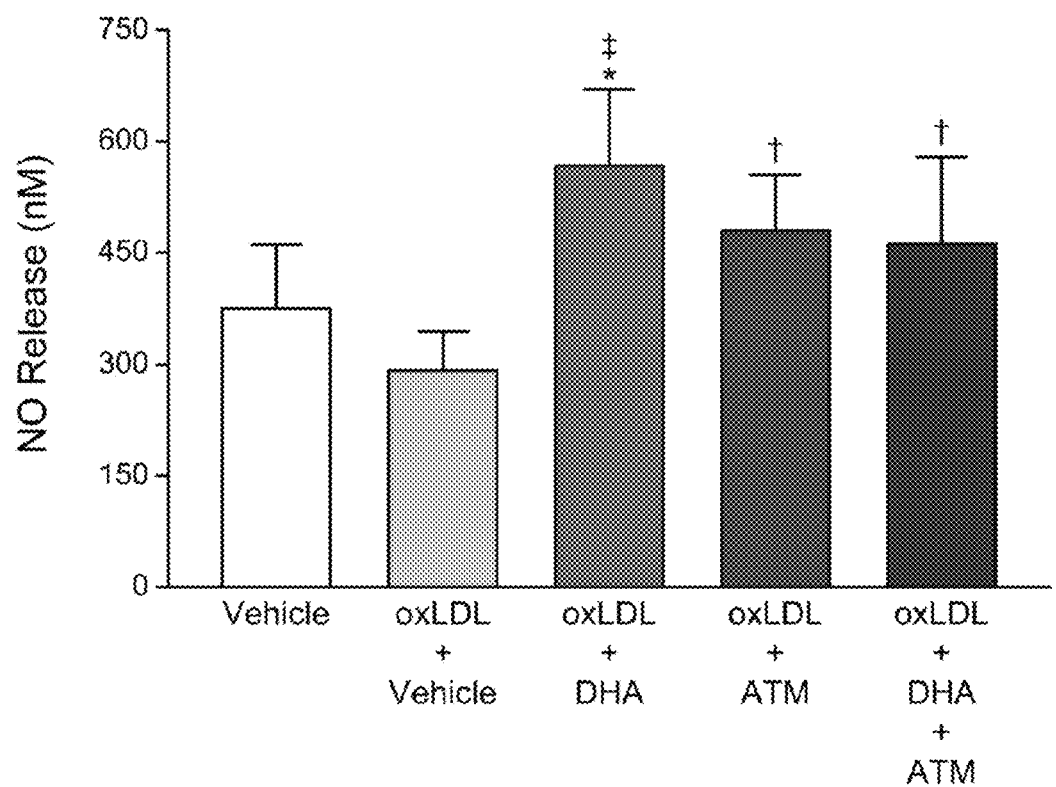
FIG. 28 shows the separate and combined effects of docosahexaenoic acid (DHA) and ATM on NO release from HUVECs exposed to oxLDL for one hour. Values are mean+/−S.D. (N=4-16). *$p<0.01$ versus vehicle alone (no oxLDL); †$p<0.05$ and ‡$p<0.01$ versus oxLDL+vehicle (Student-Newman-Keuls multiple comparisons test; overall ANOVA: $p=0.0007$, F=6.630).

As shown in FIG. 27, exposure of HUVECs to oxLDL decreased NO release from HUVECs by 22% (376±85 nM to 292±53 nM) while increasing ONOO⁻ release as compared to untreated cells. In ECs exposed to oxLDL, treatment with EPA and ATM separately increased NO release by 45% (423±163 nM) and 64% (480±75 nM), respectively. When combined, treatment with EPA+ATM increased NO release by 200% (590±190 nM) as compared to vehicle ($p<0.01$) (FIG. 27). The improvement in NO release with the EPA+ATM combination was also greater than cells treated with non-oxidized LDL ($p<0.05$). By contrast, the combination of DHA with ATM did not improve NO release as compared to ATM or DHA separately (FIG. 28).

Figure 29:
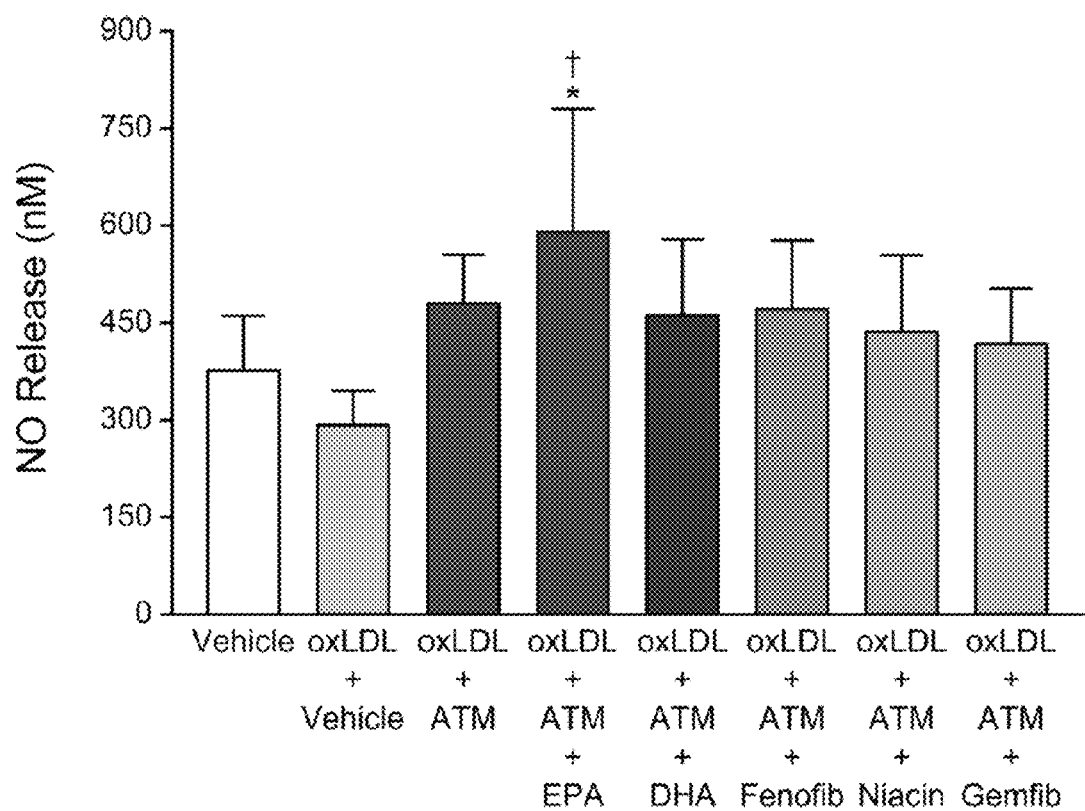
FIG. 29 shows the effects of ATM, alone or in combination with EPA, DHA, fenofibrate (Febofib), nicotinic acid (Niacin), or gemfibrozil (Gemfib) on NO release from HUVECs exposed to oxLDL. Values are mean+/−S.D. (N=4-16).*$p<0.05$ versus vehicle alone (no oxLDL); †$p<0.01$ versus oxLDL+vehicle (Student-Newman-Keuls multiple comparisons test; overall ANOVA: $p=0.0080$, F=3.309).
Figure 30:
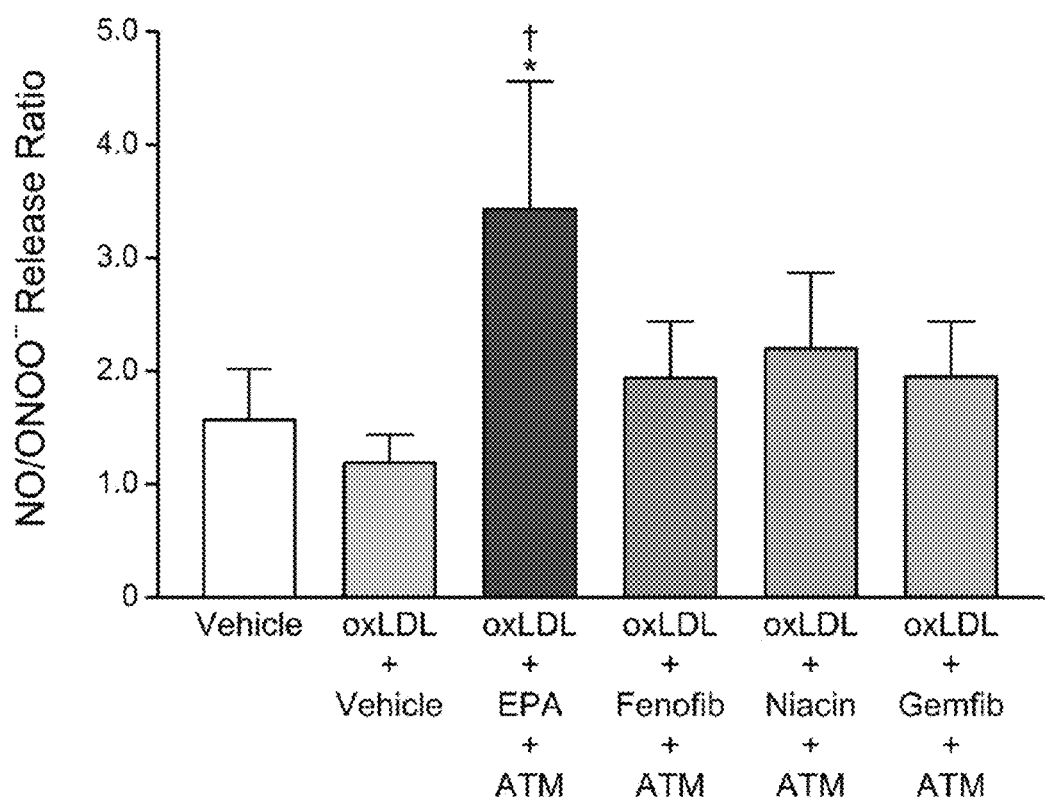
FIG. 30 shows the effects of EPA, Fenofib, Niacin and Gemfib, each in combination with ATM, on the ratio of NO to $ONOO^-$ release from HUVECs exposed to oxLDL.

When comparing all the agents, the improvement in NO with EPA was not reproduced with DHA or the other TG-lowering agents when combined with ATM (FIG. 29). Furthermore, the NO/ONOO⁻ ratio, an indicator of normal EC function, increased by approximately 3-fold with the EPA and ATM combination treatment as compared to control treatments ($p<0.05$). The improvement in the NO/ONOO⁻ ratio was not observed with other TG-lowering agents as compared to EPA (FIG. 30).

Example 9

The objective of this study is to compare dose-dependent effects of EPA, EPA-docosahexaenoic acid (DHA) combination, DHA alone, glycyrrhizin, alpha-linolenic acid (ALA), docosapentaenoic acid (DPA), arachidonic acid (AA), fenofibrate, gemfibrozil and niacin on membrane cholesterol domains that model atherosclerosis.

Membrane cholesterol domains are associated with atheroma development and formation of toxic cholesterol crystals. Agents that reduce such membrane domains would be expected to have important therapeutic benefits.

Materials

The omega-3 fatty acids, eicosapentaenoic acid (EPA), docosahexaenoic acid (DHA), glycyrrhizin, docosapentaenoic acid (DPA), alpha-linolenic acid (ALA) and the omega-6 fatty acid arachidonic acid (AA) were purchased from Sigma-Aldrich (Saint Louis, Mo.) and solubilized in redistilled ethanol to 500 µM under nitrogen atmosphere. The fatty acid stock solutions were stored at −20° C. until use. Fenofibrate, gemfibrozil and nicotinic acid were purchased from Toronto Research Chemicals (North York, Ontario, Canada) and solubilized in ethanol at 1 mM; subsequent dilutions were prepared in ethanol or aqueous buffer as needed.

Methods

Multilamellar vesicles (MLVs) were prepared as binary mixtures that include palmitoyloleoylphosphatidylcholine (POPC) (1.0 mg total phospholipid per sample) and cholesterol at an elevated cholesterol-to-phospholipid (C/P) mole ratio of 1.5:1. Component lipids (in chloroform) were transferred to 13×100 mm borosilicate culture tubes and then combined with vehicle (ethanol) or an equal volume of EPA, EPA+DHA, DHA, DPA, ALA, AA stock solutions or with other TG-lowering agents (fenofibrate, gemfibrozil, niacin), adjusted to achieve desired treatment concentrations (total drug-to-phospholipid mole ratio of 1:30), and incubated with the test agent during removal of solvent. Samples were shell-dried under nitrogen gas and placed under vacuum for 3 hours to remove residual solvent at room temperature. After desiccation, each sample was resuspended in saline buffer (0.5 mM HEPES, 154 mM NaCl, pH 7.3) to yield a final phospholipid concentration of 2.5 mg/mL. Lipid suspensions were then vortexed for 3 minutes at ambient temperature to form MLVs.

Membrane lipid vesicles were oriented for x-ray diffraction analysis as described by others (e.g., Herbette et al., *Biophys. J.*, vol. 20(2), pages 245-272 (1977)). Briefly, a 100 µL aliquot of each MLV preparation (containing 250 µg MLV) was transferred to a Lucite® sedimentation cell fitted with an aluminum foil substrate designed to collect MLVs into a single membrane pellet upon centrifugation. Samples were then loaded into a Sorvall AH-629 swinging bucket rotor (DuPont Corp., Wilmington, Del.) and centrifuged at 35,000 g, 5° C., for 90 minutes.

After centrifugal orientation, sample supernatants were aspirated and aluminum foil substrates, each supporting a single membrane pellet, were removed from the sedimentation cells. Sample pellets were dried for 5-10 minutes at ambient conditions, mounted onto curved glass supports, and placed in hermetically-sealed, brass or glass containers (for immediate analysis or temporary storage, respectively). All x-ray diffraction experiments were conducted at 20° C., 74% relative humidity. The latter was established by exposing membrane samples to saturated solutions of L-(+)-tartaric acid ($K_2C_4H_4O_6 \cdot \frac{1}{2}H_2O$) for at least 1 hour prior to experimental analysis.

Oriented membrane samples were aligned at grazing incidence with respect to a collimated, mono-chromatic CuK$_\alpha$, x-ray beam (K$_{\alpha 1}$ and K$_{\alpha 2}$ unresolved; $\lambda=1.54$ Å) produced by a Rigaku Rotaflex RU-200, high-brilliance microfocus generator (Rigaku-MSC, The Woodlands, Tex.) as previously described (Mason et al., *Biophys. J.*, vol. 55(4), pages 769-778 (1989)). The samples were initially subjected to x-ray diffraction analysis at least 12 hours after formation of the membrane pellets and retested for up to several days. Analytical x-rays were generated by electron bombardment of a rotating copper anode and are filtered through a thin nickel foil to provide monochromatic radiation ($\lambda=1.54$ Å). Collimation of the x-ray beam was achieved using a single Franks mirror. Diffraction data were collected on a one-dimensional, position-sensitive electron detector (Hecus X-ray Systems, Graz, Austria) at a sample-to-detector distance of 150 mm from the sample site.

The d-space for any given membrane multi bilayer is a measurement of the unit cell periodicity of the membrane lipid bilayer (e.g., the distance from the center of one lipid bilayer to the next including surface hydration), and is calculated from Bragg's Law, $h\lambda = d\sin\theta$, where h is the diffraction order, $\lambda$ is the wavelength of the x-ray radiation (1.54 Å), d is the membrane lipid bilayer unit cell periodicity, and $\theta$ is the Bragg angle equal to one-half the angle between the incident beam and scattered beam.

The presence of cholesterol domains in a given membrane sample results in the production of distinct Bragg (diffraction) peaks having singular periodicity values of 34 and 17 Å (typically referred to as first- and second-order cholesterol domain peaks). Under the specific temperature and relative humidity conditions established for these experiments, the second-order, 17 Å cholesterol domain peak was well-delineated from other, neighboring cholesterol and phospholipid diffraction peaks and was thus used to quantitate relative cholesterol domain peak intensity. Routines written in Origin 8.6 (OriginLab Corporation, Northampton, Mass.) were used to determine total peak area (associated with all diffraction peaks in a given pattern) against which the second-order cholesterol domain peak was normalized.

Statistical Analyses

The raw data collected in this study was normalized using internal. Data were presented as mean±S.E.M. for (N) separate samples or treatment groups. Differences between groups were analyzed using the two-tailed, Student's t-test (for comparisons between only two groups) or ANOVA followed by Dunnett or Student-Newman-Keuls multiple comparisons post-hoc analysis (for comparisons between three or more groups). Alpha error was set to 0.05 in this study.

Results

Comparative effects of eicosapentaenoic acid (EPA), docosahexaenoic acid (DHA), EPA-DHA combination treatment, fenofibrate (Fenofib), nicotinic acid (Niacin), gemfibrozil (Gemfib), glycyrrhizin (Glyc), arachidonic acid (AA), α-linolenic acid (ALA), and docosapentaenoic acid (DPA) on normalized cholesterol domain peak intensity as measured in model membrane prepared as binary mixtures of POPC and cholesterol at a 1.5:1 C/P mole ratio are reviewed in Table 2. Membranes were treated immediately with each of the various agents to achieve a total drug-to-phospholipid (D/P) mole ratio of 1:30. In each panel, diffraction peaks highlighted in red correspond to a cholesterol crystalline domain phase, which has a characteristic periodicity (d-space value) of 34 Å; peaks labeled 1 through 4 correspond to the surrounding membrane phospholipid bilayer phase, which was observed to have an average periodicity of 57 Å.

TABLE 2

Cholesterol Domain Peak Intensities for EPA and Other Agents.

| Treatment | Relative Cholesterol Domain Preak Intensity | % change Vs control | P values |
|---|---|---|---|
| Vehicle | 42.3 ± 4.3 | — | — |
| EPA (20:5; n-3)* | 14.6 ± 5.0 | −65.5 ± 17.1 | 0.0139 |
| DHA (22:6; n-3)* | 37.6 ± 2.4 | −11.1 ± 11.7 | 0.3975 |
| EPA + DHA* | 29.8 ± 7.6 | −29.6 ± 20.9 | 0.2279 |
| Fenob* | 41.7 ± 6.8 | −1.4 ± 19.1 | 0.9451 |
| Niacin* | 27.5 ± 12.2 | −35.0 ± 30.8 | 0.3157 |
| Gemfib* | 46.9 ± 12.6 | 10.9 ± 43.3 | 0.8122 |
| Glyc* | 19.1 ± 1.2 | −54.9 ± 12.3 | 0.0002 |
| AA (20:4; n-6) | 22.5 ± 4.3 | −46.8 ± 15.2 | 0.0316 |
| ALA (18:3; n-3) | 23.2 ± 0.6 | −45.2 ± 11.3 | 0.0122 |
| DPA (22:5; n-3) | 33.5 ± 2.7 | −20.8 ± 12.2 | 0.1587 |

Values are reported as mean ± SEM (N = 3-6). *P values were calculated against vehicle-treated controls using an unpaired, two-tailed Student's t-test. Values within parentheses after fatty acids denote carbon length and number of unsaturated bonds; omega-3 or −6 fatty acid classification.

The percent changes in the area of the peaks were compared to vehicle control treatment and representative diffraction patterns for each of the tested agents were calculated as shown in FIG. 31.

EPA treatment caused a pronounced and significant ($p<0.05$) reduction in cholesterol domain peaks by 65% (14.6±5.0) as compared to vehicle treatment (42.3±4.3) as shown in FIG. 32.

Model membranes were prepared as binary mixtures of POPC and cholesterol at a C/P mole ratio of 1.5:1 and treated immediately with each agent at a D/P mole ratio of 1:30 (Note: The EPA, DHA treatment agent was a 1:1 molar ratio). Relative cholesterol peak intensity values were derived by integrating the second-order cholesterol domain peak and normalizing to total phospholipid peak area associated with a given diffraction pattern. The EPA to DHA mixture was a 1:1 molar ratio. Values are mean±SEM (N=3). Samples treated with DHA did not reduce cholesterol domains (37.6±2.4); the integrated peak areas were significantly larger than those observed for EPA ($p<0.05$). The combination of EPA with DHA showed an intermediate reduction in domain formation of 30% (29.8±7.6), consistent with a lower level of EPA. The difference in domain size with the EPA+DHA combination at a 1:1 molar ratio was a non-significant −29.6% (29.8±7.6) compared to vehicle or other treatments (FIG. 32). Values are mean±SEM (N=3). *$p<0.05$ versus control; †$p<0.05$ versus DHA; § $p<0.05$ versus Fenofib (Student-Newman-Keuls multiple comparisons test; overall ANOVA: p=0.0275, F=4.326).

EPA treatment induced significant reduction in the domain peak intensity (65%, 14.6±5) compared to vehicle control. There were no significant changes in cholesterol domain size for membranes treated with either niacin (27.5±12.2) or gemfibrozil (46.9±12.6) as compared to vehicle treatment (Table 2); the cholesterol domain peaks associated with gemfibrozil treatment were numerically greater than vehicle by 11% than vehicle. A reduction in domain peak intensity was observed with niacin (−35%) but it was not statistically significant as compared to vehicle treated control samples (Table 2). Treatment with niacin was associated with substantial variation in cholesterol domain peak size compared to the other treatments. As a positive control, effects of EPA were compared to glycyrrhizin, a glycosylated sterol that has been shown to reduce cholesterol domains in model membranes. Like EPA, glycyrrhizin reduced the size of the integrated peaks associated with the cholesterol domains by 54.9% (19.1±1.2) in a highly reproducible and significant fashion (FIG. 33). Each agent was tested at D/P mole ratio of 1:30 and treated immediately with the different agents. Values are mean SEM (N=3-6). **$p<0.01$ versus control; †$p<0.05$ versus DHA; § $p<0.05$ versus Fenofib (Student-Newman-Keuls multiple comparisons test; overall ANOVA: p=0.0010, F=7.624).

DPA did not reduce domains compared to EPA (Table 2, FIG. 34, 35, 36). Treatment with ALA (18:3; n-3) and AA (20:4; n-6) also significantly reduced domain peak intensity, although to lesser extents of −46.8% and −45.2%, respectively ($p<0.05$ versus control for both) (Table 2, FIGS. 35, 36).

Dose-dependent effects of EPA on membrane cholesterol domains in model membrane prepared as binary mixtures of POPC and cholesterol at a 1.5:1 C/P mole ratio. are reviewed in Table 3. Membranes were treated immediately with EPA at the D/P mole ratios indicated. Relative cholesterol peak intensity values were derived by integrating the second-order cholesterol domain peak and normalizing to total phospholipid peak area associated with a given diffraction pattern. Values are mean±SEM (N=3). ANOVA: p=0.0798, F=3.276.

TABLE 3

Dose-Dependent Effects of EPA on Membrane Cholesterol Domains.

| Treatment* | Relative Chotesterol Domain Peak Intensity | % Change (vs. Control) | † P Values |
|---|---|---|---|
| Vehicle | 42.3 ± 4.3 | — | — |
| EPA, 1:90 | 36.0 ± 3.1 | −15.0 ± 12.6 | 0.3010 |
| EPA, 1:60 | 29.5 ± 10.9 | −30.2 ± 27.9 | 0.3373 |
| EPA, 1:30 | 14.6 ± 5.0 | −65.5 ± 17.1 | 0.0139 |

Values are reported as mean ± SEM (N = 3-6). *P values were calculated against vehicle-treated controls using an unpaired, two-tailed Student's t-test. Values within parentheses after fatty acids denote carbon length and number of unsaturated bonds; omega-3 or omega-6 fatty acid classification.

The reduction in cholesterol domain peak intensity with EPA was dose-dependent over a range of EPA to phospholipid mole ratios of 1:30 to 1:90 (Table 3, FIG. 37).

Example 10

The objective of this study was to compare the effects of EPA, fenofibrate, nicotinic acid, gemfibrozil, and vitamin E on the oxidation of small dense LDL (sdLDL) isolated from human subjects under conditions of hyperglycemia.

Materials

Eicosapentaenoic acid (EPA), fenofibrate, gemfibrozil and nicotinic acid (niacin) were purchased from Sigma-Aldrich (Saint Louis, Mo.) and solubilized separately in ethanol to 1.0 mM under nitrogen atmosphere. Vitamin E (α-tocopherol) purchased from Sigma-Aldrich was prepared in ethanol at 1.0 mM ($\varepsilon=3.06\times10^4$ $M^{-1}$ $cm^{-1}$ at 294 nm) prior to experimental use. Test compounds were further diluted in ethanol or aqueous buffer as needed. Phosphate Buffered Saline (PBS) purchased from Sigma-Aldrich was prepared in double distilled water at 10 mM (138 mM NaCl, 2.7 mM KC, pH 7.4). Glucose prepared in PBS was added to test samples to achieve a final concentration of 11.0 mM (200 mg/dL).

Methods

LDL and sdLDL were isolated from the plasma of healthy volunteers by iodixanol density gradient ultracentrifugation and adjusted to a final apolipoprotein concentration of 10 mg/mL. Sample aliquots (100 µg apolipoprotein each) were incubated with vehicle (ethanol), EPA, fenofibrate, gemfibrozil, or niacin (each at 10.0 µM) and adjusted to a final volume of 1.0 mL in glucose-treated PBS and incubated for 30 minutes at 37° C. in a shaking water bath. Lipid oxidation was initiated with 1.0 µM $CuSO_4$ and 100 µL of sample aliquots were combined with 1.0 mL thiobarbituric acid (0.5%), 10 µL trichloroacetic acid (10%), 10 µL BHT (35 mM in methanol), and 10 µL EDTA (5 mM) at different time points (up to 4 hr). Sample aliquots were incubated at 100° C. for 30 minutes and then assayed for the formation of thiobarbituric acid-reactive substances (TBARS), having a molar absorptivity ($\varepsilon$) value of $1.56\times10^5$ $M^{-1}$ $cm^{-1}$ at 532 nm and were derived principally from the reaction of thiobarbituric acid with malondialdehyde (MDA). Lipid oxidation was measured by the colorimetric detection of malondialdehyde (MDA), a marker of oxidative stress.

Statistical Analyses

Data were presented as mean±SD for (n) separate samples or experiments. Differences between groups were analyzed using the unpaired, two-tailed Student's t-test (for comparisons between only two groups) or ANOVA followed by Student-Newman-Keuls multiple comparisons post hoc analysis (for comparisons between three or more groups). Only differences with probability values less than 0.05 were considered significant.

Results

Exposure of sLDL to hyperglycemic conditions (200 mg/dL glucose) increased the sdLDL oxidation (formation of MDA) by 55% (from 3.4±0.1 to 5.3±0.3 µM) compared to non-glucose-treated controls (FIG. 38).

EPA treatment inhibited glucose-induced sdLDL oxidation in a dose-dependent fashion with an $IC_{50}$ less than 1.0 µM (FIG. 39). Further, at the highest concentration tested (10.0 µM), EPA inhibited sdLDL oxidation by 94% (5.3±0.3 µM to 0.2±0.1 µM) as compared to vehicle controls (FIG. 39). Values are mean±S.D. (N=3).**p<0.001 versus vehicle- (glucose-) treated control; †p<0.001 versus 1.0 µM EPA; § p<0.01 versus 2.5 µM EPA (Student-Newman-Keuls multiple comparisons test; overall ANOVA: p<0.0001, F=1358.7).

Treatment with fenofirbrate, niacin, and gemfibrozil did not inhibit glucose-induced sdLDL oxidation (FIG. 40 and FIG. 41).

Vitamin E failed to inhibit sdLDL oxidation. Instead, vitamin E increased sdLDL oxidation by 63% as compared to glucose-treated controls (p<0.001) (FIG. 41).

Example 11

The objectives of this study were to:
1) compare the time-dependent effects of pretreatment with EPA, alone or in combination with a statin (e.g., atorvastatin active metabolite, also referred to herein as "ATM"), to pretreatment with other triglyceride-lowering agents such as fenofibrate, niacin and gemfibrozil and DHA on endothelial cell function as indicated by changes in nitric oxide (NO) and nitroxidative ($ONOO^-$) stress release under conditions of oxidative stress using oxidized LDL (oxLDL);
2) test the effects of oxLDL treated with EPA, alone or in combination with ATM, on endothelial cell function compared to those of treatment with DHA; and
3) test the effects of pretreating LDL with EPA, alone or in combination with ATM, and then subjecting the pretreated LDL to oxidation, compared to those of DHA.

The omega-3 fatty acid, cis-5,8,11,14,17-eicosapentaenoic acid (EPA) and docosahexaenoic acid (DHA) were purchased from Sigma-Aldrich (Saint Louis, Mo.) and solubilized in redistilled ethanol to 11 mM under nitrogen atmosphere. EPA and DHA stock solutions were stored at −20° C. until use. Fenofibrate, gemfibrozil and nicotinic acid were purchased from Toronto Research Chemicals (North York, Ontario, Canada) and solubilized in ethanol at 1 mM; subsequent dilutions were prepared in ethanol or aqueous buffer as needed. Atorvastatin ortho- (o-) hydroxy (active) metabolite (ATM) was also purchased from Toronto Research Chemicals (North York, Ontario, Canada) and solubilized in ethanol at 1.0 mM.

Human umbilical vein endothelial cells (HUVECs) were obtained from healthy, female donors and isolated into primary, proliferating cell cultures (Clonetics, San Diego, Calif.). The cells were incubated in 95% air/5% $CO_2$ at 37° C. and passaged by an enzymatic (trypsin) procedure. The confluent cells (4 to $5\times10^5$ cells/35 mm dish) were plated with minimum essential medium containing 3 mM L-arginine and 0.1 mM $BH_4$ [(6R)-5,6,7,8-tetrahydrobiopterin]. Before experimental use, the cells (from second or third passage) were rinsed twice with Tyrode-HEPES buffer with 1.8 mM $CaCl_2$.

Venous blood was collected from healthy volunteers into vacutainer tubes containing sodium EDTA. Plasma was separated by centrifugation at 3000 g for 25 min at 4° C. and adjusted to a density of 1.020 g/mL with KBr. Triglyceride-rich lipoproteins (TGRL) and LDL fractions were isolated by sequential centrifugation at 70,000 rpm at 4° C. in a Beckman LE-80 ultracentrifuge using a Beckman 50.4Ti rotor (Beckman Coulter, Inc., Fullerton, Calif.). The TGRL fraction (with a relative density of <1.020) was aspirated from the top of the centrifugate and discarded, leaving an LDL-enriched infranate (with a relative density of 1.020-1.063). The LDL subfraction was retained for additional experimentation. Plasma and lipoprotein fractions were maintained at 4° C. and protected from excessive exposure to light. Prior to oxidation experiments, EDTA was removed from the lipoprotein fraction using PD-10 desalting columns (GE Healthcare, Piscataway N.J.). After equilibration of the column with phosphate buffered saline (PBS), 2.5 mL of the lipoprotein fraction was loaded on the column and the flow-through discarded. The lipoprotein was then eluted with 3 mL of PBS. The LDL fractions were further diluted with PBS to obtain a 100 µg/mL apoB100 concentration.

LDL underwent oxidation following the addition of 10 µM $CuSO_4$. To measure oxidation, 100 µL aliquots were removed and combined with 1.0 mL thiobarbituric acid (0.5%), 10 μL trichloroacetic acid (5%), 10 μL BHT (5 mg/mL in methanol), and 10 μL EDTA (5 mM). Sample aliquots were incubated at 100° C. for 20 min and then assayed for the formation of TBARS, which have a molar absorptivity (ε) value of $1.56 \times 10^5$ $M^{-1}$ $cm^{-1}$ at 532 nm and are derived principally from the reaction of thiobarbituric acid with MDA, a reactive aldehyde produced by LDL oxidation. Sample TBARS concentrations were determined spectrophotometrically by measuring sample absorbances against a standard curve derived from the hydrolysis of 1,1,3,3-tetramethoxypropane.

Concurrent measurements of NO and $ONOO^-$ were performed with tandem electrochemical nanosensors combined into one working unit with a total diameter of 200-400 nm. Their design is based on previously developed and chemically modified carbon-fiber technology. Each of the nanosensors was made by depositing a sensing material on the tip of a carbon fiber (length 4 to 5 μm, diameter 100-200 nm). The fibers were sealed with nonconductive epoxy and electrically connected to copper wires with conductive silver epoxy. Conductive films of polymeric Ni(II) tetrakis (3-methoxy-4-hydroxyphenyl) porphyrin and Mn(III) [2.2] paracyclophanyl-porphyrin were used for the NO and $ONOO^-$ sensors, respectively.

The amperometric method (with a response time of 0.1 ms) provides a quantitative signal (current) that is directly proportional to changes (from basal levels) in NO or $ONOO^-$ concentration. Amperometric measurements were performed with a Gamry III double-channel potentiostat. Basal NO or $ONOO^-$ levels were measured by differential pulse voltammetry in separate experiments.

All measurements of NO and $ONOO^-$ were performed on intact endothelial cells. The NO/$ONOO^-$ nanosensor module was positioned 5±2 μm from the surface of each individual endothelial cell using a computer-controlled M3301 micromanipulator (x-y-z resolution of 0.2 μm) and microscope (both from World Precision Instruments, Berlin, Germany) fitted with a CD camera. After establishing a background current, EPA and other TG-lowering agents (fenofibrate, niacin, and gemfibrozil), in the absence and presence of different statins, were added to the cells. Cells will then be treated with calcium ionophore (to maximally stimulate the release of nitrous molecules) and monitored continuously for changes in amperometric current.

Data are presented as mean±S.D. for (N) separate samples or treatment groups. Differences between groups were analyzed using the two-tailed, Student's t-test (for comparisons between only two groups) or ANOVA followed by Dunnett or Student-Newman-Keuls multiple comparisons post-hoc analysis (for comparisons between three or more groups). Alpha error was set to 0.05 in this study.

To assess the time-dependent effects of pretreatment (Objective 1), HUVECs were treated with vehicle or oxLDL for up to three hours following EPA pretreatment for 30 min—alone or in combination with ATM—versus DHA, fenofibrate, niacin and gemfibrozil. NO and $ONOO^-$ release were measured following stimulation with calcium. Cells were incubated with the various test agents at 10 μM and then challenged with oxLDL at 11 mg/dL (based on protein concentration) prior to stimulating maximal NO and $ONOO^-$ release with 1.0 μM calcium ionophore. Control groups were treated with vehicle alone in the absence or presence of oxLDL. The NO/$ONOO^-$ ratio was calculated as the arithmetic quotient of separate NO and ONOO-measurements. HUVECs were pretreated for 30 min with the different compounds followed by exposure to oxLDL for up to 3 hr before stimulation of NO and $ONOO^-$ release with calcium.

To test the effects of oxLDL, cells were incubated with the various test agents at 10 μM and then challenged with oxLDL at 11 mg/dL (based on protein concentration) prior to stimulating maximal NO and ONOO– release with 1.0 μM calcium ionophore. Control groups were treated with vehicle alone in the absence or presence of oxLDL. The NO/ONOO– ratio was calculated as the arithmetic quotient of separate NO and ONOO– measurements. HUVECs were pretreated for 30 min with the different compounds followed by exposure to oxLDL for up to 3 hr before stimulation of NO and ONOO– release with calcium. As shown in Table 4 and FIG. 42, all of the tested treatments improved endothelial function for up to 3 hrs if applied prior to the addition of oxLDL. The greatest improvement in the NO/$ONOO^-$ ratio was observed with the combination of EPA and ATM as it increased this ratio by 86% from 1.12±0.14 with vehicle to 2.05±0.23 with the combination treatment (p<0.001). This increase with the combination was significant as compared to DHA (1.68±0.12) or ATM (1.69±0.23) alone (p<0.05) and even EPA alone (1.73±0.20). It was also significant compared to fenofibrate (1.51±0.19), gemfibrozil (1.65±0.13) and niacin (1.45±0.14). All of the treatments improved the NO/$ONOO^-$ ratio as compared to vehicle treatment alone. Values are mean±S.D. (N=3-4). *p<0.05 and **p<0.001 versus vehicle only (no oxLDL); p<0.001 versus vehicle-then-oxLDL; § p<0.05 versus separate ATM or DHA treatments (Student-Newman-Keuls multiple comparisons test; overall ANOVA: p<0.0001, F=13.631).

TABLE 4

Effects of oxLDL on NO and $ONOO^-$ release from HUVECs pretreated with EPA, ATM, EPA/ATM combination, DHA, fenofibrate, gemfibrozil, or nicotinic acid.

| Treatment | NO | $ONOO^-$ | NO/$ONOO^-$ Ratio |
|---|---|---|---|
| Vehicle | 431 ± 20 | 208 ± 3 | 2.08 ± 0.10 |
| Vehicle, oxLDL | 294 ± 25** | 263 ± 23* | 1.12 ± 0.14** |
| EPA, oxLDL | 394 ± 43‡ | 228 ± 10 | 1.73 ± 0.20*‡ |
| ATM, oxLDL | 382 ± 25‡ | 226 ± 26 | 1.69 ± 0.23*† |
| EPA/ATM, oxLDL | 428 ± 25‡§ | 209 ± 21† | 2.05 ± 0.23‡¶ |
| DHA, oxLDL | 378 ± 5† | 229 ± 16 | 1.68 ± 0.12*† |
| Fenofib, oxLDL | 349 ± 28*† | 231 ± 22 | 1.51 ± 0.19*† |
| Gemfib, oxLDL | 377 ± 24† | 228 ± 11 | 1.65 ± 0.13*† |
| Niacin, oxLDL | 346 ± 17*† | 238 ± 20 | 1.45 ± 0.14*† |

Values are reported as mean ± S.D. (N = 3-4).
*p < 0.05 and **p < 0.001 versus vehicle-only treatment;
†p <0.05 and ‡p <0.001 versus vehicle, oxLDL treatment;
§p <0.05 versus cognate Fenofib or Niacin treatments;
¶p < 0.05 versus all other treatments (Student-Newman-Keuls multiple comparisons post hoc test; overall ANOVA—NO release data: p < 0.0001, F = 9.431;
$ONOO^-$ release data: p = 0.0099, F = 3.132;
NO/$ONOO^-$ ratio data: p < 0.0001, F = 9.972).

To test the effects of EPA-alone or in combination with ATM-versus DHA on EC function (Objective 2), HUVECs were treated with vehicle or oxLDL that was treated for 30 min with EPA, alone or in combination with ATM, or DHA. After 60 min exposure to the oxLDL that had been treated with EPA, EPA/ATM or DHA, the cells were stimulated with calcium to measure release of NO and $ONOO^-$.

Cells were co-incubated with the various test agents, each at 10 μM, and oxLDL at 11 mg/dL (based on protein concentration) prior to stimulating maximal NO and $ONOO^-$ release with 1.0 μM calcium ionophore. Control groups were treated with vehicle alone in the absence or presence of oxLDL. The NO/$ONOO^-$ ratio was calculated as the arithmetic quotient of separate NO and ONOO⁻ measurements. HUVECs were treated with oxLDL that had been already treated with the different compounds for 30 min. After 60 min, NO and ONOO release was induced with 1.0 µM calcium ionophore stimulation, and the amounts of released NO and ONOO were measured.

To test the comparative effects of EPA, DHA and EPA/ATM combination treatment, cells were co-incubated with the various test agents, each at 10 µM, and oxLDL at 11 mg/dL (based on protein concentration) prior to stimulating maximal NO and ONOO⁻ release with 1.0 µM calcium ionophore. Control groups were treated with vehicle alone in the absence or presence of oxLDL. The NO/ONOO– ratio was calculated as the arithmetic quotient of separate NO and ONOO– measurements. HUVECs were treated with oxLDL that had been already treated with the different compounds for 30 min. After 60 min, NO and ONOO– release were measured with calcium stimulation. As shown in Table 5 and FIG. 43, the greatest improvement in endothelial function were observed with the combination of EPA and ATM (1.94±0.25) by two-fold as compared to vehicle+oxLDL (0.94±0.22). This effect was significant as compared to DHA+oxLDL (1.51±0.30) or EPA+oxLDL alone (1.66±0.25). Values are mean±S.D. (N=3-4). *p<0.05 and **p<0.001 versus vehicle only (no oxLDL); †p<0.05 and ‡p<0.001 versus vehicle+oxLDL; § p<0.05 versus DHA+oxLDL (Student-Newman-Keuls multiple comparisons test; overall ANOVA: p<0.0001, F=13.958).

TABLE 5

Comparative effects of EPA, DHA, and EPA/ATM combination treatment on NO and ONOO⁻ release from HUVECs treated concomitantly with oxLDL.

| Treatment | NO | ONOO⁻ | NO/ONOO⁻ Ratio |
|---|---|---|---|
| Vehicle | 426 ± 42 | 211 ± 22 | 2.02 ± 0.29 |
| Vehicle + oxLDL | 262 ± 45** | 278 ± 43* | 0.94 ± 0.22** |
| EPA + oxLDL | 385 ± 43‡ | 232 ± 24† | 1.66 ± 0.25† |
| EPA/ATM + oxLDL | 416 ± 36‡ | 215 ± 20† | 1.94 ± 0.25‡§ |
| DHA + oxLDL | 362 ± 39‡ | 240 ± 27 | 1.51 ± 0.23*† |

Values are reported as mean ± S.D. (N = 4-7).
*p < 0.05 and **p <0.001 versus vehicle-only treatment;
†p < 0.05 and ‡p < 0.001 versus vehicle + oxLDL treatment;
§p < 0.05 versus cognate DHA treatment (Student-Newman-Keuls multiple comparisons post hoc test; overall ANOVA—NO release data: p < 0.0001, F = 15.700;
ONOO⁻ release data: p = 0.0166, F = 3.969;
NO/ONOO⁻ ratio data: p < 0.0001, F = 13.958).

To test the effects of EPA pretreatment of HUVECs combined with the effects of EPA pretreatment of LDL undergoing auto-oxidation (Objective 3), HUVECs were pretreated with EPA—alone or in combination with ATM—or DHA for 30 min. The cells were then exposed to native LDL that had been pretreated with these same agents under conditions of auto-oxidation for 2 h. After 60 min, NO and ONOO⁻ release were measured after being induced with addition of calcium.

Cells were co-incubated with the various test agents, each at 10 µM, and oxLDL or native LDL, each at 11 mg/dL (based on protein concentration), prior to stimulating maximal NO and ONOO⁻ release with 1.0 µM calcium ionophore. Control groups were treated with vehicle alone in the absence or presence of oxLDL. The NO/ONOO⁻ ratio was calculated as the arithmetic quotient of separate NO and ONOO⁻ measurements. HUVECs were pretreated with the different agents for 30 min. The cells were then exposed to LDL that had been pretreated with the different compounds under conditions of auto-oxidation for 30 min. After 60 min, NO and ONOO⁻ release were measured after being stimulated with addition of calcium.

To test the comparative effects of EPA, DHA and EPA/ATM combination treatment combination treatment on NO and ONOO– release from HUVECs treated concomitantly with native LDL (and then exposed to oxidative conditions) versus cells treated with oxLDL directly, cells were co-incubated with the various test agents, each at 10 µM, and oxLDL or native LDL, each at 11 mg/dL (based on protein concentration), prior to stimulating maximal NO and ONOO– release with 1.0 µM calcium ionophore. Control groups were treated with vehicle alone in the absence or presence of oxLDL. The NO/ONOO– ratio was calculated as the arithmetic quotient of separate NO and ONOO– measurements. HUVECs were pretreated with the different agents for 30 min. The cells were then exposed to LDL that had been pretreated with the different compounds under conditions of auto-oxidation for 30 min. After 60 min, NO and ONOO– release was measured with calcium stimulation. As shown in Table 6 and FIG. 44, the greatest improvement in endothelial function was observed with the combination of EPA and ATM+LDL (auto-oxidized) (2.19±0.33) as compared to vehicle+oxLDL (0.95±0.22); the improvement was not significant compared to vehicle+LDL (auto-oxidized) (1.53±0.20). This effect was numerically greater as compared to DHA (1.92±0.30) and EPA (2.03±0.30) alone but not in a statistically significant fashion.

TABLE 6

Comparative effects of EPA, DHA, and EPA/ATM combination pretreatment on NO and ONOO⁻ release from HUVECs treated concomitantly with native LDL undergoing oxidation. Values are mean ± S.D. (N = 3-4). **p < 0.001 versus vehicle only (no oxLDL); †p < 0.01 versus vehicle + LDL; §p < 0.001 versus vehicle + oxLDL (Student-Newman-Keuls multiple comparisons test; overall ANOVA: p < 0.0001, F = 13.436).

| Treatment | NO | ONOO⁻ | NO/ONOO⁻ Ratio |
|---|---|---|---|
| Vehicle | 430 ± 43 | 212 ± 25 | 2.03 ± 0.32 |
| Vehicle + LDL | 362 ± 30 | 237 ± 24 | 1.53 ± 0.20 |
| Vehicle + oxLDL | 263 ± 45**‡ | 278 ± 43*† | 0.95 ± 0.22**† |
| EPA + LDL | 419 ± 37§ | 207 ± 24§ | 2.03 ± 0.30§ |
| EPA/ATM + LDL | 444 ± 54†§ | 202 ± 18§ | 2.19 ± 0.33†§ |
| DHA + LDL | 406 ± 40§ | 212 ± 26§ | 1.92 ± 0.30§ |

Values are reported as mean ± S.D. (N = 4-7).
*p <0.01 and **p <0.001 versus vehicle-only treatment;
†p < 0.05 and ††p < 0.001 versus vehicle + LDL treatment;
§p < 0.01 versus vehicle + oxLDL treatment (Student-Newman-Keuls multiple comparisons post hoc test; overall ANOVA—NO release data: p < 0.0001, F = 15.995;
ONOO⁻ release data: p = 0.0017, F = 5.412;
NO/ONOO⁻ ratio data: p < 0.0001, F = 13.436).

In all of the different test conditions, the best improvement in endothelial function was observed with the combination of EPA and ATM. This was evident when the treatments were added prior to oxLDL exposure (i.e. HUVEC pretreatment) or to oxLDL that is then added to the HUVECs. Finally, the combination of EPA and ATM was also best when added to the LDL while undergoing oxidative conditions.

Example 12

An experiment to study the antioxidant effect of EPA in small dense LDL ("sdLDL") was performed. sdLDL was isolated from human plasma by isopycnic centrifugation, separated into test samples of 200 µg/mL, and incubated at 37° C. for 30 min in the absence (vehicle) or presence of EPA, fenofibrate, niacin, or gemfibrozil, each at 10.0 µM. All samples, with the exception of non-oxidized sdLDL controls, were subjected to copper-induced oxidation for 1 hour. Human umbilical vein endothelial cells (HUVECs) were incubated with the various sdLDL samples, stimulated with calcium, and monitored for nitric oxide (NO) and peroxynitrite (ONOO$^-$) release using nanosensor technology.

EPA treatment reduced sdLDL oxidation by >90% (p<0.001) compared to vehicle treatment alone. When applied directly to HUVECs, vehicle-treated, oxidized sdLDL reduced NO release by 20% as compared to non-oxidized sdLDL (from 758±40 to 610±43 nM). Following exposure to EPA-treated, oxidized sdLDL, however, HUVEC NO release (931±59 nM) increased by 53% and 23% as compared to oxidized LDL and non-oxidized sdLDL treatments, respectively. None of the other TG-lowering agents inhibited sdLDL oxidation, resulting in reduced NO release. In HUVECs challenged with oxidized sdLDL, pretreated with fenofibrate, niacin, or gemfibrozil, NO release was reduced by 21%, 45%, and 33%, respectively, as compared to effects observed with vehicle-treated, oxidized sdLDL (p<0.05).

These data demonstrate that EPA pretreatment reduced sdLDL oxidation and improved endothelial function as compared to other TG-lowering agents.

Example 13

A study was performed to test the separate and combined effects of EPA and atorvastatin o-hydroxy (active) metabolite (ATM) on endothelial function measured ex vivo in rat renal glomerular endothelial cells (ECs) exposed to oxidized LDL (oxLDL) and high glucose levels. The effects of EPA and ATM on EC function were compared to those of other TG-lowering agents (niacin and fenofibrate), as well as docosahexaenoic acid (DHA).

Healthy male Wistar Kyoto (WKY) rats, aged 7-9 weeks and weighing 250±20 g, were obtained from inbred colonies (National Institutes of Health, Bethesda, Md.). Animals were housed in a controlled environment that provided food and water ad libitum prior to the study. Food was provided in the form of a standard, purified diet (19% protein, 12% fat, 69% carbohydrates, expressed as % of total energy content in units of kcal/g) obtained from Purina TestDiet (Richmond, Ind.). Animals were sacrificed and tissue samples obtained immediately for experimentation. All procedures were conducted in accordance with standard Institutional Animal Care and Use Committee guidelines and conformed to the Guide for the Care and Use of Laboratory Animals published by the US National Institutes of Health.

EPA and DHA were purchased from Sigma-Aldrich (St. Louis, Mo.) and solubilized in ethanol to 1.0 mM under nitrogen atmosphere. ATM was purchased from Toronto Research Chemicals (North York, Ontario, Canada) and solubilized in methanol to 1.0 mM. Fenofibrate and niacin were purchased from Sigma-Aldrich and solubilized in ethanol to 1.0 mM. The calcium ionophore (Cal), A23187, was purchased from Sigma-Aldrich and prepared in aqueous buffer to 1.0 mM. All test compounds were further diluted in ethanol or aqueous buffer as needed.

Venous blood from healthy normolipidemic volunteers was collected into Na-EDTA (1 mg/mL blood) vacuum tubes after a 12-hour fast. LDL ($\delta$=1.020 to 1.063 g/mL) was separated from freshly drawn plasma by preparative ultracentrifugation as previously described. The LDL fraction was dialyzed for 96 hours against PBS containing 0.3 mM EDTA and stored at 4° C. until experimental use.

LDL was oxidized according to the methods of Huber et al. 16 Briefly, the purified LDL fraction was dialyzed against Tris/NaCl Buffer (50 mM Tris in 0.15 M NaCl, pH 8.0) to remove EDTA. Additional buffer was added to adjust the protein concentration to 30 mg/mL. LDL oxidation was initiated with 20 µM CuSO$_4$ and monitored spectrophotometrically (234 nm) over a period of 24 hours until complete. The oxLDL was then dialyzed at 4° C. with 4 L Tris buffer, filtered with a 0.22 µm filter, and stored under nitrogen at 4° C.

Immediately after sacrificing the rats, kidneys were removed, cut into 100 µm sections and transferred to a separate organ chamber containing Dulbecco's phosphate buffered saline (137 M NaCl, 2.7 M KCl, 8.1 M Na$_2$HPO$_4$, 1.5 M KH$_2$PO$_4$, 0.9 M CaCl$_2$, and 0.49 M MgCl$_2$) and 5.6 M glucose at pH 7.4.

Concurrent measurements of NO and ONOO$^-$ were performed on intact glomerular (cortical zone) endothelial cells using tandem electrochemical nanosensors, as previously described (FIG. 45).

The NO/ONOO– nanosensor was positioned near the surface of the endothelial cells using a computer-controlled M3301 micromanipulator (x-y-z resolution of 0.2 µm) and microscope (both from World Precision Instruments, Berlin, Germany) fitted with a CD camera. Each analyte was measured from amperograms and standard calibration curves collected under maximum current. The nanosensors have a high reproducibility of measurement (5% to 12%) at a constant distance from the surface of the endothelial cell. After establishing a background current, maximal NO and ONOO$^-$ release was induced by injecting Cal into the organ chamber using a nanoinjector (World Precision Instruments, Berlin Germany). Changes in current (proportional to the molar concentrations of NO or ONOO$^-$ released) were monitored continuously immediately following Cal stimulation.

Cal-stimulated changes in NO/ONOO$^-$ release were measured in glomerular endothelial cells exposed to oxLDL (11 mg/dL) and glucose (300 mg/dL) versus vehicle (for 5 min) and then treated (for 1 hr) with either EPA, ATM, or EPA+ATM (each treatment at 10.0 µM) versus vehicle. We compared the effects of EPA and ATM to DHA and to other TG-lowering agents (fenofibrate, niacin) under these same conditions. In preliminary experiments within our laboratory using human umbilical vein endothelial cells (HUVECs) exposed to oxidized LDL, EPA was found to increase NO release in a manner that was significantly enhanced by co-treatment with ATM; similar effects were not observed with DHA or any of the other TG-lowering agents (fenofibrate, niacin) in combination with ATM.

Data are presented as mean±standard deviation (SD) for (N) separate samples or experiments. Differences between groups were analyzed using the unpaired, two-tailed Student's t-test (for comparisons between only two groups) or ANOVA followed by Student-Newman-Keuls multiple comparisons post hoc analysis (for comparisons between three or more groups). Only differences with probability values less than 0.05 were considered significant.

As shown in FIGS. 46-48, simulating disease-like conditions by exposure to oxLDL and high glucose levels caused an 81% reduction (p<0.001) in endothelial NO release and a 112% increase (p<0.001) in ONOO$^-$ release as compared to untreated controls. The NO/ONOO$^-$ ratio, an indicator of eNOS coupling efficiency, decreased from 2.89 to 0.26 (p<0.001).

In ECs exposed to disease-like conditions, treatment with EPA increased NO release by 205% (p<0.001), reduced ONOO⁻ release by 27% ($p<0.05$), and increased the NO/ONOO⁻ ratio more than 4-fold (to 1.08; $p<0.01$).

ATM also improved EC function under disease-like conditions, increasing NO release by 205% ($p<0.001$), reducing ONOO⁻ release by 25% ($p<0.05$), and increasing the NO/ONOO⁻ ratio more than 4-fold ($p<0.01$). DHA, fenofibrate, and niacin had similar but quantitatively smaller effects on EC function.

EPA and ATM combination treatment increased NO release by 298% ($p<0.001$), decreased ONOO⁻ release by 32% ($p<0.05$), and increased the NO/ONOO⁻ ratio approximately 6-fold (to 1.51; $p<0.001$) as compared to vehicle treatment alone. The combined effects of EPA and ATM on NO release and the NO/ONOO⁻ ratio were significantly greater than observed for either agent alone ($p<0.05$).

These data demonstrate that EPA and ATM improve endothelial function in an ex vivo model of EC dysfunction in a manner that is significantly enhanced by their co-administration. Although the mechanism for this combinatorial effect is not fully understood, these data suggest that EPA-ATM interactions may provide atheroprotective benefits beyond changes in lipid levels alone, which may be of particular interest in patients with dyslipidemia and impaired glucose metabolism.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A method of reducing or preventing sdLDL oxidation in a subject having a high baseline serum glucose level of at least 126 mg/dL and a baseline triglyceride level of about 200 mg/dL to 499 mg/dL, the method comprising administering to the subject a pharmaceutical composition comprising eicosapentaenoic acid or a derivative thereof and further comprising a step of determining a baseline oxidized sdLDL level in the subject prior to administering the pharmaceutical composition to the subject.

2. The method of claim 1, wherein the pharmaceutical composition comprises at least 80%, at least 90%, at least 95%, or at least 96%, by weight of all fatty acids (and/or derivatives thereof) present, eicosapentaenoic acid or a derivative thereof.

3. The method of claim 1, wherein the pharmaceutical composition comprises no docosahexaenoic acid or esters thereof.

4. The method of claim 1, wherein the reduction or prevention occurs by a free radical chain-breaking mechanism.

5. The method of claim 1 further comprising determining a second oxidized sdLDL level in the subject after administering to the subject a pharmaceutical composition comprising eicosapentaenoic acid or a derivative thereof, wherein the second oxidized sdLDL level is not greater than, not significantly greater than, or lower than the baseline oxidized sdLDL level and/or wherein the second oxidized sdLDL level is not greater than, not significantly greater than, or lower than the baseline oxidized sdLDL level in comparison to a second subject who has not received the pharmaceutical composition.

6. The method of claim 5, wherein the method further comprises administering atorvastatin and/or o-hydroxyatorvastatin to the subject.

7. The method of claim 6, wherein the second oxidized sdLDL level is not greater than, not significantly greater than, or lower than the baseline oxidized sdLDL level in comparison to a second subject who has received the atorvastatin and/or the o-hydroxyatorvastatin but not the pharmaceutical composition.

8. The method of claim 6, wherein the second oxidized sdLDL level is not greater than, not significantly greater than, or lower than the baseline oxidized sdLDL level in comparison to a second subject who has received the pharmaceutical composition but not the o-hydroxyatorvastatin.

9. The method of claim 1, wherein the subject is on statin therapy, optionally stable statin therapy.

10. The method of claim 1, wherein the subject is diabetic.

11. The method of claim 1, wherein the high baseline serum glucose level is a fasting serum glucose level of at least 160 mg/dL.

12. The method of claim 1, wherein the high baseline serum glucose level is a non-fasting serum glucose level of at least 200 mg/dL.

13. A method of treating or preventing atherosclerosis in a subject by reducing or preventing sdLDL oxidation in the subject, the method comprising administering to the subject a pharmaceutical composition comprising eicosapentaenoic acid or a derivative thereof, and further comprising determining a baseline oxidized sdLDL level in the subject prior to administering the pharmaceutical composition to the subject.

* * * * *